US009669083B2

(12) United States Patent
Castado

(10) Patent No.: US 9,669,083 B2
(45) Date of Patent: Jun. 6, 2017

(54) IMMUNOGENIC COMPOSITION COMPRISING ELEMENTS OF C. DIFFICILE CDTB AND/OR CDTA PROTEINS

(71) Applicant: GLAXOSMITHKLINE BIOLOGICALS S.A., Rixensart (BE)

(72) Inventor: Cindy Castado, Rixensart (BE)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 14/653,989

(22) PCT Filed: Dec. 20, 2013

(86) PCT No.: PCT/EP2013/077762

§ 371 (c)(1),
(2) Date: Jun. 19, 2015

(87) PCT Pub. No.: WO2014/096393

PCT Pub. Date: Jun. 26, 2014

(65) Prior Publication Data

US 2015/0313985 A1 Nov. 5, 2015

(30) Foreign Application Priority Data

Dec. 23, 2012 (GB) .................................. 1223342.5

(51) Int. Cl.
*A61K 39/08* (2006.01)
*A61K 39/00* (2006.01)

(52) U.S. Cl.
CPC .... *A61K 39/08* (2013.01); *A61K 2039/55516* (2013.01); *A61K 2039/6068* (2013.01)

(58) Field of Classification Search
None
See application file for complete search history.

(56) References Cited

FOREIGN PATENT DOCUMENTS

| | | | |
|---|---|---|---|
| WO | 2010/093801 | | 8/2010 |
| WO | 2011/060431 | | 5/2011 |
| WO | WO 2012/028741 | * | 3/2012 |
| WO | 2013/112867 | | 8/2013 |

OTHER PUBLICATIONS

GST Gene Fusion System. Third Edition, Revision 2. 1997 Retrieved from http://www.personal.psu.edu/zcl1/lab/protocols/GST%20Gene%20Fusion%20System.pdf on Nov. 15, 2016.*
McTigue. J. Mol. Biol (1995) 246, 21-27, 1995.*
Gulke, et al., Characterization of the Enzymatic Component of the ADP-Ribosyltransferase Toxin CDTa from Clostridium difficile, Infection and Immunity, 69(10):6004-6011 (2001).
Barth, et al., Binary Bacterial Toxins: Biochemistry, Biology, and Applications of Common Clostridium and Bacillus Proteins, Microbiology and Molecular Biology Reviews 68(3):373-402 (2004).
Sundriyal, et al., Expression, purification and cell cytotoxicity of actin-modifying binary toxin from Clostridium difficile, Protein Expression and Purification 74(1):42-48 (2010).
Carter, et al., Binary Toxin Production in Clostridium difficile is Regulated by CdtR, a LytTR Family Response Regulator, Journal of Bacteriology 189(20): 7290-7301 (2007).

* cited by examiner

*Primary Examiner* — Oluwatosin Ogunbiyi
(74) *Attorney, Agent, or Firm* — Virginia G. Campen

(57) ABSTRACT

The present invention relates to immunogenic compositions comprising isolated *Clostridium difficile* CDTb and/or CDTa protein. In particular the isolated *Clostridium difficile* CDTb protein is suitably a truncated CDTb protein comprising the receptor binding domain or a mutated CDTb protein incapable of binding to CDTa, and the isolated *Clostridium difficile* CDTa protein is suitably a truncated CDTa protein which does not comprise the C-terminal domain. In particular the invention also relates to fusion proteins comprising a CDTa protein and a CDTb protein and also fusion proteins between an isolated *Clostridium difficile* toxin A protein and/or an isolated *Clostridium difficile* toxin B protein fused to a CDTb protein.

14 Claims, 40 Drawing Sheets

| | 20120410 : Mice immunization with C. difficile Binary Toxin formulated in AS01B Binary toxin cytotoxicity inhibition Assay on HCT116 cells : Inhibition titers on Post III pooled sera | |
|---|---|---|
| | AS01B CDTa 5µg/dose | AS01B CDTb 5µg/dose |
| Geomean | 3254 | 33629 |

| | 5µg/dose CdtB non-activated | 5µg/dose CdtB chemotrypsin-activated | 5 + 5 µg/dose + F2 CdtB non-activated | 5 + 5 µg/dose + F2 CdtB chemotrypsin-activated |
|---|---|---|---|---|
| Geomean | 225348 | 414499 | 145782 | 283643 |

| | 5µg/dose CdtB non-activated | 5µg/dose CdtB Chemotrypsin-activated | AS01B 5 + 5 µg/dose + F2 CdtB non-activated | AS01B 5 + 5 µg/dose + F2 CdtB Chemotrypsin-activated | AS03B 3µg/dose F2 |
|---|---|---|---|---|---|
| Pools D42 | | | 1205 | 1696 | 1004 |

SEQUENCE LISTING

<160> NUMBER OF SEQ ID NOS: 56

<210> SEQ ID NO 1
<211> LENGTH: 463
<212> TYPE: PRT
<213> ORGANISM: Clostridium Difficile

<400> SEQUENCE: 1

```
Met Lys Lys Phe Arg Lys His Lys Arg Ile Ser Asn Cys Ile Ser Ile
 1               5                  10                  15

Leu Leu Ile Leu Tyr Leu Thr Leu Gly Gly Leu Leu Pro Asn Asn Ile
            20                  25                  30

Tyr Ala Gln Asp Leu Gln Ser Tyr Ser Glu Lys Val Cys Asn Thr Thr
        35                  40                  45

Tyr Lys Ala Pro Ile Glu Arg Pro Glu Asp Phe Leu Lys Asp Lys Glu
    50                  55                  60

Lys Ala Lys Glu Trp Glu Arg Lys Glu Ala Glu Arg Ile Glu Gln Lys
65                  70                  75                  80

Leu Glu Arg Ser Glu Lys Glu Ala Leu Glu Ser Tyr Lys Lys Asp Ser
                85                  90                  95

Val Glu Ile Ser Lys Tyr Ser Gln Thr Arg Asn Tyr Phe Tyr Asp Tyr
            100                 105                 110

Gln Ile Glu Ala Asn Ser Arg Glu Lys Glu Tyr Lys Glu Leu Arg Asn
        115                 120                 125

Ala Ile Ser Lys Asn Lys Ile Asp Lys Pro Met Tyr Val Tyr Tyr Phe
    130                 135                 140

Glu Ser Pro Glu Lys Phe Ala Phe Asn Lys Val Ile Arg Thr Glu Asn
145                 150                 155                 160

Gln Asn Glu Ile Ser Leu Glu Lys Phe Asn Glu Phe Lys Glu Thr Ile
                165                 170                 175

Gln Asn Lys Leu Phe Lys Gln Asp Gly Phe Lys Asp Ile Ser Leu Tyr
            180                 185                 190

Glu Pro Gly Lys Gly Asp Glu Lys Pro Thr Pro Leu Leu Met His Leu
        195                 200                 205

Lys Leu Pro Arg Asn Thr Gly Met Leu Pro Tyr Thr Asn Thr Asn Asn
    210                 215                 220

Val Ser Thr Leu Ile Glu Gln Gly Tyr Ser Ile Lys Ile Asp Lys Ile
225                 230                 235                 240

Val Arg Ile Val Ile Asp Gly Lys His Tyr Ile Lys Ala Glu Ala Ser
                245                 250                 255

Val Val Ser Ser Leu Asp Phe Lys Asp Asp Val Ser Lys Gly Asp Ser
            260                 265                 270

Trp Gly Lys Ala Asn Tyr Asn Asp Trp Ser Asn Lys Leu Thr Pro Asn
        275                 280                 285

Glu Leu Ala Asp Val Asn Asp Tyr Met Arg Gly Gly Tyr Thr Ala Ile
    290                 295                 300

Asn Asn Tyr Leu Ile Ser Asn Gly Pro Val Asn Asn Pro Asn Pro Glu
305                 310                 315                 320

Leu Asp Ser Lys Ile Thr Asn Ile Glu Asn Ala Leu Lys Arg Glu Pro
                325                 330                 335
```

```
Ile Pro Thr Asn Leu Thr Val Tyr Arg Arg Ser Gly Pro Gln Glu Phe
            340                 345                 350

Gly Leu Thr Leu Thr Ser Pro Glu Tyr Asp Phe Asn Lys Leu Glu Asn
        355                 360                 365

Ile Asp Ala Phe Lys Ser Lys Trp Glu Gly Gln Ala Leu Ser Tyr Pro
    370                 375                 380

Asn Phe Ile Ser Thr Ser Ile Gly Ser Val Asn Met Ser Ala Phe Ala
385                 390                 395                 400

Lys Arg Lys Ile Val Leu Arg Ile Thr Ile Pro Lys Gly Ser Pro Gly
                405                 410                 415

Ala Tyr Leu Ser Ala Ile Pro Gly Tyr Ala Gly Glu Tyr Glu Val Leu
            420                 425                 430

Leu Asn His Gly Ser Lys Phe Lys Ile Asn Lys Ile Asp Ser Tyr Lys
        435                 440                 445

Asp Gly Thr Ile Thr Lys Leu Ile Val Asp Ala Thr Leu Ile Pro
    450                 455                 460


<210> SEQ ID NO 2
<211> LENGTH: 1392
<212> TYPE: DNA
<213> ORGANISM: Clostridium Difficile

<400> SEQUENCE: 2

atgaaaaaat ttaggaaaca taaaaggatt agtaattgta tatctatatt gttgatatta      60

tatctaactt taggtggttt gttacctaat aacatttatg cacaagactt acaaagctat     120

agtgaaaaag tttgcaatac tacttacaag gctcctatag aaagaccaga agattttctt     180

aaagataaag aaaaggctaa agaatgggaa agaaaagaag cagaaagaat agagcaaaaa     240

cttgaaagat ctgaaaaaga agcattagaa tcatataaaa aagattctgt agaaataagt     300

aaatattctc agacaagaaa ttatttttat gattatcaaa tagaagcaaa ttctcgagaa     360

aaagaatata aagaacttcg aaatgctata tcaaaaaata aaatagataa acctatgtat     420

gtctattatt ttgaatctcc agaaaaattt gcatttaata aagtaataag aacagaaaat     480

caaaacgaaa tttcattaga aaaatttaat gagtttaaag aaactataca aaacaaatta     540

tttaagcaag atggatttaa agatatttct ttatatgaac ctggaaaagg tgatgaaaaa     600

cctacaccat tacttatgca cttaaaatta cctagaaata ctggtatgtt accatataca     660

aatactaaca atgtaagtac attaatagag caaggatata gtataaaaat agataaaatt     720

gttcgtatag ttatagatgg gaagcactat attaaagcag aagcatctgt tgtaagtagt     780

cttgatttta aagatgatgt aagtaagggg gattcttggg gtaaagcaaa ttataatgat     840

tggagtaata aattaacacc taatgaactt gctgatgtaa atgattatat gcgtggagga     900

tatactgcaa ttaataatta tttaatatca aatggtccag taaataatcc taacccagaa     960

ttagattcta aaatcacaaa cattgaaaat gcattaaaac gtgaacctat tccaactaat    1020

ttaactgtat atagaagatc tggtcctcaa gaatttggtt taactcttac ttcccctgaa    1080

tatgatttta acaaactaga aaatatagat gcttttaaat caaaatggga aggacaagca    1140

ctgtcttatc caaactttat tagtactagt attggtagtg tgaatatgag tgcatttgct    1200

aaaagaaaaa tagtactacg tataactata cctaaaggtt ctcctggagc ttatctatca    1260

gctattccag gttatgcagg tgaatatgaa gtgcttttaa atcatggaag caaatttaaa    1320

atcaataaaa ttgattctta caaagatggt actataacaa aattaattgt tgatgcaaca    1380
```

```
ttgatacctt aa                                                           1392


<210> SEQ ID NO 3
<211> LENGTH: 876
<212> TYPE: PRT
<213> ORGANISM: Clostridium Difficile

<400> SEQUENCE: 3

Met Lys Ile Gln Met Arg Asn Lys Lys Val Leu Ser Phe Leu Thr Leu
 1               5                  10                  15

Thr Ala Ile Val Ser Gln Ala Leu Val Tyr Pro Val Tyr Ala Gln Thr
            20                  25                  30

Ser Thr Ser Asn His Ser Asn Lys Lys Lys Glu Ile Val Asn Glu Asp
        35                  40                  45

Ile Leu Pro Asn Asn Gly Leu Met Gly Tyr Tyr Phe Thr Asp Glu His
    50                  55                  60

Phe Lys Asp Leu Lys Leu Met Ala Pro Ile Lys Asp Gly Asn Leu Lys
65                  70                  75                  80

Phe Glu Glu Lys Lys Val Asp Lys Leu Leu Asp Lys Asp Lys Ser Asp
                85                  90                  95

Val Lys Ser Ile Arg Trp Thr Gly Arg Ile Ile Pro Ser Lys Asp Gly
            100                 105                 110

Glu Tyr Thr Leu Ser Thr Asp Arg Asp Asp Val Leu Met Gln Val Asn
        115                 120                 125

Thr Glu Ser Thr Ile Ser Asn Thr Leu Lys Val Asn Met Lys Lys Gly
    130                 135                 140

Lys Glu Tyr Lys Val Arg Ile Glu Leu Gln Asp Lys Asn Leu Gly Ser
145                 150                 155                 160

Ile Asp Asn Leu Ser Ser Pro Asn Leu Tyr Trp Glu Leu Asp Gly Met
                165                 170                 175

Lys Lys Ile Ile Pro Glu Glu Asn Leu Phe Leu Arg Asp Tyr Ser Asn
            180                 185                 190

Ile Glu Lys Asp Asp Pro Phe Ile Pro Asn Asn Asn Phe Phe Asp Pro
        195                 200                 205

Lys Leu Met Ser Asp Trp Glu Asp Glu Asp Leu Asp Thr Asp Asn Asp
    210                 215                 220

Asn Ile Pro Asp Ser Tyr Glu Arg Asn Gly Tyr Thr Ile Lys Asp Leu
225                 230                 235                 240

Ile Ala Val Lys Trp Glu Asp Ser Phe Ala Glu Gln Gly Tyr Lys Lys
                245                 250                 255

Tyr Val Ser Asn Tyr Leu Glu Ser Asn Thr Ala Gly Asp Pro Tyr Thr
            260                 265                 270

Asp Tyr Glu Lys Ala Ser Gly Ser Phe Asp Lys Ala Ile Lys Thr Glu
        275                 280                 285

Ala Arg Asp Pro Leu Val Ala Ala Tyr Pro Ile Val Gly Val Gly Met
    290                 295                 300

Glu Lys Leu Ile Ile Ser Thr Asn Glu His Ala Ser Thr Asp Gln Gly
305                 310                 315                 320

Lys Thr Val Ser Arg Ala Thr Thr Asn Ser Lys Thr Glu Ser Asn Thr
                325                 330                 335

Ala Gly Val Ser Val Asn Val Gly Tyr Gln Asn Gly Phe Thr Ala Asn
            340                 345                 350

Val Thr Thr Asn Tyr Ser His Thr Thr Asp Asn Ser Thr Ala Val Gln
        355                 360                 365
```

-continued

```
Asp Ser Asn Gly Glu Ser Trp Asn Thr Gly Leu Ser Ile Asn Lys Gly
    370                 375                 380

Glu Ser Ala Tyr Ile Asn Ala Asn Val Arg Tyr Tyr Asn Thr Gly Thr
385                 390                 395                 400

Ala Pro Met Tyr Lys Val Thr Pro Thr Thr Asn Leu Val Leu Asp Gly
                405                 410                 415

Asp Thr Leu Ser Thr Ile Lys Ala Gln Glu Asn Gln Ile Gly Asn Asn
            420                 425                 430

Leu Ser Pro Gly Asp Thr Tyr Pro Lys Lys Gly Leu Ser Pro Leu Ala
        435                 440                 445

Leu Asn Thr Met Asp Gln Phe Ser Ser Arg Leu Ile Pro Ile Asn Tyr
    450                 455                 460

Asp Gln Leu Lys Lys Leu Asp Ala Gly Lys Gln Ile Lys Leu Glu Thr
465                 470                 475                 480

Thr Gln Val Ser Gly Asn Phe Gly Thr Lys Asn Ser Ser Gly Gln Ile
                485                 490                 495

Val Thr Glu Gly Asn Ser Trp Ser Asp Tyr Ile Ser Gln Ile Asp Ser
            500                 505                 510

Ile Ser Ala Ser Ile Ile Leu Asp Thr Glu Asn Glu Ser Tyr Glu Arg
        515                 520                 525

Arg Val Thr Ala Lys Asn Leu Gln Asp Pro Glu Asp Lys Thr Pro Glu
    530                 535                 540

Leu Thr Ile Gly Glu Ala Ile Glu Lys Ala Phe Gly Ala Thr Lys Lys
545                 550                 555                 560

Asp Gly Leu Leu Tyr Phe Asn Asp Ile Pro Ile Asp Glu Ser Cys Val
                565                 570                 575

Glu Leu Ile Phe Asp Asp Asn Thr Ala Asn Lys Ile Lys Asp Ser Leu
            580                 585                 590

Lys Thr Leu Ser Asp Lys Lys Ile Tyr Asn Val Lys Leu Glu Arg Gly
        595                 600                 605

Met Asn Ile Leu Ile Lys Thr Pro Thr Tyr Phe Thr Asn Phe Asp Asp
    610                 615                 620

Tyr Asn Asn Tyr Pro Ser Thr Trp Ser Asn Val Asn Thr Thr Asn Gln
625                 630                 635                 640

Asp Gly Leu Gln Gly Ser Ala Asn Lys Leu Asn Gly Glu Thr Lys Ile
                645                 650                 655

Lys Ile Pro Met Ser Glu Leu Lys Pro Tyr Lys Arg Tyr Val Phe Ser
            660                 665                 670

Gly Tyr Ser Lys Asp Pro Leu Thr Ser Asn Ser Ile Ile Val Lys Ile
        675                 680                 685

Lys Ala Lys Glu Glu Lys Thr Asp Tyr Leu Val Pro Glu Gln Gly Tyr
    690                 695                 700

Thr Lys Phe Ser Tyr Glu Phe Glu Thr Thr Glu Lys Asp Ser Ser Asn
705                 710                 715                 720

Ile Glu Ile Thr Leu Ile Gly Ser Gly Thr Thr Tyr Leu Asp Asn Leu
                725                 730                 735

Ser Ile Thr Glu Leu Asn Ser Thr Pro Glu Ile Leu Asp Glu Pro Glu
            740                 745                 750

Val Lys Ile Pro Thr Asp Gln Glu Ile Met Asp Ala His Lys Ile Tyr
        755                 760                 765

Phe Ala Asp Leu Asn Phe Asn Pro Ser Thr Gly Asn Thr Tyr Ile Asn
    770                 775                 780

Gly Met Tyr Phe Ala Pro Thr Gln Thr Asn Lys Glu Ala Leu Asp Tyr
```

-continued

```
785                 790                 795                 800

Ile Gln Lys Tyr Arg Val Glu Ala Thr Leu Gln Tyr Ser Gly Phe Lys
                805                 810                 815

Asp Ile Gly Thr Lys Asp Lys Glu Met Arg Asn Tyr Leu Gly Asp Pro
            820                 825                 830

Asn Gln Pro Lys Thr Asn Tyr Val Asn Leu Arg Ser Tyr Phe Thr Gly
        835                 840                 845

Gly Glu Asn Ile Met Thr Tyr Lys Lys Leu Arg Ile Tyr Ala Ile Thr
    850                 855                 860

Pro Asp Asp Arg Glu Leu Leu Val Leu Ser Val Asp
865                 870                 875


<210> SEQ ID NO 4
<211> LENGTH: 2631
<212> TYPE: DNA
<213> ORGANISM: Clostridium Difficile

<400> SEQUENCE: 4

atgaaaatac aaatgaggaa taaaaaggta ttaagttttt taacacttac agctatagtt     60

agtcaagcac tagtatatcc tgtatatgct caaactagta caagtaatca ttctaataag    120

aaaaaagaaa ttgtaaatga agatatactc ccaaacaatg gattaatggg atattatttc    180

acagatgagc actttaaaga tttaaaatta atggcaccca taaaagatgg taatttaaaa    240

tttgaagaaa agaaagtaga taaacttctg gataaagaca aatcagatgt aaaatctata    300

cgatggacag gaagaataat tccttctaag gatggtgaat atacattatc aactgataga    360

gatgatgtct taatgcaagt aaatactgag agtactatat caaatacact taaagttaat    420

atgaaaaagg gtaaagaata taaagttaga atagagctac aagataaaaa tttaggttca    480

atagataatt tatcatcacc taatctttat tgggaattag atggtatgaa gaaaattata    540

ccagaagaaa atttattctt aagagattat tctaatatag aaaaagatga tccatttatc    600

ccaaataaca atttctttga cccaaagttg atgtctgatt gggaagacga agatttggat    660

acagataatg ataatatacc agattcatat gaacgaaatg gatatactat taaggactta    720

attgcagtta agtgggaaga tagttttgca gaacaaggct ataagaaata tgtatcaaat    780

tatttagagt caaatactgc tggagatcca tatacagatt atgaaaaagc ttcaggttct    840

tttgacaagg ctataaagac tgaagcaaga gatccgttag ttgcagcata tccaattgtt    900

ggagtaggta tggaaaaatt aattatatct acaaatgaac atgcctctac tgatcaaggt    960

aaaactgttt ccagagctac tactaacagt aaaactgaat ctaatacagc tggtgtgtct   1020

gttaatgtag gatatcaaaa tggattcaca gctaatgtaa ctacaaatta ttcccataca   1080

acagataatt caactgctgt tcaagatagt aatggagaat catggaatac tggattaagt   1140

ataaacaaag gagaatctgc atatataaat gcaaatgtta gatattacaa cacaggtact   1200

gcacctatgt acaaagtgac accaacaaca aatttagtgt tagatggaga tacattatca   1260

actatcaaag cacaagaaaa tcaaattggc aataatctat ctcctggaga tacttatccc   1320

aaaaaagggc tttcacctct agctcttaac acaatggatc aatttagctc tagactgatt   1380

cctataaatt atgatcaatt aaaaaaatta gatgctggaa agcaaattaa attagaaaca   1440

acacaagtaa gtggaaattt tggtacaaaa aatagttctg gacaaatagt aacagaagga   1500

aatagttggt cagactatat aagtcaaatt gacagtattt ctgcatctat tatattagat   1560

acagagaatg aatcttacga aagaagagtt actgctaaaa atttacagga tccagaagat   1620
```

-continued

```
aaaacacctg aacttacaat tggagaagca attgaaaaag cttttggcgc tactaaaaaa   1680

gatggtttgt tatattttaa tgatatacca atagatgaaa gttgtgttga actcatattt   1740

gatgataata cagccaataa gattaaagat agtttaaaaa ctttgtctga taaaaagata   1800

tataatgtta aacttgaaag aggaatgaat atacttataa aaacaccaac ttactttact   1860

aattttgatg attataataa ttaccctagt acatggagta atgtcaatac tacgaatcaa   1920

gatggtttac aaggctcagc aaataaatta aatggtgaga cgaagattaa aatccctatg   1980

tctgagctaa aaccttataa acgttatgtt tttagtggat attcaaagga tcctttaaca   2040

tctaattcaa taattgtaaa gataaaagca aaagaagaga aaacggatta tttggtacca   2100

gaacaaggat atacaaaatt tagttatgaa tttgaaacta ctgaaaaaga ttcttctaat   2160

atagagataa cattaattgg tagtggtaca acatacttag ataacttatc tattacagag   2220

ctaaatagta ctcctgaaat acttgatgaa ccagaagtta aaattccaac tgaccaagaa   2280

ataatggatg cacataaaat atattttgca gatttaaatt ttaatccaag tacaggaaat   2340

acttatataa atggtatgta ttttgcacca acacaaacta ataaagaagc tctcgattat   2400

atccaaaaat atagagttga agctacttta caatattctg gatttaaaga tattggaact   2460

aaagataaag aaatgcgtaa ttatttagga gatccaaatc agcctaaaac taattatgtt   2520

aatcttagga gttattttac aggtggagaa aatattatga catacaagaa attaagaata   2580

tatgcaatta ctccagacga tagagagtta ttagttctta gtgttgatta g            2631
```

```
<210> SEQ ID NO 5
<211> LENGTH: 421
<212> TYPE: PRT
<213> ORGANISM: Artificial Sequence
<220> FEATURE:
<223> OTHER INFORMATION: CDTa C34 construct polypeptide

<400> SEQUENCE: 5

Met Val Cys Asn Thr Thr Tyr Lys Ala Pro Ile Glu Arg Pro Glu Asp
1               5                   10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190
```

```
Ile Lys Ile Asp Lys Ile Val Arg Ile Val Ile Asp Gly Lys His Tyr
        195                 200                 205

Ile Lys Ala Glu Ala Ser Val Val Ser Ser Leu Asp Phe Lys Asp Asp
    210                 215                 220

Val Ser Lys Gly Asp Ser Trp Gly Lys Ala Asn Tyr Asn Asp Trp Ser
225                 230                 235                 240

Asn Lys Leu Thr Pro Asn Glu Leu Ala Asp Val Asn Asp Tyr Met Arg
                245                 250                 255

Gly Gly Tyr Thr Ala Ile Asn Asn Tyr Leu Ile Ser Asn Gly Pro Val
            260                 265                 270

Asn Asn Pro Asn Pro Glu Leu Asp Ser Lys Ile Thr Asn Ile Glu Asn
        275                 280                 285

Ala Leu Lys Arg Glu Pro Ile Pro Thr Asn Leu Thr Val Tyr Arg Arg
    290                 295                 300

Ser Gly Pro Gln Glu Phe Gly Leu Thr Leu Thr Ser Pro Glu Tyr Asp
305                 310                 315                 320

Phe Asn Lys Leu Glu Asn Ile Asp Ala Phe Lys Ser Lys Trp Glu Gly
                325                 330                 335

Gln Ala Leu Ser Tyr Pro Asn Phe Ile Ser Thr Ser Ile Gly Ser Val
            340                 345                 350

Asn Met Ser Ala Phe Ala Lys Arg Lys Ile Val Leu Arg Ile Thr Ile
        355                 360                 365

Pro Lys Gly Ser Pro Gly Ala Tyr Leu Ser Ala Ile Pro Gly Tyr Ala
    370                 375                 380

Gly Glu Tyr Glu Val Leu Leu Asn His Gly Ser Lys Phe Lys Ile Asn
385                 390                 395                 400

Lys Ile Asp Ser Tyr Lys Asp Gly Thr Ile Thr Lys Leu Ile Val Asp
                405                 410                 415

Ala Thr Leu Ile Pro
            420


<210> SEQ ID NO 6
<211> LENGTH: 1266
<212> TYPE: PRT
<213> ORGANISM: Artificial Sequence
<220> FEATURE:
<223> OTHER INFORMATION: CDTb C34 construct polynucleotide

<400> SEQUENCE: 6

Ala Thr Gly Gly Thr Thr Thr Gly Cys Ala Ala Thr Ala Cys Cys Ala
 1               5                  10                  15

Cys Cys Thr Ala Thr Ala Ala Ala Gly Cys Ala Cys Cys Gly Ala Thr
            20                  25                  30

Thr Gly Ala Ala Cys Gly Thr Cys Cys Gly Gly Ala Ala Gly Ala Thr
        35                  40                  45

Thr Thr Thr Cys Thr Gly Ala Ala Ala Gly Ala Thr Ala Ala Ala Gly
    50                  55                  60

Ala Ala Ala Ala Ala Gly Cys Cys Ala Ala Ala Gly Ala Ala Thr Gly
65                  70                  75                  80

Gly Gly Ala Ala Cys Gly Cys Ala Ala Ala Gly Ala Ala Gly Cys Ala
                85                  90                  95

Gly Ala Ala Cys Gly Thr Ala Thr Thr Gly Ala Ala Cys Ala Gly Ala
            100                 105                 110

Ala Ala Cys Thr Gly Gly Ala Ala Cys Gly Thr Ala Gly Cys Gly Ala
        115                 120                 125
```

-continued

```
Ala Ala Ala Ala Gly Ala Ala Gly Cys Ala Cys Thr Gly Gly Ala Ala
    130                 135                 140

Ala Gly Cys Thr Ala Cys Ala Ala Ala Ala Ala Ala Gly Ala Thr Ala
145                 150                 155                 160

Gly Cys Gly Thr Gly Gly Ala Ala Ala Thr Thr Thr Cys Ala Ala Ala
                165                 170                 175

Ala Thr Ala Thr Ala Gly Cys Cys Ala Gly Ala Cys Cys Cys Gly Cys
            180                 185                 190

Ala Ala Thr Thr Ala Thr Thr Thr Cys Thr Ala Thr Gly Ala Thr Thr
        195                 200                 205

Ala Thr Cys Ala Gly Ala Thr Thr Gly Ala Ala Gly Cys Cys Ala Ala
    210                 215                 220

Thr Ala Gly Cys Cys Gly Thr Gly Ala Ala Ala Ala Ala Gly Ala Ala
225                 230                 235                 240

Thr Ala Thr Ala Ala Ala Gly Ala Ala Cys Thr Gly Cys Gly Cys Ala
                245                 250                 255

Ala Thr Gly Cys Cys Ala Thr Thr Ala Gly Cys Ala Ala Ala Ala Ala
            260                 265                 270

Cys Ala Ala Ala Ala Thr Thr Gly Ala Thr Ala Ala Ala Cys Cys Gly
        275                 280                 285

Ala Thr Gly Thr Ala Thr Gly Thr Gly Thr Ala Thr Thr Ala Thr Thr
    290                 295                 300

Thr Cys Gly Ala Ala Ala Gly Thr Cys Cys Gly Gly Ala Ala Ala Ala
305                 310                 315                 320

Ala Thr Thr Thr Gly Cys Cys Thr Thr Thr Ala Ala Cys Ala Ala Ala
                325                 330                 335

Gly Thr Gly Ala Thr Thr Cys Gly Cys Ala Cys Cys Gly Ala Ala Ala
            340                 345                 350

Ala Thr Cys Ala Gly Ala Ala Thr Gly Ala Ala Ala Thr Thr Ala Gly
        355                 360                 365

Cys Cys Thr Gly Gly Ala Ala Ala Ala Ala Thr Thr Cys Ala Ala Thr
    370                 375                 380

Gly Ala Ala Thr Thr Thr Ala Ala Ala Gly Ala Ala Ala Cys Cys Ala
385                 390                 395                 400

Thr Thr Cys Ala Gly Ala Ala Thr Ala Ala Ala Cys Thr Gly Thr Thr
                405                 410                 415

Thr Ala Ala Ala Cys Ala Gly Gly Ala Thr Gly Gly Cys Thr Thr Thr
            420                 425                 430

Ala Ala Ala Gly Ala Thr Ala Thr Thr Thr Cys Ala Cys Thr Gly Thr
        435                 440                 445

Ala Thr Gly Ala Ala Cys Cys Gly Gly Gly Thr Ala Ala Ala Gly Gly
    450                 455                 460

Thr Gly Ala Thr Gly Ala Ala Ala Ala Ala Cys Cys Gly Ala Cys Ala
465                 470                 475                 480

Cys Cys Gly Cys Thr Gly Cys Thr Gly Ala Thr Gly Cys Ala Thr Cys
                485                 490                 495

Thr Gly Ala Ala Ala Cys Thr Gly Cys Cys Thr Cys Gly Thr Ala Ala
            500                 505                 510

Thr Ala Cys Cys Gly Gly Thr Ala Thr Gly Cys Thr Gly Cys Cys Gly
        515                 520                 525

Thr Ala Thr Ala Cys Cys Ala Ala Thr Ala Cys Cys Ala Ala Thr Ala
    530                 535                 540
```

-continued

```
Ala Thr Gly Thr Thr Ala Gly Cys Ala Cys Cys Cys Thr Gly Ala Thr
545                 550                 555                 560

Thr Gly Ala Ala Cys Ala Gly Gly Gly Cys Thr Ala Thr Ala Gly Cys
                565                 570                 575

Ala Thr Cys Ala Ala Ala Ala Thr Thr Gly Ala Thr Ala Ala Ala Ala
            580                 585                 590

Thr Thr Gly Thr Gly Cys Gly Cys Ala Thr Thr Gly Thr Gly Ala Thr
        595                 600                 605

Thr Gly Ala Thr Gly Gly Cys Ala Ala Ala Cys Ala Thr Thr Ala Thr
    610                 615                 620

Ala Thr Cys Ala Ala Ala Gly Cys Cys Gly Ala Ala Gly Cys Cys Ala
625                 630                 635                 640

Gly Cys Gly Thr Thr Gly Thr Thr Thr Cys Ala Ala Gly Cys Cys Thr
                645                 650                 655

Gly Gly Ala Thr Thr Thr Thr Ala Ala Ala Gly Ala Thr Gly Ala Thr
            660                 665                 670

Gly Thr Gly Ala Gly Cys Ala Ala Ala Gly Gly Cys Gly Ala Thr Ala
        675                 680                 685

Gly Cys Thr Gly Gly Gly Gly Thr Ala Ala Ala Gly Cys Ala Ala Ala
    690                 695                 700

Cys Thr Ala Thr Ala Ala Thr Gly Ala Thr Thr Gly Gly Ala Gly Cys
705                 710                 715                 720

Ala Ala Thr Ala Ala Ala Cys Thr Gly Ala Cys Cys Cys Cys Gly Ala
                725                 730                 735

Ala Thr Gly Ala Ala Cys Thr Gly Gly Cys Ala Gly Ala Thr Gly Thr
            740                 745                 750

Gly Ala Ala Thr Gly Ala Thr Thr Ala Thr Ala Thr Gly Cys Gly Thr
        755                 760                 765

Gly Gly Thr Gly Gly Thr Thr Ala Thr Ala Cys Cys Gly Cys Cys Ala
    770                 775                 780

Thr Thr Ala Ala Cys Ala Ala Thr Thr Ala Thr Cys Thr Gly Ala Thr
785                 790                 795                 800

Thr Ala Gly Cys Ala Ala Thr Gly Gly Thr Cys Cys Gly Gly Thr Gly
                805                 810                 815

Ala Ala Thr Ala Ala Thr Cys Cys Gly Ala Ala Thr Cys Cys Gly Gly
            820                 825                 830

Ala Ala Cys Thr Gly Gly Ala Thr Ala Gly Cys Ala Ala Ala Ala Thr
        835                 840                 845

Thr Ala Cys Cys Ala Ala Thr Ala Thr Thr Gly Ala Ala Ala Ala Thr
    850                 855                 860

Gly Cys Cys Cys Thr Gly Ala Ala Ala Cys Gly Cys Gly Ala Ala Cys
865                 870                 875                 880

Cys Gly Ala Thr Thr Cys Cys Gly Ala Cys Cys Ala Ala Thr Cys Thr
                885                 890                 895

Gly Ala Cys Cys Gly Thr Thr Thr Ala Thr Cys Gly Thr Cys Gly Thr
            900                 905                 910

Ala Gly Cys Gly Gly Thr Cys Cys Gly Cys Ala Ala Gly Ala Ala Thr
        915                 920                 925

Thr Thr Gly Gly Thr Cys Thr Gly Ala Cys Cys Cys Thr Gly Ala Cys
   930                 935                 940

Cys Ala Gly Thr Cys Cys Gly Gly Ala Ala Thr Ala Thr Gly Ala Cys
945                 950                 955                 960

Thr Thr Thr Ala Ala Cys Ala Ala Ala Cys Thr Gly Gly Ala Ala Ala
```

-continued

```
                965                 970                 975

Ala Thr Ala Thr Thr Gly Ala Thr Gly Cys Cys Thr Thr Thr Ala Ala
            980                 985                 990

Ala Ala Gly Cys Ala Ala Ala Thr Gly Gly Gly Ala Ala Gly Gly Thr
        995                 1000                1005

Cys Ala Gly Gly Cys Ala Cys Thr Gly Ala Gly Cys Thr Ala Thr Cys
    1010                1015                1020

Cys Gly Ala Ala Cys Thr Thr Thr Ala Thr Thr Ala Gly Cys Ala Cys
1025                1030                1035                1040

Cys Ala Gly Cys Ala Thr Thr Gly Gly Thr Ala Gly Cys Gly Thr Thr
                1045                1050                1055

Ala Ala Thr Ala Thr Gly Ala Gly Cys Gly Cys Ala Thr Thr Thr Gly
            1060                1065                1070

Cys Cys Ala Ala Ala Cys Gly Thr Ala Ala Ala Ala Thr Thr Gly Thr
        1075                1080                1085

Gly Cys Thr Gly Cys Gly Thr Ala Thr Thr Ala Cys Cys Ala Thr Thr
    1090                1095                1100

Cys Cys Gly Ala Ala Ala Gly Gly Thr Ala Gly Thr Cys Cys Gly Gly
1105                1110                1115                1120

Gly Thr Gly Cys Ala Thr Ala Thr Cys Thr Gly Ala Gly Cys Gly Cys
                1125                1130                1135

Ala Ala Thr Thr Cys Cys Gly Gly Gly Thr Thr Ala Thr Gly Cys Cys
            1140                1145                1150

Gly Gly Thr Gly Ala Ala Thr Ala Thr Gly Ala Ala Gly Thr Thr Cys
        1155                1160                1165

Thr Gly Cys Thr Gly Ala Ala Thr Cys Ala Thr Gly Gly Cys Ala Gly
    1170                1175                1180

Cys Ala Ala Ala Thr Thr Cys Ala Ala Ala Ala Thr Thr Ala Ala Cys
1185                1190                1195                1200

Ala Ala Ala Ala Thr Thr Gly Ala Thr Ala Gly Cys Thr Ala Thr Ala
                1205                1210                1215

Ala Ala Gly Ala Thr Gly Gly Cys Ala Cys Cys Ala Thr Thr Ala Cys
            1220                1225                1230

Cys Ala Ala Ala Cys Thr Gly Ala Thr Thr Gly Thr Thr Gly Ala Thr
        1235                1240                1245

Gly Cys Ala Ala Cys Cys Cys Thr Gly Ala Thr Thr Cys Cys Gly Thr
    1250                1255                1260

Ala Ala
1265


<210> SEQ ID NO 7
<211> LENGTH: 1067
<212> TYPE: PRT
<213> ORGANISM: Artificial Sequence
<220> FEATURE:
<223> OTHER INFORMATION: CDTb C37 construct. CDTb' (minus signal
      peptide) ligated to Glutathione-S-transferase protein
      polypeptide

<400> SEQUENCE: 7

Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45
```

-continued

```
Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Leu Gly Ser His Met Glu Ile Val Asn Glu Asp Ile
225                 230                 235                 240

Leu Pro Asn Asn Gly Leu Met Gly Tyr Tyr Phe Thr Asp Glu His Phe
                245                 250                 255

Lys Asp Leu Lys Leu Met Ala Pro Ile Lys Asp Gly Asn Leu Lys Phe
            260                 265                 270

Glu Glu Lys Lys Val Asp Lys Leu Leu Asp Lys Asp Lys Ser Asp Val
        275                 280                 285

Lys Ser Ile Arg Trp Thr Gly Arg Ile Ile Pro Ser Lys Asp Gly Glu
    290                 295                 300

Tyr Thr Leu Ser Thr Asp Arg Asp Asp Val Leu Met Gln Val Asn Thr
305                 310                 315                 320

Glu Ser Thr Ile Ser Asn Thr Leu Lys Val Asn Met Lys Lys Gly Lys
                325                 330                 335

Glu Tyr Lys Val Arg Ile Glu Leu Gln Asp Lys Asn Leu Gly Ser Ile
            340                 345                 350

Asp Asn Leu Ser Ser Pro Asn Leu Tyr Trp Glu Leu Asp Gly Met Lys
        355                 360                 365

Lys Ile Ile Pro Glu Glu Asn Leu Phe Leu Arg Asp Tyr Ser Asn Ile
    370                 375                 380

Glu Lys Asp Asp Pro Phe Ile Pro Asn Asn Asn Phe Phe Asp Pro Lys
385                 390                 395                 400

Leu Met Ser Asp Trp Glu Asp Glu Asp Leu Asp Thr Asp Asn Asp Asn
                405                 410                 415

Ile Pro Asp Ser Tyr Glu Arg Asn Gly Tyr Thr Ile Lys Asp Leu Ile
            420                 425                 430

Ala Val Lys Trp Glu Asp Ser Phe Ala Glu Gln Gly Tyr Lys Lys Tyr
        435                 440                 445

Val Ser Asn Tyr Leu Glu Ser Asn Thr Ala Gly Asp Pro Tyr Thr Asp
    450                 455                 460
```

-continued

```
Tyr Glu Lys Ala Ser Gly Ser Phe Asp Lys Ala Ile Lys Thr Glu Ala
465                 470                 475                 480

Arg Asp Pro Leu Val Ala Ala Tyr Pro Ile Val Gly Val Gly Met Glu
                485                 490                 495

Lys Leu Ile Ile Ser Thr Asn Glu His Ala Ser Thr Asp Gln Gly Lys
            500                 505                 510

Thr Val Ser Arg Ala Thr Thr Asn Ser Lys Thr Glu Ser Asn Thr Ala
        515                 520                 525

Gly Val Ser Val Asn Val Gly Tyr Gln Asn Gly Phe Thr Ala Asn Val
    530                 535                 540

Thr Thr Asn Tyr Ser His Thr Thr Asp Asn Ser Thr Ala Val Gln Asp
545                 550                 555                 560

Ser Asn Gly Glu Ser Trp Asn Thr Gly Leu Ser Ile Asn Lys Gly Glu
                565                 570                 575

Ser Ala Tyr Ile Asn Ala Asn Val Arg Tyr Tyr Asn Thr Gly Thr Ala
            580                 585                 590

Pro Met Tyr Lys Val Thr Pro Thr Thr Asn Leu Val Leu Asp Gly Asp
        595                 600                 605

Thr Leu Ser Thr Ile Lys Ala Gln Glu Asn Gln Ile Gly Asn Asn Leu
    610                 615                 620

Ser Pro Gly Asp Thr Tyr Pro Lys Lys Gly Leu Ser Pro Leu Ala Leu
625                 630                 635                 640

Asn Thr Met Asp Gln Phe Ser Ser Arg Leu Ile Pro Ile Asn Tyr Asp
                645                 650                 655

Gln Leu Lys Lys Leu Asp Ala Gly Lys Gln Ile Lys Leu Glu Thr Thr
            660                 665                 670

Gln Val Ser Gly Asn Phe Gly Thr Lys Asn Ser Ser Gly Gln Ile Val
        675                 680                 685

Thr Glu Gly Asn Ser Trp Ser Asp Tyr Ile Ser Gln Ile Asp Ser Ile
    690                 695                 700

Ser Ala Ser Ile Ile Leu Asp Thr Glu Asn Glu Ser Tyr Glu Arg Arg
705                 710                 715                 720

Val Thr Ala Lys Asn Leu Gln Asp Pro Glu Asp Lys Thr Pro Glu Leu
                725                 730                 735

Thr Ile Gly Glu Ala Ile Glu Lys Ala Phe Gly Ala Thr Lys Lys Asp
            740                 745                 750

Gly Leu Leu Tyr Phe Asn Asp Ile Pro Ile Asp Glu Ser Cys Val Glu
        755                 760                 765

Leu Ile Phe Asp Asp Asn Thr Ala Asn Lys Ile Lys Asp Ser Leu Lys
    770                 775                 780

Thr Leu Ser Asp Lys Lys Ile Tyr Asn Val Lys Leu Glu Arg Gly Met
785                 790                 795                 800

Asn Ile Leu Ile Lys Thr Pro Thr Tyr Phe Thr Asn Phe Asp Asp Tyr
                805                 810                 815

Asn Asn Tyr Pro Ser Thr Trp Ser Asn Val Asn Thr Thr Asn Gln Asp
            820                 825                 830

Gly Leu Gln Gly Ser Ala Asn Lys Leu Asn Gly Glu Thr Lys Ile Lys
        835                 840                 845

Ile Pro Met Ser Glu Leu Lys Pro Tyr Lys Arg Tyr Val Phe Ser Gly
    850                 855                 860

Tyr Ser Lys Asp Pro Leu Thr Ser Asn Ser Ile Ile Val Lys Ile Lys
865                 870                 875                 880

Ala Lys Glu Glu Lys Thr Asp Tyr Leu Val Pro Glu Gln Gly Tyr Thr
```

-continued

```
            885                 890                 895

Lys Phe Ser Tyr Glu Phe Glu Thr Thr Glu Lys Asp Ser Ser Asn Ile
            900                 905                 910

Glu Ile Thr Leu Ile Gly Ser Gly Thr Thr Tyr Leu Asp Asn Leu Ser
        915                 920                 925

Ile Thr Glu Leu Asn Ser Thr Pro Glu Ile Leu Asp Glu Pro Glu Val
    930                 935                 940

Lys Ile Pro Thr Asp Gln Glu Ile Met Asp Ala His Lys Ile Tyr Phe
945                 950                 955                 960

Ala Asp Leu Asn Phe Asn Pro Ser Thr Gly Asn Thr Tyr Ile Asn Gly
                965                 970                 975

Met Tyr Phe Ala Pro Thr Gln Thr Asn Lys Glu Ala Leu Asp Tyr Ile
            980                 985                 990

Gln Lys Tyr Arg Val Glu Ala Thr Leu Gln Tyr Ser Gly Phe Lys Asp
        995                 1000                1005

Ile Gly Thr Lys Asp Lys Glu Met Arg Asn Tyr Leu Gly Asp Pro Asn
    1010                1015                1020

Gln Pro Lys Thr Asn Tyr Val Asn Leu Arg Ser Tyr Phe Thr Gly Gly
1025                1030                1035                1040

Glu Asn Ile Met Thr Tyr Lys Lys Leu Arg Ile Tyr Ala Ile Thr Pro
                1045                1050                1055

Asp Asp Arg Glu Leu Leu Val Leu Ser Val Asp
            1060                1065
```

<210> SEQ ID NO 8
<211> LENGTH: 3204
<212> TYPE: DNA
<213> ORGANISM: Artificial Sequence
<220> FEATURE:
<223> OTHER INFORMATION: CDTb C37construct. CDTb' (minus pro-domain) ligated to Glutathione-S-transferase protein polynucleotide

<400> SEQUENCE: 8

```
atgtccccta tactaggtta ttggaaaatt aagggccttg tgcaacccac tcgacttctt      60

ttggaatatc ttgaagaaaa atatgaagag catttgtatg agcgcgatga aggtgataaa     120

tggcgaaaca aaaagtttga attgggtttg gagtttccca atcttcctta ttatattgat     180

ggtgatgtta aattaacaca gtctatggcc atcatacgtt atatagctga caagcacaac     240

atgttgggtg gttgtccaaa agagcgtgca gagatttcaa tgcttgaagg agcggttttg     300

gatattagat acggtgtttc gagaattgca tatagtaaag actttgaaac tctcaaagtt     360

gattttctta gcaagctacc tgaaatgctg aaaatgttcg aagatcgttt atgtcataaa     420

acatatttaa atggtgatca tgtaacccat cctgacttca tgttgtatga cgctcttgat     480

gttgttttat acatggaccc aatgtgcctg gatgcgttcc caaaattagt ttgttttaaa     540

aaacgtattg aagctatccc acaaattgat aagtacttga aatccagcaa gtatatagca     600

tggcctttgc agggctggca agccacgttt ggtggtggcg accatcctcc aaaatcggat     660

ctggaagttc tgttccaggg gcccctggga tcccatatgg aaattgtgaa tgaagatatt     720

ctgccgaata atggtctgat gggatactac tttaccgatg aacattttaa agatctgaaa     780

ctgatggcac cgattaaaga tggcaatctg aaatttgaag aaaaaaaagt ggataaactg     840

ctggataaag ataaaagtga tgtgaaaagc attcgttgga ccggtcgtat tattccgagc     900

aaagatggtg aatacacccct gagcaccgat cgtgatgatg ttctgatgca ggttaatacc     960
```

-continued

```
gaaagcacca ttagcaatac cctgaaagtg aatatgaaaa aaggcaaaga atataaagtg   1020
cgcattgaac tgcaggataa aaatctgggt agcattgata atctgagcag cccgaatctg   1080
tattgggaac tggatggtat gaaaaaaatc attccggaag aaaacctgtt tctgcgcgat   1140
tatagcaata ttgaaaaaga tgatccgttt attccgaata ataacttttt tgatccgaaa   1200
ctgatgagcg attgggaaga tgaagatctg gataccgata atgataatat tccggatagc   1260
tatgaacgca atggctatac cattaaagat ctgattgccg tgaaatggga agatagcttt   1320
gcagaacagg gctataagaa atatgtgagc aattatctgg aaagcaatac cgcaggcgat   1380
ccgtataccg attatgaaaa agcaagcggc agctttgata aagccattaa aaccgaagca   1440
cgtgatccgc tggttgcagc atatccgatt gttggtgttg gtatggaaaa actgattatt   1500
agcaccaatg aacatgcaag caccgatcag ggtaaaaccg ttagccgtgc aaccaccaat   1560
agcaaaaccg aaagcaatac agccggtgtt agcgttaatg ttggttatca gaatggtttt   1620
accgccaatg tgaccaccaa ttatagccat accaccgata atagcaccgc agttcaggat   1680
agcaatggtg aaagctggaa taccggtctg agcattaaca aaggtgaaag cgcatatatc   1740
aatgccaatg tgcgctatta taacaccggc accgcaccga tgtataaagt taccccgacc   1800
accaatctgg ttctggatgg tgataccctg agtaccatta aagcacaaga aaatcagatt   1860
ggcaataatc tgagtccggg tgatacctat ccgaaaaaag gtctgagtcc gctggcactg   1920
aataccatgg atcagtttag cagccgtctg attccgatta actatgatca gctgaaaaaa   1980
ctggatgccg gtaaacaaat caaactggaa accacccagg ttagcggtaa ttttggcacc   2040
aaaaattcaa gcggtcagat tgttaccgaa ggtaatagct ggtcagatta tatcagccag   2100
attgatagca ttagcgccag cattattctg gatacagaaa atgaaagcta tgaacgtcgt   2160
gtgaccgcaa aaaatctgca ggacccggaa gataaaacac cggaactgac cattggtgaa   2220
gcaattgaaa aagcatttgg tgccaccaaa aaagatggcc tgctgtattt taacgatatt   2280
ccgattgatg aaagctgcgt ggaactgatt tttgatgata ataccgccaa taaaatcaaa   2340
gatagcctga aaccctgag cgacaaaaaa atctataatg tgaaactgga acgcggtatg   2400
aatattctga ttaaaacccc gacctatttt accaattttg atgattataa caattatccg   2460
agcacttgga gcaatgtgaa taccaccaat caggatggtc tgcagggtag cgcaaataaa   2520
ctgaatggtg aaaccaaaat caaaattccg atgagcgaac tgaaaccgta taaacgttat   2580
gtgtttagcg gctatagcaa agatccgctg accagcaata gcattattgt gaaaatcaaa   2640
gccaaagaag aaaaaaccga ttatctggtt ccggaacagg gttataccaa atttagctat   2700
gaatttgaaa ccaccgaaaa agatagcagt aatattgaaa ttaccctgat tggtagcggc   2760
accacctatc tggataatct gagtattacc gaactgaata gcacaccgga aattctggat   2820
gaaccggaag tgaaaattcc gaccgatcaa gaaattatgg atgcccataa aatctatttt   2880
gccgatctga actttaatcc gagcaccggc aatacctata ttaacggcat gtattttgca   2940
ccgacccaga ccaataaaga agccctggat tatattcaga aatatcgtgt tgaagccacc   3000
ctgcagtata gcggttttaa agatattggc accaaagata aagaaatgcg taattatctg   3060
ggcgatccga atcagccgaa aaccaattat gttaatctgc gcagctattt taccggtggc   3120
gaaaacatta tgacctacaa aaaactgcgc atttatgcca ttacaccgga tgatcgtgaa   3180
ctgctggttc tgagcgttga ttaa                                           3204
```

<210> SEQ ID NO 9
<211> LENGTH: 667

<212> TYPE: PRT
<213> ORGANISM: Artificial Sequence
<220> FEATURE:
<223> OTHER INFORMATION: CDTb C40 construct. CDTb'' (minus pro-domain and signal peptide) polypeptide

<400> SEQUENCE: 9

```
Leu Met Ser Asp Trp Glu Asp Glu Asp Leu Asp Thr Asp Asn Asp Asn
 1               5                  10                  15

Ile Pro Asp Ser Tyr Glu Arg Asn Gly Tyr Thr Ile Lys Asp Leu Ile
            20                  25                  30

Ala Val Lys Trp Glu Asp Ser Phe Ala Glu Gln Gly Tyr Lys Lys Tyr
        35                  40                  45

Val Ser Asn Tyr Leu Glu Ser Asn Thr Ala Gly Asp Pro Tyr Thr Asp
    50                  55                  60

Tyr Glu Lys Ala Ser Gly Ser Phe Asp Lys Ala Ile Lys Thr Glu Ala
65                  70                  75                  80

Arg Asp Pro Leu Val Ala Ala Tyr Pro Ile Val Gly Val Gly Met Glu
                85                  90                  95

Lys Leu Ile Ile Ser Thr Asn Glu His Ala Ser Thr Asp Gln Gly Lys
            100                 105                 110

Thr Val Ser Arg Ala Thr Thr Asn Ser Lys Thr Glu Ser Asn Thr Ala
        115                 120                 125

Gly Val Ser Val Asn Val Gly Tyr Gln Asn Gly Phe Thr Ala Asn Val
    130                 135                 140

Thr Thr Asn Tyr Ser His Thr Thr Asp Asn Ser Thr Ala Val Gln Asp
145                 150                 155                 160

Ser Asn Gly Glu Ser Trp Asn Thr Gly Leu Ser Ile Asn Lys Gly Glu
                165                 170                 175

Ser Ala Tyr Ile Asn Ala Asn Val Arg Tyr Tyr Asn Thr Gly Thr Ala
            180                 185                 190

Pro Met Tyr Lys Val Thr Pro Thr Thr Asn Leu Val Leu Asp Gly Asp
        195                 200                 205

Thr Leu Ser Thr Ile Lys Ala Gln Glu Asn Gln Ile Gly Asn Asn Leu
    210                 215                 220

Ser Pro Gly Asp Thr Tyr Pro Lys Lys Gly Leu Ser Pro Leu Ala Leu
225                 230                 235                 240

Asn Thr Met Asp Gln Phe Ser Ser Arg Leu Ile Pro Ile Asn Tyr Asp
                245                 250                 255

Gln Leu Lys Lys Leu Asp Ala Gly Lys Gln Ile Lys Leu Glu Thr Thr
            260                 265                 270

Gln Val Ser Gly Asn Phe Gly Thr Lys Asn Ser Ser Gly Gln Ile Val
        275                 280                 285

Thr Glu Gly Asn Ser Trp Ser Asp Tyr Ile Ser Gln Ile Asp Ser Ile
    290                 295                 300

Ser Ala Ser Ile Ile Leu Asp Thr Glu Asn Glu Ser Tyr Glu Arg Arg
305                 310                 315                 320

Val Thr Ala Lys Asn Leu Gln Asp Pro Glu Asp Lys Thr Pro Glu Leu
                325                 330                 335

Thr Ile Gly Glu Ala Ile Glu Lys Ala Phe Gly Ala Thr Lys Lys Asp
            340                 345                 350

Gly Leu Leu Tyr Phe Asn Asp Ile Pro Ile Asp Glu Ser Cys Val Glu
        355                 360                 365

Leu Ile Phe Asp Asp Asn Thr Ala Asn Lys Ile Lys Asp Ser Leu Lys
    370                 375                 380
```

```
Thr Leu Ser Asp Lys Lys Ile Tyr Asn Val Lys Leu Glu Arg Gly Met
385                 390                 395                 400

Asn Ile Leu Ile Lys Thr Pro Thr Tyr Phe Thr Asn Phe Asp Asp Tyr
                405                 410                 415

Asn Asn Tyr Pro Ser Thr Trp Ser Asn Val Asn Thr Thr Asn Gln Asp
            420                 425                 430

Gly Leu Gln Gly Ser Ala Asn Lys Leu Asn Gly Glu Thr Lys Ile Lys
        435                 440                 445

Ile Pro Met Ser Glu Leu Lys Pro Tyr Lys Arg Tyr Val Phe Ser Gly
    450                 455                 460

Tyr Ser Lys Asp Pro Leu Thr Ser Asn Ser Ile Ile Val Lys Ile Lys
465                 470                 475                 480

Ala Lys Glu Glu Lys Thr Asp Tyr Leu Val Pro Glu Gln Gly Tyr Thr
                485                 490                 495

Lys Phe Ser Tyr Glu Phe Glu Thr Thr Glu Lys Asp Ser Ser Asn Ile
            500                 505                 510

Glu Ile Thr Leu Ile Gly Ser Gly Thr Thr Tyr Leu Asp Asn Leu Ser
        515                 520                 525

Ile Thr Glu Leu Asn Ser Thr Pro Glu Ile Leu Asp Glu Pro Glu Val
    530                 535                 540

Lys Ile Pro Thr Asp Gln Glu Ile Met Asp Ala His Lys Ile Tyr Phe
545                 550                 555                 560

Ala Asp Leu Asn Phe Asn Pro Ser Thr Gly Asn Thr Tyr Ile Asn Gly
                565                 570                 575

Met Tyr Phe Ala Pro Thr Gln Thr Asn Lys Glu Ala Leu Asp Tyr Ile
            580                 585                 590

Gln Lys Tyr Arg Val Glu Ala Thr Leu Gln Tyr Ser Gly Phe Lys Asp
        595                 600                 605

Ile Gly Thr Lys Asp Lys Glu Met Arg Asn Tyr Leu Gly Asp Pro Asn
    610                 615                 620

Gln Pro Lys Thr Asn Tyr Val Asn Leu Arg Ser Tyr Phe Thr Gly Gly
625                 630                 635                 640

Glu Asn Ile Met Thr Tyr Lys Lys Leu Arg Ile Tyr Ala Ile Thr Pro
                645                 650                 655

Asp Asp Arg Glu Leu Leu Val Leu Ser Val Asp
            660                 665
```

```
<210> SEQ ID NO 10
<211> LENGTH: 420
<212> TYPE: PRT
<213> ORGANISM: Artificial Sequence
<220> FEATURE:
<223> OTHER INFORMATION: C44 construct. CDTa mutation E428Q polypeptide

<400> SEQUENCE: 10

Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80
```

-continued

```
Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Ser Leu Asp Phe Lys Asp Asp
    210                 215                 220

Val Ser Lys Gly Asp Ser Trp Gly Lys Ala Asn Tyr Asn Asp Trp Ser
225                 230                 235                 240

Asn Lys Leu Thr Pro Asn Glu Leu Ala Asp Val Asn Asp Tyr Met Arg
                245                 250                 255

Gly Gly Tyr Thr Ala Ile Asn Asn Tyr Leu Ile Ser Asn Gly Pro Val
            260                 265                 270

Asn Asn Pro Asn Pro Glu Leu Asp Ser Lys Ile Thr Asn Ile Glu Asn
        275                 280                 285

Ala Leu Lys Arg Glu Pro Ile Pro Thr Asn Leu Thr Val Tyr Arg Arg
    290                 295                 300

Ser Gly Pro Gln Glu Phe Gly Leu Thr Leu Thr Ser Pro Glu Tyr Asp
305                 310                 315                 320

Phe Asn Lys Leu Glu Asn Ile Asp Ala Phe Lys Ser Lys Trp Glu Gly
                325                 330                 335

Gln Ala Leu Ser Tyr Pro Asn Phe Ile Ser Thr Ser Ile Gly Ser Val
            340                 345                 350

Asn Met Ser Ala Phe Ala Lys Arg Lys Ile Val Leu Arg Ile Thr Ile
        355                 360                 365

Pro Lys Gly Ser Pro Gly Ala Tyr Leu Ser Ala Ile Pro Gly Tyr Ala
    370                 375                 380

Gly Tyr Glu Val Leu Leu Asn His Gly Ser Lys Phe Lys Ile Asn Lys
385                 390                 395                 400

Ile Asp Ser Tyr Lys Asp Gly Thr Ile Thr Lys Leu Ile Val Asp Ala
                405                 410                 415

Thr Leu Ile Pro
            420
```

<210> SEQ ID NO 11
<211> LENGTH: 1266
<212> TYPE: DNA
<213> ORGANISM: Artificial Sequence
<220> FEATURE:
<223> OTHER INFORMATION: CDTa mutation E428Q polynucleotide

<400> SEQUENCE: 11

```
atggtttgca ataccaccta taaagcaccg attgaacgtc cggaagattt tctgaaagat     60
```

-continued

```
aaagaaaaag ccaaagaatg ggaacgcaaa gaagcagaac gtattgaaca gaaactggaa    120

cgtagcgaaa aagaagcact ggaaagctac aaaaaagata gcgtggaaat ttcaaaatat    180

agccagaccc gcaattattt ctatgattat cagattgaag ccaatagccg tgaaaaagaa    240

tataaagaac tgcgcaatgc cattagcaaa aacaaaattg ataaaccgat gtatgtgtat    300

tatttcgaaa gtccggaaaa atttgccttt aacaaagtga ttcgcaccga aaatcagaat    360

gaaattagcc tggaaaaatt caatgaattt aaagaaacca ttcagaataa actgtttaaa    420

caggatggct ttaaagatat ttcactgtat gaaccgggta aaggtgatga aaaaccgaca    480

ccgctgctga tgcatctgaa actgcctcgt aataccggta tgctgccgta taccaatacc    540

aataatgtta gcaccctgat tgaacagggc tatagcatca aaattgataa aattgtgcgc    600

attgtgattg atggcaaaca ttatatcaaa gccgaagcca gcgttgtttc aagcctggat    660

tttaaagatg atgtgagcaa aggcgatagc tggggtaaag caaactataa tgattggagc    720

aataaactga ccccgaatga actggcagat gtgaatgatt atatgcgtgg tggttatacc    780

gccattaaca attatctgat tagcaatggt ccggtgaata atccgaatcc ggaactggat    840

agcaaaatta ccaatattga aaatgccctg aaacgcgaac cgattccgac caatctgacc    900

gtttatcgtc gtagcggtcc gcaagaattt ggtctgaccc tgaccagtcc ggaatatgac    960

tttaacaaac tggaaaatat tgatgccttt aaaagcaaat gggaaggtca ggcactgagc   1020

tatccgaact ttattagcac cagcattggt agcgttaata tgagcgcatt tgccaaacgt   1080

aaaattgtgc tgcgtattac cattccgaaa ggtagtccgg gtgcatatct gagcgcaatt   1140

ccgggttatg ccggtcaata tgaagttctg ctgaatcatg gcagcaaatt caaaattaac   1200

aaaattgata gctataaaga tggcaccatt accaaactga ttgttgatgc aaccctgatt   1260

ccgtaa                                                               1266
```

```
<210> SEQ ID NO 12
<211> LENGTH: 420
<212> TYPE: PRT
<213> ORGANISM: Artificial Sequence
<220> FEATURE:
<223> OTHER INFORMATION: C54 construct. CDTa mutation E430Q polypeptide

<400> SEQUENCE: 12

Met Val Cys Asn Thr Thr Tyr Lys Ala Pro Ile Glu Arg Pro Glu Asp
1               5                   10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140
```

```
Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Ser Leu Asp Phe Lys Asp Asp
    210                 215                 220

Val Ser Lys Gly Asp Ser Trp Gly Lys Ala Asn Tyr Asn Asp Trp Ser
225                 230                 235                 240

Asn Lys Leu Thr Pro Asn Glu Leu Ala Asp Val Asn Asp Tyr Met Arg
                245                 250                 255

Gly Gly Tyr Thr Ala Ile Asn Asn Tyr Leu Ile Ser Asn Gly Pro Val
            260                 265                 270

Asn Asn Pro Asn Pro Glu Leu Asp Ser Lys Ile Thr Asn Ile Glu Asn
        275                 280                 285

Ala Leu Lys Arg Glu Pro Ile Pro Thr Asn Leu Thr Val Tyr Arg Arg
    290                 295                 300

Ser Gly Pro Gln Glu Phe Gly Leu Thr Leu Thr Ser Pro Glu Tyr Asp
305                 310                 315                 320

Phe Asn Lys Leu Glu Asn Ile Asp Ala Phe Lys Ser Lys Trp Glu Gly
                325                 330                 335

Gln Ala Leu Ser Tyr Pro Asn Phe Ile Ser Thr Ser Ile Gly Ser Val
            340                 345                 350

Asn Met Ser Ala Phe Ala Lys Arg Lys Ile Val Leu Arg Ile Thr Ile
        355                 360                 365

Pro Lys Gly Ser Pro Gly Ala Tyr Leu Ser Ala Ile Pro Gly Tyr Ala
    370                 375                 380

Gly Glu Tyr Val Leu Leu Asn His Gly Ser Lys Phe Lys Ile Asn Lys
385                 390                 395                 400

Ile Asp Ser Tyr Lys Asp Gly Thr Ile Thr Lys Leu Ile Val Asp Ala
                405                 410                 415

Thr Leu Ile Pro
            420


<210>  SEQ ID NO 13
<211> LENGTH: 198
<212> TYPE: PRT
<213> ORGANISM: Artificial Sequence
<220> FEATURE:
<223> OTHER INFORMATION: CDTa N terminal domain (residue 44 to residue
      240) polypeptide

<400> SEQUENCE: 13

Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80
```

```
Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile
        195
```

```
<210> SEQ ID NO 14
<211> LENGTH: 226
<212> TYPE: PRT
<213> ORGANISM: Artificial Sequence
<220> FEATURE:
<223> OTHER INFORMATION: C49 construct. CDTa Nterminal domain without
      signal peptide, with the linker existing between
      the N-term domain and the C-term domain
      (containing the enzymatic activity). This
      construct covers the fragment from amino acid 44
      to aa 268 polypeptide sequence.

<400> SEQUENCE: 14

Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205
```

```
Ile Lys Ala Glu Ala Ser Val Val Ser Ser Leu Asp Phe Lys Asp Asp
    210                 215                 220

Val Ser
225


<210> SEQ ID NO 15
<211> LENGTH: 218
<212> TYPE: PRT
<213> ORGANISM: Artificial Sequence
<220> FEATURE:
<223> OTHER INFORMATION: C50 construct. CDTa without signal peptide and
      the linker existing between the Nterminal and Cterminal domains of
      CDTa. This construct covers the fragment from aa 44 to aa 260
      polypeptide sequence.

<400> SEQUENCE: 15

Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Ser
    210                 215


<210> SEQ ID NO 16
<211> LENGTH: 834
<212> TYPE: PRT
<213> ORGANISM: Artificial Sequence
<220> FEATURE:
<223> OTHER INFORMATION: Polypeptide sequence of CDTb with pro-domain
      removed (CDTb')

<400> SEQUENCE: 16

Glu Ile Val Asn Glu Asp Ile Leu Pro Asn Asn Gly Leu Met Gly Tyr
 1               5                  10                  15

Tyr Phe Thr Asp Glu His Phe Lys Asp Leu Lys Leu Met Ala Pro Ile
            20                  25                  30

Lys Asp Gly Asn Leu Lys Phe Glu Glu Lys Lys Val Asp Lys Leu Leu
```

```
        35                  40                  45

Asp Lys Asp Lys Ser Asp Val Lys Ser Ile Arg Trp Thr Gly Arg Ile
    50                  55                  60

Ile Pro Ser Lys Asp Gly Glu Tyr Thr Leu Ser Thr Asp Arg Asp Asp
65                  70                  75                  80

Val Leu Met Gln Val Asn Thr Glu Ser Thr Ile Ser Asn Thr Leu Lys
                85                  90                  95

Val Asn Met Lys Lys Gly Lys Glu Tyr Lys Val Arg Ile Glu Leu Gln
            100                 105                 110

Asp Lys Asn Leu Gly Ser Ile Asp Asn Leu Ser Ser Pro Asn Leu Tyr
        115                 120                 125

Trp Glu Leu Asp Gly Met Lys Lys Ile Ile Pro Glu Glu Asn Leu Phe
    130                 135                 140

Leu Arg Asp Tyr Ser Asn Ile Glu Lys Asp Asp Pro Phe Ile Pro Asn
145                 150                 155                 160

Asn Asn Phe Phe Asp Pro Lys Leu Met Ser Asp Trp Glu Asp Glu Asp
                165                 170                 175

Leu Asp Thr Asp Asn Asp Asn Ile Pro Asp Ser Tyr Glu Arg Asn Gly
            180                 185                 190

Tyr Thr Ile Lys Asp Leu Ile Ala Val Lys Trp Glu Asp Ser Phe Ala
        195                 200                 205

Glu Gln Gly Tyr Lys Lys Tyr Val Ser Asn Tyr Leu Glu Ser Asn Thr
    210                 215                 220

Ala Gly Asp Pro Tyr Thr Asp Tyr Glu Lys Ala Ser Gly Ser Phe Asp
225                 230                 235                 240

Lys Ala Ile Lys Thr Glu Ala Arg Asp Pro Leu Val Ala Ala Tyr Pro
                245                 250                 255

Ile Val Gly Val Gly Met Glu Lys Leu Ile Ile Ser Thr Asn Glu His
            260                 265                 270

Ala Ser Thr Asp Gln Gly Lys Thr Val Ser Arg Ala Thr Thr Asn Ser
        275                 280                 285

Lys Thr Glu Ser Asn Thr Ala Gly Val Ser Val Asn Val Gly Tyr Gln
    290                 295                 300

Asn Gly Phe Thr Ala Asn Val Thr Thr Asn Tyr Ser His Thr Thr Asp
305                 310                 315                 320

Asn Ser Thr Ala Val Gln Asp Ser Asn Gly Glu Ser Trp Asn Thr Gly
                325                 330                 335

Leu Ser Ile Asn Lys Gly Glu Ser Ala Tyr Ile Asn Ala Asn Val Arg
            340                 345                 350

Tyr Tyr Asn Thr Gly Thr Ala Pro Met Tyr Lys Val Thr Pro Thr Thr
        355                 360                 365

Asn Leu Val Leu Asp Gly Asp Thr Leu Ser Thr Ile Lys Ala Gln Glu
    370                 375                 380

Asn Gln Ile Gly Asn Asn Leu Ser Pro Gly Asp Thr Tyr Pro Lys Lys
385                 390                 395                 400

Gly Leu Ser Pro Leu Ala Leu Asn Thr Met Asp Gln Phe Ser Ser Arg
                405                 410                 415

Leu Ile Pro Ile Asn Tyr Asp Gln Leu Lys Lys Leu Asp Ala Gly Lys
            420                 425                 430

Gln Ile Lys Leu Glu Thr Thr Gln Val Ser Gly Asn Phe Gly Thr Lys
        435                 440                 445

Asn Ser Ser Gly Gln Ile Val Thr Glu Gly Asn Ser Trp Ser Asp Tyr
    450                 455                 460
```

```
Ile Ser Gln Ile Asp Ser Ile Ser Ala Ser Ile Ile Leu Asp Thr Glu
465                 470                 475                 480

Asn Glu Ser Tyr Glu Arg Arg Val Thr Ala Lys Asn Leu Gln Asp Pro
                485                 490                 495

Glu Asp Lys Thr Pro Glu Leu Thr Ile Gly Glu Ala Ile Glu Lys Ala
            500                 505                 510

Phe Gly Ala Thr Lys Lys Asp Gly Leu Leu Tyr Phe Asn Asp Ile Pro
        515                 520                 525

Ile Asp Glu Ser Cys Val Glu Leu Ile Phe Asp Asp Asn Thr Ala Asn
    530                 535                 540

Lys Ile Lys Asp Ser Leu Lys Thr Leu Ser Asp Lys Lys Ile Tyr Asn
545                 550                 555                 560

Val Lys Leu Glu Arg Gly Met Asn Ile Leu Ile Lys Thr Pro Thr Tyr
                565                 570                 575

Phe Thr Asn Phe Asp Asp Tyr Asn Asn Tyr Pro Ser Thr Trp Ser Asn
            580                 585                 590

Val Asn Thr Thr Asn Gln Asp Gly Leu Gln Gly Ser Ala Asn Lys Leu
        595                 600                 605

Asn Gly Glu Thr Lys Ile Lys Ile Pro Met Ser Glu Leu Lys Pro Tyr
    610                 615                 620

Lys Arg Tyr Val Phe Ser Gly Tyr Ser Lys Asp Pro Leu Thr Ser Asn
625                 630                 635                 640

Ser Ile Ile Val Lys Ile Lys Ala Lys Glu Glu Lys Thr Asp Tyr Leu
                645                 650                 655

Val Pro Glu Gln Gly Tyr Thr Lys Phe Ser Tyr Glu Phe Glu Thr Thr
            660                 665                 670

Glu Lys Asp Ser Ser Asn Ile Glu Ile Thr Leu Ile Gly Ser Gly Thr
        675                 680                 685

Thr Tyr Leu Asp Asn Leu Ser Ile Thr Glu Leu Asn Ser Thr Pro Glu
    690                 695                 700

Ile Leu Asp Glu Pro Glu Val Lys Ile Pro Thr Asp Gln Glu Ile Met
705                 710                 715                 720

Asp Ala His Lys Ile Tyr Phe Ala Asp Leu Asn Phe Asn Pro Ser Thr
                725                 730                 735

Gly Asn Thr Tyr Ile Asn Gly Met Tyr Phe Ala Pro Thr Gln Thr Asn
            740                 745                 750

Lys Glu Ala Leu Asp Tyr Ile Gln Lys Tyr Arg Val Glu Ala Thr Leu
        755                 760                 765

Gln Tyr Ser Gly Phe Lys Asp Ile Gly Thr Lys Asp Lys Glu Met Arg
    770                 775                 780

Asn Tyr Leu Gly Asp Pro Asn Gln Pro Lys Thr Asn Tyr Val Asn Leu
785                 790                 795                 800

Arg Ser Tyr Phe Thr Gly Gly Glu Asn Ile Met Thr Tyr Lys Lys Leu
                805                 810                 815

Arg Ile Tyr Ala Ile Thr Pro Asp Asp Arg Glu Leu Leu Val Leu Ser
            820                 825                 830

Val Asp


<210> SEQ ID NO 17
<211> LENGTH: 2511
<212> TYPE: DNA
<213> ORGANISM: Artificial Sequence
<220> FEATURE:
<223> OTHER INFORMATION: Polypeptide sequence of CDTb with pro-domain
```

removed (CDTb')

<400> SEQUENCE: 17

```
catatggaaa ttgtgaatga agatattctg ccgaataatg gtctgatggg atactacttt     60
accgatgaac attttaaaga tctgaaactg atggcaccga ttaaagatgg caatctgaaa    120
tttgaagaaa aaaaagtgga taaactgctg gataaagata aaagtgatgt gaaaagcatt    180
cgttggaccg gtcgtattat tccgagcaaa gatggtgaat acaccctgag caccgatcgt    240
gatgatgttc tgatgcaggt taataccgaa agcaccatta gcaataccct gaaagtgaat    300
atgaaaaaag gcaaagaata taaagtgcgc attgaactgc aggataaaaa tctgggtagc    360
attgataatc tgagcagccc gaatctgtat tgggaactgg atggtatgaa aaaaatcatt    420
ccggaagaaa acctgtttct gcgcgattat agcaatattg aaaaagatga tccgtttatt    480
ccgaataata actttttga tccgaaactg atgagcgatt gggaagatga agatctggat    540
accgataatg ataatattcc ggatagctat gaacgcaatg gctataccat taaagatctg    600
attgccgtga aatgggaaga tagctttgca gaacagggct ataagaaata tgtgagcaat    660
tatctggaaa gcaataccgc aggcgatccg tataccgatt atgaaaaagc aagcggcagc    720
tttgataaag ccattaaaac cgaagcacgt gatccgctgg ttgcagcata tccgattgtt    780
ggtgttggta tggaaaaact gattattagc accaatgaac atgcaagcac cgatcagggt    840
aaaaccgtta gccgtgcaac caccaatagc aaaaccgaaa gcaatacagc cggtgttagc    900
gttaatgttg gttatcagaa tggttttacc gccaatgtga ccaccaatta tagccatacc    960
accgataata gcaccgcagt tcaggatagc aatggtgaaa gctggaatac cggtctgagc   1020
attaacaaag gtgaaagcgc atatatcaat gccaatgtgc gctattataa caccggcacc   1080
gcaccgatgt ataaagttac cccgaccacc aatctggttc tggatggtga taccctgagt   1140
accattaaag cacaagaaaa tcagattggc aataatctga gtccgggtga tacctatccg   1200
aaaaaaggtc tgagtccgct ggcactgaat accatggatc agtttagcag ccgtctgatt   1260
ccgattaact atgatcagct gaaaaaactg gatgccggta aacaaatcaa actggaaacc   1320
acccaggtta gcggtaattt tggcaccaaa aattcaagcg gtcagattgt taccgaaggt   1380
aatagctggt cagattatat cagccagatt gatagcatta gcgccagcat tattctggat   1440
acagaaaatg aaagctatga acgtcgtgtg accgcaaaaa atctgcagga cccggaagat   1500
aaaacaccgg aactgaccat tggtgaagca attgaaaaag catttggtgc caccaaaaaa   1560
gatggcctgc tgtattttaa cgatattccg attgatgaaa gctgcgtgga actgattttt   1620
gatgataata ccgccaataa aatcaaagat agcctgaaaa ccctgagcga caaaaaaatc   1680
tataatgtga aactggaacg cggtatgaat attctgatta aaccccgac ctattttacc   1740
aattttgatg attataacaa ttatccgagc acttggagca atgtgaatac caccaatcag   1800
gatggtctgc agggtagcgc aaataaactg aatggtgaaa ccaaaatcaa aattccgatg   1860
agcgaactga aaccgtataa acgttatgtg tttagcggct atagcaaaga tccgctgacc   1920
agcaatagca ttattgtgaa aatcaaagcc aaagaagaaa aaaccgatta tctggttccg   1980
gaacagggtt ataccaaatt tagctatgaa tttgaaacca ccgaaaaaga tagcagtaat   2040
attgaaatta ccctgattgg tagcggcacc acctatctgg ataatctgag tattaccgaa   2100
ctgaatagca caccggaaat tctggatgaa ccggaagtga aaattccgac cgatcaagaa   2160
attatggatg cccataaaat ctattttgcc gatctgaact ttaatccgag caccggcaat   2220
acctatatta acggcatgta ttttgcaccg acccagacca ataaagaagc cctggattat   2280
```

```
attcagaaat atcgtgttga agccaccctg cagtatagcg gttttaaaga tattggcacc   2340

aaagataaag aaatgcgtaa ttatctgggc gatccgaatc agccgaaaac caattatgtt   2400

aatctgcgca gctattttac cggtggcgaa aacattatga cctacaaaaa actgcgcatt   2460

tatgccatta caccggatga tcgtgaactg ctggttctga gcgttgatta a            2511


<210> SEQ ID NO 18
<211> LENGTH: 966
<212> TYPE: PRT
<213> ORGANISM: Artificial Sequence
<220> FEATURE:
<223> OTHER INFORMATION: sequence of Fusion 1 (F1)

<400> SEQUENCE: 18

Met Gly Trp Gln Thr Ile Asp Gly Lys Lys Tyr Tyr Phe Asn Thr Asn
 1               5                  10                  15

Thr Ala Ile Ala Ser Thr Gly Tyr Thr Ile Ile Asn Gly Lys His Phe
            20                  25                  30

Tyr Phe Asn Thr Asp Gly Ile Met Gln Ile Gly Val Phe Lys Gly Pro
        35                  40                  45

Asn Gly Phe Glu Tyr Phe Ala Pro Ala Asn Thr Asp Ala Asn Asn Ile
    50                  55                  60

Glu Gly Gln Ala Ile Leu Tyr Gln Asn Glu Phe Leu Thr Leu Asn Gly
65                  70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
    130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
    210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
        275                 280                 285

Gln Ile Gly Val Phe Lys Gly Pro Asn Gly Phe Glu Tyr Phe Ala Pro
    290                 295                 300

Ala Asn Thr Asp Ala Asn Asn Ile Glu Gly Gln Ala Ile Leu Tyr Gln
305                 310                 315                 320
```

-continued

```
Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
            420                 425                 430

Gln Asn Arg Phe Leu Tyr Leu His Asp Asn Ile Tyr Tyr Phe Gly Asn
        435                 440                 445

Asn Ser Lys Ala Ala Thr Gly Trp Val Thr Ile Asp Gly Asn Arg Tyr
    450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
            500                 505                 510

Ala Asn Asn Ile Glu Gly Gln Ala Ile Arg Tyr Gln Asn Arg Phe Leu
        515                 520                 525

His Leu Leu Gly Lys Ile Tyr Tyr Phe Gly Asn Asn Ser Lys Ala Val
    530                 535                 540

Thr Gly Trp Gln Thr Ile Asn Gly Lys Val Tyr Tyr Phe Met Pro Asp
545                 550                 555                 560

Thr Ala Met Ala Ala Ala Gly Gly Leu Phe Glu Ile Asp Gly Val Ile
                565                 570                 575

Tyr Phe Phe Gly Val Asp Gly Val Lys Ala Pro Gly Phe Val Ser Ile
            580                 585                 590

Asn Asp Asn Lys His Tyr Phe Asp Asp Ser Gly Val Met Lys Val Gly
        595                 600                 605

Tyr Thr Glu Ile Asp Gly Lys His Phe Tyr Phe Ala Glu Asn Gly Glu
    610                 615                 620

Met Gln Ile Gly Val Phe Asn Thr Glu Asp Gly Phe Lys Tyr Phe Ala
625                 630                 635                 640

His His Asn Glu Asp Leu Gly Asn Glu Glu Gly Glu Glu Ile Ser Tyr
                645                 650                 655

Ser Gly Ile Leu Asn Phe Asn Asn Lys Ile Tyr Tyr Phe Asp Asp Ser
            660                 665                 670

Phe Thr Ala Val Val Gly Trp Lys Asp Leu Glu Asp Gly Ser Lys Tyr
        675                 680                 685

Tyr Phe Asp Glu Asp Thr Ala Glu Ala Tyr Ile Gly Leu Ser Leu Ile
    690                 695                 700

Asn Asp Gly Gln Tyr Tyr Phe Asn Asp Asp Gly Ile Met Gln Val Gly
705                 710                 715                 720

Phe Val Thr Ile Asn Asp Lys Val Phe Tyr Phe Ser Asp Ser Gly Ile
                725                 730                 735

Ile Glu Ser Gly Val Gln Asn Ile Asp Asp Asn Tyr Phe Tyr Ile Asp
```

```
        740                 745                 750

Asp Asn Gly Ile Val Gln Ile Gly Val Phe Asp Thr Ser Asp Gly Tyr
            755                 760                 765

Lys Tyr Phe Ala Pro Ala Asn Thr Val Asn Asp Asn Ile Tyr Gly Gln
    770                 775                 780

Ala Val Glu Tyr Ser Gly Leu Val Arg Val Gly Glu Asp Val Tyr Tyr
785                 790                 795                 800

Phe Gly Glu Thr Tyr Thr Ile Glu Thr Gly Trp Ile Tyr Asp Met Glu
                805                 810                 815

Asn Glu Ser Asp Lys Tyr Tyr Phe Asn Pro Glu Thr Lys Lys Ala Cys
            820                 825                 830

Lys Gly Ile Asn Leu Ile Asp Asp Ile Lys Tyr Tyr Phe Asp Glu Lys
        835                 840                 845

Gly Ile Met Arg Thr Gly Leu Ile Ser Phe Glu Asn Asn Asn Tyr Tyr
    850                 855                 860

Phe Asn Glu Asn Gly Glu Met Gln Phe Gly Tyr Ile Asn Ile Glu Asp
865                 870                 875                 880

Lys Met Phe Tyr Phe Gly Glu Asp Gly Val Met Gln Ile Gly Val Phe
                885                 890                 895

Asn Thr Pro Asp Gly Phe Lys Tyr Phe Ala His Gln Asn Thr Leu Asp
            900                 905                 910

Glu Asn Phe Glu Gly Glu Ser Ile Asn Tyr Thr Gly Trp Leu Asp Leu
        915                 920                 925

Asp Glu Lys Arg Tyr Tyr Phe Thr Asp Glu Tyr Ile Ala Ala Thr Gly
    930                 935                 940

Ser Val Ile Ile Asp Gly Glu Glu Tyr Tyr Phe Asp Pro Asp Thr Ala
945                 950                 955                 960

Gln Leu Val Ile Ser Glu
                965


<210> SEQ ID NO 19
<211> LENGTH: 966
<212> TYPE: PRT
<213> ORGANISM: Artificial Sequence
<220> FEATURE:
<223> OTHER INFORMATION: sequence of Fusion 2 (F2)

<400> SEQUENCE: 19

Met Gly Trp Gln Thr Ile Asp Gly Lys Lys Tyr Tyr Phe Asn Thr Asn
1               5                   10                  15

Thr Ala Ile Ala Ser Thr Gly Tyr Thr Ile Ile Asn Gly Lys His Phe
            20                  25                  30

Tyr Phe Asn Thr Asp Gly Ile Met Gln Ile Gly Val Phe Lys Gly Pro
        35                  40                  45

Asn Gly Phe Glu Tyr Phe Ala Pro Ala Asn Thr Asp Ala Asn Asn Ile
    50                  55                  60

Glu Gly Gln Ala Ile Leu Tyr Gln Asn Glu Phe Leu Thr Leu Asn Gly
65                  70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
```

-continued

```
    130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
    210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
        275                 280                 285

Gln Ile Gly Val Phe Lys Gly Pro Asn Gly Phe Glu Tyr Phe Ala Pro
    290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
            420                 425                 430

Gln Asn Arg Phe Leu Tyr Leu His Asp Asn Ile Tyr Tyr Phe Gly Asn
        435                 440                 445

Asn Ser Lys Ala Ala Thr Gly Trp Val Thr Ile Asp Gly Asn Arg Tyr
    450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
            500                 505                 510

Ala Asn Asn Ile Glu Gly Gln Ala Ile Arg Tyr Gln Asn Arg Phe Leu
        515                 520                 525

His Leu Leu Gly Lys Ile Tyr Tyr Phe Gly Asn Asn Ser Lys Ala Val
    530                 535                 540

Thr Gly Trp Gln Thr Ile Asn Gly Lys Val Tyr Tyr Phe Met Pro Asp
545                 550                 555                 560
```

-continued

```
Thr Ala Met Ala Ala Ala Gly Gly Leu Asn Gln Ile Gly Asp Tyr Lys
                565                 570                 575

Tyr Tyr Phe Asn Ser Asp Gly Val Met Gln Lys Gly Phe Val Ser Ile
            580                 585                 590

Asn Asp Asn Lys His Tyr Phe Asp Asp Ser Gly Val Met Lys Val Gly
        595                 600                 605

Tyr Thr Glu Ile Asp Gly Lys His Phe Tyr Phe Ala Glu Asn Gly Glu
    610                 615                 620

Met Gln Ile Gly Val Phe Asn Thr Glu Asp Gly Phe Lys Tyr Phe Ala
625                 630                 635                 640

His His Asn Glu Asp Leu Gly Asn Glu Glu Gly Glu Glu Ile Ser Tyr
                645                 650                 655

Ser Gly Ile Leu Asn Phe Asn Asn Lys Ile Tyr Tyr Phe Asp Asp Ser
            660                 665                 670

Phe Thr Ala Val Val Gly Trp Lys Asp Leu Glu Asp Gly Ser Lys Tyr
        675                 680                 685

Tyr Phe Asp Glu Asp Thr Ala Glu Ala Tyr Ile Gly Leu Ser Leu Ile
    690                 695                 700

Asn Asp Gly Gln Tyr Tyr Phe Asn Asp Asp Gly Ile Met Gln Val Gly
705                 710                 715                 720

Phe Val Thr Ile Asn Asp Lys Val Phe Tyr Phe Ser Asp Ser Gly Ile
                725                 730                 735

Ile Glu Ser Gly Val Gln Asn Ile Asp Asp Asn Tyr Phe Tyr Ile Asp
            740                 745                 750

Asp Asn Gly Ile Val Gln Ile Gly Val Phe Asp Thr Ser Asp Gly Tyr
        755                 760                 765

Lys Tyr Phe Ala Pro Ala Asn Thr Val Asn Asp Asn Ile Tyr Gly Gln
    770                 775                 780

Ala Val Glu Tyr Ser Gly Leu Val Arg Val Gly Glu Asp Val Tyr Tyr
785                 790                 795                 800

Phe Gly Glu Thr Tyr Thr Ile Glu Thr Gly Trp Ile Tyr Asp Met Glu
                805                 810                 815

Asn Glu Ser Asp Lys Tyr Tyr Phe Asn Pro Glu Thr Lys Lys Ala Cys
            820                 825                 830

Lys Gly Ile Asn Leu Ile Asp Asp Ile Lys Tyr Tyr Phe Asp Glu Lys
        835                 840                 845

Gly Ile Met Arg Thr Gly Leu Ile Ser Phe Glu Asn Asn Asn Tyr Tyr
    850                 855                 860

Phe Asn Glu Asn Gly Glu Met Gln Phe Gly Tyr Ile Asn Ile Glu Asp
865                 870                 875                 880

Lys Met Phe Tyr Phe Gly Glu Asp Gly Val Met Gln Ile Gly Val Phe
                885                 890                 895

Asn Thr Pro Asp Gly Phe Lys Tyr Phe Ala His Gln Asn Thr Leu Asp
            900                 905                 910

Glu Asn Phe Glu Gly Glu Ser Ile Asn Tyr Thr Gly Trp Leu Asp Leu
        915                 920                 925

Asp Glu Lys Arg Tyr Tyr Phe Thr Asp Glu Tyr Ile Ala Ala Thr Gly
    930                 935                 940

Ser Val Ile Ile Asp Gly Glu Glu Tyr Tyr Phe Asp Pro Asp Thr Ala
945                 950                 955                 960

Gln Leu Val Ile Ser Glu
                965
```

<210> SEQ ID NO 20
<211> LENGTH: 833
<212> TYPE: PRT
<213> ORGANISM: Artificial Sequence
<220> FEATURE:
<223> OTHER INFORMATION: sequence of Fusion 3 (F3)

<400> SEQUENCE: 20

Met Gly Trp Gln Thr Ile Asp Gly Lys Lys Tyr Tyr Phe Asn Thr Asn
1 5 10 15

Thr Ala Ile Ala Ser Thr Gly Tyr Thr Ile Ile Asn Gly Lys His Phe
20 25 30

Tyr Phe Asn Thr Asp Gly Ile Met Gln Ile Gly Val Phe Lys Gly Pro
35 40 45

Asn Gly Phe Glu Tyr Phe Ala Pro Ala Asn Thr Asp Ala Asn Asn Ile
50 55 60

Glu Gly Gln Ala Ile Leu Tyr Gln Asn Glu Phe Leu Thr Leu Asn Gly
65 70 75 80

Lys Lys Tyr Tyr Phe Gly Ser Asp Ser Lys Ala Val Thr Gly Trp Arg
85 90 95

Ile Ile Asn Asn Lys Lys Tyr Tyr Phe Asn Pro Asn Asn Ala Ile Ala
100 105 110

Ala Ile His Leu Cys Thr Ile Asn Asn Asp Lys Tyr Tyr Phe Ser Tyr
115 120 125

Asp Gly Ile Leu Gln Asn Gly Tyr Ile Thr Ile Glu Arg Asn Asn Phe
130 135 140

Tyr Phe Asp Ala Asn Asn Glu Ser Lys Met Val Thr Gly Val Phe Lys
145 150 155 160

Gly Pro Asn Gly Phe Glu Tyr Phe Ala Pro Ala Asn Thr His Asn Asn
165 170 175

Asn Ile Glu Gly Gln Ala Ile Val Tyr Gln Asn Lys Phe Leu Thr Leu
180 185 190

Asn Gly Lys Lys Tyr Tyr Phe Asp Asn Asp Ser Lys Ala Val Thr Gly
195 200 205

Trp Gln Thr Ile Asp Gly Lys Lys Tyr Tyr Phe Asn Leu Asn Thr Ala
210 215 220

Glu Ala Ala Thr Gly Trp Gln Thr Ile Asp Gly Lys Lys Tyr Tyr Phe
225 230 235 240

Asn Leu Asn Thr Ala Glu Ala Ala Thr Gly Trp Gln Thr Ile Asp Gly
245 250 255

Lys Lys Tyr Tyr Phe Asn Thr Asn Thr Phe Ile Ala Ser Thr Gly Tyr
260 265 270

Thr Ser Ile Asn Gly Lys His Phe Tyr Phe Asn Thr Asp Gly Ile Met
275 280 285

Gln Ile Gly Val Phe Lys Gly Pro Asn Gly Phe Glu Tyr Phe Ala Pro
290 295 300

Ala Asn Thr Asp Ala Asn Asn Ile Glu Gly Gln Ala Ile Leu Tyr Gln
305 310 315 320

Asn Lys Phe Leu Thr Leu Asn Gly Lys Lys Tyr Tyr Phe Gly Ser Asp
325 330 335

Ser Lys Ala Val Thr Gly Leu Arg Thr Ile Asp Gly Lys Lys Tyr Tyr
340 345 350

Phe Asn Thr Asn Thr Ala Val Ala Val Thr Gly Trp Gln Thr Ile Asn
355 360 365

```
Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
            420                 425                 430

Gln Asn Arg Phe Leu Tyr Leu His Asp Asn Ile Tyr Tyr Phe Gly Asn
        435                 440                 445

Asn Ser Lys Ala Ala Thr Gly Trp Val Thr Ile Asp Gly Asn Arg Tyr
    450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala His His Asn Glu Asp
            500                 505                 510

Leu Gly Asn Glu Glu Gly Glu Glu Ile Ser Tyr Ser Gly Ile Leu Asn
        515                 520                 525

Phe Asn Asn Lys Ile Tyr Tyr Phe Asp Asp Ser Phe Thr Ala Val Val
    530                 535                 540

Gly Trp Lys Asp Leu Glu Asp Gly Ser Lys Tyr Tyr Phe Asp Glu Asp
545                 550                 555                 560

Thr Ala Glu Ala Tyr Ile Gly Leu Ser Leu Ile Asn Asp Gly Gln Tyr
                565                 570                 575

Tyr Phe Asn Asp Asp Gly Ile Met Gln Val Gly Phe Val Thr Ile Asn
            580                 585                 590

Asp Lys Val Phe Tyr Phe Ser Asp Ser Gly Ile Ile Glu Ser Gly Val
        595                 600                 605

Gln Asn Ile Asp Asp Asn Tyr Phe Tyr Ile Asp Asp Asn Gly Ile Val
    610                 615                 620

Gln Ile Gly Val Phe Asp Thr Ser Asp Gly Tyr Lys Tyr Phe Ala Pro
625                 630                 635                 640

Ala Asn Thr Val Asn Asp Asn Ile Tyr Gly Gln Ala Val Glu Tyr Ser
                645                 650                 655

Gly Leu Val Arg Val Gly Glu Asp Val Tyr Tyr Phe Gly Glu Thr Tyr
            660                 665                 670

Thr Ile Glu Thr Gly Trp Ile Tyr Asp Met Glu Asn Glu Ser Asp Lys
        675                 680                 685

Tyr Tyr Phe Asn Pro Glu Thr Lys Lys Ala Cys Lys Gly Ile Asn Leu
    690                 695                 700

Ile Asp Asp Ile Lys Tyr Tyr Phe Asp Glu Lys Gly Ile Met Arg Thr
705                 710                 715                 720

Gly Leu Ile Ser Phe Glu Asn Asn Asn Tyr Tyr Phe Asn Glu Asn Gly
                725                 730                 735

Glu Met Gln Phe Gly Tyr Ile Asn Ile Glu Asp Lys Met Phe Tyr Phe
            740                 745                 750

Gly Glu Asp Gly Val Met Gln Ile Gly Val Phe Asn Thr Pro Asp Gly
        755                 760                 765

Phe Lys Tyr Phe Ala His Gln Asn Thr Leu Asp Glu Asn Phe Glu Gly
    770                 775                 780

Glu Ser Ile Asn Tyr Thr Gly Trp Leu Asp Leu Asp Glu Lys Arg Tyr
```

785 790 795 800

Tyr Phe Thr Asp Glu Tyr Ile Ala Ala Thr Gly Ser Val Ile Ile Asp
805 810 815

Gly Glu Glu Tyr Tyr Phe Asp Pro Asp Thr Ala Gln Leu Val Ile Ser
820 825 830

Glu

<210> SEQ ID NO 21
<211> LENGTH: 1057
<212> TYPE: PRT
<213> ORGANISM: Artificial Sequence
<220> FEATURE:
<223> OTHER INFORMATION: sequence of Fusion 4 (F4)

<400> SEQUENCE: 21

Met Gly Trp Gln Thr Ile Asp Gly Lys Lys Tyr Tyr Phe Asn Thr Asn
1 5 10 15

Thr Ala Ile Ala Ser Thr Gly Tyr Thr Ile Ile Asn Gly Lys His Phe
20 25 30

Tyr Phe Asn Thr Asp Gly Ile Met Gln Ile Gly Val Phe Lys Gly Pro
35 40 45

Asn Gly Phe Glu Tyr Phe Ala Pro Ala Asn Thr Asp Ala Asn Asn Ile
50 55 60

Glu Gly Gln Ala Ile Leu Tyr Gln Asn Glu Phe Leu Thr Leu Asn Gly
65 70 75 80

Lys Lys Tyr Tyr Phe Gly Ser Asp Ser Lys Ala Val Thr Gly Trp Arg
85 90 95

Ile Ile Asn Asn Lys Lys Tyr Tyr Phe Asn Pro Asn Asn Ala Ile Ala
100 105 110

Ala Ile His Leu Cys Thr Ile Asn Asn Asp Lys Tyr Tyr Phe Ser Tyr
115 120 125

Asp Gly Ile Leu Gln Asn Gly Tyr Ile Thr Ile Glu Arg Asn Asn Phe
130 135 140

Tyr Phe Asp Ala Asn Asn Glu Ser Lys Met Val Thr Gly Val Phe Lys
145 150 155 160

Gly Pro Asn Gly Phe Glu Tyr Phe Ala Pro Ala Asn Thr His Asn Asn
165 170 175

Asn Ile Glu Gly Gln Ala Ile Val Tyr Gln Asn Lys Phe Leu Thr Leu
180 185 190

Asn Gly Lys Lys Tyr Tyr Phe Asp Asn Asp Ser Lys Ala Val Thr Gly
195 200 205

Trp Gln Thr Ile Asp Gly Lys Lys Tyr Tyr Phe Asn Leu Asn Thr Ala
210 215 220

Glu Ala Ala Thr Gly Trp Gln Thr Ile Asp Gly Lys Lys Tyr Tyr Phe
225 230 235 240

Asn Leu Asn Thr Ala Glu Ala Ala Thr Gly Trp Gln Thr Ile Asp Gly
245 250 255

Lys Lys Tyr Tyr Phe Asn Thr Asn Thr Phe Ile Ala Ser Thr Gly Tyr
260 265 270

Thr Ser Ile Asn Gly Lys His Phe Tyr Phe Asn Thr Asp Gly Ile Met
275 280 285

Gln Ile Gly Val Phe Lys Gly Pro Asn Gly Phe Glu Tyr Phe Ala Pro
290 295 300

Ala Asn Thr Asp Ala Asn Asn Ile Glu Gly Gln Ala Ile Leu Tyr Gln
305 310 315 320

-continued

```
Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
            420                 425                 430

Gln Asn Arg Phe Leu Tyr Leu His Asp Asn Ile Tyr Tyr Phe Gly Asn
        435                 440                 445

Asn Ser Lys Ala Ala Thr Gly Trp Val Thr Ile Asp Gly Asn Arg Tyr
    450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
            500                 505                 510

Ala Asn Asn Ile Glu Gly Gln Ala Ile Arg Tyr Gln Asn Arg Phe Leu
        515                 520                 525

His Leu Leu Gly Lys Ile Tyr Tyr Phe Gly Asn Asn Ser Lys Ala Val
    530                 535                 540

Thr Gly Trp Gln Thr Ile Asn Gly Lys Val Tyr Tyr Phe Met Pro Asp
545                 550                 555                 560

Thr Ala Met Ala Ala Ala Gly Gly Glu Thr Ile Ile Asp Asp Lys Asn
                565                 570                 575

Tyr Tyr Phe Asn Gln Ser Gly Val Leu Gln Thr Gly Val Phe Ser Thr
            580                 585                 590

Glu Asp Gly Phe Lys Tyr Phe Ala Pro Ala Asn Thr Leu Asp Glu Asn
        595                 600                 605

Leu Glu Gly Glu Ala Ile Asp Phe Thr Gly Lys Leu Ile Ile Asp Glu
    610                 615                 620

Asn Ile Tyr Tyr Phe Asp Asp Asn Tyr Arg Gly Ala Val Glu Trp Lys
625                 630                 635                 640

Glu Leu Asp Gly Glu Met His Tyr Phe Ser Pro Glu Thr Gly Lys Ala
                645                 650                 655

Phe Lys Gly Leu Asn Gln Ile Gly Asp Tyr Lys Tyr Tyr Phe Asn Ser
            660                 665                 670

Asp Gly Val Met Gln Lys Gly Phe Val Ser Ile Asn Asp Asn Lys His
        675                 680                 685

Tyr Phe Asp Asp Ser Gly Val Met Lys Val Gly Tyr Thr Glu Ile Asp
    690                 695                 700

Gly Lys His Phe Tyr Phe Ala Glu Asn Gly Glu Met Gln Ile Gly Val
705                 710                 715                 720

Phe Asn Thr Glu Asp Gly Phe Lys Tyr Phe Ala His His Asn Glu Asp
                725                 730                 735
```

```
Leu Gly Asn Glu Glu Gly Glu Glu Ile Ser Tyr Ser Gly Ile Leu Asn
            740                 745                 750

Phe Asn Asn Lys Ile Tyr Tyr Phe Asp Asp Ser Phe Thr Ala Val Val
        755                 760                 765

Gly Trp Lys Asp Leu Glu Asp Gly Ser Lys Tyr Tyr Phe Asp Glu Asp
    770                 775                 780

Thr Ala Glu Ala Tyr Ile Gly Leu Ser Leu Ile Asn Asp Gly Gln Tyr
785                 790                 795                 800

Tyr Phe Asn Asp Asp Gly Ile Met Gln Val Gly Phe Val Thr Ile Asn
                805                 810                 815

Asp Lys Val Phe Tyr Phe Ser Asp Ser Gly Ile Ile Glu Ser Gly Val
            820                 825                 830

Gln Asn Ile Asp Asp Asn Tyr Phe Tyr Ile Asp Asp Asn Gly Ile Val
        835                 840                 845

Gln Ile Gly Val Phe Asp Thr Ser Asp Gly Tyr Lys Tyr Phe Ala Pro
    850                 855                 860

Ala Asn Thr Val Asn Asp Asn Ile Tyr Gly Gln Ala Val Glu Tyr Ser
865                 870                 875                 880

Gly Leu Val Arg Val Gly Glu Asp Val Tyr Tyr Phe Gly Glu Thr Tyr
                885                 890                 895

Thr Ile Glu Thr Gly Trp Ile Tyr Asp Met Glu Asn Glu Ser Asp Lys
            900                 905                 910

Tyr Tyr Phe Asn Pro Glu Thr Lys Lys Ala Cys Lys Gly Ile Asn Leu
        915                 920                 925

Ile Asp Asp Ile Lys Tyr Tyr Phe Asp Glu Lys Gly Ile Met Arg Thr
    930                 935                 940

Gly Leu Ile Ser Phe Glu Asn Asn Asn Tyr Tyr Phe Asn Glu Asn Gly
945                 950                 955                 960

Glu Met Gln Phe Gly Tyr Ile Asn Ile Glu Asp Lys Met Phe Tyr Phe
                965                 970                 975

Gly Glu Asp Gly Val Met Gln Ile Gly Val Phe Asn Thr Pro Asp Gly
            980                 985                 990

Phe Lys Tyr Phe Ala His Gln Asn Thr Leu Asp Glu Asn Phe Glu Gly
        995                 1000                1005

Glu Ser Ile Asn Tyr Thr Gly Trp Leu Asp Leu Asp Glu Lys Arg Tyr
    1010                1015                1020

Tyr Phe Thr Asp Glu Tyr Ile Ala Ala Thr Gly Ser Val Ile Ile Asp
1025                1030                1035                1040

Gly Glu Glu Tyr Tyr Phe Asp Pro Asp Thr Ala Gln Leu Val Ile Ser
                1045                1050                1055

Glu


<210> SEQ ID NO 22
<211> LENGTH: 971
<212> TYPE: PRT
<213> ORGANISM: Artificial Sequence
<220> FEATURE:
<223> OTHER INFORMATION: sequence of Fusion 5 (F5)

<400> SEQUENCE: 22

Met Gly Trp Gln Thr Ile Asp Gly Lys Lys Tyr Tyr Phe Asn Thr Asn
1               5                   10                  15

Thr Ala Ile Ala Ser Thr Gly Tyr Thr Ile Ile Asn Gly Lys His Phe
            20                  25                  30

Tyr Phe Asn Thr Asp Gly Ile Met Gln Ile Gly Val Phe Lys Gly Pro
```

-continued

```
        35                  40                  45

Asn Gly Phe Glu Tyr Phe Ala Pro Ala Asn Thr Asp Ala Asn Asn Ile
    50                  55                  60

Glu Gly Gln Ala Ile Leu Tyr Gln Asn Glu Phe Leu Thr Leu Asn Gly
65                  70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
    130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
    210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
        275                 280                 285

Gln Ile Gly Val Phe Lys Gly Pro Asn Gly Phe Glu Tyr Phe Ala Pro
    290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
            420                 425                 430

Gln Asn Arg Phe Leu Tyr Leu His Asp Asn Ile Tyr Tyr Phe Gly Asn
        435                 440                 445

Asn Ser Lys Ala Ala Thr Gly Trp Val Thr Ile Asp Gly Asn Arg Tyr
    450                 455                 460
```

-continued

```
Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
            500                 505                 510

Ala Asn Asn Ile Glu Gly Gln Ala Ile Arg Tyr Gln Asn Arg Phe Leu
        515                 520                 525

His Leu Leu Gly Lys Ile Tyr Tyr Phe Gly Asn Asn Ser Lys Ala Val
    530                 535                 540

Thr Gly Trp Gln Thr Ile Asn Gly Lys Val Tyr Tyr Phe Met Pro Asp
545                 550                 555                 560

Thr Ala Met Ala Ala Ala Gly Gly Leu Phe Glu Ile Asp Gly Val Ile
                565                 570                 575

Tyr Phe Phe Gly Val Asp Gly Val Lys Ala Pro Gly Ile Tyr Gly Gly
            580                 585                 590

Gly Phe Val Ser Ile Asn Asp Asn Lys His Tyr Phe Asp Asp Ser Gly
        595                 600                 605

Val Met Lys Val Gly Tyr Thr Glu Ile Asp Gly Lys His Phe Tyr Phe
    610                 615                 620

Ala Glu Asn Gly Glu Met Gln Ile Gly Val Phe Asn Thr Glu Asp Gly
625                 630                 635                 640

Phe Lys Tyr Phe Ala His His Asn Glu Asp Leu Gly Asn Glu Glu Gly
                645                 650                 655

Glu Glu Ile Ser Tyr Ser Gly Ile Leu Asn Phe Asn Asn Lys Ile Tyr
            660                 665                 670

Tyr Phe Asp Asp Ser Phe Thr Ala Val Val Gly Trp Lys Asp Leu Glu
        675                 680                 685

Asp Gly Ser Lys Tyr Tyr Phe Asp Glu Asp Thr Ala Glu Ala Tyr Ile
    690                 695                 700

Gly Leu Ser Leu Ile Asn Asp Gly Gln Tyr Tyr Phe Asn Asp Asp Gly
705                 710                 715                 720

Ile Met Gln Val Gly Phe Val Thr Ile Asn Asp Lys Val Phe Tyr Phe
                725                 730                 735

Ser Asp Ser Gly Ile Ile Glu Ser Gly Val Gln Asn Ile Asp Asp Asn
            740                 745                 750

Tyr Phe Tyr Ile Asp Asp Asn Gly Ile Val Gln Ile Gly Val Phe Asp
        755                 760                 765

Thr Ser Asp Gly Tyr Lys Tyr Phe Ala Pro Ala Asn Thr Val Asn Asp
    770                 775                 780

Asn Ile Tyr Gly Gln Ala Val Glu Tyr Ser Gly Leu Val Arg Val Gly
785                 790                 795                 800

Glu Asp Val Tyr Tyr Phe Gly Glu Thr Tyr Thr Ile Glu Thr Gly Trp
                805                 810                 815

Ile Tyr Asp Met Glu Asn Glu Ser Asp Lys Tyr Tyr Phe Asn Pro Glu
            820                 825                 830

Thr Lys Lys Ala Cys Lys Gly Ile Asn Leu Ile Asp Asp Ile Lys Tyr
        835                 840                 845

Tyr Phe Asp Glu Lys Gly Ile Met Arg Thr Gly Leu Ile Ser Phe Glu
    850                 855                 860

Asn Asn Asn Tyr Tyr Phe Asn Glu Asn Gly Glu Met Gln Phe Gly Tyr
865                 870                 875                 880
```

-continued

```
Ile Asn Ile Glu Asp Lys Met Phe Tyr Phe Gly Glu Asp Gly Val Met
                885                 890                 895

Gln Ile Gly Val Phe Asn Thr Pro Asp Gly Phe Lys Tyr Phe Ala His
            900                 905                 910

Gln Asn Thr Leu Asp Glu Asn Phe Glu Gly Glu Ser Ile Asn Tyr Thr
        915                 920                 925

Gly Trp Leu Asp Leu Asp Glu Lys Arg Tyr Tyr Phe Thr Asp Glu Tyr
    930                 935                 940

Ile Ala Ala Thr Gly Ser Val Ile Ile Asp Gly Glu Glu Tyr Tyr Phe
945                 950                 955                 960

Asp Pro Asp Thr Ala Gln Leu Val Ile Ser Glu
                965                 970
```

<210> SEQ ID NO 23
<211> LENGTH: 3339
<212> TYPE: DNA
<213> ORGANISM: Artificial Sequence
<220> FEATURE:
<223> OTHER INFORMATION: nucleotide sequence of F54 Gly

<400> SEQUENCE: 23

```
atggcaaccg gttggcagac catcgatggc aaaaaatatt attttaatac caacaccgca     60

attgcaagca ccggctatac cattatcaac ggcaaacact tttattttaa caccgacggc    120

attatgcaga ttggtgtgtt taaaggtccg aacggctttg aatactttgc accggcaaat    180

accgatgcca ataatattga aggccaggcc attctgtatc agaatgaatt tctgaccctg    240

aacggcaaaa aatactactt tggcagcgat agcaaagcag ttaccggttg gcgcatcatc    300

aacaataaga aatattactt caacccgaat aatgcaattg cagcaattca tctgtgcacc    360

attaacaacg acaaatatta tttcagctat gacggtattc tgcagaatgg ctacattacc    420

atcgaacgca acaactttta tttcgatgcc aacaacgaaa gcaaaatggt gaccggtgtt    480

ttcaaaggcc ctaatggttt tgagtatttc gctccggcaa acacccataa taacaacatt    540

gaaggtcagg cgatcgttta tcagaacaaa ttcctgacgc tgaatggtaa gaaatactat    600

ttcgataatg acagcaaagc cgtgaccggc tggcagacaa ttgacgggaa gaaatattac    660

tttaatctga ataccgcaga agcagcaacc ggttggcaaa cgatcgacgg taaaaagtac    720

tacttcaacc tgaacacagc cgaagcagcc acaggatggc agactattga tggaaaaaaa    780

tactatttca acaccaacac ctttattgca tctaccggtt ataccagcat taacggtaaa    840

catttctact tcaacaccga tggtatcatg cagatcggcg ttttcaaagg tccaaatggt    900

ttcgaatact ttgcccctgc caatacagat gcaaataaca tcgagggtca ggcaatcctg    960

taccaaaaca aatttctgac cctgaatggg aaaaaatatt actttggtag cgattctaaa   1020

gccgttaccg gtctgcgtac cattgatggt aaaaaatact actttaatac gaatacagcc   1080

gttgcggtta caggctggca gaccattaac gggaaaaaat actattttaa cacaaatacc   1140

agcattgcct caacgggtta taccattatt tcgggtaaac acttctactt taataccgat   1200

ggtattatgc aaatcggagt ctttaaagga cctgatgggt tcgaatattt tgcgcctgcg   1260

aacactgatg cgaacaatat cgaaggacag gcaatccgct atcagaatcg ctttctgtat   1320

ctgcacgaca acatctatta ttttggcaac aattcaaaag cagccaccgg ctgggttaca   1380

attgatggca accgctacta tttcgaaccg aataccgcaa tgggtgcaaa tggctacaaa   1440

accatcgata ataaaaattt ctattttcgc aacggtctgc cgcagatcgg ggtatttaaa   1500

ggtagcaacg gcttcgaata cttcgctcca gcgaatacgg acgcgaacaa tattgagggt   1560
```

```
caagcgattc gttatcaaaa ccgttttctg catctgctgg gcaaaatcta ctactttggc   1620

aataacagta aagcagttac tggatggcag acaatcaatg gtaaagtgta ctattttatg   1680

ccggataccg ccatggcagc agccggtggt ctgtttgaaa ttgatggcgt gatctatttt   1740

tttggtgtgg atggtgttaa agcaccggga atatacggtg gtaccggctt tgtgaccgtg   1800

ggtgatgata aatactattt caatccgatt aacggtggtg cagcgagcat tggcgaaacc   1860

atcatcgatg acaaaaacta ttatttcaac cagagcggtg tgctgcagac cggtgtgttt   1920

agcaccgaag atggctttaa atattttgcg ccagcgaaca ccctggatga aaacctggaa   1980

ggcgaagcga ttgattttac cggcaaactg atcatcgatg aaaacatcta ttacttcgat   2040

gataactatc gtggtgcggt ggaatggaaa gaactggatg gcgaaatgca ttattttttct   2100

ccggaaaccg gtaaagcgtt taaaggcctg aaccagatcg gcgattacaa atactacttc   2160

aacagcgatg gcgtgatgca gaaaggcttt gtgagcatca acgataacaa acactatttc   2220

gatgatagcg gtgtgatgaa agtgggctat accgaaattg atggcaaaca tttctacttc   2280

gcggaaaacg gcgaaatgca gattggcgtg ttcaataccg aagatggttt caaatacttc   2340

gcgcaccata acgaagatct gggtaacgaa gaaggcgaag aaattagcta tagcggcatc   2400

ctgaacttca acaacaaaat ctactacttt gatgatagct ttaccgcggt ggtgggctgg   2460

aaagatctgg aagatggcag caaatattat ttcgatgaag ataccgcgga agcgtatatt   2520

ggcctgagcc tgattaacga tggccagtac tattttaacg atgatggcat tatgcaggtg   2580

ggtttcgtga ccattaatga taaagtgttc tatttcagcg atagcggcat tattgaaagc   2640

ggcgtgcaga acattgatga taactacttc tacatcgatg ataacggcat tgtgcagatc   2700

ggcgtttttg ataccagcga tggctacaaa tatttcgcac cggccaatac cgtgaacgat   2760

aacatttatg gccaggcggt ggaatatagc ggtctggtgc gtgtgggcga agatgtgtat   2820

tatttcggcg aaacctatac catcgaaacc ggctggattt atgatatgga aaacgaaagc   2880

gataaatatt actttaatcc ggaaacgaaa aaagcgtgca aaggcattaa cctgatcgat   2940

gatatcaaat actattttga tgaaaaaggc attatgcgta ccggtctgat tagcttcgaa   3000

aacaacaact attacttcaa cgaaaacggt gaaatgcagt tcggctacat caacatcgaa   3060

gataaaatgt tctacttcgg cgaagatggt gttatgcaga ttggtgtttt taacaccccg   3120

gatggcttca aatactttgc ccatcagaat accctggatg aaaatttcga aggtgaaagc   3180

attaactata ccggctggct ggatctggat gaaaaacgct actacttcac cgatgaatac   3240

attgcggcga ccggcagcgt gattattgat ggcgaagaat actacttcga tccggatacc   3300

gcgcagctgg tgattagcga acatcatcat catcaccat                          3339
```

<210> SEQ ID NO 24
<211> LENGTH: 1113
<212> TYPE: PRT
<213> ORGANISM: Artificial Sequence
<220> FEATURE:
<223> OTHER INFORMATION: amino acid of F54Gly

<400> SEQUENCE: 24

```
Met Ala Thr Gly Trp Gln Thr Ile Asp Gly Lys Lys Tyr Tyr Phe Asn
 1               5                  10                  15

Thr Asn Thr Ala Ile Ala Ser Thr Gly Tyr Thr Ile Ile Asn Gly Lys
            20                  25                  30

His Phe Tyr Phe Asn Thr Asp Gly Ile Met Gln Ile Gly Val Phe Lys
        35                  40                  45
```

```
Gly Pro Asn Gly Phe Glu Tyr Phe Ala Pro Ala Asn Thr Asp Ala Asn
    50                  55                  60

Asn Ile Glu Gly Gln Ala Ile Leu Tyr Gln Asn Glu Phe Leu Thr Leu
65                  70                  75                  80

Asn Gly Lys Lys Tyr Tyr Phe Gly Ser Asp Ser Lys Ala Val Thr Gly
                85                  90                  95

Trp Arg Ile Ile Asn Asn Lys Lys Tyr Tyr Phe Asn Pro Asn Asn Ala
            100                 105                 110

Ile Ala Ala Ile His Leu Cys Thr Ile Asn Asn Asp Lys Tyr Tyr Phe
        115                 120                 125

Ser Tyr Asp Gly Ile Leu Gln Asn Gly Tyr Ile Thr Ile Glu Arg Asn
    130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
    210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
            260                 265                 270

Gly Tyr Thr Ser Ile Asn Gly Lys His Phe Tyr Phe Asn Thr Asp Gly
        275                 280                 285

Ile Met Gln Ile Gly Val Phe Lys Gly Pro Asn Gly Phe Glu Tyr Phe
    290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
                325                 330                 335

Ser Asp Ser Lys Ala Val Thr Gly Leu Arg Thr Ile Asp Gly Lys Lys
            340                 345                 350

Tyr Tyr Phe Asn Thr Asn Thr Ala Val Ala Val Thr Gly Trp Gln Thr
        355                 360                 365

Ile Asn Gly Lys Lys Tyr Tyr Phe Asn Thr Asn Thr Ser Ile Ala Ser
    370                 375                 380

Thr Gly Tyr Thr Ile Ile Ser Gly Lys His Phe Tyr Phe Asn Thr Asp
385                 390                 395                 400

Gly Ile Met Gln Ile Gly Val Phe Lys Gly Pro Asp Gly Phe Glu Tyr
                405                 410                 415

Phe Ala Pro Ala Asn Thr Asp Ala Asn Asn Ile Glu Gly Gln Ala Ile
            420                 425                 430

Arg Tyr Gln Asn Arg Phe Leu Tyr Leu His Asp Asn Ile Tyr Tyr Phe
        435                 440                 445

Gly Asn Asn Ser Lys Ala Ala Thr Gly Trp Val Thr Ile Asp Gly Asn
    450                 455                 460
```

-continued

```
Arg Tyr Tyr Phe Glu Pro Asn Thr Ala Met Gly Ala Asn Gly Tyr Lys
465                 470                 475                 480

Thr Ile Asp Asn Lys Asn Phe Tyr Phe Arg Asn Gly Leu Pro Gln Ile
                485                 490                 495

Gly Val Phe Lys Gly Ser Asn Gly Phe Glu Tyr Phe Ala Pro Ala Asn
            500                 505                 510

Thr Asp Ala Asn Asn Ile Glu Gly Gln Ala Ile Arg Tyr Gln Asn Arg
        515                 520                 525

Phe Leu His Leu Leu Gly Lys Ile Tyr Tyr Phe Gly Asn Asn Ser Lys
    530                 535                 540

Ala Val Thr Gly Trp Gln Thr Ile Asn Gly Lys Val Tyr Tyr Phe Met
545                 550                 555                 560

Pro Asp Thr Ala Met Ala Ala Ala Gly Gly Leu Phe Glu Ile Asp Gly
                565                 570                 575

Val Ile Tyr Phe Phe Gly Val Asp Gly Val Lys Ala Pro Gly Ile Tyr
            580                 585                 590

Gly Gly Thr Gly Phe Val Thr Val Gly Asp Asp Lys Tyr Tyr Phe Asn
        595                 600                 605

Pro Ile Asn Gly Gly Ala Ala Ser Ile Gly Glu Thr Ile Ile Asp Asp
    610                 615                 620

Lys Asn Tyr Tyr Phe Asn Gln Ser Gly Val Leu Gln Thr Gly Val Phe
625                 630                 635                 640

Ser Thr Glu Asp Gly Phe Lys Tyr Phe Ala Pro Ala Asn Thr Leu Asp
                645                 650                 655

Glu Asn Leu Glu Gly Glu Ala Ile Asp Phe Thr Gly Lys Leu Ile Ile
            660                 665                 670

Asp Glu Asn Ile Tyr Tyr Phe Asp Asp Asn Tyr Arg Gly Ala Val Glu
        675                 680                 685

Trp Lys Glu Leu Asp Gly Glu Met His Tyr Phe Ser Pro Glu Thr Gly
    690                 695                 700

Lys Ala Phe Lys Gly Leu Asn Gln Ile Gly Asp Tyr Lys Tyr Tyr Phe
705                 710                 715                 720

Asn Ser Asp Gly Val Met Gln Lys Gly Phe Val Ser Ile Asn Asp Asn
                725                 730                 735

Lys His Tyr Phe Asp Asp Ser Gly Val Met Lys Val Gly Tyr Thr Glu
            740                 745                 750

Ile Asp Gly Lys His Phe Tyr Phe Ala Glu Asn Gly Glu Met Gln Ile
        755                 760                 765

Gly Val Phe Asn Thr Glu Asp Gly Phe Lys Tyr Phe Ala His His Asn
    770                 775                 780

Glu Asp Leu Gly Asn Glu Glu Gly Glu Glu Ile Ser Tyr Ser Gly Ile
785                 790                 795                 800

Leu Asn Phe Asn Asn Lys Ile Tyr Tyr Phe Asp Asp Ser Phe Thr Ala
                805                 810                 815

Val Val Gly Trp Lys Asp Leu Glu Asp Gly Ser Lys Tyr Tyr Phe Asp
            820                 825                 830

Glu Asp Thr Ala Glu Ala Tyr Ile Gly Leu Ser Leu Ile Asn Asp Gly
        835                 840                 845

Gln Tyr Tyr Phe Asn Asp Asp Gly Ile Met Gln Val Gly Phe Val Thr
    850                 855                 860

Ile Asn Asp Lys Val Phe Tyr Phe Ser Asp Ser Gly Ile Ile Glu Ser
865                 870                 875                 880

Gly Val Gln Asn Ile Asp Asp Asn Tyr Phe Tyr Ile Asp Asp Asn Gly
```

-continued

```
                885                 890                 895

Ile Val Gln Ile Gly Val Phe Asp Thr Ser Asp Gly Tyr Lys Tyr Phe
            900                 905                 910

Ala Pro Ala Asn Thr Val Asn Asp Asn Ile Tyr Gly Gln Ala Val Glu
        915                 920                 925

Tyr Ser Gly Leu Val Arg Val Gly Glu Asp Val Tyr Tyr Phe Gly Glu
    930                 935                 940

Thr Tyr Thr Ile Glu Thr Gly Trp Ile Tyr Asp Met Glu Asn Glu Ser
945                 950                 955                 960

Asp Lys Tyr Tyr Phe Asn Pro Glu Thr Lys Lys Ala Cys Lys Gly Ile
                965                 970                 975

Asn Leu Ile Asp Asp Ile Lys Tyr Tyr Phe Asp Glu Lys Gly Ile Met
            980                 985                 990

Arg Thr Gly Leu Ile Ser Phe Glu Asn Asn Asn Tyr Tyr Phe Asn Glu
        995                 1000                1005

Asn Gly Glu Met Gln Phe Gly Tyr Ile Asn Ile Glu Asp Lys Met Phe
    1010                1015                1020

Tyr Phe Gly Glu Asp Gly Val Met Gln Ile Gly Val Phe Asn Thr Pro
1025                1030                1035                1040

Asp Gly Phe Lys Tyr Phe Ala His Gln Asn Thr Leu Asp Glu Asn Phe
                1045                1050                1055

Glu Gly Glu Ser Ile Asn Tyr Thr Gly Trp Leu Asp Leu Asp Glu Lys
            1060                1065                1070

Arg Tyr Tyr Phe Thr Asp Glu Tyr Ile Ala Ala Thr Gly Ser Val Ile
        1075                1080                1085

Ile Asp Gly Glu Glu Tyr Tyr Phe Asp Pro Asp Thr Ala Gln Leu Val
    1090                1095                1100

Ile Ser Glu His His His His His His
1105                1110
```

<210> SEQ ID NO 25
<211> LENGTH: 3324
<212> TYPE: DNA
<213> ORGANISM: Artificial Sequence
<220> FEATURE:
<223> OTHER INFORMATION: nucleotide sequence of F54 New

<400> SEQUENCE: 25

```
atggcaaccg gttggcagac catcgatggc aaaaaatatt attttaatac caacaccgca     60

attgcaagca ccggctatac cattatcaac ggcaaacact tttattttaa caccgacggc    120

attatgcaga ttggtgtgtt taaaggtccg aacggctttg aatactttgc accggcaaat    180

accgatgcca ataatattga aggccaggcc attctgtatc agaatgaatt tctgaccctg    240

aacggcaaaa aatactactt tggcagcgat agcaaagcag ttaccggttg gcgcatcatc    300

aacaataaga aatattactt caacccgaat aatgcaattg cagcaattca tctgtgcacc    360

attaacaacg acaaatatta tttcagctat gacggtattc tgcagaatgg ctacattacc    420

atcgaacgca acaactttta tttcgatgcc aacaacgaaa gcaaaatggt gaccggtgtt    480

ttcaaaggcc ctaatggttt tgagtatttc gctccggcaa acacccataa taacaacatt    540

gaaggtcagg cgatcgttta tcagaacaaa ttcctgacgc tgaatggtaa gaaatactat    600

ttcgataatg acagcaaagc cgtgaccggc tggcagacaa ttgacgggaa gaaatattac    660

tttaatctga ataccgcaga agcagcaacc ggttggcaaa cgatcgacgg taaaaagtac    720

tacttcaacc tgaacacagc cgaagcagcc acaggatggc agactattga tggaaaaaaa    780
```

-continued

```
tactatttca acaccaacac ctttattgca tctaccggtt ataccagcat taacggtaaa    840
catttctact tcaacaccga tggtatcatg cagatcggcg ttttcaaagg tccaaatggt    900
ttcgaatact ttgcccctgc caatacagat gcaaataaca tcgagggtca ggcaatcctg    960
taccaaaaca aatttctgac cctgaatggg aaaaaatatt actttggtag cgattctaaa   1020
gccgttaccg gtctgcgtac cattgatggt aaaaaatact actttaatac gaatacagcc   1080
gttgcggtta caggctggca gaccattaac gggaaaaaat actattttaa cacaaatacc   1140
agcattgcct caacgggtta taccattatt tcgggtaaac acttctactt taataccgat   1200
ggtattatgc aaatcggagt ctttaaagga cctgatgggt tcgaatattt tgcgcctgcg   1260
aacactgatg cgaacaatat cgaaggacag gcaatccgct atcagaatcg ctttctgtat   1320
ctgcacgaca acatctatta ttttggcaac aattcaaaag cagccaccgg ctgggttaca   1380
attgatggca accgctacta tttcgaaccg aataccgcaa tgggtgcaaa tggctacaaa   1440
accatcgata ataaaaattt ctattttcgc aacggtctgc cgcagatcgg ggtatttaaa   1500
ggtagcaacg gcttcgaata cttcgctcca gcgaatacgg acgcgaacaa tattgagggt   1560
caagcgattc gttatcaaaa ccgttttctg catctgctgg gcaaaatcta ctactttggc   1620
aataacagta aagcagttac tggatggcag acaatcaatg gtaaagtgta ctattttatg   1680
ccggataccg ccatggcagc agccggtggt ctgtttgaaa ttgatggcgt gatctatttt   1740
tttggtgtgg atggtgttaa agcagttacc ggctttgtga ccgtgggtga tgataaatac   1800
tatttcaatc cgattaacgg tggtgcagcg agcattggcg aaaccatcat cgatgacaaa   1860
aactattatt tcaaccagag cggtgtgctg cagaccggtg tgtttagcac cgaagatggc   1920
tttaaatatt ttgcgccagc gaacaccctg gatgaaaacc tggaaggcga agcgattgat   1980
tttaccggca aactgatcat cgatgaaaac atctattact tcgatgataa ctatcgtggt   2040
gcggtggaat ggaaagaact ggatggcgaa atgcattatt tttctccgga aaccggtaaa   2100
gcgtttaaag gcctgaacca gatcggcgat tacaaatact acttcaacag cgatggcgtg   2160
atgcagaaag gctttgtgag catcaacgat aacaaacact atttcgatga tagcggtgtg   2220
atgaaagtgg gctataccga aattgatggc aaacatttct acttcgcgga aaacggcgaa   2280
atgcagattg gcgtgttcaa taccgaagat ggtttcaaat acttcgcgca ccataacgaa   2340
gatctgggta acgaagaagg cgaagaaatt agctatagcg gcatcctgaa cttcaacaac   2400
aaaatctact actttgatga tagctttacc gcggtggtgg gctggaaaga tctggaagat   2460
ggcagcaaat attatttcga tgaagatacc gcggaagcgt atattggcct gagcctgatt   2520
aacgatggcc agtactattt taacgatgat ggcattatgc aggtgggttt cgtgaccatt   2580
aatgataaag tgttctattt cagcgatagc ggcattattg aaagcggcgt gcagaacatt   2640
gatgataact acttctacat cgatgataac ggcattgtgc agatcggcgt ttttgatacc   2700
agcgatggct acaaatattt cgcaccggcc aataccgtga acgataacat ttatggccag   2760
gcggtggaat atagcggtct ggtgcgtgtg ggcgaagatg tgtattattt cggcgaaacc   2820
tataccatcg aaaccggctg gatttatgat atggaaaacg aaagcgataa atattacttt   2880
aatccggaaa cgaaaaaagc gtgcaaaggc attaacctga tcgatgatat caaatactat   2940
tttgatgaaa aaggcattat gcgtaccggt ctgattagct tcgaaaacaa caactattac   3000
ttcaacgaaa acggtgaaat gcagttcggc tacatcaaca tcgaagataa aatgttctac   3060
ttcggcgaag atggtgttat gcagattggt gtttttaaca ccccggatgg cttcaaatac   3120
```

-continued

```
tttgcccatc agaataccct ggatgaaaat ttcgaaggtg aaagcattaa ctataccggc   3180

tggctggatc tggatgaaaa acgctactac ttcaccgatg aatacattgc ggcgaccggc   3240

agcgtgatta ttgatggcga agaatactac ttcgatccgg ataccgcgca gctggtgatt   3300

agcgaacatc atcatcatca ccat                                          3324
```

<210> SEQ ID NO 26
<211> LENGTH: 1108
<212> TYPE: PRT
<213> ORGANISM: Artificial Sequence
<220> FEATURE:
<223> OTHER INFORMATION: 26 F54 New

<400> SEQUENCE: 26

```
Met Ala Thr Gly Trp Gln Thr Ile Asp Gly Lys Lys Tyr Tyr Phe Asn
 1               5                  10                  15

Thr Asn Thr Ala Ile Ala Ser Thr Gly Tyr Thr Ile Ile Asn Gly Lys
            20                  25                  30

His Phe Tyr Phe Asn Thr Asp Gly Ile Met Gln Ile Gly Val Phe Lys
        35                  40                  45

Gly Pro Asn Gly Phe Glu Tyr Phe Ala Pro Ala Asn Thr Asp Ala Asn
    50                  55                  60

Asn Ile Glu Gly Gln Ala Ile Leu Tyr Gln Asn Glu Phe Leu Thr Leu
65                  70                  75                  80

Asn Gly Lys Lys Tyr Tyr Phe Gly Ser Asp Ser Lys Ala Val Thr Gly
                85                  90                  95

Trp Arg Ile Ile Asn Asn Lys Lys Tyr Tyr Phe Asn Pro Asn Asn Ala
            100                 105                 110

Ile Ala Ala Ile His Leu Cys Thr Ile Asn Asn Asp Lys Tyr Tyr Phe
        115                 120                 125

Ser Tyr Asp Gly Ile Leu Gln Asn Gly Tyr Ile Thr Ile Glu Arg Asn
    130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
    210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
            260                 265                 270

Gly Tyr Thr Ser Ile Asn Gly Lys His Phe Tyr Phe Asn Thr Asp Gly
        275                 280                 285

Ile Met Gln Ile Gly Val Phe Lys Gly Pro Asn Gly Phe Glu Tyr Phe
    290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
```

-continued

```
                325                 330                 335

Ser Asp Ser Lys Ala Val Thr Gly Leu Arg Thr Ile Asp Gly Lys Lys
            340                 345                 350

Tyr Tyr Phe Asn Thr Asn Thr Ala Val Ala Val Thr Gly Trp Gln Thr
        355                 360                 365

Ile Asn Gly Lys Lys Tyr Tyr Phe Asn Thr Asn Thr Ser Ile Ala Ser
    370                 375                 380

Thr Gly Tyr Thr Ile Ile Ser Gly Lys His Phe Tyr Phe Asn Thr Asp
385                 390                 395                 400

Gly Ile Met Gln Ile Gly Val Phe Lys Gly Pro Asp Gly Phe Glu Tyr
                405                 410                 415

Phe Ala Pro Ala Asn Thr Asp Ala Asn Asn Ile Glu Gly Gln Ala Ile
            420                 425                 430

Arg Tyr Gln Asn Arg Phe Leu Tyr Leu His Asp Asn Ile Tyr Tyr Phe
        435                 440                 445

Gly Asn Asn Ser Lys Ala Ala Thr Gly Trp Val Thr Ile Asp Gly Asn
    450                 455                 460

Arg Tyr Tyr Phe Glu Pro Asn Thr Ala Met Gly Ala Asn Gly Tyr Lys
465                 470                 475                 480

Thr Ile Asp Asn Lys Asn Phe Tyr Phe Arg Asn Gly Leu Pro Gln Ile
                485                 490                 495

Gly Val Phe Lys Gly Ser Asn Gly Phe Glu Tyr Phe Ala Pro Ala Asn
            500                 505                 510

Thr Asp Ala Asn Asn Ile Glu Gly Gln Ala Ile Arg Tyr Gln Asn Arg
        515                 520                 525

Phe Leu His Leu Leu Gly Lys Ile Tyr Tyr Phe Gly Asn Asn Ser Lys
    530                 535                 540

Ala Val Thr Gly Trp Gln Thr Ile Asn Gly Lys Val Tyr Tyr Phe Met
545                 550                 555                 560

Pro Asp Thr Ala Met Ala Ala Ala Gly Gly Leu Phe Glu Ile Asp Gly
                565                 570                 575

Val Ile Tyr Phe Phe Gly Val Asp Gly Val Lys Ala Val Thr Gly Phe
            580                 585                 590

Val Thr Val Gly Asp Asp Lys Tyr Tyr Phe Asn Pro Ile Asn Gly Gly
        595                 600                 605

Ala Ala Ser Ile Gly Glu Thr Ile Ile Asp Asp Lys Asn Tyr Tyr Phe
    610                 615                 620

Asn Gln Ser Gly Val Leu Gln Thr Gly Val Phe Ser Thr Glu Asp Gly
625                 630                 635                 640

Phe Lys Tyr Phe Ala Pro Ala Asn Thr Leu Asp Glu Asn Leu Glu Gly
                645                 650                 655

Glu Ala Ile Asp Phe Thr Gly Lys Leu Ile Ile Asp Glu Asn Ile Tyr
            660                 665                 670

Tyr Phe Asp Asp Asn Tyr Arg Gly Ala Val Glu Trp Lys Glu Leu Asp
        675                 680                 685

Gly Glu Met His Tyr Phe Ser Pro Glu Thr Gly Lys Ala Phe Lys Gly
    690                 695                 700

Leu Asn Gln Ile Gly Asp Tyr Lys Tyr Tyr Phe Asn Ser Asp Gly Val
705                 710                 715                 720

Met Gln Lys Gly Phe Val Ser Ile Asn Asp Asn Lys His Tyr Phe Asp
                725                 730                 735

Asp Ser Gly Val Met Lys Val Gly Tyr Thr Glu Ile Asp Gly Lys His
            740                 745                 750
```

```
Phe Tyr Phe Ala Glu Asn Gly Glu Met Gln Ile Gly Val Phe Asn Thr
        755                 760                 765

Glu Asp Gly Phe Lys Tyr Phe Ala His His Asn Glu Asp Leu Gly Asn
    770                 775                 780

Glu Glu Gly Glu Glu Ile Ser Tyr Ser Gly Ile Leu Asn Phe Asn Asn
785                 790                 795                 800

Lys Ile Tyr Tyr Phe Asp Asp Ser Phe Thr Ala Val Val Gly Trp Lys
                805                 810                 815

Asp Leu Glu Asp Gly Ser Lys Tyr Tyr Phe Asp Glu Asp Thr Ala Glu
            820                 825                 830

Ala Tyr Ile Gly Leu Ser Leu Ile Asn Asp Gly Gln Tyr Tyr Phe Asn
        835                 840                 845

Asp Asp Gly Ile Met Gln Val Gly Phe Val Thr Ile Asn Asp Lys Val
    850                 855                 860

Phe Tyr Phe Ser Asp Ser Gly Ile Ile Glu Ser Gly Val Gln Asn Ile
865                 870                 875                 880

Asp Asp Asn Tyr Phe Tyr Ile Asp Asp Asn Gly Ile Val Gln Ile Gly
                885                 890                 895

Val Phe Asp Thr Ser Asp Gly Tyr Lys Tyr Phe Ala Pro Ala Asn Thr
            900                 905                 910

Val Asn Asp Asn Ile Tyr Gly Gln Ala Val Glu Tyr Ser Gly Leu Val
        915                 920                 925

Arg Val Gly Glu Asp Val Tyr Tyr Phe Gly Glu Thr Tyr Thr Ile Glu
    930                 935                 940

Thr Gly Trp Ile Tyr Asp Met Glu Asn Glu Ser Asp Lys Tyr Tyr Phe
945                 950                 955                 960

Asn Pro Glu Thr Lys Lys Ala Cys Lys Gly Ile Asn Leu Ile Asp Asp
                965                 970                 975

Ile Lys Tyr Tyr Phe Asp Glu Lys Gly Ile Met Arg Thr Gly Leu Ile
            980                 985                 990

Ser Phe Glu Asn Asn Asn Tyr Tyr Phe Asn Glu Asn Gly Glu Met Gln
        995                 1000                1005

Phe Gly Tyr Ile Asn Ile Glu Asp Lys Met Phe Tyr Phe Gly Glu Asp
    1010                1015                1020

Gly Val Met Gln Ile Gly Val Phe Asn Thr Pro Asp Gly Phe Lys Tyr
1025                1030                1035                1040

Phe Ala His Gln Asn Thr Leu Asp Glu Asn Phe Glu Gly Glu Ser Ile
                1045                1050                1055

Asn Tyr Thr Gly Trp Leu Asp Leu Asp Glu Lys Arg Tyr Tyr Phe Thr
            1060                1065                1070

Asp Glu Tyr Ile Ala Ala Thr Gly Ser Val Ile Ile Asp Gly Glu Glu
        1075                1080                1085

Tyr Tyr Phe Asp Pro Asp Thr Ala Gln Leu Val Ile Ser Glu His His
    1090                1095                1100

His His His His
1105
```

<210> SEQ ID NO 27
<211> LENGTH: 3387
<212> TYPE: DNA
<213> ORGANISM: Artificial Sequence
<220> FEATURE:
<223> OTHER INFORMATION: nucleotide sequence of F5 ToxB

<400> SEQUENCE: 27

-continued

```
atggcaaccg gttggcagac catcgatggc aaaaaatatt attttaatac caacaccgca     60
attgcaagca ccggctatac cattatcaac ggcaaacact tttattttaa caccgacggc    120
attatgcaga ttggtgtgtt taaaggtccg aacggctttg aatactttgc accggcaaat    180
accgatgcca ataatattga aggccaggcc attctgtatc agaatgaatt tctgaccctg    240
aacggcaaaa aatactactt tggcagcgat agcaaagcag ttaccggttg gcgcatcatc    300
aacaataaga aatattactt caacccgaat aatgcaattg cagcaattca tctgtgcacc    360
attaacaacg acaaatatta tttcagctat gacggtattc tgcagaatgg ctacattacc    420
atcgaacgca acaactttta tttcgatgcc aacaacgaaa gcaaaatggt gaccggtgtt    480
ttcaaaggcc ctaatggttt tgagtatttc gctccggcaa acacccataa taacaacatt    540
gaaggtcagg cgatcgttta tcagaacaaa ttcctgacgc tgaatggtaa gaaatactat    600
ttcgataatg acagcaaagc cgtgaccggc tggcagacaa ttgacgggaa gaaatattac    660
tttaatctga ataccgcaga agcagcaacc ggttggcaaa cgatcgacgg taaaaagtac    720
tacttcaacc tgaacacagc cgaagcagcc acaggatggc agactattga tggaaaaaaa    780
tactatttca acaccaacac ctttattgca tctaccggtt ataccagcat taacggtaaa    840
catttctact tcaacaccga tggtatcatg cagatcggcg ttttcaaagg tccaaatggt    900
ttcgaatact ttgcccctgc caatacagat gcaaataaca tcgagggtca ggcaatcctg    960
taccaaaaca aatttctgac cctgaatggg aaaaaatatt actttggtag cgattctaaa   1020
gccgttaccg gtctgcgtac cattgatggt aaaaaatact actttaatac gaatacagcc   1080
gttgcggtta caggctggca gaccattaac gggaaaaaat actattttaa cacaaatacc   1140
agcattgcct caacgggtta taccattatt tcgggtaaac acttctactt taataccgat   1200
ggtattatgc aaatcggagt ctttaaagga cctgatgggt tcgaatattt tgcgcctgcg   1260
aacactgatg cgaacaatat cgaaggacag gcaatccgct atcagaatcg ctttctgtat   1320
ctgcacgaca acatctatta ttttggcaac aattcaaaag cagccaccgg ctgggttaca   1380
attgatggca accgctacta tttcgaaccg aataccgcaa tgggtgcaaa tggctacaaa   1440
accatcgata ataaaaattt ctattttcgc aacggtctgc cgcagatcgg ggtatttaaa   1500
ggtagcaacg gcttcgaata cttcgctcca gcgaatacgg acgcgaacaa tattgagggt   1560
caagcgattc gttatcaaaa ccgttttctg catctgctgg gcaaaatcta ctactttggc   1620
aataacagta aagcagttac tggatggcag acaatcaatg gtaaagtgta ctattttatg   1680
ccggataccg ccatggcagc agccggtggt ctgtttgaaa ttgatggcgt gatctatttt   1740
tttggtgtgg atggtgttaa agcagtgagc ggtctgattt atattaacga tagcctgtat   1800
tactttaaac caccggtgaa taacctgatt accggctttg tgaccgtggg tgatgataaa   1860
tactatttca atccgattaa cggtggtgca gcgagcattg gcgaaaccat catcgatgac   1920
aaaaactatt atttcaacca gagcggtgtg ctgcagaccg gtgtgtttag caccgaagat   1980
ggctttaaat attttgcgcc agcgaacacc ctggatgaaa acctggaagg cgaagcgatt   2040
gattttaccg gcaaactgat catcgatgaa aacatctatt acttcgatga taactatcgt   2100
ggtgcggtgg aatggaaaga actggatggc gaaatgcatt atttttctcc ggaaaccggt   2160
aaagcgttta aaggcctgaa ccagatcggc gattacaaat actacttcaa cagcgatggc   2220
gtgatgcaga aaggctttgt gagcatcaac gataacaaac actatttcga tgatagcggt   2280
gtgatgaaag tgggctatac cgaaattgat ggcaaacatt tctacttcgc ggaaaacggc   2340
```

```
gaaatgcaga ttggcgtgtt caataccgaa gatggtttca aatacttcgc gcaccataac   2400

gaagatctgg gtaacgaaga aggcgaagaa attagctata gcggcatcct gaacttcaac   2460

aacaaaatct actactttga tgatagcttt accgcggtgg tgggctggaa agatctggaa   2520

gatggcagca aatattattt cgatgaagat accgcggaag cgtatattgg cctgagcctg   2580

attaacgatg gccagtacta ttttaacgat gatggcatta tgcaggtggg tttcgtgacc   2640

attaatgata aagtgttcta tttcagcgat agcggcatta ttgaaagcgg cgtgcagaac   2700

attgatgata actacttcta catcgatgat aacggcattg tgcagatcgg cgtttttgat   2760

accagcgatg gctacaaata tttcgcaccg gccaataccg tgaacgataa catttatggc   2820

caggcggtgg aatatagcgg tctggtgcgt gtgggcgaag atgtgtatta tttcggcgaa   2880

acctatacca tcgaaaccgg ctggatttat gatatggaaa acgaaagcga taaatattac   2940

tttaatccgg aaacgaaaaa agcgtgcaaa ggcattaacc tgatcgatga tatcaaatac   3000

tattttgatg aaaaaggcat tatgcgtacc ggtctgatta gcttcgaaaa caacaactat   3060

tacttcaacg aaaacggtga aatgcagttc ggctacatca acatcgaaga taaaatgttc   3120

tacttcggcg aagatggtgt tatgcagatt ggtgttttta acaccccgga tggcttcaaa   3180

tactttgccc atcagaatac cctggatgaa aatttcgaag gtgaaagcat taactatacc   3240

ggctggctgg atctggatga aaaacgctac tacttcaccg atgaatacat tgcggcgacc   3300

ggcagcgtga ttattgatgg cgaagaatac tacttcgatc cggataccgc gcagctggtg   3360

attagcgaac atcatcatca tcaccat                                     3387
```

<210> SEQ ID NO 28
<211> LENGTH: 1129
<212> TYPE: PRT
<213> ORGANISM: Artificial Sequence
<220> FEATURE:
<223> OTHER INFORMATION: amino acid sequence of F5 ToxB

<400> SEQUENCE: 28

```
Met Ala Thr Gly Trp Gln Thr Ile Asp Gly Lys Lys Tyr Tyr Phe Asn
 1               5                  10                  15

Thr Asn Thr Ala Ile Ala Ser Thr Gly Tyr Thr Ile Ile Asn Gly Lys
            20                  25                  30

His Phe Tyr Phe Asn Thr Asp Gly Ile Met Gln Ile Gly Val Phe Lys
        35                  40                  45

Gly Pro Asn Gly Phe Glu Tyr Phe Ala Pro Ala Asn Thr Asp Ala Asn
    50                  55                  60

Asn Ile Glu Gly Gln Ala Ile Leu Tyr Gln Asn Glu Phe Leu Thr Leu
65                  70                  75                  80

Asn Gly Lys Lys Tyr Tyr Phe Gly Ser Asp Ser Lys Ala Val Thr Gly
                85                  90                  95

Trp Arg Ile Ile Asn Asn Lys Lys Tyr Tyr Phe Asn Pro Asn Asn Ala
            100                 105                 110

Ile Ala Ala Ile His Leu Cys Thr Ile Asn Asn Asp Lys Tyr Tyr Phe
        115                 120                 125

Ser Tyr Asp Gly Ile Leu Gln Asn Gly Tyr Ile Thr Ile Glu Arg Asn
    130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175
```

```
Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
    210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
            260                 265                 270

Gly Tyr Thr Ser Ile Asn Gly Lys His Phe Tyr Phe Asn Thr Asp Gly
        275                 280                 285

Ile Met Gln Ile Gly Val Phe Lys Gly Pro Asn Gly Phe Glu Tyr Phe
    290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
                325                 330                 335

Ser Asp Ser Lys Ala Val Thr Gly Leu Arg Thr Ile Asp Gly Lys Lys
            340                 345                 350

Tyr Tyr Phe Asn Thr Asn Thr Ala Val Ala Val Thr Gly Trp Gln Thr
        355                 360                 365

Ile Asn Gly Lys Lys Tyr Tyr Phe Asn Thr Asn Thr Ser Ile Ala Ser
    370                 375                 380

Thr Gly Tyr Thr Ile Ile Ser Gly Lys His Phe Tyr Phe Asn Thr Asp
385                 390                 395                 400

Gly Ile Met Gln Ile Gly Val Phe Lys Gly Pro Asp Gly Phe Glu Tyr
                405                 410                 415

Phe Ala Pro Ala Asn Thr Asp Ala Asn Asn Ile Glu Gly Gln Ala Ile
            420                 425                 430

Arg Tyr Gln Asn Arg Phe Leu Tyr Leu His Asp Asn Ile Tyr Tyr Phe
        435                 440                 445

Gly Asn Asn Ser Lys Ala Ala Thr Gly Trp Val Thr Ile Asp Gly Asn
    450                 455                 460

Arg Tyr Tyr Phe Glu Pro Asn Thr Ala Met Gly Ala Asn Gly Tyr Lys
465                 470                 475                 480

Thr Ile Asp Asn Lys Asn Phe Tyr Phe Arg Asn Gly Leu Pro Gln Ile
                485                 490                 495

Gly Val Phe Lys Gly Ser Asn Gly Phe Glu Tyr Phe Ala Pro Ala Asn
            500                 505                 510

Thr Asp Ala Asn Asn Ile Glu Gly Gln Ala Ile Arg Tyr Gln Asn Arg
        515                 520                 525

Phe Leu His Leu Leu Gly Lys Ile Tyr Tyr Phe Gly Asn Asn Ser Lys
    530                 535                 540

Ala Val Thr Gly Trp Gln Thr Ile Asn Gly Lys Val Tyr Tyr Phe Met
545                 550                 555                 560

Pro Asp Thr Ala Met Ala Ala Ala Gly Gly Leu Phe Glu Ile Asp Gly
                565                 570                 575

Val Ile Tyr Phe Phe Gly Val Asp Gly Val Lys Ala Val Ser Gly Leu
            580                 585                 590

Ile Tyr Ile Asn Asp Ser Leu Tyr Tyr Phe Lys Pro Pro Val Asn Asn
```

```
        595                 600                 605

Leu Ile Thr Gly Phe Val Thr Val Gly Asp Asp Lys Tyr Tyr Phe Asn
    610                 615                 620

Pro Ile Asn Gly Gly Ala Ala Ser Ile Gly Glu Thr Ile Ile Asp Asp
625                 630                 635                 640

Lys Asn Tyr Tyr Phe Asn Gln Ser Gly Val Leu Gln Thr Gly Val Phe
                645                 650                 655

Ser Thr Glu Asp Gly Phe Lys Tyr Phe Ala Pro Ala Asn Thr Leu Asp
            660                 665                 670

Glu Asn Leu Glu Gly Glu Ala Ile Asp Phe Thr Gly Lys Leu Ile Ile
        675                 680                 685

Asp Glu Asn Ile Tyr Tyr Phe Asp Asp Asn Tyr Arg Gly Ala Val Glu
    690                 695                 700

Trp Lys Glu Leu Asp Gly Glu Met His Tyr Phe Ser Pro Glu Thr Gly
705                 710                 715                 720

Lys Ala Phe Lys Gly Leu Asn Gln Ile Gly Asp Tyr Lys Tyr Tyr Phe
                725                 730                 735

Asn Ser Asp Gly Val Met Gln Lys Gly Phe Val Ser Ile Asn Asp Asn
            740                 745                 750

Lys His Tyr Phe Asp Asp Ser Gly Val Met Lys Val Gly Tyr Thr Glu
        755                 760                 765

Ile Asp Gly Lys His Phe Tyr Phe Ala Glu Asn Gly Glu Met Gln Ile
    770                 775                 780

Gly Val Phe Asn Thr Glu Asp Gly Phe Lys Tyr Phe Ala His His Asn
785                 790                 795                 800

Glu Asp Leu Gly Asn Glu Glu Gly Glu Glu Ile Ser Tyr Ser Gly Ile
                805                 810                 815

Leu Asn Phe Asn Asn Lys Ile Tyr Tyr Phe Asp Asp Ser Phe Thr Ala
            820                 825                 830

Val Val Gly Trp Lys Asp Leu Glu Asp Gly Ser Lys Tyr Tyr Phe Asp
        835                 840                 845

Glu Asp Thr Ala Glu Ala Tyr Ile Gly Leu Ser Leu Ile Asn Asp Gly
    850                 855                 860

Gln Tyr Tyr Phe Asn Asp Asp Gly Ile Met Gln Val Gly Phe Val Thr
865                 870                 875                 880

Ile Asn Asp Lys Val Phe Tyr Phe Ser Asp Ser Gly Ile Ile Glu Ser
                885                 890                 895

Gly Val Gln Asn Ile Asp Asp Asn Tyr Phe Tyr Ile Asp Asp Asn Gly
            900                 905                 910

Ile Val Gln Ile Gly Val Phe Asp Thr Ser Asp Gly Tyr Lys Tyr Phe
        915                 920                 925

Ala Pro Ala Asn Thr Val Asn Asp Asn Ile Tyr Gly Gln Ala Val Glu
    930                 935                 940

Tyr Ser Gly Leu Val Arg Val Gly Glu Asp Val Tyr Tyr Phe Gly Glu
945                 950                 955                 960

Thr Tyr Thr Ile Glu Thr Gly Trp Ile Tyr Asp Met Glu Asn Glu Ser
                965                 970                 975

Asp Lys Tyr Tyr Phe Asn Pro Glu Thr Lys Lys Ala Cys Lys Gly Ile
            980                 985                 990

Asn Leu Ile Asp Asp Ile Lys Tyr Tyr Phe Asp Glu Lys Gly Ile Met
        995                 1000                1005

Arg Thr Gly Leu Ile Ser Phe Glu Asn Asn Asn Tyr Tyr Phe Asn Glu
    1010                1015                1020
```

```
Asn Gly Glu Met Gln Phe Gly Tyr Ile Asn Ile Glu Asp Lys Met Phe
1025                1030                1035                1040

Tyr Phe Gly Glu Asp Gly Val Met Gln Ile Gly Val Phe Asn Thr Pro
                1045                1050                1055

Asp Gly Phe Lys Tyr Phe Ala His Gln Asn Thr Leu Asp Glu Asn Phe
            1060                1065                1070

Glu Gly Glu Ser Ile Asn Tyr Thr Gly Trp Leu Asp Leu Asp Glu Lys
        1075                1080                1085

Arg Tyr Tyr Phe Thr Asp Glu Tyr Ile Ala Ala Thr Gly Ser Val Ile
    1090                1095                1100

Ile Asp Gly Glu Glu Tyr Tyr Phe Asp Pro Asp Thr Ala Gln Leu Val
1105                1110                1115                1120

Ile Ser Glu His His His His His His
                1125


<210> SEQ ID NO 29
<211> LENGTH: 2985
<212> TYPE: DNA
<213> ORGANISM: Artificial Sequence
<220> FEATURE:
<223> OTHER INFORMATION: nucleotide sequence of F52 new

<400> SEQUENCE: 29

atggcaaccg gttggcagac catcgatggc aaaaaatatt attttaatac caacaccgca     60

attgcaagca ccggctatac cattatcaac ggcaaacact tttattttaa caccgacggc    120

attatgcaga ttggtgtgtt taaaggtccg aacggctttg aatactttgc accggcaaat    180

accgatgcca ataatattga aggccaggcc attctgtatc agaatgaatt tctgaccctg    240

aacggcaaaa aatactactt tggcagcgat agcaaagcag ttaccggttg gcgcatcatc    300

aacaataaga aatattactt caacccgaat aatgcaattg cagcaattca tctgtgcacc    360

attaacaacg acaaatatta tttcagctat gacggtattc tgcagaatgg ctacattacc    420

atcgaacgca acaactttta tttcgatgcc aacaacgaaa gcaaaatggt gaccggtgtt    480

ttcaaaggcc ctaatggttt tgagtatttc gctccggcaa acacccataa taacaacatt    540

gaaggtcagg cgatcgttta tcagaacaaa ttcctgacgc tgaatggtaa gaaatactat    600

ttcgataatg acagcaaagc cgtgaccggc tggcagacaa ttgacgggaa gaaatattac    660

tttaatctga ataccgcaga agcagcaacc ggttggcaaa cgatcgacgg taaaaagtac    720

tacttcaacc tgaacacagc cgaagcagcc acaggatggc agactattga tggaaaaaaa    780

tactatttca acaccaacac ctttattgca tctaccggtt ataccagcat taacggtaaa    840

catttctact tcaacaccga tggtatcatg cagatcggcg ttttcaaagg tccaaatggt    900

ttcgaatact ttgcccctgc caatacagat gcaaataaca tcgagggtca ggcaatcctg    960

taccaaaaca aatttctgac cctgaatggg aaaaaatatt actttggtag cgattctaaa   1020

gccgttaccg gtctgcgtac cattgatggt aaaaaatact actttaatac gaatacagcc   1080

gttgcggtta caggctggca gaccattaac gggaaaaaat actattttaa cacaaatacc   1140

agcattgcct caacgggtta taccattatt tcgggtaaac acttctactt taataccgat   1200

ggtattatgc aaatcggagt ctttaaagga cctgatgggt tcgaatattt tgcgcctgcg   1260

aacactgatg cgaacaatat cgaaggacag gcaatccgct atcagaatcg ctttctgtat   1320

ctgcacgaca acatctatta ttttggcaac aattcaaaag cagccaccgg ctgggttaca   1380

attgatggca accgctacta tttcgaaccg aataccgcaa tgggtgcaaa tggctacaaa   1440
```

accatcgata ataaaaattt ctattttcgc aacggtctgc cgcagatcgg ggtatttaaa 1500
ggtagcaacg gcttcgaata cttcgctcca gcgaatacgg acgcgaacaa tattgagggt 1560
caagcgattc gttatcaaaa ccgttttctg catctgctgg gcaaaatcta ctactttggc 1620
aataacagta aagcagttac tggatggcag acaatcaatg gtaaagtgta ctattttatg 1680
ccggataccg ccatggcagc agccggtggt ctgtttgaaa ttgatggcgt gatctatttt 1740
tttggtgtgg atggtgttaa agcagtgaaa ggcctgaacc agatcggcga ttacaaatac 1800
tacttcaaca gcgatggcgt gatgcagaaa ggctttgtga gcatcaacga taacaaacac 1860
tatttcgatg atagcggtgt gatgaaagtg ggctataccg aaattgatgg caaacatttc 1920
tacttcgcgg aaaacggcga aatgcagatt ggcgtgttca ataccgaaga tggtttcaaa 1980
tacttcgcgc accataacga agatctgggt aacgaagaag gcgaagaaat tagctatagc 2040
ggcatcctga acttcaacaa caaaatctac tactttgatg atagctttac cgcggtggtg 2100
ggctggaaag atctggaaga tggcagcaaa tattatttcg atgaagatac cgcggaagcg 2160
tatattggcc tgagcctgat taacgatggc cagtactatt ttaacgatga tggcattatg 2220
caggtgggtt tcgtgaccat taatgataaa gtgttctatt tcagcgatag cggcattatt 2280
gaaagcggcg tgcagaacat tgatgataac tacttctaca tcgatgataa cggcattgtg 2340
cagatcggcg tttttgatac cagcgatggc tacaaatatt tcgcaccggc caataccgtg 2400
aacgataaca tttatggcca ggcggtggaa tatagcggtc tggtgcgtgt gggcgaagat 2460
gtgtattatt tcggcgaaac ctataccatc gaaaccggct ggatttatga tatggaaaac 2520
gaaagcgata aatattactt taatccggaa acgaaaaaag cgtgcaaagg cattaacctg 2580
atcgatgata tcaaatacta ttttgatgaa aaaggcatta tgcgtaccgg tctgattagc 2640
ttcgaaaaca acaactatta cttcaacgaa aacggtgaaa tgcagttcgg ctacatcaac 2700
atcgaagata aaatgttcta cttcggcgaa gatggtgtta tgcagattgg tgtttttaac 2760
accccggatg gcttcaaata ctttgcccat cagaataccc tggatgaaaa tttcgaaggt 2820
gaaagcatta actataccgg ctggctggat ctggatgaaa aacgctacta cttcaccgat 2880
gaatacattg cggcgaccgg cagcgtgatt attgatggcg aagaatacta cttcgatccg 2940
gataccgcgc agctggtgat tagcgaacat catcatcatc accat 2985

<210> SEQ ID NO 30
<211> LENGTH: 995
<212> TYPE: PRT
<213> ORGANISM: Artificial Sequence
<220> FEATURE:
<223> OTHER INFORMATION: amino acid sequence of F52 New

<400> SEQUENCE: 30

Met Ala Thr Gly Trp Gln Thr Ile Asp Gly Lys Lys Tyr Tyr Phe Asn
1 5 10 15

Thr Asn Thr Ala Ile Ala Ser Thr Gly Tyr Thr Ile Ile Asn Gly Lys
20 25 30

His Phe Tyr Phe Asn Thr Asp Gly Ile Met Gln Ile Gly Val Phe Lys
35 40 45

Gly Pro Asn Gly Phe Glu Tyr Phe Ala Pro Ala Asn Thr Asp Ala Asn
50 55 60

Asn Ile Glu Gly Gln Ala Ile Leu Tyr Gln Asn Glu Phe Leu Thr Leu
65 70 75 80

Asn Gly Lys Lys Tyr Tyr Phe Gly Ser Asp Ser Lys Ala Val Thr Gly

-continued

```
                85                  90                  95

Trp Arg Ile Ile Asn Asn Lys Lys Tyr Tyr Phe Asn Pro Asn Asn Ala
            100                 105                 110

Ile Ala Ala Ile His Leu Cys Thr Ile Asn Asn Asp Lys Tyr Tyr Phe
        115                 120                 125

Ser Tyr Asp Gly Ile Leu Gln Asn Gly Tyr Ile Thr Ile Glu Arg Asn
    130                 135                 140

Asn Phe Tyr Phe Asp Ala Asn Asn Glu Ser Lys Met Val Thr Gly Val
145                 150                 155                 160

Phe Lys Gly Pro Asn Gly Phe Glu Tyr Phe Ala Pro Ala Asn Thr His
                165                 170                 175

Asn Asn Asn Ile Glu Gly Gln Ala Ile Val Tyr Gln Asn Lys Phe Leu
            180                 185                 190

Thr Leu Asn Gly Lys Lys Tyr Tyr Phe Asp Asn Asp Ser Lys Ala Val
        195                 200                 205

Thr Gly Trp Gln Thr Ile Asp Gly Lys Lys Tyr Tyr Phe Asn Leu Asn
    210                 215                 220

Thr Ala Glu Ala Ala Thr Gly Trp Gln Thr Ile Asp Gly Lys Lys Tyr
225                 230                 235                 240

Tyr Phe Asn Leu Asn Thr Ala Glu Ala Ala Thr Gly Trp Gln Thr Ile
                245                 250                 255

Asp Gly Lys Lys Tyr Tyr Phe Asn Thr Asn Thr Phe Ile Ala Ser Thr
            260                 265                 270

Gly Tyr Thr Ser Ile Asn Gly Lys His Phe Tyr Phe Asn Thr Asp Gly
        275                 280                 285

Ile Met Gln Ile Gly Val Phe Lys Gly Pro Asn Gly Phe Glu Tyr Phe
    290                 295                 300

Ala Pro Ala Asn Thr Asp Ala Asn Asn Ile Glu Gly Gln Ala Ile Leu
305                 310                 315                 320

Tyr Gln Asn Lys Phe Leu Thr Leu Asn Gly Lys Lys Tyr Tyr Phe Gly
                325                 330                 335

Ser Asp Ser Lys Ala Val Thr Gly Leu Arg Thr Ile Asp Gly Lys Lys
            340                 345                 350

Tyr Tyr Phe Asn Thr Asn Thr Ala Val Ala Val Thr Gly Trp Gln Thr
        355                 360                 365

Ile Asn Gly Lys Lys Tyr Tyr Phe Asn Thr Asn Thr Ser Ile Ala Ser
    370                 375                 380

Thr Gly Tyr Thr Ile Ile Ser Gly Lys His Phe Tyr Phe Asn Thr Asp
385                 390                 395                 400

Gly Ile Met Gln Ile Gly Val Phe Lys Gly Pro Asp Gly Phe Glu Tyr
                405                 410                 415

Phe Ala Pro Ala Asn Thr Asp Ala Asn Asn Ile Glu Gly Gln Ala Ile
            420                 425                 430

Arg Tyr Gln Asn Arg Phe Leu Tyr Leu His Asp Asn Ile Tyr Tyr Phe
        435                 440                 445

Gly Asn Asn Ser Lys Ala Ala Thr Gly Trp Val Thr Ile Asp Gly Asn
    450                 455                 460

Arg Tyr Tyr Phe Glu Pro Asn Thr Ala Met Gly Ala Asn Gly Tyr Lys
465                 470                 475                 480

Thr Ile Asp Asn Lys Asn Phe Tyr Phe Arg Asn Gly Leu Pro Gln Ile
                485                 490                 495

Gly Val Phe Lys Gly Ser Asn Gly Phe Glu Tyr Phe Ala Pro Ala Asn
            500                 505                 510
```

```
Thr Asp Ala Asn Asn Ile Glu Gly Gln Ala Ile Arg Tyr Gln Asn Arg
        515                 520                 525

Phe Leu His Leu Leu Gly Lys Ile Tyr Tyr Phe Gly Asn Asn Ser Lys
    530                 535                 540

Ala Val Thr Gly Trp Gln Thr Ile Asn Gly Lys Val Tyr Tyr Phe Met
545                 550                 555                 560

Pro Asp Thr Ala Met Ala Ala Ala Gly Gly Leu Phe Glu Ile Asp Gly
                565                 570                 575

Val Ile Tyr Phe Phe Gly Val Asp Gly Val Lys Ala Val Lys Gly Leu
            580                 585                 590

Asn Gln Ile Gly Asp Tyr Lys Tyr Tyr Phe Asn Ser Asp Gly Val Met
        595                 600                 605

Gln Lys Gly Phe Val Ser Ile Asn Asp Asn Lys His Tyr Phe Asp Asp
    610                 615                 620

Ser Gly Val Met Lys Val Gly Tyr Thr Glu Ile Asp Gly Lys His Phe
625                 630                 635                 640

Tyr Phe Ala Glu Asn Gly Glu Met Gln Ile Gly Val Phe Asn Thr Glu
                645                 650                 655

Asp Gly Phe Lys Tyr Phe Ala His His Asn Glu Asp Leu Gly Asn Glu
            660                 665                 670

Glu Gly Glu Glu Ile Ser Tyr Ser Gly Ile Leu Asn Phe Asn Asn Lys
        675                 680                 685

Ile Tyr Tyr Phe Asp Asp Ser Phe Thr Ala Val Val Gly Trp Lys Asp
    690                 695                 700

Leu Glu Asp Gly Ser Lys Tyr Tyr Phe Asp Glu Asp Thr Ala Glu Ala
705                 710                 715                 720

Tyr Ile Gly Leu Ser Leu Ile Asn Asp Gly Gln Tyr Tyr Phe Asn Asp
                725                 730                 735

Asp Gly Ile Met Gln Val Gly Phe Val Thr Ile Asn Asp Lys Val Phe
            740                 745                 750

Tyr Phe Ser Asp Ser Gly Ile Ile Glu Ser Gly Val Gln Asn Ile Asp
        755                 760                 765

Asp Asn Tyr Phe Tyr Ile Asp Asp Asn Gly Ile Val Gln Ile Gly Val
    770                 775                 780

Phe Asp Thr Ser Asp Gly Tyr Lys Tyr Phe Ala Pro Ala Asn Thr Val
785                 790                 795                 800

Asn Asp Asn Ile Tyr Gly Gln Ala Val Glu Tyr Ser Gly Leu Val Arg
                805                 810                 815

Val Gly Glu Asp Val Tyr Tyr Phe Gly Glu Thr Tyr Thr Ile Glu Thr
            820                 825                 830

Gly Trp Ile Tyr Asp Met Glu Asn Glu Ser Asp Lys Tyr Tyr Phe Asn
        835                 840                 845

Pro Glu Thr Lys Lys Ala Cys Lys Gly Ile Asn Leu Ile Asp Asp Ile
    850                 855                 860

Lys Tyr Tyr Phe Asp Glu Lys Gly Ile Met Arg Thr Gly Leu Ile Ser
865                 870                 875                 880

Phe Glu Asn Asn Asn Tyr Tyr Phe Asn Glu Asn Gly Glu Met Gln Phe
                885                 890                 895

Gly Tyr Ile Asn Ile Glu Asp Lys Met Phe Tyr Phe Gly Glu Asp Gly
            900                 905                 910

Val Met Gln Ile Gly Val Phe Asn Thr Pro Asp Gly Phe Lys Tyr Phe
        915                 920                 925
```

```
Ala His Gln Asn Thr Leu Asp Glu Asn Phe Glu Gly Glu Ser Ile Asn
    930                 935                 940

Tyr Thr Gly Trp Leu Asp Leu Asp Glu Lys Arg Tyr Tyr Phe Thr Asp
945                 950                 955                 960

Glu Tyr Ile Ala Ala Thr Gly Ser Val Ile Ile Asp Gly Glu Glu Tyr
                965                 970                 975

Tyr Phe Asp Pro Asp Thr Ala Gln Leu Val Ile Ser Glu His His His
            980                 985                 990

His His His
        995
```

<210> SEQ ID NO 31
<211> LENGTH: 2710
<212> TYPE: PRT
<213> ORGANISM: Clostridium Difficile

<400> SEQUENCE: 31

```
Met Ser Leu Ile Ser Lys Glu Glu Leu Ile Lys Leu Ala Tyr Ser Ile
 1               5                  10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
               245                 250                 255

Glu Leu Leu Asn Arg Gly Asn Leu Ala Ala Ala Ser Asp Ile Val Arg
           260                 265                 270

Leu Leu Ala Leu Lys Asn Phe Gly Gly Val Tyr Leu Asp Val Asp Met
       275                 280                 285

Leu Pro Gly Ile His Ser Asp Leu Phe Lys Thr Ile Ser Arg Pro Ser
   290                 295                 300
```

-continued

Ser Ile Gly Leu Asp Arg Trp Glu Met Ile Lys Leu Glu Ala Ile Met
305 310 315 320

Lys Tyr Lys Lys Tyr Ile Asn Asn Tyr Thr Ser Glu Asn Phe Asp Lys
325 330 335

Leu Asp Gln Gln Leu Lys Asp Asn Phe Lys Leu Ile Ile Glu Ser Lys
340 345 350

Ser Glu Lys Ser Glu Ile Phe Ser Lys Leu Glu Asn Leu Asn Val Ser
355 360 365

Asp Leu Glu Ile Lys Ile Ala Phe Ala Leu Gly Ser Val Ile Asn Gln
370 375 380

Ala Leu Ile Ser Lys Gln Gly Ser Tyr Leu Thr Asn Leu Val Ile Glu
385 390 395 400

Gln Val Lys Asn Arg Tyr Gln Phe Leu Asn Gln His Leu Asn Pro Ala
405 410 415

Ile Glu Ser Asp Asn Asn Phe Thr Asp Thr Thr Lys Ile Phe His Asp
420 425 430

Ser Leu Phe Asn Ser Ala Thr Ala Glu Asn Ser Met Phe Leu Thr Lys
435 440 445

Ile Ala Pro Tyr Leu Gln Val Gly Phe Met Pro Glu Ala Arg Ser Thr
450 455 460

Ile Ser Leu Ser Gly Pro Gly Ala Tyr Ala Ser Ala Tyr Tyr Asp Phe
465 470 475 480

Ile Asn Leu Gln Glu Asn Thr Ile Glu Lys Thr Leu Lys Ala Ser Asp
485 490 495

Leu Ile Glu Phe Lys Phe Pro Glu Asn Asn Leu Ser Gln Leu Thr Glu
500 505 510

Gln Glu Ile Asn Ser Leu Trp Ser Phe Asp Gln Ala Ser Ala Lys Tyr
515 520 525

Gln Phe Glu Lys Tyr Val Arg Asp Tyr Thr Gly Gly Ser Leu Ser Glu
530 535 540

Asp Asn Gly Val Asp Phe Asn Lys Asn Thr Ala Leu Asp Lys Asn Tyr
545 550 555 560

Leu Leu Asn Asn Lys Ile Pro Ser Asn Asn Val Glu Glu Ala Gly Ser
565 570 575

Lys Asn Tyr Val His Tyr Ile Ile Gln Leu Gln Gly Asp Asp Ile Ser
580 585 590

Tyr Glu Ala Thr Cys Asn Leu Phe Ser Lys Asn Pro Lys Asn Ser Ile
595 600 605

Ile Ile Gln Arg Asn Met Asn Glu Ser Ala Lys Ser Tyr Phe Leu Ser
610 615 620

Asp Asp Gly Glu Ser Ile Leu Glu Leu Asn Lys Tyr Arg Ile Pro Glu
625 630 635 640

Arg Leu Lys Asn Lys Glu Lys Val Lys Val Thr Phe Ile Gly His Gly
645 650 655

Lys Asp Glu Phe Asn Thr Ser Glu Phe Ala Arg Leu Ser Val Asp Ser
660 665 670

Leu Ser Asn Glu Ile Ser Ser Phe Leu Asp Thr Ile Lys Leu Asp Ile
675 680 685

Ser Pro Lys Asn Val Glu Val Asn Leu Leu Gly Cys Asn Met Phe Ser
690 695 700

Tyr Asp Phe Asn Val Glu Glu Thr Tyr Pro Gly Lys Leu Leu Leu Ser
705 710 715 720

```
Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
    770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
            820                 825                 830

Ser Ile Gly Asp Tyr Ile Tyr Tyr Glu Lys Leu Glu Pro Val Lys Asn
        835                 840                 845

Ile Ile His Asn Ser Ile Asp Asp Leu Ile Asp Glu Phe Asn Leu Leu
    850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
            900                 905                 910

Val Glu Thr Glu Lys Glu Ile Phe Ser Lys Tyr Ser Glu His Ile Thr
        915                 920                 925

Lys Glu Ile Ser Thr Ile Lys Asn Ser Ile Ile Thr Asp Val Asn Gly
    930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
            980                 985                 990

Ala Gln Leu Phe Ser Thr Gly Leu Asn Thr Ile Tyr Asp Ser Ile Gln
        995                 1000                1005

Leu Val Asn Leu Ile Ser Asn Ala Val Asn Asp Thr Ile Asn Val Leu
    1010                1015                1020

Pro Thr Ile Thr Glu Gly Ile Pro Ile Val Ser Thr Ile Leu Asp Gly
1025                1030                1035                1040

Ile Asn Leu Gly Ala Ala Ile Lys Glu Leu Leu Asp Glu His Asp Pro
                1045                1050                1055

Leu Leu Lys Lys Glu Leu Glu Ala Lys Val Gly Val Leu Ala Ile Asn
            1060                1065                1070

Met Ser Leu Ser Ile Ala Ala Thr Val Ala Ser Ile Val Gly Ile Gly
        1075                1080                1085

Ala Glu Val Thr Ile Phe Leu Leu Pro Ile Ala Gly Ile Ser Ala Gly
    1090                1095                1100

Ile Pro Ser Leu Val Asn Asn Glu Leu Ile Leu His Asp Lys Ala Thr
1105                1110                1115                1120

Ser Val Val Asn Tyr Phe Asn His Leu Ser Glu Ser Lys Lys Tyr Gly
                1125                1130                1135

Pro Leu Lys Thr Glu Asp Asp Lys Ile Leu Val Pro Ile Asp Asp Leu
```

```
            1140                1145                1150

Val Ile Ser Glu Ile Asp Phe Asn Asn Asn Ser Ile Lys Leu Gly Thr
        1155                1160                1165

Cys Asn Ile Leu Ala Met Glu Gly Gly Ser Gly His Thr Val Thr Gly
    1170                1175                1180

Asn Ile Asp His Phe Phe Ser Ser Pro Ser Ile Ser Ser His Ile Pro
1185                1190                1195                1200

Ser Leu Ser Ile Tyr Ser Ala Ile Gly Ile Glu Thr Glu Asn Leu Asp
                1205                1210                1215

Phe Ser Lys Lys Ile Met Met Leu Pro Asn Ala Pro Ser Arg Val Phe
            1220                1225                1230

Trp Trp Glu Thr Gly Ala Val Pro Gly Leu Arg Ser Leu Glu Asn Asp
        1235                1240                1245

Gly Thr Arg Leu Leu Asp Ser Ile Arg Asp Leu Tyr Pro Gly Lys Phe
    1250                1255                1260

Tyr Trp Arg Phe Tyr Ala Phe Phe Asp Tyr Ala Ile Thr Thr Leu Lys
1265                1270                1275                1280

Pro Val Tyr Glu Asp Thr Asn Ile Lys Ile Lys Leu Asp Lys Asp Thr
                1285                1290                1295

Arg Asn Phe Ile Met Pro Thr Ile Thr Thr Asn Glu Ile Arg Asn Lys
            1300                1305                1310

Leu Ser Tyr Ser Phe Asp Gly Ala Gly Gly Thr Tyr Ser Leu Leu Leu
        1315                1320                1325

Ser Ser Tyr Pro Ile Ser Thr Asn Ile Asn Leu Ser Lys Asp Asp Leu
    1330                1335                1340

Trp Ile Phe Asn Ile Asp Asn Glu Val Arg Glu Ile Ser Ile Glu Asn
1345                1350                1355                1360

Gly Thr Ile Lys Lys Gly Lys Leu Ile Lys Asp Val Leu Ser Lys Ile
                1365                1370                1375

Asp Ile Asn Lys Asn Lys Leu Ile Ile Gly Asn Gln Thr Ile Asp Phe
            1380                1385                1390

Ser Gly Asp Ile Asp Asn Lys Asp Arg Tyr Ile Phe Leu Thr Cys Glu
        1395                1400                1405

Leu Asp Asp Lys Ile Ser Leu Ile Ile Glu Ile Asn Leu Val Ala Lys
    1410                1415                1420

Ser Tyr Ser Leu Leu Leu Ser Gly Asp Lys Asn Tyr Leu Ile Ser Asn
1425                1430                1435                1440

Leu Ser Asn Thr Ile Glu Lys Ile Asn Thr Leu Gly Leu Asp Ser Lys
                1445                1450                1455

Asn Ile Ala Tyr Asn Tyr Thr Asp Glu Ser Asn Asn Lys Tyr Phe Gly
            1460                1465                1470

Ala Ile Ser Lys Thr Ser Gln Lys Ser Ile Ile His Tyr Lys Lys Asp
        1475                1480                1485

Ser Lys Asn Ile Leu Glu Phe Tyr Asn Asp Ser Thr Leu Glu Phe Asn
    1490                1495                1500

Ser Lys Asp Phe Ile Ala Glu Asp Ile Asn Val Phe Met Lys Asp Asp
1505                1510                1515                1520

Ile Asn Thr Ile Thr Gly Lys Tyr Tyr Val Asp Asn Asn Thr Asp Lys
                1525                1530                1535

Ser Ile Asp Phe Ser Ile Ser Leu Val Ser Lys Asn Gln Val Lys Val
            1540                1545                1550

Asn Gly Leu Tyr Leu Asn Glu Ser Val Tyr Ser Ser Tyr Leu Asp Phe
        1555                1560                1565
```

```
Val Lys Asn Ser Asp Gly His His Asn Thr Ser Asn Phe Met Asn Leu
    1570                1575                1580

Phe Leu Asp Asn Ile Ser Phe Trp Lys Leu Phe Gly Phe Glu Asn Ile
1585                1590                1595                1600

Asn Phe Val Ile Asp Lys Tyr Phe Thr Leu Val Gly Lys Thr Asn Leu
                1605                1610                1615

Gly Tyr Val Glu Phe Ile Cys Asp Asn Asn Lys Asn Ile Asp Ile Tyr
            1620                1625                1630

Phe Gly Glu Trp Lys Thr Ser Ser Ser Lys Ser Thr Ile Phe Ser Gly
        1635                1640                1645

Asn Gly Arg Asn Val Val Val Glu Pro Ile Tyr Asn Pro Asp Thr Gly
    1650                1655                1660

Glu Asp Ile Ser Thr Ser Leu Asp Phe Ser Tyr Glu Pro Leu Tyr Gly
1665                1670                1675                1680

Ile Asp Arg Tyr Ile Asn Lys Val Leu Ile Ala Pro Asp Leu Tyr Thr
                1685                1690                1695

Ser Leu Ile Asn Ile Asn Thr Asn Tyr Tyr Ser Asn Glu Tyr Tyr Pro
            1700                1705                1710

Glu Ile Ile Val Leu Asn Pro Asn Thr Phe His Lys Lys Val Asn Ile
        1715                1720                1725

Asn Leu Asp Ser Ser Ser Phe Glu Tyr Lys Trp Ser Thr Glu Gly Ser
    1730                1735                1740

Asp Phe Ile Leu Val Arg Tyr Leu Glu Glu Ser Asn Lys Lys Ile Leu
1745                1750                1755                1760

Gln Lys Ile Arg Ile Lys Gly Ile Leu Ser Asn Thr Gln Ser Phe Asn
                1765                1770                1775

Lys Met Ser Ile Asp Phe Lys Asp Ile Lys Lys Leu Ser Leu Gly Tyr
            1780                1785                1790

Ile Met Ser Asn Phe Lys Ser Phe Asn Ser Glu Asn Glu Leu Asp Arg
        1795                1800                1805

Asp His Leu Gly Phe Lys Ile Ile Asp Asn Lys Thr Tyr Tyr Tyr Asp
    1810                1815                1820

Glu Asp Ser Lys Leu Val Lys Gly Leu Ile Asn Ile Asn Asn Ser Leu
1825                1830                1835                1840

Phe Tyr Phe Asp Pro Ile Glu Phe Asn Leu Val Thr Gly Trp Gln Thr
                1845                1850                1855

Ile Asn Gly Lys Lys Tyr Tyr Phe Asp Ile Asn Thr Gly Ala Ala Leu
            1860                1865                1870

Thr Ser Tyr Lys Ile Ile Asn Gly Lys His Phe Tyr Phe Asn Asn Asp
        1875                1880                1885

Gly Val Met Gln Leu Gly Val Phe Lys Gly Pro Asp Gly Phe Glu Tyr
    1890                1895                1900

Phe Ala Pro Ala Asn Thr Gln Asn Asn Asn Ile Glu Gly Gln Ala Ile
1905                1910                1915                1920

Val Tyr Gln Ser Lys Phe Leu Thr Leu Asn Gly Lys Lys Tyr Tyr Phe
                1925                1930                1935

Asp Asn Asn Ser Lys Ala Val Thr Gly Trp Arg Ile Ile Asn Asn Glu
            1940                1945                1950

Lys Tyr Tyr Phe Asn Pro Asn Asn Ala Ile Ala Ala Val Gly Leu Gln
        1955                1960                1965

Val Ile Asp Asn Asn Lys Tyr Tyr Phe Asn Pro Asp Thr Ala Ile Ile
    1970                1975                1980
```

-continued

```
Ser Lys Gly Trp Gln Thr Val Asn Gly Ser Arg Tyr Tyr Phe Asp Thr
1985                1990                1995                2000

Asp Thr Ala Ile Ala Phe Asn Gly Tyr Lys Thr Ile Asp Gly Lys His
                2005                2010                2015

Phe Tyr Phe Asp Ser Asp Cys Val Val Lys Ile Gly Val Phe Ser Thr
            2020                2025                2030

Ser Asn Gly Phe Glu Tyr Phe Ala Pro Ala Asn Thr Tyr Asn Asn Asn
        2035                2040                2045

Ile Glu Gly Gln Ala Ile Val Tyr Gln Ser Lys Phe Leu Thr Leu Asn
    2050                2055                2060

Gly Lys Lys Tyr Tyr Phe Asp Asn Asn Ser Lys Ala Val Thr Gly Leu
2065                2070                2075                2080

Gln Thr Ile Asp Ser Lys Lys Tyr Tyr Phe Asn Thr Asn Thr Ala Glu
                2085                2090                2095

Ala Ala Thr Gly Trp Gln Thr Ile Asp Gly Lys Lys Tyr Tyr Phe Asn
            2100                2105                2110

Thr Asn Thr Ala Glu Ala Ala Thr Gly Trp Gln Thr Ile Asp Gly Lys
        2115                2120                2125

Lys Tyr Tyr Phe Asn Thr Asn Thr Ala Ile Ala Ser Thr Gly Tyr Thr
    2130                2135                2140

Ile Ile Asn Gly Lys His Phe Tyr Phe Asn Thr Asp Gly Ile Met Gln
2145                2150                2155                2160

Ile Gly Val Phe Lys Gly Pro Asn Gly Phe Glu Tyr Phe Ala Pro Ala
                2165                2170                2175

Asn Thr Asp Ala Asn Asn Ile Glu Gly Gln Ala Ile Leu Tyr Gln Asn
            2180                2185                2190

Glu Phe Leu Thr Leu Asn Gly Lys Lys Tyr Tyr Phe Gly Ser Asp Ser
        2195                2200                2205

Lys Ala Val Thr Gly Trp Arg Ile Ile Asn Asn Lys Lys Tyr Tyr Phe
    2210                2215                2220

Asn Pro Asn Asn Ala Ile Ala Ala Ile His Leu Cys Thr Ile Asn Asn
2225                2230                2235                2240

Asp Lys Tyr Tyr Phe Ser Tyr Asp Gly Ile Leu Gln Asn Gly Tyr Ile
                2245                2250                2255

Thr Ile Glu Arg Asn Asn Phe Tyr Phe Asp Ala Asn Asn Glu Ser Lys
            2260                2265                2270

Met Val Thr Gly Val Phe Lys Gly Pro Asn Gly Phe Glu Tyr Phe Ala
        2275                2280                2285

Pro Ala Asn Thr His Asn Asn Asn Ile Glu Gly Gln Ala Ile Val Tyr
    2290                2295                2300

Gln Asn Lys Phe Leu Thr Leu Asn Gly Lys Lys Tyr Tyr Phe Asp Asn
2305                2310                2315                2320

Asp Ser Lys Ala Val Thr Gly Trp Gln Thr Ile Asp Gly Lys Lys Tyr
                2325                2330                2335

Tyr Phe Asn Leu Asn Thr Ala Glu Ala Ala Thr Gly Trp Gln Thr Ile
            2340                2345                2350

Asp Gly Lys Lys Tyr Tyr Phe Asn Leu Asn Thr Ala Glu Ala Ala Thr
        2355                2360                2365

Gly Trp Gln Thr Ile Asp Gly Lys Lys Tyr Tyr Phe Asn Thr Asn Thr
    2370                2375                2380

Phe Ile Ala Ser Thr Gly Tyr Thr Ser Ile Asn Gly Lys His Phe Tyr
2385                2390                2395                2400

Phe Asn Thr Asp Gly Ile Met Gln Ile Gly Val Phe Lys Gly Pro Asn
```

-continued

```
                2405                2410                2415

Gly Phe Glu Tyr Phe Ala Pro Ala Asn Thr Asp Ala Asn Asn Ile Glu
            2420                2425                2430

Gly Gln Ala Ile Leu Tyr Gln Asn Lys Phe Leu Thr Leu Asn Gly Lys
        2435                2440                2445

Lys Tyr Tyr Phe Gly Ser Asp Ser Lys Ala Val Thr Gly Leu Arg Thr
    2450                2455                2460

Ile Asp Gly Lys Lys Tyr Tyr Phe Asn Thr Asn Thr Ala Val Ala Val
2465                2470                2475                2480

Thr Gly Trp Gln Thr Ile Asn Gly Lys Lys Tyr Tyr Phe Asn Thr Asn
                2485                2490                2495

Thr Ser Ile Ala Ser Thr Gly Tyr Thr Ile Ile Ser Gly Lys His Phe
            2500                2505                2510

Tyr Phe Asn Thr Asp Gly Ile Met Gln Ile Gly Val Phe Lys Gly Pro
        2515                2520                2525

Asp Gly Phe Glu Tyr Phe Ala Pro Ala Asn Thr Asp Ala Asn Asn Ile
    2530                2535                2540

Glu Gly Gln Ala Ile Arg Tyr Gln Asn Arg Phe Leu Tyr Leu His Asp
2545                2550                2555                2560

Asn Ile Tyr Tyr Phe Gly Asn Asn Ser Lys Ala Ala Thr Gly Trp Val
                2565                2570                2575

Thr Ile Asp Gly Asn Arg Tyr Tyr Phe Glu Pro Asn Thr Ala Met Gly
            2580                2585                2590

Ala Asn Gly Tyr Lys Thr Ile Asp Asn Lys Asn Phe Tyr Phe Arg Asn
        2595                2600                2605

Gly Leu Pro Gln Ile Gly Val Phe Lys Gly Ser Asn Gly Phe Glu Tyr
    2610                2615                2620

Phe Ala Pro Ala Asn Thr Asp Ala Asn Asn Ile Glu Gly Gln Ala Ile
2625                2630                2635                2640

Arg Tyr Gln Asn Arg Phe Leu His Leu Leu Gly Lys Ile Tyr Tyr Phe
                2645                2650                2655

Gly Asn Asn Ser Lys Ala Val Thr Gly Trp Gln Thr Ile Asn Gly Lys
            2660                2665                2670

Val Tyr Tyr Phe Met Pro Asp Thr Ala Met Ala Ala Ala Gly Gly Leu
        2675                2680                2685

Phe Glu Ile Asp Gly Val Ile Tyr Phe Phe Gly Val Asp Gly Val Lys
    2690                2695                2700

Ala Pro Gly Ile Tyr Gly
2705                2710


<210> SEQ ID NO 32
<211> LENGTH: 2366
<212> TYPE: PRT
<213> ORGANISM: Clostridium difficile

<400> SEQUENCE: 32

Met Ser Leu Val Asn Arg Lys Gln Leu Glu Lys Met Ala Asn Val Arg
 1               5                  10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60
```

-continued

```
Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
```

-continued

```
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
        755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
        835                 840                 845

Ser Asp Ser Ile Asn Tyr Ile Lys Asp Glu Phe Lys Leu Ile Glu Ser
    850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910
```

```
Thr Glu Lys Thr Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
    930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr Ile Thr Asp Ala Ala Lys Val Val
        995                 1000                1005

Glu Leu Val Ser Thr Ala Leu Asp Glu Thr Ile Asp Leu Leu Pro Thr
    1010                1015                1020

Leu Ser Glu Gly Leu Pro Ile Ile Ala Thr Ile Ile Asp Gly Val Ser
1025                1030                1035                1040

Leu Gly Ala Ala Ile Lys Glu Leu Ser Glu Thr Ser Asp Pro Leu Leu
                1045                1050                1055

Arg Gln Glu Ile Glu Ala Lys Ile Gly Ile Met Ala Val Asn Leu Thr
            1060                1065                1070

Thr Ala Thr Thr Ala Ile Ile Thr Ser Ser Leu Gly Ile Ala Ser Gly
        1075                1080                1085

Phe Ser Ile Leu Leu Val Pro Leu Ala Gly Ile Ser Ala Gly Ile Pro
    1090                1095                1100

Ser Leu Val Asn Asn Glu Leu Val Leu Arg Asp Lys Ala Thr Lys Val
1105                1110                1115                1120

Val Asp Tyr Phe Lys His Val Ser Leu Val Glu Thr Glu Gly Val Phe
                1125                1130                1135

Thr Leu Leu Asp Asp Lys Ile Met Met Pro Gln Asp Asp Leu Val Ile
            1140                1145                1150

Ser Glu Ile Asp Phe Asn Asn Asn Ser Ile Val Leu Gly Lys Cys Glu
        1155                1160                1165

Ile Trp Arg Met Glu Gly Gly Ser Gly His Thr Val Thr Asp Asp Ile
    1170                1175                1180

Asp His Phe Phe Ser Ala Pro Ser Ile Thr Tyr Arg Glu Pro His Leu
1185                1190                1195                1200

Ser Ile Tyr Asp Val Leu Glu Val Gln Lys Glu Glu Leu Asp Leu Ser
                1205                1210                1215

Lys Asp Leu Met Val Leu Pro Asn Ala Pro Asn Arg Val Phe Ala Trp
            1220                1225                1230

Glu Thr Gly Trp Thr Pro Gly Leu Arg Ser Leu Glu Asn Asp Gly Thr
        1235                1240                1245

Lys Leu Leu Asp Arg Ile Arg Asp Asn Tyr Glu Gly Glu Phe Tyr Trp
    1250                1255                1260

Arg Tyr Phe Ala Phe Ile Ala Asp Ala Leu Ile Thr Thr Leu Lys Pro
1265                1270                1275                1280

Arg Tyr Glu Asp Thr Asn Ile Arg Ile Asn Leu Asp Ser Asn Thr Arg
                1285                1290                1295

Ser Phe Ile Val Pro Ile Ile Thr Thr Glu Tyr Ile Arg Glu Lys Leu
            1300                1305                1310

Ser Tyr Ser Phe Tyr Gly Ser Gly Gly Thr Tyr Ala Leu Ser Leu Ser
        1315                1320                1325
```

-continued

```
Gln Tyr Asn Met Gly Ile Asn Ile Glu Leu Ser Glu Ser Asp Val Trp
    1330                1335                1340

Ile Ile Asp Val Asp Asn Val Val Arg Asp Val Thr Ile Glu Ser Asp
1345                1350                1355                1360

Lys Ile Lys Lys Gly Asp Leu Ile Glu Gly Ile Leu Ser Thr Leu Ser
                1365                1370                1375

Ile Glu Glu Asn Lys Ile Ile Leu Asn Ser His Glu Ile Asn Phe Ser
            1380                1385                1390

Gly Glu Val Asn Gly Ser Asn Gly Phe Val Ser Leu Thr Phe Ser Ile
        1395                1400                1405

Leu Glu Gly Ile Asn Ala Ile Ile Glu Val Asp Leu Leu Ser Lys Ser
    1410                1415                1420

Tyr Lys Leu Leu Ile Ser Gly Glu Leu Lys Ile Leu Met Leu Asn Ser
1425                1430                1435                1440

Asn His Ile Gln Gln Lys Ile Asp Tyr Ile Gly Phe Asn Ser Glu Leu
                1445                1450                1455

Gln Lys Asn Ile Pro Tyr Ser Phe Val Asp Ser Glu Gly Lys Glu Asn
            1460                1465                1470

Gly Phe Ile Asn Gly Ser Thr Lys Glu Gly Leu Phe Val Ser Glu Leu
        1475                1480                1485

Pro Asp Val Val Leu Ile Ser Lys Val Tyr Met Asp Asp Ser Lys Pro
    1490                1495                1500

Ser Phe Gly Tyr Tyr Ser Asn Asn Leu Lys Asp Val Lys Val Ile Thr
1505                1510                1515                1520

Lys Asp Asn Val Asn Ile Leu Thr Gly Tyr Tyr Leu Lys Asp Asp Ile
                1525                1530                1535

Lys Ile Ser Leu Ser Leu Thr Leu Gln Asp Glu Lys Thr Ile Lys Leu
            1540                1545                1550

Asn Ser Val His Leu Asp Glu Ser Gly Val Ala Glu Ile Leu Lys Phe
        1555                1560                1565

Met Asn Arg Lys Gly Asn Thr Asn Thr Ser Asp Ser Leu Met Ser Phe
    1570                1575                1580

Leu Glu Ser Met Asn Ile Lys Ser Ile Phe Val Asn Phe Leu Gln Ser
1585                1590                1595                1600

Asn Ile Lys Phe Ile Leu Asp Ala Asn Phe Ile Ile Ser Gly Thr Thr
                1605                1610                1615

Ser Ile Gly Gln Phe Glu Phe Ile Cys Asp Glu Asn Asp Asn Ile Gln
            1620                1625                1630

Pro Tyr Phe Ile Lys Phe Asn Thr Leu Glu Thr Asn Tyr Thr Leu Tyr
        1635                1640                1645

Val Gly Asn Arg Gln Asn Met Ile Val Glu Pro Asn Tyr Asp Leu Asp
    1650                1655                1660

Asp Ser Gly Asp Ile Ser Ser Thr Val Ile Asn Phe Ser Gln Lys Tyr
1665                1670                1675                1680

Leu Tyr Gly Ile Asp Ser Cys Val Asn Lys Val Val Ile Ser Pro Asn
                1685                1690                1695

Ile Tyr Thr Asp Glu Ile Asn Ile Thr Pro Val Tyr Glu Thr Asn Asn
            1700                1705                1710

Thr Tyr Pro Glu Val Ile Val Leu Asp Ala Asn Tyr Ile Asn Glu Lys
        1715                1720                1725

Ile Asn Val Asn Ile Asn Asp Leu Ser Ile Arg Tyr Val Trp Ser Asn
    1730                1735                1740

Asp Gly Asn Asp Phe Ile Leu Met Ser Thr Ser Glu Glu Asn Lys Val
```

```
1745                1750                1755                1760

Ser Gln Val Lys Ile Arg Phe Val Asn Val Phe Lys Asp Lys Thr Leu
                1765                1770                1775

Ala Asn Lys Leu Ser Phe Asn Phe Ser Asp Lys Gln Asp Val Pro Val
            1780                1785                1790

Ser Glu Ile Ile Leu Ser Phe Thr Pro Ser Tyr Tyr Glu Asp Gly Leu
        1795                1800                1805

Ile Gly Tyr Asp Leu Gly Leu Val Ser Leu Tyr Asn Glu Lys Phe Tyr
    1810                1815                1820

Ile Asn Asn Phe Gly Met Met Val Ser Gly Leu Ile Tyr Ile Asn Asp
1825                1830                1835                1840

Ser Leu Tyr Tyr Phe Lys Pro Pro Val Asn Asn Leu Ile Thr Gly Phe
                1845                1850                1855

Val Thr Val Gly Asp Asp Lys Tyr Tyr Phe Asn Pro Ile Asn Gly Gly
            1860                1865                1870

Ala Ala Ser Ile Gly Glu Thr Ile Ile Asp Asp Lys Asn Tyr Tyr Phe
        1875                1880                1885

Asn Gln Ser Gly Val Leu Gln Thr Gly Val Phe Ser Thr Glu Asp Gly
    1890                1895                1900

Phe Lys Tyr Phe Ala Pro Ala Asn Thr Leu Asp Glu Asn Leu Glu Gly
1905                1910                1915                1920

Glu Ala Ile Asp Phe Thr Gly Lys Leu Ile Ile Asp Glu Asn Ile Tyr
                1925                1930                1935

Tyr Phe Asp Asp Asn Tyr Arg Gly Ala Val Glu Trp Lys Glu Leu Asp
            1940                1945                1950

Gly Glu Met His Tyr Phe Ser Pro Glu Thr Gly Lys Ala Phe Lys Gly
        1955                1960                1965

Leu Asn Gln Ile Gly Asp Tyr Lys Tyr Tyr Phe Asn Ser Asp Gly Val
    1970                1975                1980

Met Gln Lys Gly Phe Val Ser Ile Asn Asp Asn Lys His Tyr Phe Asp
1985                1990                1995                2000

Asp Ser Gly Val Met Lys Val Gly Tyr Thr Glu Ile Asp Gly Lys His
                2005                2010                2015

Phe Tyr Phe Ala Glu Asn Gly Glu Met Gln Ile Gly Val Phe Asn Thr
            2020                2025                2030

Glu Asp Gly Phe Lys Tyr Phe Ala His His Asn Glu Asp Leu Gly Asn
        2035                2040                2045

Glu Glu Gly Glu Glu Ile Ser Tyr Ser Gly Ile Leu Asn Phe Asn Asn
    2050                2055                2060

Lys Ile Tyr Tyr Phe Asp Asp Ser Phe Thr Ala Val Val Gly Trp Lys
2065                2070                2075                2080

Asp Leu Glu Asp Gly Ser Lys Tyr Tyr Phe Asp Glu Asp Thr Ala Glu
                2085                2090                2095

Ala Tyr Ile Gly Leu Ser Leu Ile Asn Asp Gly Gln Tyr Tyr Phe Asn
            2100                2105                2110

Asp Asp Gly Ile Met Gln Val Gly Phe Val Thr Ile Asn Asp Lys Val
        2115                2120                2125

Phe Tyr Phe Ser Asp Ser Gly Ile Ile Glu Ser Gly Val Gln Asn Ile
    2130                2135                2140

Asp Asp Asn Tyr Phe Tyr Ile Asp Asp Asn Gly Ile Val Gln Ile Gly
2145                2150                2155                2160

Val Phe Asp Thr Ser Asp Gly Tyr Lys Tyr Phe Ala Pro Ala Asn Thr
                2165                2170                2175
```

```
Val Asn Asp Asn Ile Tyr Gly Gln Ala Val Glu Tyr Ser Gly Leu Val
            2180                2185                2190

Arg Val Gly Glu Asp Val Tyr Tyr Phe Gly Glu Thr Tyr Thr Ile Glu
        2195                2200                2205

Thr Gly Trp Ile Tyr Asp Met Glu Asn Glu Ser Asp Lys Tyr Tyr Phe
    2210                2215                2220

Asn Pro Glu Thr Lys Lys Ala Cys Lys Gly Ile Asn Leu Ile Asp Asp
2225                2230                2235                2240

Ile Lys Tyr Tyr Phe Asp Glu Lys Gly Ile Met Arg Thr Gly Leu Ile
                2245                2250                2255

Ser Phe Glu Asn Asn Asn Tyr Tyr Phe Asn Glu Asn Gly Glu Met Gln
            2260                2265                2270

Phe Gly Tyr Ile Asn Ile Glu Asp Lys Met Phe Tyr Phe Gly Glu Asp
        2275                2280                2285

Gly Val Met Gln Ile Gly Val Phe Asn Thr Pro Asp Gly Phe Lys Tyr
    2290                2295                2300

Phe Ala His Gln Asn Thr Leu Asp Glu Asn Phe Glu Gly Glu Ser Ile
2305                2310                2315                2320

Asn Tyr Thr Gly Trp Leu Asp Leu Asp Glu Lys Arg Tyr Tyr Phe Thr
                2325                2330                2335

Asp Glu Tyr Ile Ala Ala Thr Gly Ser Val Ile Ile Asp Gly Glu Glu
            2340                2345                2350

Tyr Tyr Phe Asp Pro Asp Thr Ala Gln Leu Val Ile Ser Glu
        2355                2360                2365


<210> SEQ ID NO 33
<211> LENGTH: 667
<212> TYPE: PRT
<213> ORGANISM: Artificial Sequence
<220> FEATURE:
<223> OTHER INFORMATION: amino acid sequence of CDTb" C39 when expressed
      in fusion with GST.

<400> SEQUENCE: 33

Leu Met Ser Asp Trp Glu Asp Glu Asp Leu Asp Thr Asp Asn Asp Asn
 1               5                  10                  15

Ile Pro Asp Ser Tyr Glu Arg Asn Gly Tyr Thr Ile Lys Asp Leu Ile
            20                  25                  30

Ala Val Lys Trp Glu Asp Ser Phe Ala Glu Gln Gly Tyr Lys Lys Tyr
        35                  40                  45

Val Ser Asn Tyr Leu Glu Ser Asn Thr Ala Gly Asp Pro Tyr Thr Asp
    50                  55                  60

Tyr Glu Lys Ala Ser Gly Ser Phe Asp Lys Ala Ile Lys Thr Glu Ala
65                  70                  75                  80

Arg Asp Pro Leu Val Ala Ala Tyr Pro Ile Val Gly Val Gly Met Glu
                85                  90                  95

Lys Leu Ile Ile Ser Thr Asn Glu His Ala Ser Thr Asp Gln Gly Lys
            100                 105                 110

Thr Val Ser Arg Ala Thr Thr Asn Ser Lys Thr Glu Ser Asn Thr Ala
        115                 120                 125

Gly Val Ser Val Asn Val Gly Tyr Gln Asn Gly Phe Thr Ala Asn Val
    130                 135                 140

Thr Thr Asn Tyr Ser His Thr Thr Asp Asn Ser Thr Ala Val Gln Asp
145                 150                 155                 160

Ser Asn Gly Glu Ser Trp Asn Thr Gly Leu Ser Ile Asn Lys Gly Glu
```

-continued

```
                165                 170                 175

Ser Ala Tyr Ile Asn Ala Asn Val Arg Tyr Tyr Asn Thr Gly Thr Ala
            180                 185                 190

Pro Met Tyr Lys Val Thr Pro Thr Thr Asn Leu Val Leu Asp Gly Asp
        195                 200                 205

Thr Leu Ser Thr Ile Lys Ala Gln Glu Asn Gln Ile Gly Asn Asn Leu
    210                 215                 220

Ser Pro Gly Asp Thr Tyr Pro Lys Lys Gly Leu Ser Pro Leu Ala Leu
225                 230                 235                 240

Asn Thr Met Asp Gln Phe Ser Ser Arg Leu Ile Pro Ile Asn Tyr Asp
                245                 250                 255

Gln Leu Lys Lys Leu Asp Ala Gly Lys Gln Ile Lys Leu Glu Thr Thr
            260                 265                 270

Gln Val Ser Gly Asn Phe Gly Thr Lys Asn Ser Ser Gly Gln Ile Val
        275                 280                 285

Thr Glu Gly Asn Ser Trp Ser Asp Tyr Ile Ser Gln Ile Asp Ser Ile
    290                 295                 300

Ser Ala Ser Ile Ile Leu Asp Thr Glu Asn Glu Ser Tyr Glu Arg Arg
305                 310                 315                 320

Val Thr Ala Lys Asn Leu Gln Asp Pro Glu Asp Lys Thr Pro Glu Leu
                325                 330                 335

Thr Ile Gly Glu Ala Ile Glu Lys Ala Phe Gly Ala Thr Lys Lys Asp
            340                 345                 350

Gly Leu Leu Tyr Phe Asn Asp Ile Pro Ile Asp Glu Ser Cys Val Glu
        355                 360                 365

Leu Ile Phe Asp Asp Asn Thr Ala Asn Lys Ile Lys Asp Ser Leu Lys
    370                 375                 380

Thr Leu Ser Asp Lys Lys Ile Tyr Asn Val Lys Leu Glu Arg Gly Met
385                 390                 395                 400

Asn Ile Leu Ile Lys Thr Pro Thr Tyr Phe Thr Asn Phe Asp Asp Tyr
                405                 410                 415

Asn Asn Tyr Pro Ser Thr Trp Ser Asn Val Asn Thr Thr Asn Gln Asp
            420                 425                 430

Gly Leu Gln Gly Ser Ala Asn Lys Leu Asn Gly Glu Thr Lys Ile Lys
        435                 440                 445

Ile Pro Met Ser Glu Leu Lys Pro Tyr Lys Arg Tyr Val Phe Ser Gly
    450                 455                 460

Tyr Ser Lys Asp Pro Leu Thr Ser Asn Ser Ile Ile Val Lys Ile Lys
465                 470                 475                 480

Ala Lys Glu Glu Lys Thr Asp Tyr Leu Val Pro Glu Gln Gly Tyr Thr
                485                 490                 495

Lys Phe Ser Tyr Glu Phe Glu Thr Thr Glu Lys Asp Ser Ser Asn Ile
            500                 505                 510

Glu Ile Thr Leu Ile Gly Ser Gly Thr Thr Tyr Leu Asp Asn Leu Ser
        515                 520                 525

Ile Thr Glu Leu Asn Ser Thr Pro Glu Ile Leu Asp Glu Pro Glu Val
    530                 535                 540

Lys Ile Pro Thr Asp Gln Glu Ile Met Asp Ala His Lys Ile Tyr Phe
545                 550                 555                 560

Ala Asp Leu Asn Phe Asn Pro Ser Thr Gly Asn Thr Tyr Ile Asn Gly
                565                 570                 575

Met Tyr Phe Ala Pro Thr Gln Thr Asn Lys Glu Ala Leu Asp Tyr Ile
            580                 585                 590
```

```
Gln Lys Tyr Arg Val Glu Ala Thr Leu Gln Tyr Ser Gly Phe Lys Asp
        595                 600                 605

Ile Gly Thr Lys Asp Lys Glu Met Arg Asn Tyr Leu Gly Asp Pro Asn
    610                 615                 620

Gln Pro Lys Thr Asn Tyr Val Asn Leu Arg Ser Tyr Phe Thr Gly Gly
625                 630                 635                 640

Glu Asn Ile Met Thr Tyr Lys Lys Leu Arg Ile Tyr Ala Ile Thr Pro
                645                 650                 655

Asp Asp Arg Glu Leu Leu Val Leu Ser Val Asp
            660                 665


<210> SEQ ID NO 34
<211> LENGTH: 266
<212> TYPE: PRT
<213> ORGANISM: Artificial Sequence
<220> FEATURE:
<223> OTHER INFORMATION: amino acid sequence of CdtB receptor binding
      domain with linker in N-term of sequence, from aa
      620-876 (C52)

<400> SEQUENCE: 34

Met Thr Asn Phe Asp Asp Tyr Asn Asn Tyr Pro Ser Thr Trp Ser Asn
 1               5                  10                  15

Val Asn Thr Thr Asn Gln Asp Gly Leu Gln Gly Ser Ala Asn Lys Leu
            20                  25                  30

Asn Gly Glu Thr Lys Ile Lys Ile Pro Met Ser Glu Leu Lys Pro Tyr
        35                  40                  45

Lys Arg Tyr Val Phe Ser Gly Tyr Ser Lys Asp Pro Leu Thr Ser Asn
    50                  55                  60

Ser Ile Ile Val Lys Ile Lys Ala Lys Glu Glu Lys Thr Asp Tyr Leu
65                  70                  75                  80

Val Pro Glu Gln Gly Tyr Thr Lys Phe Ser Tyr Glu Phe Glu Thr Thr
                85                  90                  95

Glu Lys Asp Ser Ser Asn Ile Glu Ile Thr Leu Ile Gly Ser Gly Thr
            100                 105                 110

Thr Tyr Leu Asp Asn Leu Ser Ile Thr Glu Leu Asn Ser Thr Pro Glu
        115                 120                 125

Ile Leu Asp Glu Pro Glu Val Lys Ile Pro Thr Asp Gln Glu Ile Met
    130                 135                 140

Asp Ala His Lys Ile Tyr Phe Ala Asp Leu Asn Phe Asn Pro Ser Thr
145                 150                 155                 160

Gly Asn Thr Tyr Ile Asn Gly Met Tyr Phe Ala Pro Thr Gln Thr Asn
                165                 170                 175

Lys Glu Ala Leu Asp Tyr Ile Gln Lys Tyr Arg Val Glu Ala Thr Leu
            180                 185                 190

Gln Tyr Ser Gly Phe Lys Asp Ile Gly Thr Lys Asp Lys Glu Met Arg
        195                 200                 205

Asn Tyr Leu Gly Asp Pro Asn Gln Pro Lys Thr Asn Tyr Val Asn Leu
    210                 215                 220

Arg Ser Tyr Phe Thr Gly Gly Glu Asn Ile Met Thr Tyr Lys Lys Leu
225                 230                 235                 240

Arg Ile Tyr Ala Ile Thr Pro Asp Asp Arg Glu Leu Leu Val Leu Ser
                245                 250                 255

Val Asp Gly Gly His His His His His His
            260                 265
```

<210> SEQ ID NO 35
<211> LENGTH: 801
<212> TYPE: DNA
<213> ORGANISM: Artificial Sequence
<220> FEATURE:
<223> OTHER INFORMATION: Nucleotide sequence of C52

<400> SEQUENCE: 35

```
atgaccaatt ttgatgatta taacaattat ccgagcactt ggagcaatgt gaataccacc     60

aatcaggatg gtctgcaggg tagcgcaaat aaactgaatg gtgaaaccaa aatcaaaatt    120

ccgatgagcg aactgaaacc gtataaacgt tatgtgttta gcggctatag caaagatccg    180

ctgaccagca atagcattat tgtgaaaatc aaagccaaag aagaaaaaac cgattatctg    240

gttccggaac agggttatac caaatttagc tatgaatttg aaaccaccga aaaagatagc    300

agtaatattg aaattaccct gattggtagc ggcaccacct atctggataa tctgagtatt    360

accgaactga atagcacacc ggaaattctg gatgaaccgg aagtgaaaat tccgaccgat    420

caagaaatta tggatgccca taaaatctat tttgccgatc tgaactttaa tccgagcacc    480

ggcaatacct atattaacgg catgtatttt gcaccgaccc agaccaataa agaagccctg    540

gattatattc agaaatatcg tgttgaagcc accctgcagt atagcggttt taaagatatt    600

ggcaccaaag ataaagaaat gcgtaattat ctgggcgatc cgaatcagcc gaaaaccaat    660

tatgttaatc tgcgcagcta ttttaccggt ggcgaaaaca ttatgaccta caaaaaactg    720

cgcatttatg ccattacacc ggatgatcgt gaactgctgg ttctgagcgt tgatggcggt    780

caccaccatc atcatcatta a                                              801
```

<210> SEQ ID NO 36
<211> LENGTH: 250
<212> TYPE: PRT
<213> ORGANISM: Artificial Sequence
<220> FEATURE:
<223> OTHER INFORMATION: amino acid sequence of CdtB receptor binding
domain without linker in N-term of sequence, from
aa 636-876 (C55)

<400> SEQUENCE: 36

```
Met Asn Thr Thr Asn Gln Asp Gly Leu Gln Gly Ser Ala Asn Lys Leu
 1               5                  10                  15

Asn Gly Glu Thr Lys Ile Lys Ile Pro Met Ser Glu Leu Lys Pro Tyr
            20                  25                  30

Lys Arg Tyr Val Phe Ser Gly Tyr Ser Lys Asp Pro Leu Thr Ser Asn
        35                  40                  45

Ser Ile Ile Val Lys Ile Lys Ala Lys Glu Glu Lys Thr Asp Tyr Leu
    50                  55                  60

Val Pro Glu Gln Gly Tyr Thr Lys Phe Ser Tyr Glu Phe Glu Thr Thr
65                  70                  75                  80

Glu Lys Asp Ser Ser Asn Ile Glu Ile Thr Leu Ile Gly Ser Gly Thr
                85                  90                  95

Thr Tyr Leu Asp Asn Leu Ser Ile Thr Glu Leu Asn Ser Thr Pro Glu
            100                 105                 110

Ile Leu Asp Glu Pro Glu Val Lys Ile Pro Thr Asp Gln Glu Ile Met
        115                 120                 125

Asp Ala His Lys Ile Tyr Phe Ala Asp Leu Asn Phe Asn Pro Ser Thr
    130                 135                 140

Gly Asn Thr Tyr Ile Asn Gly Met Tyr Phe Ala Pro Thr Gln Thr Asn
145                 150                 155                 160
```

```
Lys Glu Ala Leu Asp Tyr Ile Gln Lys Tyr Arg Val Glu Ala Thr Leu
                165                 170                 175

Gln Tyr Ser Gly Phe Lys Asp Ile Gly Thr Lys Asp Lys Glu Met Arg
            180                 185                 190

Asn Tyr Leu Gly Asp Pro Asn Gln Pro Lys Thr Asn Tyr Val Asn Leu
        195                 200                 205

Arg Ser Tyr Phe Thr Gly Gly Glu Asn Ile Met Thr Tyr Lys Lys Leu
    210                 215                 220

Arg Ile Tyr Ala Ile Thr Pro Asp Asp Arg Glu Leu Leu Val Leu Ser
225                 230                 235                 240

Val Asp Gly Gly His His His His His His
                245                 250
```

<210> SEQ ID NO 37
<211> LENGTH: 753
<212> TYPE: DNA
<213> ORGANISM: Artificial Sequence
<220> FEATURE:
<223> OTHER INFORMATION: nucleotide sequence of C55

<400> SEQUENCE: 37

```
atgaatacca ccaatcagga tggtctgcag ggtagcgcaa ataaactgaa tggtgaaacc     60

aaaatcaaaa ttccgatgag cgaactgaaa ccgtataaac gttatgtgtt tagcggctat    120

agcaaagatc cgctgaccag caatagcatt attgtgaaaa tcaaagccaa agaagaaaaa    180

accgattatc tggttccgga acagggttat accaaattta gctatgaatt tgaaaccacc    240

gaaaaagata gcagtaatat tgaaattacc ctgattggta gcggcaccac ctatctggat    300

aatctgagta ttaccgaact gaatagcaca ccggaaattc tggatgaacc ggaagtgaaa    360

attccgaccg atcaagaaat tatggatgcc cataaaatct attttgccga tctgaacttt    420

aatccgagca ccggcaatac ctatattaac ggcatgtatt ttgcaccgac ccagaccaat    480

aaagaagccc tggattatat tcagaaatat cgtgttgaag ccaccctgca gtatagcggt    540

tttaaagata ttggcaccaa agataaagaa atgcgtaatt atctgggcga tccgaatcag    600

ccgaaaacca attatgttaa tctgcgcagc tattttaccg gtggcgaaaa cattatgacc    660

tacaaaaaac tgcgcattta tgccattaca ccggatgatc gtgaactgct ggttctgagc    720

gttgatggcg gtcaccacca tcatcatcat taa                                 753
```

<210> SEQ ID NO 38
<211> LENGTH: 170
<212> TYPE: PRT
<213> ORGANISM: Artificial Sequence
<220> FEATURE:
<223> OTHER INFORMATION: amino acid sequence of CDTb prodomain sequence
      (long, aa43-211) (C58)

<400> SEQUENCE: 38

```
Met Glu Ile Val Asn Glu Asp Ile Leu Pro Asn Asn Gly Leu Met Gly
 1               5                  10                  15

Tyr Tyr Phe Thr Asp Glu His Phe Lys Asp Leu Lys Leu Met Ala Pro
            20                  25                  30

Ile Lys Asp Gly Asn Leu Lys Phe Glu Glu Lys Lys Val Asp Lys Leu
        35                  40                  45

Leu Asp Lys Asp Lys Ser Asp Val Lys Ser Ile Arg Trp Thr Gly Arg
    50                  55                  60

Ile Ile Pro Ser Lys Asp Gly Glu Tyr Thr Leu Ser Thr Asp Arg Asp
```

```
65                  70                  75                  80

Asp Val Leu Met Gln Val Asn Thr Glu Ser Thr Ile Ser Asn Thr Leu
                85                  90                  95

Lys Val Asn Met Lys Lys Gly Lys Glu Tyr Lys Val Arg Ile Glu Leu
            100                 105                 110

Gln Asp Lys Asn Leu Gly Ser Ile Asp Asn Leu Ser Ser Pro Asn Leu
        115                 120                 125

Tyr Trp Glu Leu Asp Gly Met Lys Lys Ile Ile Pro Glu Glu Asn Leu
    130                 135                 140

Phe Leu Arg Asp Tyr Ser Asn Ile Glu Lys Asp Asp Pro Phe Ile Pro
145                 150                 155                 160

Asn Asn Asn Phe Phe Asp Pro Lys Leu Met
                165                 170


<210> SEQ ID NO 39
<211> LENGTH: 145
<212> TYPE: PRT
<213> ORGANISM: Artificial Sequence
<220> FEATURE:
<223> OTHER INFORMATION: amino acid sequence of CDTb prodomain sequence
      (short, aa43-186) (C59)

<400> SEQUENCE: 39

Met Glu Ile Val Asn Glu Asp Ile Leu Pro Asn Asn Gly Leu Met Gly
 1               5                  10                  15

Tyr Tyr Phe Thr Asp Glu His Phe Lys Asp Leu Lys Leu Met Ala Pro
            20                  25                  30

Ile Lys Asp Gly Asn Leu Lys Phe Glu Glu Lys Lys Val Asp Lys Leu
        35                  40                  45

Leu Asp Lys Asp Lys Ser Asp Val Lys Ser Ile Arg Trp Thr Gly Arg
    50                  55                  60

Ile Ile Pro Ser Lys Asp Gly Glu Tyr Thr Leu Ser Thr Asp Arg Asp
65                  70                  75                  80

Asp Val Leu Met Gln Val Asn Thr Glu Ser Thr Ile Ser Asn Thr Leu
                85                  90                  95

Lys Val Asn Met Lys Lys Gly Lys Glu Tyr Lys Val Arg Ile Glu Leu
            100                 105                 110

Gln Asp Lys Asn Leu Gly Ser Ile Asp Asn Leu Ser Ser Pro Asn Leu
        115                 120                 125

Tyr Trp Glu Leu Asp Gly Met Lys Lys Ile Ile Pro Glu Glu Asn Leu
    130                 135                 140

Phe
145


<210> SEQ ID NO 40
<211> LENGTH: 489
<212> TYPE: PRT
<213> ORGANISM: Artificial Sequence
<220> FEATURE:
<223> OTHER INFORMATION: amino acid sequence of Fusion CDTa N-term with
      linker (aa44-268) to CDTb receptor binding domain
      with linker in N term of sequence (aa621-876)
      (C60)

<400> SEQUENCE: 40

Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30
```

-continued

```
Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Ser Leu Asp Phe Lys Asp Asp
    210                 215                 220

Thr Asn Phe Asp Asp Tyr Asn Asn Tyr Pro Ser Thr Trp Ser Asn Val
225                 230                 235                 240

Asn Thr Thr Asn Gln Asp Gly Leu Gln Gly Ser Ala Asn Lys Leu Asn
                245                 250                 255

Gly Glu Thr Lys Ile Lys Ile Pro Met Ser Glu Leu Lys Pro Tyr Lys
            260                 265                 270

Arg Tyr Val Phe Ser Gly Tyr Ser Lys Asp Pro Leu Thr Ser Asn Ser
        275                 280                 285

Ile Ile Val Lys Ile Lys Ala Lys Glu Glu Lys Thr Asp Tyr Leu Val
    290                 295                 300

Pro Glu Gln Gly Tyr Thr Lys Phe Ser Tyr Glu Phe Glu Thr Thr Glu
305                 310                 315                 320

Lys Asp Ser Ser Asn Ile Glu Ile Thr Leu Ile Gly Ser Gly Thr Thr
                325                 330                 335

Tyr Leu Asp Asn Leu Ser Ile Thr Glu Leu Asn Ser Thr Pro Glu Ile
            340                 345                 350

Leu Asp Glu Pro Glu Val Lys Ile Pro Thr Asp Gln Glu Ile Met Asp
        355                 360                 365

Ala His Lys Ile Tyr Phe Ala Asp Leu Asn Phe Asn Pro Ser Thr Gly
    370                 375                 380

Asn Thr Tyr Ile Asn Gly Met Tyr Phe Ala Pro Thr Gln Thr Asn Lys
385                 390                 395                 400

Glu Ala Leu Asp Tyr Ile Gln Lys Tyr Arg Val Glu Ala Thr Leu Gln
                405                 410                 415

Tyr Ser Gly Phe Lys Asp Ile Gly Thr Lys Asp Lys Glu Met Arg Asn
            420                 425                 430

Tyr Leu Gly Asp Pro Asn Gln Pro Lys Thr Asn Tyr Val Asn Leu Arg
        435                 440                 445
```

```
Ser Tyr Phe Thr Gly Gly Glu Asn Ile Met Thr Tyr Lys Lys Leu Arg
    450                 455                 460

Ile Tyr Ala Ile Thr Pro Asp Asp Arg Glu Leu Leu Val Leu Ser Val
465                 470                 475                 480

Asp Gly Gly His His His His His His
                485


<210> SEQ ID NO 41
<211> LENGTH: 473
<212> TYPE: PRT
<213> ORGANISM: Artificial Sequence
<220> FEATURE:
<223> OTHER INFORMATION: amino acid sequence of Fusion CDTa N-term with
      linker (aa44-268) to CDTb receptor binding domain
      without linker in N term of sequence (aa636-876)
      (C61)

<400> SEQUENCE: 41

Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Ser Leu Asp Phe Lys Asp Asp
    210                 215                 220

Asn Thr Thr Asn Gln Asp Gly Leu Gln Gly Ser Ala Asn Lys Leu Asn
225                 230                 235                 240

Gly Glu Thr Lys Ile Lys Ile Pro Met Ser Glu Leu Lys Pro Tyr Lys
                245                 250                 255

Arg Tyr Val Phe Ser Gly Tyr Ser Lys Asp Pro Leu Thr Ser Asn Ser
            260                 265                 270

Ile Ile Val Lys Ile Lys Ala Lys Glu Glu Lys Thr Asp Tyr Leu Val
        275                 280                 285

Pro Glu Gln Gly Tyr Thr Lys Phe Ser Tyr Glu Phe Glu Thr Thr Glu
    290                 295                 300
```

-continued

Lys Asp Ser Ser Asn Ile Glu Ile Thr Leu Ile Gly Ser Gly Thr Thr
305 310 315 320

Tyr Leu Asp Asn Leu Ser Ile Thr Glu Leu Asn Ser Thr Pro Glu Ile
325 330 335

Leu Asp Glu Pro Glu Val Lys Ile Pro Thr Asp Gln Glu Ile Met Asp
340 345 350

Ala His Lys Ile Tyr Phe Ala Asp Leu Asn Phe Asn Pro Ser Thr Gly
355 360 365

Asn Thr Tyr Ile Asn Gly Met Tyr Phe Ala Pro Thr Gln Thr Asn Lys
370 375 380

Glu Ala Leu Asp Tyr Ile Gln Lys Tyr Arg Val Glu Ala Thr Leu Gln
385 390 395 400

Tyr Ser Gly Phe Lys Asp Ile Gly Thr Lys Asp Lys Glu Met Arg Asn
405 410 415

Tyr Leu Gly Asp Pro Asn Gln Pro Lys Thr Asn Tyr Val Asn Leu Arg
420 425 430

Ser Tyr Phe Thr Gly Gly Glu Asn Ile Met Thr Tyr Lys Lys Leu Arg
435 440 445

Ile Tyr Ala Ile Thr Pro Asp Asp Arg Glu Leu Leu Val Leu Ser Val
450 455 460

Asp Gly Gly His His His His His His
465 470

<210> SEQ ID NO 42
<211> LENGTH: 482
<212> TYPE: PRT
<213> ORGANISM: Artificial Sequence
<220> FEATURE:
<223> OTHER INFORMATION: amino acid sequence of Fusion CDTa N-term without linker (aa44-260) to CDTb receptor binding domain with linker in N term of sequence (aa621-876) (C62)

<400> SEQUENCE: 42

Met Val Cys Asn Thr Thr Tyr Lys Ala Pro Ile Glu Arg Pro Glu Asp
1 5 10 15

Phe Leu Lys Asp Lys Glu Lys Ala Lys Glu Trp Glu Arg Lys Glu Ala
20 25 30

Glu Arg Ile Glu Gln Lys Leu Glu Arg Ser Glu Lys Glu Ala Leu Glu
35 40 45

Ser Tyr Lys Lys Asp Ser Val Glu Ile Ser Lys Tyr Ser Gln Thr Arg
50 55 60

Asn Tyr Phe Tyr Asp Tyr Gln Ile Glu Ala Asn Ser Arg Glu Lys Glu
65 70 75 80

Tyr Lys Glu Leu Arg Asn Ala Ile Ser Lys Asn Lys Ile Asp Lys Pro
85 90 95

Met Tyr Val Tyr Tyr Phe Glu Ser Pro Glu Lys Phe Ala Phe Asn Lys
100 105 110

Val Ile Arg Thr Glu Asn Gln Asn Glu Ile Ser Leu Glu Lys Phe Asn
115 120 125

Glu Phe Lys Glu Thr Ile Gln Asn Lys Leu Phe Lys Gln Asp Gly Phe
130 135 140

Lys Asp Ile Ser Leu Tyr Glu Pro Gly Lys Gly Asp Glu Lys Pro Thr
145 150 155 160

Pro Leu Leu Met His Leu Lys Leu Pro Arg Asn Thr Gly Met Leu Pro
165 170 175

```
Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Thr Asn Phe Asp Asp Tyr Asn
    210                 215                 220

Asn Tyr Pro Ser Thr Trp Ser Asn Val Asn Thr Thr Asn Gln Asp Gly
225                 230                 235                 240

Leu Gln Gly Ser Ala Asn Lys Leu Asn Gly Glu Thr Lys Ile Lys Ile
                245                 250                 255

Pro Met Ser Glu Leu Lys Pro Tyr Lys Arg Tyr Val Phe Ser Gly Tyr
            260                 265                 270

Ser Lys Asp Pro Leu Thr Ser Asn Ser Ile Ile Val Lys Ile Lys Ala
        275                 280                 285

Lys Glu Glu Lys Thr Asp Tyr Leu Val Pro Glu Gln Gly Tyr Thr Lys
    290                 295                 300

Phe Ser Tyr Glu Phe Glu Thr Thr Glu Lys Asp Ser Ser Asn Ile Glu
305                 310                 315                 320

Ile Thr Leu Ile Gly Ser Gly Thr Thr Tyr Leu Asp Asn Leu Ser Ile
                325                 330                 335

Thr Glu Leu Asn Ser Thr Pro Glu Ile Leu Asp Glu Pro Glu Val Lys
            340                 345                 350

Ile Pro Thr Asp Gln Glu Ile Met Asp Ala His Lys Ile Tyr Phe Ala
        355                 360                 365

Asp Leu Asn Phe Asn Pro Ser Thr Gly Asn Thr Tyr Ile Asn Gly Met
    370                 375                 380

Tyr Phe Ala Pro Thr Gln Thr Asn Lys Glu Ala Leu Asp Tyr Ile Gln
385                 390                 395                 400

Lys Tyr Arg Val Glu Ala Thr Leu Gln Tyr Ser Gly Phe Lys Asp Ile
                405                 410                 415

Gly Thr Lys Asp Lys Glu Met Arg Asn Tyr Leu Gly Asp Pro Asn Gln
            420                 425                 430

Pro Lys Thr Asn Tyr Val Asn Leu Arg Ser Tyr Phe Thr Gly Gly Glu
        435                 440                 445

Asn Ile Met Thr Tyr Lys Lys Leu Arg Ile Tyr Ala Ile Thr Pro Asp
    450                 455                 460

Asp Arg Glu Leu Leu Val Leu Ser Val Asp Gly Gly His His His His
465                 470                 475                 480

His His
```

<210> SEQ ID NO 43
<211> LENGTH: 466
<212> TYPE: PRT
<213> ORGANISM: Artificial Sequence
<220> FEATURE:
<223> OTHER INFORMATION: amino acid sequence of Fusion CDTa N-term without linker (aa44-260) to CDTb receptor binding domain without linker in N term of sequence (aa636-876) (C63)

<400> SEQUENCE: 43

```
Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
```

```
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Asn Thr Thr Asn Gln Asp Gly
    210                 215                 220

Leu Gln Gly Ser Ala Asn Lys Leu Asn Gly Glu Thr Lys Ile Lys Ile
225                 230                 235                 240

Pro Met Ser Glu Leu Lys Pro Tyr Lys Arg Tyr Val Phe Ser Gly Tyr
                245                 250                 255

Ser Lys Asp Pro Leu Thr Ser Asn Ser Ile Ile Val Lys Ile Lys Ala
            260                 265                 270

Lys Glu Glu Lys Thr Asp Tyr Leu Val Pro Glu Gln Gly Tyr Thr Lys
        275                 280                 285

Phe Ser Tyr Glu Phe Glu Thr Thr Glu Lys Asp Ser Ser Asn Ile Glu
    290                 295                 300

Ile Thr Leu Ile Gly Ser Gly Thr Thr Tyr Leu Asp Asn Leu Ser Ile
305                 310                 315                 320

Thr Glu Leu Asn Ser Thr Pro Glu Ile Leu Asp Glu Pro Glu Val Lys
                325                 330                 335

Ile Pro Thr Asp Gln Glu Ile Met Asp Ala His Lys Ile Tyr Phe Ala
            340                 345                 350

Asp Leu Asn Phe Asn Pro Ser Thr Gly Asn Thr Tyr Ile Asn Gly Met
        355                 360                 365

Tyr Phe Ala Pro Thr Gln Thr Asn Lys Glu Ala Leu Asp Tyr Ile Gln
    370                 375                 380

Lys Tyr Arg Val Glu Ala Thr Leu Gln Tyr Ser Gly Phe Lys Asp Ile
385                 390                 395                 400

Gly Thr Lys Asp Lys Glu Met Arg Asn Tyr Leu Gly Asp Pro Asn Gln
                405                 410                 415

Pro Lys Thr Asn Tyr Val Asn Leu Arg Ser Tyr Phe Thr Gly Gly Glu
            420                 425                 430

Asn Ile Met Thr Tyr Lys Lys Leu Arg Ile Tyr Ala Ile Thr Pro Asp
        435                 440                 445

Asp Arg Glu Leu Leu Val Leu Ser Val Asp Gly Gly His His His His
    450                 455                 460
```

```
His His
465

<210> SEQ ID NO 44
<211> LENGTH: 1231
<212> TYPE: PRT
<213> ORGANISM: Artificial Sequence
<220> FEATURE:
<223> OTHER INFORMATION: amino acid sequence of Fusion F2- CDTb receptor
      binding domain with linker in N term of sequence
      (aa621-876) (C64)

<400> SEQUENCE: 44

Met Gly Trp Gln Thr Ile Asp Gly Lys Lys Tyr Tyr Phe Asn Thr Asn
1               5                   10                  15

Thr Ala Ile Ala Ser Thr Gly Tyr Thr Ile Ile Asn Gly Lys His Phe
            20                  25                  30

Tyr Phe Asn Thr Asp Gly Ile Met Gln Ile Gly Val Phe Lys Gly Pro
        35                  40                  45

Asn Gly Phe Glu Tyr Phe Ala Pro Ala Asn Thr Asp Ala Asn Asn Ile
    50                  55                  60

Glu Gly Gln Ala Ile Leu Tyr Gln Asn Glu Phe Leu Thr Leu Asn Gly
65                  70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
    130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
    210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
        275                 280                 285

Gln Ile Gly Val Phe Lys Gly Pro Asn Gly Phe Glu Tyr Phe Ala Pro
    290                 295                 300

Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335
```

-continued

```
Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
            420                 425                 430

Gln Asn Arg Phe Leu Tyr Leu His Asp Asn Ile Tyr Tyr Phe Gly Asn
        435                 440                 445

Asn Ser Lys Ala Ala Thr Gly Trp Val Thr Ile Asp Gly Asn Arg Tyr
    450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
            500                 505                 510

Ala Asn Asn Ile Glu Gly Gln Ala Ile Arg Tyr Gln Asn Arg Phe Leu
        515                 520                 525

His Leu Leu Gly Lys Ile Tyr Tyr Phe Gly Asn Asn Ser Lys Ala Val
    530                 535                 540

Thr Gly Trp Gln Thr Ile Asn Gly Lys Val Tyr Tyr Phe Met Pro Asp
545                 550                 555                 560

Thr Ala Met Ala Ala Ala Gly Gly Leu Asn Gln Ile Gly Asp Tyr Lys
                565                 570                 575

Tyr Tyr Phe Asn Ser Asp Gly Val Met Gln Lys Gly Phe Val Ser Ile
            580                 585                 590

Asn Asp Asn Lys His Tyr Phe Asp Asp Ser Gly Val Met Lys Val Gly
        595                 600                 605

Tyr Thr Glu Ile Asp Gly Lys His Phe Tyr Phe Ala Glu Asn Gly Glu
    610                 615                 620

Met Gln Ile Gly Val Phe Asn Thr Glu Asp Gly Phe Lys Tyr Phe Ala
625                 630                 635                 640

His His Asn Glu Asp Leu Gly Asn Glu Glu Gly Glu Glu Ile Ser Tyr
                645                 650                 655

Ser Gly Ile Leu Asn Phe Asn Asn Lys Ile Tyr Tyr Phe Asp Asp Ser
            660                 665                 670

Phe Thr Ala Val Val Gly Trp Lys Asp Leu Glu Asp Gly Ser Lys Tyr
        675                 680                 685

Tyr Phe Asp Glu Asp Thr Ala Glu Ala Tyr Ile Gly Leu Ser Leu Ile
    690                 695                 700

Asn Asp Gly Gln Tyr Tyr Phe Asn Asp Asp Gly Ile Met Gln Val Gly
705                 710                 715                 720

Phe Val Thr Ile Asn Asp Lys Val Phe Tyr Phe Ser Asp Ser Gly Ile
                725                 730                 735

Ile Glu Ser Gly Val Gln Asn Ile Asp Asp Asn Tyr Phe Tyr Ile Asp
            740                 745                 750

Asp Asn Gly Ile Val Gln Ile Gly Val Phe Asp Thr Ser Asp Gly Tyr
```

-continued

```
        755                 760                 765

Lys Tyr Phe Ala Pro Ala Asn Thr Val Asn Asp Asn Ile Tyr Gly Gln
    770                 775                 780

Ala Val Glu Tyr Ser Gly Leu Val Arg Val Gly Glu Asp Val Tyr Tyr
785                 790                 795                 800

Phe Gly Glu Thr Tyr Thr Ile Glu Thr Gly Trp Ile Tyr Asp Met Glu
                805                 810                 815

Asn Glu Ser Asp Lys Tyr Tyr Phe Asn Pro Glu Thr Lys Lys Ala Cys
            820                 825                 830

Lys Gly Ile Asn Leu Ile Asp Asp Ile Lys Tyr Tyr Phe Asp Glu Lys
        835                 840                 845

Gly Ile Met Arg Thr Gly Leu Ile Ser Phe Glu Asn Asn Asn Tyr Tyr
    850                 855                 860

Phe Asn Glu Asn Gly Glu Met Gln Phe Gly Tyr Ile Asn Ile Glu Asp
865                 870                 875                 880

Lys Met Phe Tyr Phe Gly Glu Asp Gly Val Met Gln Ile Gly Val Phe
                885                 890                 895

Asn Thr Pro Asp Gly Phe Lys Tyr Phe Ala His Gln Asn Thr Leu Asp
            900                 905                 910

Glu Asn Phe Glu Gly Glu Ser Ile Asn Tyr Thr Gly Trp Leu Asp Leu
        915                 920                 925

Asp Glu Lys Arg Tyr Tyr Phe Thr Asp Glu Tyr Ile Ala Ala Thr Gly
    930                 935                 940

Ser Val Ile Ile Asp Gly Glu Glu Tyr Tyr Phe Asp Pro Asp Thr Ala
945                 950                 955                 960

Gln Leu Val Ile Ser Glu Thr Asn Phe Asp Asp Tyr Asn Asn Tyr Pro
                965                 970                 975

Ser Thr Trp Ser Asn Val Asn Thr Thr Asn Gln Asp Gly Leu Gln Gly
            980                 985                 990

Ser Ala Asn Lys Leu Asn Gly Glu Thr Lys Ile Lys Ile Pro Met Ser
        995                 1000                1005

Glu Leu Lys Pro Tyr Lys Arg Tyr Val Phe Ser Gly Tyr Ser Lys Asp
    1010                1015                1020

Pro Leu Thr Ser Asn Ser Ile Ile Val Lys Ile Lys Ala Lys Glu Glu
1025                1030                1035                1040

Lys Thr Asp Tyr Leu Val Pro Glu Gln Gly Tyr Thr Lys Phe Ser Tyr
                1045                1050                1055

Glu Phe Glu Thr Thr Glu Lys Asp Ser Ser Asn Ile Glu Ile Thr Leu
            1060                1065                1070

Ile Gly Ser Gly Thr Thr Tyr Leu Asp Asn Leu Ser Ile Thr Glu Leu
        1075                1080                1085

Asn Ser Thr Pro Glu Ile Leu Asp Glu Pro Glu Val Lys Ile Pro Thr
    1090                1095                1100

Asp Gln Glu Ile Met Asp Ala His Lys Ile Tyr Phe Ala Asp Leu Asn
1105                1110                1115                1120

Phe Asn Pro Ser Thr Gly Asn Thr Tyr Ile Asn Gly Met Tyr Phe Ala
                1125                1130                1135

Pro Thr Gln Thr Asn Lys Glu Ala Leu Asp Tyr Ile Gln Lys Tyr Arg
            1140                1145                1150

Val Glu Ala Thr Leu Gln Tyr Ser Gly Phe Lys Asp Ile Gly Thr Lys
        1155                1160                1165

Asp Lys Glu Met Arg Asn Tyr Leu Gly Asp Pro Asn Gln Pro Lys Thr
    1170                1175                1180
```

```
Asn Tyr Val Asn Leu Arg Ser Tyr Phe Thr Gly Gly Glu Asn Ile Met
1185                1190                1195                1200

Thr Tyr Lys Lys Leu Arg Ile Tyr Ala Ile Thr Pro Asp Asp Arg Glu
                1205                1210                1215

Leu Leu Val Leu Ser Val Asp Gly Gly His His His His His His
            1220                1225                1230


<210> SEQ ID NO 45
<211> LENGTH: 1219
<212> TYPE: PRT
<213> ORGANISM: Artificial Sequence
<220> FEATURE:
<223> OTHER INFORMATION: amino acid sequence of Fusion of F2 to CDTb
      receptor binding domain without linker in N term
      of sequence (aa636-876) with 2 heterogeneous Gly
      residues between F2 and CTDb sequences (C65)

<400> SEQUENCE: 45

Met Gly Trp Gln Thr Ile Asp Gly Lys Lys Tyr Tyr Phe Asn Thr Asn
 1               5                  10                  15

Thr Ala Ile Ala Ser Thr Gly Tyr Thr Ile Ile Asn Gly Lys His Phe
            20                  25                  30

Tyr Phe Asn Thr Asp Gly Ile Met Gln Ile Gly Val Phe Lys Gly Pro
        35                  40                  45

Asn Gly Phe Glu Tyr Phe Ala Pro Ala Asn Thr Asp Ala Asn Asn Ile
    50                  55                  60

Glu Gly Gln Ala Ile Leu Tyr Gln Asn Glu Phe Leu Thr Leu Asn Gly
65                  70                  75                  80

Lys Lys Tyr Tyr Phe Gly Ser Asp Ser Lys Ala Val Thr Gly Trp Arg
                85                  90                  95

Ile Ile Asn Asn Lys Lys Tyr Tyr Phe Asn Pro Asn Asn Ala Ile Ala
            100                 105                 110

Ala Ile His Leu Cys Thr Ile Asn Asn Asp Lys Tyr Tyr Phe Ser Tyr
        115                 120                 125

Asp Gly Ile Leu Gln Asn Gly Tyr Ile Thr Ile Glu Arg Asn Asn Phe
    130                 135                 140

Tyr Phe Asp Ala Asn Asn Glu Ser Lys Met Val Thr Gly Val Phe Lys
145                 150                 155                 160

Gly Pro Asn Gly Phe Glu Tyr Phe Ala Pro Ala Asn Thr His Asn Asn
                165                 170                 175

Asn Ile Glu Gly Gln Ala Ile Val Tyr Gln Asn Lys Phe Leu Thr Leu
            180                 185                 190

Asn Gly Lys Lys Tyr Tyr Phe Asp Asn Asp Ser Lys Ala Val Thr Gly
        195                 200                 205

Trp Gln Thr Ile Asp Gly Lys Lys Tyr Tyr Phe Asn Leu Asn Thr Ala
    210                 215                 220

Glu Ala Ala Thr Gly Trp Gln Thr Ile Asp Gly Lys Lys Tyr Tyr Phe
225                 230                 235                 240

Asn Leu Asn Thr Ala Glu Ala Ala Thr Gly Trp Gln Thr Ile Asp Gly
                245                 250                 255

Lys Lys Tyr Tyr Phe Asn Thr Asn Thr Phe Ile Ala Ser Thr Gly Tyr
            260                 265                 270

Thr Ser Ile Asn Gly Lys His Phe Tyr Phe Asn Thr Asp Gly Ile Met
        275                 280                 285

Gln Ile Gly Val Phe Lys Gly Pro Asn Gly Phe Glu Tyr Phe Ala Pro
    290                 295                 300
```

```
Ala Asn Thr Asp Ala Asn Asn Ile Glu Gly Gln Ala Ile Leu Tyr Gln
305                 310                 315                 320

Asn Lys Phe Leu Thr Leu Asn Gly Lys Lys Tyr Tyr Phe Gly Ser Asp
                325                 330                 335

Ser Lys Ala Val Thr Gly Leu Arg Thr Ile Asp Gly Lys Lys Tyr Tyr
            340                 345                 350

Phe Asn Thr Asn Thr Ala Val Ala Val Thr Gly Trp Gln Thr Ile Asn
        355                 360                 365

Gly Lys Lys Tyr Tyr Phe Asn Thr Asn Thr Ser Ile Ala Ser Thr Gly
    370                 375                 380

Tyr Thr Ile Ile Ser Gly Lys His Phe Tyr Phe Asn Thr Asp Gly Ile
385                 390                 395                 400

Met Gln Ile Gly Val Phe Lys Gly Pro Asp Gly Phe Glu Tyr Phe Ala
                405                 410                 415

Pro Ala Asn Thr Asp Ala Asn Asn Ile Glu Gly Gln Ala Ile Arg Tyr
            420                 425                 430

Gln Asn Arg Phe Leu Tyr Leu His Asp Asn Ile Tyr Tyr Phe Gly Asn
        435                 440                 445

Asn Ser Lys Ala Ala Thr Gly Trp Val Thr Ile Asp Gly Asn Arg Tyr
    450                 455                 460

Tyr Phe Glu Pro Asn Thr Ala Met Gly Ala Asn Gly Tyr Lys Thr Ile
465                 470                 475                 480

Asp Asn Lys Asn Phe Tyr Phe Arg Asn Gly Leu Pro Gln Ile Gly Val
                485                 490                 495

Phe Lys Gly Ser Asn Gly Phe Glu Tyr Phe Ala Pro Ala Asn Thr Asp
            500                 505                 510

Ala Asn Asn Ile Glu Gly Gln Ala Ile Arg Tyr Gln Asn Arg Phe Leu
        515                 520                 525

His Leu Leu Gly Lys Ile Tyr Tyr Phe Gly Asn Asn Ser Lys Ala Val
    530                 535                 540

Thr Gly Trp Gln Thr Ile Asn Gly Lys Val Tyr Tyr Phe Met Pro Asp
545                 550                 555                 560

Thr Ala Met Ala Ala Ala Gly Gly Leu Asn Gln Ile Gly Asp Tyr Lys
                565                 570                 575

Tyr Tyr Phe Asn Ser Asp Gly Val Met Gln Lys Gly Phe Val Ser Ile
            580                 585                 590

Asn Asp Asn Lys His Tyr Phe Asp Asp Ser Gly Val Met Lys Val Gly
        595                 600                 605

Tyr Thr Glu Ile Asp Gly Lys His Phe Tyr Phe Ala Glu Asn Gly Glu
    610                 615                 620

Met Gln Ile Gly Val Phe Asn Thr Glu Asp Gly Phe Lys Tyr Phe Ala
625                 630                 635                 640

His His Asn Glu Asp Leu Gly Asn Glu Glu Gly Glu Glu Ile Ser Tyr
                645                 650                 655

Ser Gly Ile Leu Asn Phe Asn Asn Lys Ile Tyr Tyr Phe Asp Asp Ser
            660                 665                 670

Phe Thr Ala Val Val Gly Trp Lys Asp Leu Glu Asp Gly Ser Lys Tyr
        675                 680                 685

Tyr Phe Asp Glu Asp Thr Ala Glu Ala Tyr Ile Gly Leu Ser Leu Ile
    690                 695                 700

Asn Asp Gly Gln Tyr Tyr Phe Asn Asp Asp Gly Ile Met Gln Val Gly
705                 710                 715                 720
```

-continued

```
Phe Val Thr Ile Asn Asp Lys Val Phe Tyr Phe Ser Asp Ser Gly Ile
                725                 730                 735

Ile Glu Ser Gly Val Gln Asn Ile Asp Asp Asn Tyr Phe Tyr Ile Asp
            740                 745                 750

Asp Asn Gly Ile Val Gln Ile Gly Val Phe Asp Thr Ser Asp Gly Tyr
        755                 760                 765

Lys Tyr Phe Ala Pro Ala Asn Thr Val Asn Asp Asn Ile Tyr Gly Gln
    770                 775                 780

Ala Val Glu Tyr Ser Gly Leu Val Arg Val Gly Glu Asp Val Tyr Tyr
785                 790                 795                 800

Phe Gly Glu Thr Tyr Thr Ile Glu Thr Gly Trp Ile Tyr Asp Met Glu
                805                 810                 815

Asn Glu Ser Asp Lys Tyr Tyr Phe Asn Pro Glu Thr Lys Lys Ala Cys
            820                 825                 830

Lys Gly Ile Asn Leu Ile Asp Asp Ile Lys Tyr Tyr Phe Asp Glu Lys
        835                 840                 845

Gly Ile Met Arg Thr Gly Leu Ile Ser Phe Glu Asn Asn Asn Tyr Tyr
    850                 855                 860

Phe Asn Glu Asn Gly Glu Met Gln Phe Gly Tyr Ile Asn Ile Glu Asp
865                 870                 875                 880

Lys Met Phe Tyr Phe Gly Glu Asp Gly Val Met Gln Ile Gly Val Phe
                885                 890                 895

Asn Thr Pro Asp Gly Phe Lys Tyr Phe Ala His Gln Asn Thr Leu Asp
            900                 905                 910

Glu Asn Phe Glu Gly Glu Ser Ile Asn Tyr Thr Gly Trp Leu Asp Leu
        915                 920                 925

Asp Glu Lys Arg Tyr Tyr Phe Thr Asp Glu Tyr Ile Ala Ala Thr Gly
    930                 935                 940

Ser Val Ile Ile Asp Gly Glu Glu Tyr Tyr Phe Asp Pro Asp Thr Ala
945                 950                 955                 960

Gln Leu Val Ile Ser Glu Gly Gly Asn Val Asn Thr Thr Asn Gln Asp
                965                 970                 975

Gly Leu Gln Gly Ser Ala Asn Lys Leu Asn Gly Glu Thr Lys Ile Lys
            980                 985                 990

Ile Pro Met Ser Glu Leu Lys Pro Tyr Lys Arg Tyr Val Phe Ser Gly
        995                 1000                1005

Tyr Ser Lys Asp Pro Leu Thr Ser Asn Ser Ile Ile Val Lys Ile Lys
    1010                1015                1020

Ala Lys Glu Glu Lys Thr Asp Tyr Leu Val Pro Glu Gln Gly Tyr Thr
1025                1030                1035                1040

Lys Phe Ser Tyr Glu Phe Glu Thr Thr Glu Lys Asp Ser Ser Asn Ile
                1045                1050                1055

Glu Ile Thr Leu Ile Gly Ser Gly Thr Thr Tyr Leu Asp Asn Leu Ser
            1060                1065                1070

Ile Thr Glu Leu Asn Ser Thr Pro Glu Ile Leu Asp Glu Pro Glu Val
        1075                1080                1085

Lys Ile Pro Thr Asp Gln Glu Ile Met Asp Ala His Lys Ile Tyr Phe
    1090                1095                1100

Ala Asp Leu Asn Phe Asn Pro Ser Thr Gly Asn Thr Tyr Ile Asn Gly
1105                1110                1115                1120

Met Tyr Phe Ala Pro Thr Gln Thr Asn Lys Glu Ala Leu Asp Tyr Ile
                1125                1130                1135

Gln Lys Tyr Arg Val Glu Ala Thr Leu Gln Tyr Ser Gly Phe Lys Asp
```

```
            1140                1145                1150

Ile Gly Thr Lys Asp Lys Glu Met Arg Asn Tyr Leu Gly Asp Pro Asn
        1155                1160                1165

Gln Pro Lys Thr Asn Tyr Val Asn Leu Arg Ser Tyr Phe Thr Gly Gly
    1170                1175                1180

Glu Asn Ile Met Thr Tyr Lys Lys Leu Arg Ile Tyr Ala Ile Thr Pro
1185                1190                1195                1200

Asp Asp Arg Glu Leu Leu Val Leu Ser Val Asp Gly Gly His His His
                1205                1210                1215

His His His


<210> SEQ ID NO 46
<211> LENGTH: 419
<212> TYPE: PRT
<213> ORGANISM: Artificial Sequence
<220> FEATURE:
<223> OTHER INFORMATION: amino acid sequence of CDTa without signal
      peptide, with two mutations (E428Q, E430Q, aa
      44-463) (C67)

<400> SEQUENCE: 46

Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Ser Leu Asp Phe Lys Asp Asp
    210                 215                 220

Val Ser Lys Gly Asp Ser Trp Gly Lys Ala Asn Tyr Asn Asp Trp Ser
225                 230                 235                 240

Asn Lys Leu Thr Pro Asn Glu Leu Ala Asp Val Asn Asp Tyr Met Arg
                245                 250                 255

Gly Gly Tyr Thr Ala Ile Asn Asn Tyr Leu Ile Ser Asn Gly Pro Val
            260                 265                 270
```

```
Asn Asn Pro Asn Pro Glu Leu Asp Ser Lys Ile Thr Asn Ile Glu Asn
        275                 280                 285

Ala Leu Lys Arg Glu Pro Ile Pro Thr Asn Leu Thr Val Tyr Arg Arg
    290                 295                 300

Ser Gly Pro Gln Glu Phe Gly Leu Thr Leu Thr Ser Pro Glu Tyr Asp
305                 310                 315                 320

Phe Asn Lys Leu Glu Asn Ile Asp Ala Phe Lys Ser Lys Trp Glu Gly
                325                 330                 335

Gln Ala Leu Ser Tyr Pro Asn Phe Ile Ser Thr Ser Ile Gly Ser Val
            340                 345                 350

Asn Met Ser Ala Phe Ala Lys Arg Lys Ile Val Leu Arg Ile Thr Ile
        355                 360                 365

Pro Lys Gly Ser Pro Gly Ala Tyr Leu Ser Ala Ile Pro Gly Tyr Ala
    370                 375                 380

Gly Tyr Val Leu Leu Asn His Gly Ser Lys Phe Lys Ile Asn Lys Ile
385                 390                 395                 400

Asp Ser Tyr Lys Asp Gly Thr Ile Thr Lys Leu Ile Val Asp Ala Thr
                405                 410                 415

Leu Ile Pro


<210> SEQ ID NO 47
<211> LENGTH: 1266
<212> TYPE: DNA
<213> ORGANISM: Artificial Sequence
<220> FEATURE:
<223> OTHER INFORMATION: nucleotide sequence of C67

<400> SEQUENCE: 47

atggtttgca ataccaccta taaagcaccg attgaacgtc cggaagattt tctgaaagat     60

aaagaaaaag ccaaagaatg ggaacgcaaa gaagcagaac gtattgaaca gaaactggaa    120

cgtagcgaaa aagaagcact ggaaagctac aaaaaagata gcgtggaaat ttcaaaatat    180

agccagaccc gcaattattt ctatgattat cagattgaag ccaatagccg tgaaaaagaa    240

tataaagaac tgcgcaatgc cattagcaaa aacaaaattg ataaaccgat gtatgtgtat    300

tatttcgaaa gtccggaaaa atttgccttt aacaaagtga ttcgcaccga aaatcagaat    360

gaaattagcc tggaaaaatt caatgaattt aaagaaacca ttcagaataa actgtttaaa    420

caggatggct ttaaagatat ttcactgtat gaaccgggta aaggtgatga aaaaccgaca    480

ccgctgctga tgcatctgaa actgcctcgt aataccggta tgctgccgta taccaatacc    540

aataatgtta gcaccctgat tgaacagggc tatagcatca aaattgataa aattgtgcgc    600

attgtgattg atggcaaaca ttatatcaaa gccgaagcca gcgttgtttc aagcctggat    660

tttaaagatg atgtgagcaa aggcgatagc tggggtaaag caaactataa tgattggagc    720

aataaactga ccccgaatga actggcagat gtgaatgatt atatgcgtgg tggttatacc    780

gccattaaca attatctgat tagcaatggt ccggtgaata atccgaatcc ggaactggat    840

agcaaaatta ccaatattga aaatgccctg aaacgcgaac cgattccgac caatctgacc    900

gtttatcgtc gtagcggtcc gcaagaattt ggtctgaccc tgaccagtcc ggaatatgac    960

tttaacaaac tggaaaatat tgatgccttt aaaagcaaat gggaaggtca ggcactgagc   1020

tatccgaact ttattagcac cagcattggt agcgttaata tgagcgcatt tgccaaacgt   1080

aaaattgtgc tgcgtattac cattccgaaa ggtagtccgg gtgcatatct gagcgcaatt   1140

ccgggttatg ccggtcaata tcaggttctg ctgaatcatg gcagcaaatt caaaattaac   1200
```

```
aaaattgata gctataaaga tggcaccatt accaaactga ttgttgatgc aaccctgatt   1260

ccgtaa                                                              1266


<210> SEQ ID NO 48
<211> LENGTH: 421
<212> TYPE: PRT
<213> ORGANISM: Artificial Sequence
<220> FEATURE:
<223> OTHER INFORMATION: amino acid sequence of CDTa without signal
      peptide, with seven mutations (R345A, Q350A,
      N385A, R402A, S388F, E428Q, E430Q, aa 44-463)
      (C69)

<400> SEQUENCE: 48

Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Ser Leu Asp Phe Lys Asp Asp
    210                 215                 220

Val Ser Lys Gly Asp Ser Trp Gly Lys Ala Asn Tyr Asn Asp Trp Ser
225                 230                 235                 240

Asn Lys Leu Thr Pro Asn Glu Leu Ala Asp Val Asn Asp Tyr Met Arg
                245                 250                 255

Gly Gly Tyr Thr Ala Ile Asn Asn Tyr Leu Ile Ser Asn Gly Pro Val
            260                 265                 270

Asn Asn Pro Asn Pro Glu Leu Asp Ser Lys Ile Thr Asn Ile Glu Asn
        275                 280                 285

Ala Leu Lys Arg Glu Pro Ile Pro Thr Asn Leu Thr Val Tyr Ala Arg
    290                 295                 300

Ser Gly Pro Ala Glu Phe Gly Leu Thr Leu Thr Ser Pro Glu Tyr Asp
305                 310                 315                 320

Phe Asn Lys Leu Glu Asn Ile Asp Ala Phe Lys Ser Lys Trp Glu Gly
                325                 330                 335
```

```
Gln Ala Leu Ser Tyr Pro Ala Phe Ile Phe Thr Ser Ile Gly Ser Val
            340                 345                 350

Asn Met Ser Ala Phe Ala Lys Ala Lys Ile Val Leu Arg Ile Thr Ile
        355                 360                 365

Pro Lys Gly Ser Pro Gly Ala Tyr Leu Ser Ala Ile Pro Gly Tyr Ala
    370                 375                 380

Gly Gln Tyr Gln Val Leu Leu Asn His Gly Ser Lys Phe Lys Ile Asn
385                 390                 395                 400

Lys Ile Asp Ser Tyr Lys Asp Gly Thr Ile Thr Lys Leu Ile Val Asp
                405                 410                 415

Ala Thr Leu Ile Pro
            420
```

<210> SEQ ID NO 49
<211> LENGTH: 1263
<212> TYPE: DNA
<213> ORGANISM: Artificial Sequence
<220> FEATURE:
<223> OTHER INFORMATION: nucleotide sequence of C69

<400> SEQUENCE: 49

```
atggtttgca ataccaccta taaagcaccg attgaacgtc cggaagattt tctgaaagat      60

aaagaaaaag ccaaagaatg ggaacgcaaa gaagcagaac gtattgaaca gaaactggaa     120

cgtagcgaaa aagaagcact ggaaagctac aaaaaagata gcgtggaaat ttcaaaatat     180

agccagaccc gcaattattt ctatgattat cagattgaag ccaatagccg tgaaaaagaa     240

tataaagaac tgcgcaatgc cattagcaaa aacaaaattg ataaaccgat gtatgtgtat     300

tatttcgaaa gtccggaaaa atttgccttt aacaaagtga ttcgcaccga aaatcagaat     360

gaaattagcc tggaaaaatt caatgaattt aaagaaacca ttcagaataa actgtttaaa     420

caggatggct ttaaagatat ttcactgtat gaaccgggta aaggtgatga aaaaccgaca     480

ccgctgctga tgcatctgaa actgcctcgt aataccggta tgctgccgta taccaatacc     540

aataatgtta gcaccctgat tgaacagggc tatagcatca aaattgataa aattgtgcgc     600

attgtgattg atggcaaaca ttatatcaaa gccgaagcca gcgttgtttc aagcctggat     660

tttaaagatg atgtgagcaa aggcgatagc tggggtaaag caaactataa tgattggagc     720

aataaactga ccccgaatga actggcagat gtgaatgatt atatgcgtgg tggttatacc     780

gccattaaca attatctgat tagcaatggt ccggtgaata atccgaatcc ggaactggat     840

agcaaaatta ccaatattga aaatgccctg aaacgcgaac cgattccgac caatctgacc     900

gtttatgcac gtagcggtcc ggcagaattt ggtctgaccc tgaccagtcc ggaatatgac     960

tttaacaaac tggaaaatat tgatgccttt aaaagcaaat gggaaggtca ggcactgagc    1020

tatccggcat ttattttcac cagcattggt agcgttaata tgagcgcatt tgccaaagca    1080

aaaattgtgc tgcgtattac cattccgaaa ggtagtccgg gtgcatatct gagcgcaatt    1140

ccgggttatg ccggtcagta tcaggttctg ctgaatcatg gcagcaaatt caaaattaac    1200

aaaattgata gctataaaga tggcaccatt accaaactga ttgttgatgc aaccctgatt    1260

ccg                                                                  1263
```

<210> SEQ ID NO 50
<211> LENGTH: 672
<212> TYPE: PRT
<213> ORGANISM: Artificial Sequence
<220> FEATURE:

<223> OTHER INFORMATION: amino acid sequence of CDTb without signal
sequence and prodomain (mature fragment based on
MS data) with Ca2+ binding motif mutation
(aa212-876, mut Asp-9-11-13 Ala) (C97)

<400> SEQUENCE: 50

```
Met Ser Asp Trp Glu Asp Glu Asp Leu Ala Thr Ala Asn Ala Asn Ile
 1               5                  10                  15

Pro Asp Ser Tyr Glu Arg Asn Gly Tyr Thr Ile Lys Asp Leu Ile Ala
            20                  25                  30

Val Lys Trp Glu Asp Ser Phe Ala Glu Gln Gly Tyr Lys Lys Tyr Val
        35                  40                  45

Ser Asn Tyr Leu Glu Ser Asn Thr Ala Gly Asp Pro Tyr Thr Asp Tyr
    50                  55                  60

Glu Lys Ala Ser Gly Ser Phe Asp Lys Ala Ile Lys Thr Glu Ala Arg
65                  70                  75                  80

Asp Pro Leu Val Ala Ala Tyr Pro Ile Val Gly Val Gly Met Glu Lys
                85                  90                  95

Leu Ile Ile Ser Thr Asn Glu His Ala Ser Thr Asp Gln Gly Lys Thr
            100                 105                 110

Val Ser Arg Ala Thr Thr Asn Ser Lys Thr Glu Ser Asn Thr Ala Gly
        115                 120                 125

Val Ser Val Asn Val Gly Tyr Gln Asn Gly Phe Thr Ala Asn Val Thr
    130                 135                 140

Thr Asn Tyr Ser His Thr Thr Asp Asn Ser Thr Ala Val Gln Asp Ser
145                 150                 155                 160

Asn Gly Glu Ser Trp Asn Thr Gly Leu Ser Ile Asn Lys Gly Glu Ser
                165                 170                 175

Ala Tyr Ile Asn Ala Asn Val Arg Tyr Tyr Asn Thr Gly Thr Ala Pro
            180                 185                 190

Met Tyr Lys Val Thr Pro Thr Thr Asn Leu Val Leu Asp Gly Asp Thr
        195                 200                 205

Leu Ser Thr Ile Lys Ala Gln Glu Asn Gln Ile Gly Asn Asn Leu Ser
    210                 215                 220

Pro Gly Asp Thr Tyr Pro Lys Lys Gly Leu Ser Pro Leu Ala Leu Asn
225                 230                 235                 240

Thr Met Asp Gln Phe Ser Ser Arg Leu Ile Pro Ile Asn Tyr Asp Gln
                245                 250                 255

Leu Lys Lys Leu Asp Ala Gly Lys Gln Ile Lys Leu Glu Thr Thr Gln
            260                 265                 270

Val Ser Gly Asn Phe Gly Thr Lys Asn Ser Ser Gly Gln Ile Val Thr
        275                 280                 285

Glu Gly Asn Ser Trp Ser Asp Tyr Ile Ser Gln Ile Asp Ser Ile Ser
    290                 295                 300

Ala Ser Ile Ile Leu Asp Thr Glu Asn Glu Ser Tyr Glu Arg Arg Val
305                 310                 315                 320

Thr Ala Lys Asn Leu Gln Asp Pro Glu Asp Lys Thr Pro Glu Leu Thr
                325                 330                 335

Ile Gly Glu Ala Ile Glu Lys Ala Phe Gly Ala Thr Lys Lys Asp Gly
            340                 345                 350

Leu Leu Tyr Phe Asn Asp Ile Pro Ile Asp Glu Ser Cys Val Glu Leu
        355                 360                 365

Ile Phe Asp Asp Asn Thr Ala Asn Lys Ile Lys Asp Ser Leu Lys Thr
    370                 375                 380
```

```
Leu Ser Asp Lys Lys Ile Tyr Asn Val Lys Leu Glu Arg Gly Met Asn
385                 390                 395                 400

Ile Leu Ile Lys Thr Pro Thr Tyr Phe Thr Asn Phe Asp Asp Tyr Asn
                405                 410                 415

Asn Tyr Pro Ser Thr Trp Ser Asn Val Asn Thr Thr Asn Gln Asp Gly
            420                 425                 430

Leu Gln Gly Ser Ala Asn Lys Leu Asn Gly Glu Thr Lys Ile Lys Ile
        435                 440                 445

Pro Met Ser Glu Leu Lys Pro Tyr Lys Arg Tyr Val Phe Ser Gly Tyr
    450                 455                 460

Ser Lys Asp Pro Leu Thr Ser Asn Ser Ile Ile Val Lys Ile Lys Ala
465                 470                 475                 480

Lys Glu Glu Lys Thr Asp Tyr Leu Val Pro Glu Gln Gly Tyr Thr Lys
                485                 490                 495

Phe Ser Tyr Glu Phe Glu Thr Thr Glu Lys Asp Ser Ser Asn Ile Glu
            500                 505                 510

Ile Thr Leu Ile Gly Ser Gly Thr Thr Tyr Leu Asp Asn Leu Ser Ile
        515                 520                 525

Thr Glu Leu Asn Ser Thr Pro Glu Ile Leu Asp Glu Pro Glu Val Lys
    530                 535                 540

Ile Pro Thr Asp Gln Glu Ile Met Asp Ala His Lys Ile Tyr Phe Ala
545                 550                 555                 560

Asp Leu Asn Phe Asn Pro Ser Thr Gly Asn Thr Tyr Ile Asn Gly Met
                565                 570                 575

Tyr Phe Ala Pro Thr Gln Thr Asn Lys Glu Ala Leu Asp Tyr Ile Gln
            580                 585                 590

Lys Tyr Arg Val Glu Ala Thr Leu Gln Tyr Ser Gly Phe Lys Asp Ile
        595                 600                 605

Gly Thr Lys Asp Lys Glu Met Arg Asn Tyr Leu Gly Asp Pro Asn Gln
    610                 615                 620

Pro Lys Thr Asn Tyr Val Asn Leu Arg Ser Tyr Phe Thr Gly Gly Glu
625                 630                 635                 640

Asn Ile Met Thr Tyr Lys Lys Leu Arg Ile Tyr Ala Ile Thr Pro Asp
                645                 650                 655

Asp Arg Glu Leu Leu Val Leu Ser Val Asp His His His His His His
            660                 665                 670
```

<210> SEQ ID NO 51
<211> LENGTH: 672
<212> TYPE: PRT
<213> ORGANISM: Artificial Sequence
<220> FEATURE:
<223> OTHER INFORMATION: amino acid sequence of CDTb with prodomain removed (CDTb'', aa212-876) (C55)

<400> SEQUENCE: 51

```
Met Ser Asp Trp Glu Asp Glu Asp Leu Asp Thr Asp Asn Asp Asn Ile
 1               5                  10                  15

Pro Asp Ser Tyr Glu Arg Asn Gly Tyr Thr Ile Lys Asp Leu Ile Ala
            20                  25                  30

Val Lys Trp Glu Asp Ser Phe Ala Glu Gln Gly Tyr Lys Lys Tyr Val
        35                  40                  45

Ser Asn Tyr Leu Glu Ser Asn Thr Ala Gly Asp Pro Tyr Thr Asp Tyr
    50                  55                  60

Glu Lys Ala Ser Gly Ser Phe Asp Lys Ala Ile Lys Thr Glu Ala Arg
65                  70                  75                  80
```

```
Asp Pro Leu Val Ala Ala Tyr Pro Ile Val Gly Val Gly Met Glu Lys
                85                  90                  95

Leu Ile Ile Ser Thr Asn Glu His Ala Ser Thr Asp Gln Gly Lys Thr
            100                 105                 110

Val Ser Arg Ala Thr Thr Asn Ser Lys Thr Glu Ser Asn Thr Ala Gly
        115                 120                 125

Val Ser Val Asn Val Gly Tyr Gln Asn Gly Phe Thr Ala Asn Val Thr
    130                 135                 140

Thr Asn Tyr Ser His Thr Thr Asp Asn Ser Thr Ala Val Gln Asp Ser
145                 150                 155                 160

Asn Gly Glu Ser Trp Asn Thr Gly Leu Ser Ile Asn Lys Gly Glu Ser
                165                 170                 175

Ala Tyr Ile Asn Ala Asn Val Arg Tyr Tyr Asn Thr Gly Thr Ala Pro
            180                 185                 190

Met Tyr Lys Val Thr Pro Thr Thr Asn Leu Val Leu Asp Gly Asp Thr
        195                 200                 205

Leu Ser Thr Ile Lys Ala Gln Glu Asn Gln Ile Gly Asn Asn Leu Ser
    210                 215                 220

Pro Gly Asp Thr Tyr Pro Lys Lys Gly Leu Ser Pro Leu Ala Leu Asn
225                 230                 235                 240

Thr Met Asp Gln Phe Ser Ser Arg Leu Ile Pro Ile Asn Tyr Asp Gln
                245                 250                 255

Leu Lys Lys Leu Asp Ala Gly Lys Gln Ile Lys Leu Glu Thr Thr Gln
            260                 265                 270

Val Ser Gly Asn Phe Gly Thr Lys Asn Ser Ser Gly Gln Ile Val Thr
        275                 280                 285

Glu Gly Asn Ser Trp Ser Asp Tyr Ile Ser Gln Ile Asp Ser Ile Ser
    290                 295                 300

Ala Ser Ile Ile Leu Asp Thr Glu Asn Glu Ser Tyr Glu Arg Arg Val
305                 310                 315                 320

Thr Ala Lys Asn Leu Gln Asp Pro Glu Asp Lys Thr Pro Glu Leu Thr
                325                 330                 335

Ile Gly Glu Ala Ile Glu Lys Ala Phe Gly Ala Thr Lys Lys Asp Gly
            340                 345                 350

Leu Leu Tyr Phe Asn Asp Ile Pro Ile Asp Glu Ser Cys Val Glu Leu
        355                 360                 365

Ile Phe Asp Asp Asn Thr Ala Asn Lys Ile Lys Asp Ser Leu Lys Thr
    370                 375                 380

Leu Ser Asp Lys Lys Ile Tyr Asn Val Lys Leu Glu Arg Gly Met Asn
385                 390                 395                 400

Ile Leu Ile Lys Thr Pro Thr Tyr Phe Thr Asn Phe Asp Asp Tyr Asn
                405                 410                 415

Asn Tyr Pro Ser Thr Trp Ser Asn Val Asn Thr Thr Asn Gln Asp Gly
            420                 425                 430

Leu Gln Gly Ser Ala Asn Lys Leu Asn Gly Glu Thr Lys Ile Lys Ile
        435                 440                 445

Pro Met Ser Glu Leu Lys Pro Tyr Lys Arg Tyr Val Phe Ser Gly Tyr
    450                 455                 460

Ser Lys Asp Pro Leu Thr Ser Asn Ser Ile Ile Val Lys Ile Lys Ala
465                 470                 475                 480

Lys Glu Glu Lys Thr Asp Tyr Leu Val Pro Glu Gln Gly Tyr Thr Lys
                485                 490                 495
```

```
Phe Ser Tyr Glu Phe Glu Thr Thr Glu Lys Asp Ser Ser Asn Ile Glu
            500                 505                 510

Ile Thr Leu Ile Gly Ser Gly Thr Thr Tyr Leu Asp Asn Leu Ser Ile
        515                 520                 525

Thr Glu Leu Asn Ser Thr Pro Glu Ile Leu Asp Glu Pro Glu Val Lys
    530                 535                 540

Ile Pro Thr Asp Gln Glu Ile Met Asp Ala His Lys Ile Tyr Phe Ala
545                 550                 555                 560

Asp Leu Asn Phe Asn Pro Ser Thr Gly Asn Thr Tyr Ile Asn Gly Met
                565                 570                 575

Tyr Phe Ala Pro Thr Gln Thr Asn Lys Glu Ala Leu Asp Tyr Ile Gln
            580                 585                 590

Lys Tyr Arg Val Glu Ala Thr Leu Gln Tyr Ser Gly Phe Lys Asp Ile
        595                 600                 605

Gly Thr Lys Asp Lys Glu Met Arg Asn Tyr Leu Gly Asp Pro Asn Gln
    610                 615                 620

Pro Lys Thr Asn Tyr Val Asn Leu Arg Ser Tyr Phe Thr Gly Gly Glu
625                 630                 635                 640

Asn Ile Met Thr Tyr Lys Lys Leu Arg Ile Tyr Ala Ile Thr Pro Asp
                645                 650                 655

Asp Arg Glu Leu Leu Val Leu Ser Val Asp His His His His His His
            660                 665                 670


<210> SEQ ID NO 52
<211> LENGTH: 427
<212> TYPE: PRT
<213> ORGANISM: Artificial Sequence
<220> FEATURE:
<223> OTHER INFORMATION: amino acid sequence of CDTa without signal
      peptide, with five mutations (R345A, Q350A, N385A,
      R402A, S388F, aa 44-463) (C107)

<400> SEQUENCE: 52

Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
```

```
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Ser Leu Asp Phe Lys Asp Asp
    210                 215                 220

Val Ser Lys Gly Asp Ser Trp Gly Lys Ala Asn Tyr Asn Asp Trp Ser
225                 230                 235                 240

Asn Lys Leu Thr Pro Asn Glu Leu Ala Asp Val Asn Asp Tyr Met Arg
                245                 250                 255

Gly Gly Tyr Thr Ala Ile Asn Asn Tyr Leu Ile Ser Asn Gly Pro Val
            260                 265                 270

Asn Asn Pro Asn Pro Glu Leu Asp Ser Lys Ile Thr Asn Ile Glu Asn
        275                 280                 285

Ala Leu Lys Arg Glu Pro Ile Pro Thr Asn Leu Thr Val Tyr Ala Arg
    290                 295                 300

Ser Gly Pro Ala Glu Phe Gly Leu Thr Leu Thr Ser Pro Glu Tyr Asp
305                 310                 315                 320

Phe Asn Lys Leu Glu Asn Ile Asp Ala Phe Lys Ser Lys Trp Glu Gly
                325                 330                 335

Gln Ala Leu Ser Tyr Pro Ala Phe Ile Phe Thr Ser Ile Gly Ser Val
            340                 345                 350

Asn Met Ser Ala Phe Ala Lys Ala Lys Ile Val Leu Arg Ile Thr Ile
        355                 360                 365

Pro Lys Gly Ser Pro Gly Ala Tyr Leu Ser Ala Ile Pro Gly Tyr Ala
    370                 375                 380

Gly Glu Tyr Glu Val Leu Leu Asn His Gly Ser Lys Phe Lys Ile Asn
385                 390                 395                 400

Lys Ile Asp Ser Tyr Lys Asp Gly Thr Ile Thr Lys Leu Ile Val Asp
                405                 410                 415

Ala Thr Leu Ile Pro His His His His His His
            420                 425
```

<210> SEQ ID NO 53
<211> LENGTH: 1287
<212> TYPE: DNA
<213> ORGANISM: Artificial Sequence
<220> FEATURE:
<223> OTHER INFORMATION: Polynucleotide sequence of CDTa without signal peptide, with five mutations (R345A, Q350A, N385A, R402A, S388F, aa 44-463) (C107)

<400> SEQUENCE: 53

```
atggtttgca ataccaccta taaagcaccg attgaacgtc cggaagattt tctgaaagat     60

aaagaaaaag ccaaagaatg ggaacgcaaa gaagcagaac gtattgaaca gaaactggaa    120

cgtagcgaaa aagaagcact ggaaagctac aaaaaagata gcgtggaaat ttcaaaatat    180

agccagaccc gcaattattt ctatgattat cagattgaag ccaatagccg tgaaaaagaa    240

tataaagaac tgcgcaatgc cattagcaaa aacaaaattg ataaaccgat gtatgtgtat    300

tatttcgaaa gtccggaaaa atttgccttt aacaaagtga ttcgcaccga aaatcagaat    360

gaaattagcc tggaaaaatt caatgaattt aaagaaacca ttcagaataa actgtttaaa    420

caggatggct ttaaagatat ttcactgtat gaaccgggta aaggtgatga aaaaccgaca    480

ccgctgctga tgcatctgaa actgcctcgt aataccggta tgctgccgta taccaatacc    540

aataatgtta gcaccctgat tgaacagggc tatagcatca aaattgataa aattgtgcgc    600
```

-continued

```
attgtgattg atggcaaaca ttatatcaaa gccgaagcca gcgttgtttc aagcctggat    660

tttaaagatg atgtgagcaa aggcgatagc tggggtaaag caaactataa tgattggagc    720

aataaactga ccccgaatga actggcagat gtgaatgatt atatgcgtgg tggttatacc    780

gccattaaca attatctgat tagcaatggt ccggtgaata atccgaatcc ggaactggat    840

agcaaaatta ccaatattga aaatgccctg aaacgcgaac cgattccgac caatctgacc    900

gtttatgcac gtagcggtcc ggcagaattt ggtctgaccc tgaccagtcc ggaatatgac    960

tttaacaaac tggaaaatat tgatgccttt aaaagcaaat gggaaggtca ggcactgagc   1020

tatccggcat ttattttcac cagcattggt agcgttaata tgagcgcatt tgccaaagca   1080

aaaattgtgc tgcgtattac cattccgaaa ggtagtccgg gtgcatatct gagcgcaatt   1140

ccgggttatg ccggtgaata tgaagttctg ctgaatcatg gcagcaaatt caaaattaac   1200

aaaattgata gctataaaga tggcaccatt accaaactga ttgttgatgc aaccctgatt   1260

ccgcaccacc atcatcatca ttaataa                                       1287
```

```
<210> SEQ ID NO 54
<211> LENGTH: 427
<212> TYPE: PRT
<213> ORGANISM: Artificial Sequence
<220> FEATURE:
<223> OTHER INFORMATION: Amino acid sequence of CDTa without signal
      peptide, with six mutations (R345A, Q350A, N385A,
      R402A, S388F, E430Q, aa 44-463) (C108)

<400> SEQUENCE: 54

Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Ser Leu Asp Phe Lys Asp Asp
    210                 215                 220

Val Ser Lys Gly Asp Ser Trp Gly Lys Ala Asn Tyr Asn Asp Trp Ser
```

```
225                 230                 235                 240

Asn Lys Leu Thr Pro Asn Glu Leu Ala Asp Val Asn Asp Tyr Met Arg
                245                 250                 255

Gly Gly Tyr Thr Ala Ile Asn Asn Tyr Leu Ile Ser Asn Gly Pro Val
            260                 265                 270

Asn Asn Pro Asn Pro Glu Leu Asp Ser Lys Ile Thr Asn Ile Glu Asn
        275                 280                 285

Ala Leu Lys Arg Glu Pro Ile Pro Thr Asn Leu Thr Val Tyr Ala Arg
    290                 295                 300

Ser Gly Pro Ala Glu Phe Gly Leu Thr Leu Thr Ser Pro Glu Tyr Asp
305                 310                 315                 320

Phe Asn Lys Leu Glu Asn Ile Asp Ala Phe Lys Ser Lys Trp Glu Gly
                325                 330                 335

Gln Ala Leu Ser Tyr Pro Ala Phe Ile Phe Thr Ser Ile Gly Ser Val
            340                 345                 350

Asn Met Ser Ala Phe Ala Lys Ala Lys Ile Val Leu Arg Ile Thr Ile
        355                 360                 365

Pro Lys Gly Ser Pro Gly Ala Tyr Leu Ser Ala Ile Pro Gly Tyr Ala
    370                 375                 380

Gly Glu Tyr Gln Val Leu Leu Asn His Gly Ser Lys Phe Lys Ile Asn
385                 390                 395                 400

Lys Ile Asp Ser Tyr Lys Asp Gly Thr Ile Thr Lys Leu Ile Val Asp
                405                 410                 415

Ala Thr Leu Ile Pro His His His His His His
            420                 425


<210> SEQ ID NO 55
<211> LENGTH: 1287
<212> TYPE: DNA
<213> ORGANISM: Artificial Sequence
<220> FEATURE:
<223> OTHER INFORMATION: Polynucleotide sequence of CDTa without signal
      peptide, with six mutations (R345A, Q350A, N385A,
      R402A, S388F, E430Q, aa 44-463) (C108)

<400> SEQUENCE: 55

atggtttgca ataccaccta taaagcaccg attgaacgtc cggaagattt tctgaaagat      60

aaagaaaaag ccaaagaatg ggaacgcaaa gaagcagaac gtattgaaca gaaactggaa     120

cgtagcgaaa aagaagcact ggaaagctac aaaaaagata gcgtggaaat ttcaaaatat     180

agccagaccc gcaattattt ctatgattat cagattgaag ccaatagccg tgaaaaagaa     240

tataaagaac tgcgcaatgc cattagcaaa aacaaaattg ataaaccgat gtatgtgtat     300

tatttcgaaa gtccggaaaa atttgccttt aacaaagtga ttcgcaccga aaatcagaat     360

gaaattagcc tggaaaaatt caatgaattt aaagaaacca ttcagaataa actgtttaaa     420

caggatggct ttaaagatat ttcactgtat gaaccgggta aaggtgatga aaaaccgaca     480

ccgctgctga tgcatctgaa actgcctcgt aataccggta tgctgccgta taccaatacc     540

aataatgtta gcaccctgat tgaacagggc tatagcatca aaattgataa aattgtgcgc     600

attgtgattg atggcaaaca ttatatcaaa gccgaagcca gcgttgtttc aagcctggat     660

tttaaagatg atgtgagcaa aggcgatagc tggggtaaag caaactataa tgattggagc     720

aataaactga ccccgaatga actggcagat gtgaatgatt atatgcgtgg tggttatacc     780

gccattaaca attatctgat tagcaatggt ccggtgaata atccgaatcc ggaactggat     840

agcaaaatta ccaatattga aaatgccctg aaacgcgaac cgattccgac caatctgacc     900
```

```
gtttatgcac gtagcggtcc ggcagaattt ggtctgaccc tgaccagtcc ggaatatgac    960

tttaacaaac tggaaaatat tgatgccttt aaaagcaaat gggaaggtca ggcactgagc   1020

tatccggcat ttattttcac cagcattggt agcgttaata tgagcgcatt tgccaaagca   1080

aaaattgtgc tgcgtattac cattccgaaa ggtagtccgg gtgcatatct gagcgcaatt   1140

ccgggttatg ccggtgaata tcaagttctg ctgaatcatg gcagcaaatt caaaattaac   1200

aaaattgata gctataaaga tggcaccatt accaaactga ttgttgatgc aaccctgatt   1260

ccgcaccacc atcatcatca ttaataa                                       1287


<210> SEQ ID NO 56
<211> LENGTH: 427
<212> TYPE: PRT
<213> ORGANISM: Artificial Sequence
<220> FEATURE:
<223> OTHER INFORMATION: Amino acid sequence of CDTa without signal
      peptide, with six mutations (R345A, Q350A, N385A,
      R402A, S388F, E428Q, aa 44-463) (C110

<400> SEQUENCE: 56

Met Val Cys Asn Thr Thr Tyr Lys Ala Pro Ile Glu Arg Pro Glu Asp
 1               5                  10                  15

Phe Leu Lys Asp Lys Glu Lys Ala Lys Glu Trp Glu Arg Lys Glu Ala
            20                  25                  30

Glu Arg Ile Glu Gln Lys Leu Glu Arg Ser Glu Lys Glu Ala Leu Glu
        35                  40                  45

Ser Tyr Lys Lys Asp Ser Val Glu Ile Ser Lys Tyr Ser Gln Thr Arg
    50                  55                  60

Asn Tyr Phe Tyr Asp Tyr Gln Ile Glu Ala Asn Ser Arg Glu Lys Glu
65                  70                  75                  80

Tyr Lys Glu Leu Arg Asn Ala Ile Ser Lys Asn Lys Ile Asp Lys Pro
                85                  90                  95

Met Tyr Val Tyr Tyr Phe Glu Ser Pro Glu Lys Phe Ala Phe Asn Lys
            100                 105                 110

Val Ile Arg Thr Glu Asn Gln Asn Glu Ile Ser Leu Glu Lys Phe Asn
        115                 120                 125

Glu Phe Lys Glu Thr Ile Gln Asn Lys Leu Phe Lys Gln Asp Gly Phe
    130                 135                 140

Lys Asp Ile Ser Leu Tyr Glu Pro Gly Lys Gly Asp Glu Lys Pro Thr
145                 150                 155                 160

Pro Leu Leu Met His Leu Lys Leu Pro Arg Asn Thr Gly Met Leu Pro
                165                 170                 175

Tyr Thr Asn Thr Asn Asn Val Ser Thr Leu Ile Glu Gln Gly Tyr Ser
            180                 185                 190

Ile Lys Ile Asp Lys Ile Val Arg Ile Val Ile Asp Gly Lys His Tyr
        195                 200                 205

Ile Lys Ala Glu Ala Ser Val Val Ser Ser Leu Asp Phe Lys Asp Asp
    210                 215                 220

Val Ser Lys Gly Asp Ser Trp Gly Lys Ala Asn Tyr Asn Asp Trp Ser
225                 230                 235                 240

Asn Lys Leu Thr Pro Asn Glu Leu Ala Asp Val Asn Asp Tyr Met Arg
                245                 250                 255

Gly Gly Tyr Thr Ala Ile Asn Asn Tyr Leu Ile Ser Asn Gly Pro Val
            260                 265                 270

Asn Asn Pro Asn Pro Glu Leu Asp Ser Lys Ile Thr Asn Ile Glu Asn
```

-continued

```
        275                 280                 285

Ala Leu Lys Arg Glu Pro Ile Pro Thr Asn Leu Thr Val Tyr Ala Arg
    290                 295                 300

Ser Gly Pro Ala Glu Phe Gly Leu Thr Leu Thr Ser Pro Glu Tyr Asp
305                 310                 315                 320

Phe Asn Lys Leu Glu Asn Ile Asp Ala Phe Lys Ser Lys Trp Glu Gly
                325                 330                 335

Gln Ala Leu Ser Tyr Pro Ala Phe Ile Phe Thr Ser Ile Gly Ser Val
            340                 345                 350

Asn Met Ser Ala Phe Ala Lys Ala Lys Ile Val Leu Arg Ile Thr Ile
        355                 360                 365

Pro Lys Gly Ser Pro Gly Ala Tyr Leu Ser Ala Ile Pro Gly Tyr Ala
    370                 375                 380

Gly Gln Tyr Glu Val Leu Leu Asn His Gly Ser Lys Phe Lys Ile Asn
385                 390                 395                 400

Lys Ile Asp Ser Tyr Lys Asp Gly Thr Ile Thr Lys Leu Ile Val Asp
                405                 410                 415

Ala Thr Leu Ile Pro His His His His His His
            420                 425
```

IMMUNOGENIC COMPOSITION COMPRISING ELEMENTS OF C. DIFFICILE CDTB AND/OR CDTA PROTEINS

This application is filed pursuant to 35 U.S.C. §371 as a United States National Phase Application of International Patent Application Serial No. PCT/EP2013/077762 filed Dec. 20, 2013, which claims priority to United Kingdom Application No. GB 1223342.5 filed Dec. 23, 2012, and the entire contents of each of the foregoing applications are hereby incorporated by reference.

BACKGROUND

*C. difficile* is the most important cause of nosocomial intestinal infections and is the major cause of pseudomembranous colitis in humans (Bartlett et al *Am. J. Clin. Nutr.* 11 suppl:2521-6 (1980)). The overall associated mortality rate for individuals infected with *C. difficile* was calculated to be 5.99% within 3 months of diagnosis, with higher mortality associated with advanced age, being 13.5% in patients over 80 years (Karas et al *Journal of Infection* 561:1-9 (2010)). The current treatment for *C. difficile* infection is the administration of antibiotics (metronidazole and vancomycin), however there has been evidence of strains which are resistant to these antibiotics (Shah et al., Expert Rev. Anti Infect. Ther. 8(5), 555-564 (2010)). Accordingly there is a need for immunogenic compositions capable of inducing antibodies to, and/or a protective immune response to, *C. difficile.*

The enterotoxicity of *C. difficile* is primarily due to the action of two toxins, toxin A and toxin B. These are both potent cytotoxins (Lyerly et al Current Microbiology 21:29-32 (1990).

It has been demonstrated that fragments of toxin A, in particular fragments of the C-terminal domain, can lead to a protective immune response in hamsters (Lyerly et al Current Microbiology 21:29-32 (1990)), WO96/12802 and WO00/61762. However the present inventors have demonstrated that antibodies against toxin A and toxin B alone are not sufficient in order to prevent disease caused by certain strains, in particular serogroup 078 and 027 strains. For this reason vaccines which are capable of protecting against these strains are still required.

Some strains, but not all, also express the binary toxin (CDT). Similar to many other binary toxins, CDT is composed of two components—an enzymatically active component (CDTa) and a catalytically inert transport component (CDTb). The catalytically inert component facilitates translocation of the CDTa into the target cell.

CDTa has an ADP-ribosylating activity, which transfers the ADP-ribose moiety of NAD/NADPH to the monomeric actin (G-actin) in the target cell and thus preventing its polymerization to F-actin and resulting in disruption of the cytoskeleton and eventual cell death (Sundriyal et al, Protein expression and Purification 74 (2010) 42-48).

WO2013/112867 (Merck) describes vaccines against *Clostridium difficile* comprising recombinant *C. difficile* Toxin A and Toxin B and binary toxin A (CDTa) proteins comprising specifically defined mutations relative to the native toxin sequence that are described as substantially reducing or eliminating toxicity, in combination with binary toxin B (CDTb).

The present inventors have found, that binary toxin can be used to provide an improved vaccine against *C. difficile* particularly providing protection against several of the most concerning *C. difficile* strains (such as the 027 and 078 strains). Furthermore the present inventors have demonstrated, for the first time, that only CDTa or CDTb (not both) is required in order to generate antibodies which are capable of neutralizing strains expressing binary toxin. In addition the inventors have demonstrated, for the first time, that CDTa proteins comprising mutations which reduce the ADP-ribosylating activity of CDTa, are still capable of raising an immune response. In addition, the inventors have demonstrated that truncated CDTa proteins are capable of raising an immune response. Similarly the inventors have demonstrated that truncated CDTb proteins are capable of raising an immune response, that CDTb can raise an immune response when it is in its monomeric or polymeric form and that fusion proteins comprising CDTa and CDTb or CDTb fused to isolated toxin A and/or isolated toxin B are capable of raising an immune response. Finally, the inventors have demonstrated that an immunogenic composition comprising binary toxin can be improved by adding an adjuvant, in particular an adjuvant comprising an immunologically active saponin presented in the form of a liposome or an oil in water emulsion.

SUMMARY OF INVENTION

In a first aspect of the invention there is provided an immunogenic composition comprising an isolated *Clostridium difficile* CDTb protein wherein the composition does not further comprise an isolated protein having at least 70%, 75%, 80%, 85%, 90%, 95%, 98%, 99% or 100% similarity to SEQ ID NO: 1, SEQ ID NO: 31 or SEQ ID NO: 32.

In a second aspect of the invention there is provided an immunogenic composition comprising isolated *Clostridium difficile* CDTb protein wherein the isolated *Clostridium difficile* CDTb protein is a truncated CDTb protein comprising the receptor binding domain.

In a third aspect of the invention there is provided an immunogenic composition comprising isolated *Clostridium difficile* CDTb protein wherein the isolated *Clostridium difficile* CDTb protein is a mutated CDTb protein incapable of binding to CDTa.

In a fourth aspect of the invention there is provided an immunogenic composition comprising isolated *Clostridium difficile* CDTa protein wherein the isolated *Clostridium difficile* CDTa protein is a truncated CDTa protein which does not comprise the C-terminal domain.

In a fifth aspect the present invention provides an immunogenic composition comprising a fusion protein comprising a CDTa protein and a CDTb protein.

In a sixth aspect the present invention provides an immunogenic composition comprising a fusion protein between an isolated *Clostridium difficile* toxin A protein and/or an isolated *Clostridium difficile* toxin B protein fused to a CDTb protein.

In a seventh aspect the present invention provides a vaccine comprising the immunogenic composition of any one of the first five aspects and a pharmaceutically acceptable excipient.

In an eighth aspect the present invention provides the immunogenic composition of any one of the first five aspects or the vaccine of the sixth aspect, for use in the treatment or prevention of disease e.g. *C. difficile* disease.

In a ninth aspect the present invention provides the use of an immunogenic composition of any one of the first five aspects or the vaccine of the sixth aspect in the preparation of a medicament for the prevention or treatment of disease e.g. *C. difficile* disease.

In a tenth aspect the present invention provides a method of preventing or treating *C. difficile* disease comprising administering an immunogenic composition of any one of the first six aspects or the vaccine of the seventh aspect to a mammalian subject.

In a further aspect of the invention there is provided an immunogenic composition comprising an isolated *Clostridium difficile* CDTb protein.

In a further aspect of the invention there is provided an immunogenic composition comprising either an isolated *Clostridium difficile* CDTb protein or an isolated CDTa protein but does not comprise both an isolated CDTb protein and an isolated CDTa protein.

Novel polypeptides and nucleotides as defined herein also form further aspects of the invention.

BRIEF DESCRIPTION OF THE DRAWINGS

FIG. 1 (comprising FIGS. 1*a*-1*h*)—Graphs describing the size distribution of the different CdtA, CdtB and CdtA-CdtB fusion constructions as determined by sedimentation velocity analytical ultracentrifugation:

FIG. 2 (comprising FIGS. 2*a*-2*c*)—SDS PAGE profiles of CdtA, CdtB and CdtA-CdtB fusion constructions after purification:

DETAILED DESCRIPTION

Binary Toxin

Figure 1A:
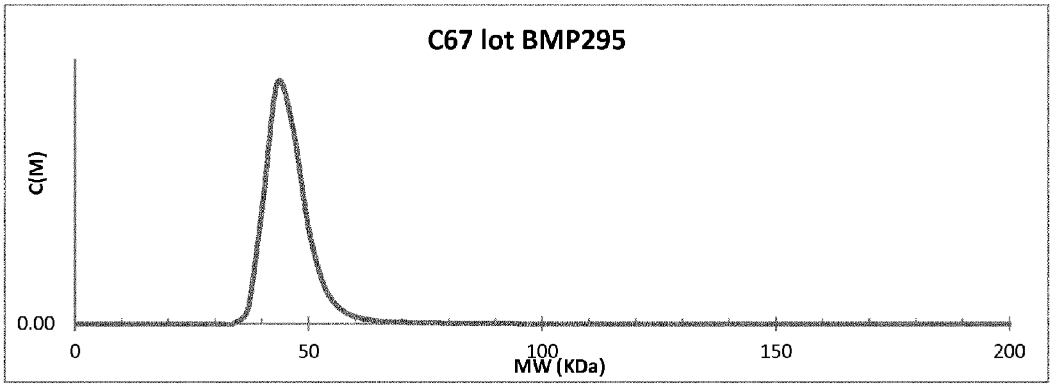
FIG. 1*a*: AUC of C67 (CdtA (aa44-463) mut E428Q-E430Q

The *Clostridium difficile* binary toxin comprises two different proteins, CDTa and CDTb. During infection CDTb is activated by proteolytic cleavage by a chymotrypsin-like protease to produce a CDTb protein lacking the prodomain (also referred to as CDTb"). Note that CDTb" also lacks the CDTb signal sequence, a CDTb protein lacking the signal sequence but not lacking the prodomain is referred to as CDTb'. After proteolytic activation the CDTb oligomerises and binds to CDTa to form the complete 'binary toxin'. The binding of the binary toxin to the cell receptors leads to receptor-mediated endocytosis. As the endosome acidifies the CDTb binding domain undergoes conformational changes that allow the CDTb oligomer to form a pore, the pore formation triggers translocation of the ADP-ribosyltransferase domain (CDTa) into the target cell.

CDTb

The present invention provides an immunogenic composition comprising an isolated *Clostridium difficile* CDTb protein. The present invention also provides an immunogenic composition comprising an isolated *Clostridium difficile* CDTb protein as the sole *C. difficile* antigen. As used herein the term "as the sole *C. difficile* antigen" means that the immunogenic composition comprising an isolated *Clostridium difficile* CDTb protein as the sole *C. difficile* antigen does not also comprise another antigen from *C. difficile* e.g. the immunogenic composition does not also comprise a toxin A, toxin B or CDTa protein.

The present invention provides an immunogenic composition comprising an isolated *Clostridium difficile* CDTb protein wherein the composition does not further comprise an isolated protein having at least 70%, 75%, 80%, 85%, 90%, 95%, 98%, 99% or 100% similarity to SEQ ID NO: 1, SEQ ID NO: 31 or SEQ ID NO: 32. According to the invention as herein described the term 'CDTb protein' encompasses SEQ ID NO:3 or fragments or variants of SEQ ID NO:3.

In one embodiment of this first aspect of the invention, the composition does not comprise an isolated *Clostridium difficile* CDTa protein.

In one embodiment of this aspect the isolated *Clostridium difficile* CDTb protein is or comprises (i) SEQ ID NO: 3; or (ii) a variant of CDTb having at least 80%, 85%, 88%, 90%, 92%, 95%, 98%, 99%, 100% sequence identity to SEQ ID NO:3; or (iii) a fragment of CDTb having at least 30, 50, 80, 100, 120, 150, 200, 250 or 300 contiguous amino acids of SEQ ID NO:3.

In one such aspect there is provided an immunogenic composition wherein the isolated *Clostridium difficile* CDTb protein is a variant of CDTb having at least 80%, 85%, 88%, 90%, 92%, 95%, 98%, 99%, 100% sequence identity to SEQ ID NO:3.

In another aspect there is provided an immunogenic composition wherein the isolated *Clostridium difficile* CDTb protein is a fragment of CDTb having at least 30, 50, 80, 100, 120, 150, 200, 250, 300, 350, 400, 450, 500, 550, 600, 650, 700, 750, 800 or 850 contiguous amino acids of SEQ ID NO: 3.

CDTb comprises multiple domains, in particular CDTb comprises a signal peptide and a prodomain both of which are cleaved as explained in the section entitled "Binary Toxin" above.

In one embodiment the isolated *Clostridium difficile* CDTb protein is a truncated CDTb protein with the signal peptide removed. The term 'truncated CDTb protein with the signal peptide removed' refers to a fragment or variant of SEQ ID NO: 3 with substantially all of the signal peptide removed (therefore which does not comprise amino acids corresponding to substantially all of the signal peptide), there may be a few amino acids of the signal peptide remaining, for example 2, 5, 10, 15 or 20 amino acids of the signal peptide may remain. The signal peptide corresponds to amino acids 1-48 (encompassing amino acids 1-42) of SEQ ID NO: 3 or their equivalents in a binary toxin protein isolated from a different strain of *C. difficile*, for example amino acids 1-42 of the amino acid sequence of CDTb from strain CD196 (Perelle, M. et al Infect. Immun., 65 (1997), pp. 1402-1407).

Suitably in this embodiment the isolated *Clostridium difficile* CDTb protein is or comprises (i) SEQ ID NO: 7 or SEQ ID NO: 16; or (ii) a variant of CDTb having at least 80%, 85%, 88%, 90%, 92%, 95%, 98%, 99%, 100% sequence identity to SEQ ID NO: 7 or SEQ ID NO:16; or (iii) a fragment of CDTb having at least 30, 50, 80, 100, 120, 150, 200, 250, 300, 350, 400, 450, 500, 550, 600, 650, 700, 750 or 800 contiguous amino acids of SEQ ID NO: 7 or SEQ ID NO:16. In one embodiment the truncated CDTb protein with the signal peptide removed is or comprises a variant of CDTb having at least 80%, 85%, 88%, 90%, 92%, 95%, 98%, 99%, 100% sequence identity to SEQ ID NO: 7 or SEQ ID NO:16. In a further embodiment the isolated truncated CDTb protein with the signal peptide removed is or comprises a fragment of CDTb having at least 30, 50, 80, 100, 120, 150, 200, 250, 300, 350, 400, 450, 500, 550, 600, 650, 700, 750, or 800 contiguous amino acids of SEQ ID NO: 7 or SEQ ID NO:16.

In one embodiment the isolated *Clostridium difficile* CDTb protein is a truncated CDTb protein with the prodomain removed. The term 'truncated CDTb protein with the prodomain removed' refers to a fragment or variant of SEQ ID NO: 3 with substantially all of the prodomain removed (therefore which does not comprise amino acids corresponding to substantially all of the prodomain), there may be a few amino acids of the prodomain remaining, for example 2, 5, 10, 15 or 20 amino acids of the prodomain may remain. The prodomain corresponds to amino acids 48-211 (encompassing amino acids 48-166) of SEQ ID NO:3 or their equivalents in a binary toxin protein isolated from a different strain of *C. difficile*. Optionally the truncated CDTb protein with the prodomain removed also lacks the CDTb signal sequence, the CDTb signal sequence corresponds to amino acids 1-48 (encompassing amino acids 1-42) of SEQ ID NO:3 or their equivalents in a different strain. The term 'truncated CDTb protein with the prodomain removed' may also refer to a fragment or variant of SEQ ID NO: 3 which is capable of oligomerising and binding to CDTa. In this embodiment of the invention the isolated *Clostridium difficile* CDTb protein suitably is or comprises (i) SEQ ID NO: 9 or SEQ ID NO: 51; or (ii) a variant of CDTb having at least 80%, 85%, 88%, 90%, 92%, 95%, 98%, 99%, 100% sequence identity to SEQ ID NO:9 or SEQ ID NO: 51; or (iii) a fragment of CDTb having at least 30, 50, 80, 100, 120, 150, 200, 250, 300, 350, 400, 450, 500, 550, 600 or 650 contiguous amino acids of SEQ ID NO:9 or SEQ ID NO: 51.

In one embodiment the truncated CDTb protein with the prodomain removed is or comprises a variant of CDTb having at least 80%, 85%, 88%, 90%, 92%, 95%, 98%, 99%, 100% sequence identity to SEQ ID NO:9. In a further embodiment the isolated truncated CDTb protein with the prodomain removed is or comprises a fragment of CDTb having at least 30, 50, 80, 100, 120, 150, 200, 250, 300, 350, 400, 450, 500, 550, 600, 650, 700, 750, or 800 contiguous amino acids of SEQ ID NO:9.

CDTb also comprises a receptor binding domain. In one embodiment the isolated *Clostridium difficile* CDTb protein is a truncated CDTb protein comprising the receptor binding domain. The term 'truncated CDTb protein comprising the receptor binding domain' refers to a fragment or variant of SEQ ID NO:3 with substantially all but the receptor binding domain removed (therefore which does not comprise amino acids corresponding to substantially all of the protein except for the receptor binding domain), there may be a few amino acids in addition to the receptor binding domain remaining, for example 2, 5, 10, 15 or 20 amino acids except for/in addition to the receptor binding domain. In one version, the receptor binding domain corresponds to amino acids 620-876 of SEQ ID NO:3, or their equivalents in a binary toxin protein isolated from a different strain of *C. difficile*. In another version, the receptor binding domain corresponds to amino acids 636-876 of SEQ ID NO:3 or their equivalents in a binary toxin protein isolated from a different strain of *C. difficile*.

In this embodiment the isolated *Clostridium difficile* CDTb protein suitably is or comprises (i) SEQ ID NO: 34 or SEQ ID NO: 36; or (i) a variant of CDTb having at least 80%, 85%, 88%, 90%, 92%, 95%, 98%, 99%, 100% sequence identity to SEQ ID NO: 34 or SEQ ID NO: 36; or (iii) a fragment of CDTb having at least 30, 50, 80, 100, 120, 150 or 200 contiguous amino acids of SEQ ID NO: 34 or SEQ ID NO: 36.

In another embodiment of this aspect of the invention, the isolated *Clostridium difficile* CDTb protein is a mutated CDTb protein incapable of binding to CDTa.

In this embodiment the isolated *Clostridium difficile* CDTb protein suitably is or comprises (i) SEQ ID NO: 50; or (i) a variant of CDTb having at least 80%, 85%, 88%, 90%, 92%, 95%, 98%, 99%, 100% sequence identity to SEQ ID NO: 50; or (iii) a fragment of CDTb having at least 30, 50, 80, 100, 120, 150, 200, 250 or 300 contiguous amino acids of SEQ ID NO: 50.

The CDTb protein varies in amino acid sequence between different strains, for this reason the amino acid numbering may differ between strains. For this reason the term 'equivalents in a different strain' refers to amino acids which correspond to those of a reference strain (e.g., *C. difficile* R20291 from which SEQ ID NO:1 and SEQ ID NO:3 are derived), but which are found in a toxin from a different strain and which may thus be numbered differently. A region of 'equivalent' amino acids may be determined by aligning the sequences of the toxins from the different strains. Example binary toxin producing strains of *C. difficile* include CD196, CCUG 20309, R8637, IS81, IS93, IS51, IS58, R6786, R7605, R10456 and R5989. The amino acids numbers provided throughout refer to those of reference strain R20291.

In one embodiment the isolated *Clostridium difficile* CDTb protein is a monomer of CDTb. In a further embodiment the isolated *Clostridium difficile* CDTb protein is a multimer of CDTb. In a further embodiment the isolated *Clostridium difficile* CDTb protein is a heptamer of CDTb.

In a second aspect the present invention provides immunogenic compositions comprising isolated *Clostridium difficile* CDTb protein wherein the isolated *Clostridium difficile* CDTb protein is a truncated CDTb protein comprising the receptor binding domain. In one embodiment of this aspect the isolated *Clostridium difficile* CDTb protein suitably is or comprises (i) SEQ ID NO: 34 or SEQ ID NO: 36; or (i) a variant of CDTb having at least 80%, 85%, 88%, 90%, 92%, 95%, 98%, 99%, 100% sequence identity to SEQ ID NO: 34 or SEQ ID NO: 36; or (iii) a fragment of CDTb having at least 30, 50, 80, 100, 120, 150 or 200 contiguous amino acids of SEQ ID NO: 34 or SEQ ID NO: 36.

In a third aspect the invention provides immunogenic compositions comprising isolated *Clostridium difficile* CDTb protein wherein the isolated *Clostridium difficile* CDTb protein is a mutated CDTb protein incapable of binding to CDTa. In one embodiment of this aspect, the isolated *Clostridium difficile* CDTb protein suitably is or comprises (i) SEQ ID NO: 50; or (i) a variant of CDTb having at least 80%, 85%, 88%, 90%, 92%, 95%, 98%, 99%, 100% sequence identity to SEQ ID NO: 50; or (iii) a fragment of CDTb having at least 30, 50, 80, 100, 120, 150, 200, 250 or 300 contiguous amino acids of SEQ ID NO: 50.

In one embodiment of the second and third aspects of the invention, the immunogenic composition comprises/further comprises an isolated *Clostridium difficile* CDTa protein comprising (i) SEQ ID NO: 1; or (ii) a variant of CDTa having at least 80%, 85%, 88%, 90%, 92%, 95%, 98%, 99%, 100% sequence identity to SEQ ID NO:1; or (iii) a fragment of CDTa having at least at least 30, 50, 80, 100, 120, 150, 200, 250, 300, 350 or 400 contiguous amino acids of SEQ ID NO:1.

CDTa

The present invention also provides immunogenic compositions comprising an isolated *Clostridium difficile* CDTa protein. The present invention also provides immunogenic compositions comprising an isolated *Clostridium difficile* CDTa protein as the sole *C. difficile* antigen. As used herein the term "as the sole *C. difficile* antigen" means that the immunogenic composition comprising an isolated *Clostridium difficile* CDTa protein as the sole *C. difficile* antigen does not also comprise another antigen from *C. difficile* e.g. the immunogenic composition does not also comprise a toxin A, toxin B or CDTb protein. According to the invention as herein described the term 'CDTa protein' encompasses SEQ ID NO:1 or fragments or variants of SEQ ID NO:1. In one embodiment the isolated *Clostridium difficile* CDTa protein comprises a variant of CDTa having at least 80%, 85%, 88%, 90%, 92%, 95%, 98%, 99%, 100% sequence identity to SEQ ID NO:1. In a further embodiment the isolated *Clostridium difficile* CDTa protein comprises a fragment of CDTa having at least at least 30, 50, 80, 100, 120, 150, 200, 250, 300, 350 or 400 contiguous amino acids of SEQ ID NO:1.

CDTa comprises two domains, the C-terminal domain is responsible for the ADP ribosyltransferase activity whilst the N-terminal domain is responsible for interacting with CDTb.

In one embodiment of the first three aspects of the invention, the immunogenic composition comprises/further comprises an isolated *Clostridium difficile* CDTa protein. Suitably the isolated *Clostridium difficile* CDTa protein is a truncated CDTa protein. "A truncated CDTa protein" as used herein means a CDTa protein that does not achieve its full length or its proper form, and thus is missing some of the amino acid residues that are present in full length CDTa of SEQ ID NO: 1, and which cannot perform the function for which it was intended because its structure is incapable of doing so, e.g. ADP ribosyltransferase activity and/or interacting with CDTb.

Suitably the isolated *Clostridium difficile* CDTa protein is a truncated CDTa protein which does not comprise the C-terminal domain. The term 'truncated CDTa protein which does not comprise the C-terminal domain' refers to a fragment or variant of SEQ ID NO:1 which does not comprise a substantial portion of the C-terminal domain, there may be a few amino acids of the C-terminal domain remaining, for example, 2, 5, 10, 15, 20, 25, 30, 35 or 50 amino acids of the C-terminal domain may remain. The C-terminal domain corresponds to amino acids 267-463 of SEQ ID NO:1 or their equivalents in a CDTa protein isolated from a different strain of *C. difficile*. In this embodiment the truncated *Clostridium difficile* CDTa protein suitably is or comprises (i) SEQ ID NO: 14 or SEQ ID NO: 15

(i) a variant of CDTa having at least 80%, 85%, 88%, 90%, 92%, 95%, 98%, 99%, 100% sequence identity to SEQ ID NO: 14 or SEQ ID NO: 15; or (iii) a fragment of CDTa having at least 30, 50, 80, 100, 120, 150, or 190 contiguous amino acids of SEQ ID NO: 14 or SEQ ID NO: 15.

In one embodiment the truncated CDTa protein which does not comprise the C-terminal domain is a variant of CDTa having at least 80%, 85%, 88%, 90%, 92%, 95%, 98%, 99%, 100% sequence identity to SEQ ID NO:13. In a further embodiment the truncated CDTa protein which does not comprise the C-terminal domain is a variant of CDTa having at least 30, 50, 80, 100, 120, 150, or 190 contiguous amino acids of SEQ ID NO:13.

In a fourth aspect the invention provides an immunogenic composition comprising isolated *Clostridium difficile* CDTa protein wherein the isolated *Clostridium difficile* CDTa protein is a truncated CDTa protein which does not comprise the C-terminal domain. In one embodiment of this aspect, the isolated *Clostridium difficile* CDTa protein suitably is or comprises (i) SEQ ID NO: 14 or SEQ ID NO: 15; or (ii) a variant of CDTa having at least 80%, 85%, 88%, 90%, 92%, 95%, 98%, 99%, 100% sequence identity to SEQ ID NO:14 or SEQ ID NO: 15; or (iii) a fragment of CDTa having at least 30, 50, 80, 100, 120, 150, or 190 contiguous amino acids of SEQ ID NO:14 or SEQ ID NO: 15.

In a further embodiment of any of the aspects of the invention, the isolated *Clostridium difficile* CDTa protein suitably contains a mutation which reduces its ADP-ribosyltransferase activity. For example the isolated *Clostridium difficile* CDTa protein has a mutation from glutamate to another amino acid at position 428. The term 'has a mutation at position 428' refers to CDTa proteins which have a mutation at this exact location but also to a CDTa protein which is isolated from a different strain and which has a mutation at an equivalent position. The CDTa protein varies in amino acid sequence between different strains, for this reason the amino acid numbering may differ between strains, thus a CDTa protein from a different strain may have a corresponding glutamate which is not number 428 in sequence. In one embodiment the isolated *Clostridium difficile* CDTa protein has a mutation from glutamate to glutamine at position 428.

In a further embodiment of any of the aspects of the invention, the isolated *Clostridium difficile* CDTa protein suitably has a mutation from glutamate to a different amino acid at position 430, the term 'has a mutation at position 430' refers to proteins which have this exact location but also to a CDTa protein which is isolated from a different strain and which has a mutation at an equivalent position. In one embodiment the isolated *Clostridium difficile* CDTa protein has a mutation from glutamate to glutamine at position 430.

In a further embodiment of any of the aspects of the invention, the isolated *Clostridium difficile* CDTa protein suitably is or comprises (i) SEQ ID NO: 46; SEQ ID NO: 48; SEQ ID NO: 52; or SEQ ID NO: 54; or (ii) a variant of CDTa having at least 80%, 85%, 88%, 90%, 92%, 95%, 98%, 99%, 100% sequence identity to SEQ ID NO: 46; SEQ ID NO: 48; SEQ ID NO: 52; or SEQ ID NO: 54; or (iii) a fragment of CDTa having at least 30, 50, 80, 100, 120, 150, 200, 250, 300, 350 or 400 contiguous amino acids of SEQ ID ID NO: 46; SEQ ID NO: 48; SEQ ID NO: 52; or SEQ ID NO: 54.

In a further embodiment of any of the aspects of the invention, the isolated *Clostridium difficile* CDTa protein suitably is or comprises (i) SEQ ID NO: 48; or (ii) a variant of CDTa having at least 80%, 85%, 88%, 90%, 92%, 95%, 98%, 99%, 100% sequence identity to SEQ ID NO: 48; or (iii) a fragment of CDTa having at least 30, 50, 80, 100, 120, 150, 200, 250, 300, 350 or 400 contiguous amino acids of SEQ ID ID NO: 48.

Immunogenic Compositions with CDTa and/or CDTb

In a further embodiment there is provided an immunogenic composition which comprises a CDTb protein but does not comprise a CDTa protein, for example the immunogenic composition does not comprise a variant of CDTa having at least 95%, 98%, 99%, or 100% sequence identity to SEQ ID NO:1 or a fragment of CDTa having at least at least 250, 400 or 450. contiguous amino acids of SEQ ID NO:1.

In a further embodiment there is provided an immunogenic composition which comprises a CDTa protein but does not comprise a CDTb protein, for example the immunogenic composition does not comprise a variant of CDTb having at least 95%, 98%, 99%, or 100% sequence identity to SEQ ID NO:3 or a fragment of CDTb having at least 700, 750, or 800 contiguous amino acids of CDTb.

In a further embodiment there is provided an immunogenic composition which comprises either an isolated *Clostridium difficile* CDTb protein or an isolated CDTa protein but does not comprise both an isolated CDTb protein and an isolated CDTa protein.

In a further embodiment there is provided a fusion protein comprising a CDTa protein and a CDTb protein. In another embodiment there is provided immunogenic compositions comprising a fusion protein comprising a CDTa protein and a CDTb protein.

Fusion Proteins Comprising a CDTa Protein and a CDTb Protein

In a fifth aspect, the invention provides immunogenic compositions comprising a fusion protein comprising a CDTa protein and a CDTb protein. In one embodiment of this aspect, the CDTa protein suitably is truncated. For example, the CDTa protein suitably does not comprise the C-terminal domain. In this aspect, the CDTb protein suitably is truncated. In this embodiment, the CDTb protein suitably comprises the receptor binding domain.

In one embodiment of this aspect of the invention, the fusion protein suitably is or comprises (i) SEQ ID NO: 40; SEQ ID NO: 41; SEQ ID NO: 42; or SEQ ID NO: 43; or (ii) a variant having at least 80%, 85%, 88%, 90%, 92%, 95%, 98%, 99%, 100% sequence identity to SEQ ID NO: 40; SEQ ID NO: 41; SEQ ID NO: 42; or SEQ ID NO: 43; or (iii) a fragment having at least 30, 50, 80, 100, 120, 150, 200, 250, 300, 350 or 400 contiguous amino acids of SEQ ID NO: 40; SEQ ID NO: 41; SEQ ID NO: 42; or SEQ ID NO: 43.

"Fusion polypeptide" or "fusion protein" refers to a protein having at least two heterologous polypeptides (e.g. at least two *Mycobacterium* sp. polypeptides) covalently linked, either directly or via an amino acid linker. It may also refer to a protein having at least two heterologous polypeptides linked non-covalently. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. This term also refers to conservatively modified variants, polymorphic variants, alleles, mutants, immunogenic fragments, and interspecies homologs of the antigens that make up the fusion protein.

The term "fused" refers to the linkage e.g. covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46 (1985); Murphy et al., Proc. Natl. Acad. Sci. USA 83:8258-8262 (1986); U.S. Pat. No. 4,935,233 and U.S. Pat. No. 4,751,180. The linker sequence may generally be from 1 to about 50 amino acids in length for example 1, 5, 10, 15, 20, 25, 30, 35 or 40 amino acids in length. Linker sequences are not required when the first and second polypeptides have non-essential N-terminal amino acid regions that can be used to separate the functional domains and prevent steric interference.

In one embodiment of any of the aspects of the invention, the immunogenic composition elicits antibodies that neutralize CDTa or CDTb or both. In a further embodiment the composition elicits antibodies that neutralize binary toxin.

Whether a composition elicits antibodies against a toxin can be measured by immunising mice with the immunogenic composition, collecting sera and analysing the anti-toxin titres of the sera using by ELISA. The sera should be compared to a reference sample obtained from mice which have not been immunised. The composition of the invention elicits antibodies that neutralise CDTa if the sera against the polypeptide gives an ELISA readout more than 10%, 20%, 30%, 50%, 70%, 80%, 90%, or 100% higher than the reference sample.

In a further embodiment the immunogenic compositions of the invention elicits a protective immune response in a mammalian host against strains of *C. difficile*. In one embodiment the mammalian host is selected from the group consisting of mouse, rabbit, guinea pig, non-human primate, monkey and human. In one embodiment the mammalian host is a mouse. In a further embodiment the mammalian host is a human.

Whether an immunogenic composition elicits a protective immune response in a mammalian host against strains of *C. difficile* can be determined using a challenge assay. In such an assay the mammalian host is vaccinated with the immunogenic composition and challenged by exposure to *C. difficile*, the time which the mammal survives after challenge is compared with the time which a reference mammal that has not been immunised with the immunogenic composition survives. An immunogenic composition elicits a protective immune response if a mammal immunised with the immunogenic composition survives at least 10%, 20%, 30%, 50%, 80%, 80%, 90%, or 100% longer than a reference mammal which has not been immunised after challenge with *C. difficile*.

Toxin A and Toxin B

In one embodiment of any of the aspects of the invention, the immunogenic compositions of the invention further comprise an isolated *Clostridium difficile* toxin A protein and/or an isolated *C. difficile* toxin B protein.

The term 'isolated *Clostridium difficile* toxin A protein' refers to a fragment or variant of SEQ ID NO: 31. In one embodiment the isolated *Clostridium difficile* toxin A protein is a fragment comprising 50, 100, 150, 200, 250, 300, 500, 750, 1000, 1250, 1500, 1750, 2000 or 2500 contiguous amino acids of SEQ ID NO:31. In one embodiment the isolated *Clostridium difficile* toxin A protein is a variant comprising 80%, 85%, 90%, 92%, 95%, 98%, 99% or 100% identity to SEQ ID NO:31.

The term 'isolated *Clostridium difficile* toxin B protein' refers to a fragment or variant of SEQ ID NO: 32. In one embodiment the isolated *Clostridium difficile* toxin B protein is a fragment comprising 50, 100, 150, 200, 250, 300, 500, 750, 1000, 1250, 1500, 1750 or 2000 SEQ ID NO:32. In one embodiment the isolated *Clostridium difficile* toxin B protein is a variant comprising 80%, 85%, 90%, 92%, 95%, 98%, 99% or 100% identity to SEQ ID NO:32.

In one embodiment the isolated *Clostridium difficile* toxin A protein comprises a repeating domain fragment. The term 'toxin A repeating domain' refers to the C-terminal domain of the toxin A protein from *C. difficile*, comprising repeated sequences. The toxin A repeating domain refers to amino acids 1832-2710 of toxin A from strain VPI10463 (ATCC43255) and their equivalents in a different strain, the sequence of amino acids 1832-2710 from strain VPI10463 (ATCC43255) corresponds to amino acids 1832-2710 of SEQ ID NO: 31. In a further embodiment the isolated *Clostridium difficile* toxin A protein comprises a fragment of the toxin A N-terminal domain. The toxin A N-terminal domain refers to amino acids 1-1831 of toxin A from strain VBI10463 (ATCC43255) and their equivalents in a different strain, the sequence of amino acids 1-1831 of SEQ ID NO: 31.

In one embodiment the isolated *Clostridium difficile* toxin B protein comprises a toxin B repeating domain fragment. The term 'toxin B repeating domain' refers to the C-terminal domain of the toxin B protein from *C. difficile*. This domain refers to amino acids 1834-2366 from strain VPI10463 (ATCC43255) and their equivalents in a different strain, the sequence of amino acids 1834-2366 from strain VPI10463 (ATCC43255) corresponds to amino acids 1834-2366 of SEQ ID NO: 32. In a further embodiment the isolated *Clostridium difficile* toxin B protein comprises a fragment of the toxin B N-terminal domain. The toxin B N-terminal domain refers to amino acids 1-1833 of toxin B from strain VBI10463 (ATCC43255) and their equivalents in a different strain, the sequence of amino acids 1-1833 of SEQ ID NO: 32.

The *C. difficile* toxins A and B are conserved proteins, however the sequence differs a small amount between strains, moreover the amino acid sequence for toxins A and B in different strains may differ in number of amino acids.

For these reasons the terms toxin A repeating domain and/or toxin B repeating domain to refer to a sequence which is a variant with 90%, 95%, 98%, 99% or 100% sequence identity to amino acids 1832-2710 of SEQ ID NO: 31 or a variant with 90%, 95%, 98%, 99% or 100% sequence identity to amino acids 1834-2366 of SEQ ID NO:32. Similarly the terms toxin a N-terminal domain and/or toxin B N terminal domain refer to a sequence which is avariant with 90%, 95%, 98%, 99% or 100% sequence identity to amino acids 1-1831 of SEQ ID NO:31 or a variant with 90%, 95%, 98%, 99% or 100% sequence identity to amino acids 1-1833 of SEQ ID NO:32.

Furthermore the amino acid numbering may differ between the C-terminal domains of toxin A (or toxin B) from one strain and toxin A (or toxin B) from another strain. For this reason the term 'equivalents in a different strain' refers to amino acids which correspond to those of a reference strain (e.g., *C. difficile* VPI10463), but which are found in a toxin from a different strain and which may thus be numbered differently. A region of 'equivalent' amino acids may be determined by aligning the sequences of the toxins from the different strains. The amino acids numbers provided throughout refer to those of strain VPI10463.

In a further embodiment of any of the aspects of the invention, the isolated *C. difficile* toxin A protein and the isolated *C. difficile* toxin B protein form a fusion protein. In one embodiment the fusion protein is 80%, 85%, 90%, 95%, 98%, 99% or 100% identical to a sequence selected from the group consisting of SEQ ID NO: 18, 19, 20, 21, 22, 24, 26, 28 and 30. In a further embodiment the fusion protein is a fragment of at least 800, 850, 900 or 950 contiguous amino acids of a sequence selected from the group consisting of SEQ ID NO: 18, 19, 20, 21, 22, 24, 26, 28 and 30.

In a further embodiment of any of the aspects of the invention the immunogenic composition comprises/further comprises a fusion protein between an isolated *Clostridium difficile* toxin A protein and/or an isolated *Clostridium difficile* toxin B protein fused to a CDTb protein or to a truncated CDTb protein. In one embodiment there is provided a fusion protein comprising a fragment of toxin A, a fragment of toxin B and a CDTb protein, for example the fusion protein may comprise a fragment or variant of SEQ ID NO:18, 19, 20, 21, 22, 24, 26, 28 or 30 fused to a CDTb protein. For example the fusion protein may comprise a fragment or variant of SEQ ID NO:18, 19, 20, 21, 22, 24, 26, 28 or 30 fused to a truncated CDTb protein.

In one embodiment the fusion protein suitably is or comprises (i) SEQ ID NO: 44 or SEQ ID NO: 45; or (ii) a variant having at least 80%, 85%, 90%, 95%, 98%, 99% or 100% sequence identity to SEQ ID NO: 44 or SEQ ID NO: 45; or (iii) a fragment of at least 800, 850, 900 or 950 contiguous amino acids of a sequence selected from the group consisting of SEQ ID NO: 44 or SEQ ID NO: 45.

Fragments

The term "fragment" as defined herein may refer to a fragment comprising a T cell epitope. T cell epitopes are short contiguous stretches of amino acids which are recognised by T cells (e.g. CD4+ or CD8+ T cells). Identification of T cell epitopes may be achieved through epitope mapping experiments which are well known to the person skilled in the art (see, for example, Paul, *Fundamental Immunology,* 3rd ed., 243-247 (1993); Beiβbarth et al *Bioinformatics* 2005 21(Suppl. 1):i29-i37).

Suitably the fragments of the invention are immunogenic fragments. "Immunogenic fragments" according to the present invention will typically comprise at least 9 contiguous amino acids from the full length polypeptide sequence (e.g. at least 10), such as at least 12 contiguous amino acids (e.g. at least 15 or at least 20 contiguous amino acids), in particular at least 50 contiguous amino acids, such as at least 100 contiguous amino acids (for example at least 200 contiguous amino acids). Suitably the immunogenic fragments will be at least 20%, such as at least 50%, at least 70% or at least 80% of the length of the full length polypeptide sequence.

It will be understood that in a diverse out-bred population, such as humans, different HLA types mean that specific epitopes may not be recognised by all members of the population. Consequently, to maximise the level of recognition and scale of immune response to a polypeptide, it is generally desirable that an immunogenic fragment contains a plurality of the epitopes from the full length sequence (suitably all epitopes).

Variants

"Variants" or "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences.

In respect of variants of a protein sequence, the skilled person will recognise that individual substitutions, deletions or additions to polypeptide, which alters, adds or deletes a single amino acid or a small percentage of amino acids is a "conservatively modified variant" where the alteration(s) results in the substitution of an amino acid with a functionally similar amino acid or the substitution/deletion/addition of residues which do not substantially impact the biological function of the variant.

Conservative substitution tables providing functionally similar amino acids are well known in the art. Such conservatively modified variants are in addition to and do not exclude polymorphic variants, interspecies homologs, and alleles of the invention.

A polypeptide of the invention (such as a CDTa protein or a CDTb protein) may contain a number of conservative substitutions (for example, 1-50, such as 1-25, in particular 1-10, and especially 1 amino acid residue(s) may be altered) when compared to the reference sequence. In general, such conservative substitutions will fall within one of the amino-acid groupings specified below, though in some circumstances other substitutions may be possible without substantially affecting the immunogenic properties of the antigen. The following eight groups each contain amino acids that are typically conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* 1984).

Suitably such substitutions do not occur in the region of an epitope, and do not therefore have a significant impact on the immunogenic properties of the antigen.

Polypeptide variants may also include those wherein additional amino acids are inserted compared to the reference sequence, for example, such insertions may occur at 1-10 locations (such as 1-5 locations, suitably 1 or 2 locations, in particular 1 location) and may, for example, involve the addition of 50 or fewer amino acids at each location (such as 20 or fewer, in particular 10 or fewer, especially 5 or fewer). Suitably such insertions do not occur in the region of an epitope, and do not therefore have a significant impact on the immunogenic properties of the antigen. One example of insertions includes a short stretch of histidine residues (e.g. 2-6 residues) to aid expression and/or purification of the antigen in question.

Polypeptide variants include those wherein amino acids have been deleted compared to the reference sequence, for example, such deletions may occur at 1-10 locations (such as 1-5 locations, suitably 1 or 2 locations, in particular 1 location) and may, for example, involve the deletion of 50 or fewer amino acids at each location (such as 20 or fewer, in particular 10 or fewer, especially 5 or fewer). Suitably such deletions do not occur in the region of an epitope, and do not therefore have a significant impact on the immunogenic properties of the antigen.

The skilled person will recognise that a particular polypeptide variant may comprise substitutions, deletions and additions (or any combination thereof).

Variants preferably exhibit at least about 70% identity, more preferably at least about 80% identity and most preferably at least about 90% identity (such as at least about 95%, at least about 98% or at least about 99%) to the associated reference sequence.

The terms "identical" or percent "identity," in the context of two or more nucleic acids or polypeptide sequences, refer to two or more sequences or sub-sequences that are the same or have a specified percentage of amino acid residues or nucleotides that are the same (i.e., 70% identity, optionally 75%, 80%, 85%, 90%, 95%, 98% or 99% identity over a specified region), when compared and aligned for maximum correspondence over a comparison window, or designated region as measured using, for example, one of the following sequence comparison algorithms or by manual alignment and visual inspection. Such sequences are then said to be "substantially identical." This definition also refers to the compliment of a test sequence. Optionally, the identity exists over a region that is at least about 25 to about 50 amino acids or nucleotides in length, or optionally over a region that is 75-100 amino acids or nucleotides in length. Suitably, the comparison is performed over a window corresponding to the entire length of the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, references to a segment in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Polynucleotide Identification and Characterisation

Polynucleotides encoding the *Clostridium difficile* CDTa, CDTb, Toxin A and Toxin B proteins of the invention may be identified, prepared and/or manipulated using any of a variety of well established techniques. For example, a polynucleotide may be identified, as described in more detail below, by screening a microarray of cDNAs. Such screens may be performed, for example, using a Synteni microarray (Palo Alto, Calif.) according to the manufacturer's instructions (and essentially as described by Schena et al., *Proc. Natl. Acad. Sci. USA* 93:10614-10619 (1996) and Heller et al., *Proc. Natl. Acad. Sci. USA* 94:2150-2155 (1997)). Alternatively, polynucleotides may be amplified from cDNA prepared from cells expressing the proteins described herein, such as *M. tuberculosis* cells. Such polynucleotides may be amplified via polymerase chain reaction (PCR). For this approach, sequence-specific primers may be designed based on the sequences provided herein, and may be purchased or synthesised.

An amplified portion of a polynucleotide may be used to isolate a full length gene from a suitable library (e.g., a *M. tuberculosis* cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridisation techniques, a partial sequence may be labeled (e.g., by nick-translation or end-labeling with $^{32}P$) using well known techniques. A bacterial or bacteriophage library is then generally screened by hybridising filters containing denatured bacterial colonies (or lawns containing phage plaques) with the labeled probe (see Sambrook et al., *Molecular Cloning: A Laboratory Manual* (2000)). Hybridising colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then be assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22-30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186 (1988)), which uses restriction enzymes to generate a fragment in the known region of the gene. The fragment is then circularised by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridises to a polyA region or vector sequence, to identify sequences that are 5' and 3' of a known sequence. Additional techniques include capture PCR (Lagerstrom et al., *PCR Methods Applic.* 1:111-19 (1991)) and walking PCR (Parker et al., *Nucl. Acids. Res.* 19:3055-60 (1991)). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

Polynucleotide sequences or fragments thereof which encode the *Clostridium difficile* CDTa, CDTb, Toxin A and Toxin B proteins, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

Natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognised by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesised, in whole or in part, using chemical methods well known in the art (see Caruthers, M. H. et al., *Nucl. Acids Res. Symp. Ser.* pp. 215-223 (1980), Horn et al., *Nucl. Acids Res. Symp. Ser.* pp. 225-232 (1980)). Alternatively, the protein itself may be produced using chemical methods to synthesize the amino acid sequence of a polypeptide, or a portion thereof. For example, peptide synthesis can be performed using various solid-phase techniques (Roberge et al., *Science* 269:202-204 (1995)) and automated synthesis may be achieved, for example, using the ABI 431A Peptide Synthesizer (Perkin Elmer, Palo Alto, Calif.).

A newly synthesised peptide may be substantially purified by preparative high performance liquid chromatography (e.g., Creighton, *Proteins, Structures and Molecular Principles* (1983)) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into an appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning, A Laboratory Manual* (2000), and Ausubel et al., *Current Protocols in Molecular Biology* (updated annually).

A variety of expression vector/host systems may be utilised to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 μlasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 μlasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503-5509 (1989)); and the like. pGEX Vectors (Promega, Madison, Wis.; GE Healthcare.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae* or *Pichia* such as *Pichia pastoris* for example, a number of vectors containing constitutive or inducible promoters such as alpha factor, alcohol oxidase, and PGH may be used. Other vectors containing constitutive or inducible promoters include GAP, PGK, GAL and ADH. For reviews, see Ausubel et al. (supra) and Grant et al., *Methods Enzymol.* 153:516-544 (1987) and Romas et al. *Yeast* 8 423-88 (1992).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in *McGraw Hill Yearbook of Science and Technology pp.* 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells. Methods and protocols for working with adenovirus vectors are reviewed in Wold, *Adenovirus Methods and Protocols,* 1998. Additional references regarding use of adenovirus vectors can be found in *Adenovirus: A Medical Dictionary, Bibliography, and Annotated Research Guide to Internet References,* 2004.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-32 (1977)) and adenine phosphoribosyltransferase (Lowy et al., *Cell* 22:817-23 (1990)) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilise indole in place of tryptophan, or hisD, which allows cells to utilise histinol in place of histidine (Hartman & Mulligan, *Proc. Natl. Acad. Sci. U.S.A.* 85:8047-51 (1988)). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridisations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilising monoclonal antibodies reactive to two non-interfering epitopes on a given polypeptide may be preferred for some applications, but a competitive binding assay may also be employed. These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labelled hybridisation or PCR probes for detecting sequences related to polynucleotides include oligolabeling, nick translation, end-labelling or PCR amplification using a labelled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilised immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilised metal ion affinity chromatography) as described in Porath et al., *Prot. Exp. Purif.* 3:263-281 (1992) while the enterokinase cleavage site provides a means for purifying the desired polypeptide from the fusion protein. A discussion of vectors which contain fusion proteins is provided in Kroll et al., *DNA Cell Biol.* 12:441-453 (1993)).

Polypeptide Compositions

Generally, a polypeptide of use in the invention (for example the *Clostridium difficile* CDTa, CDTb, Toxin A and Toxin B proteins) will be an isolated polypeptide (i.e. separated from those components with which it may usually be found in nature).

For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Polypeptides for use in the invention, immunogenic fragments thereof, and other variants having less than about 100 amino acids, and generally less than about 50 amino acids, may also be generated by synthetic means, using techniques well known to those of ordinary skill in the art. For example, such polypeptides may be synthesised using any of the commercially available solid-phase techniques, such as the Merrifield solid-phase synthesis method, where amino acids are sequentially added to a growing amino acid chain. See Merrifield, *J. Am. Chem. Soc.* 85:2149-2146 (1963). Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, examples of such proteins include tetanus, tuberculosis and hepatitis proteins (see, e.g., Stoute et al., *New Engl. J. Med.* 336:86-91 (1997)). A fusion partner may, for example, assist in providing T helper epitopes (an immunological fusion partner), preferably T helper epitopes recognised by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46 (1985); Murphy et al., *Proc. Natl. Acad. Sci. USA* 83:8258-8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

Adjuvants

In a further embodiment of any of the aspects of the invention, the immunogenic composition further comprises an adjuvant. In one embodiment the adjuvant comprises aluminium hydroxide or aluminium phosphate. Alternatively the immunogenic composition of the invention may comprise an aluminium-free adjuvant, the immunogenic composition is formulated with an adjuvant that is free of aluminum or aluminum salts, that is, an aluminum-free adjuvant or adjuvant system.

In certain embodiments, the immunogenic composition is formulated with an adjuvant comprising an immunologically active saponin fraction presented in the form of a liposome. The adjuvant may further comprise a lipopolysaccharide. The adjuvant may include QS21. For example, in one embodiment, the adjuvant contains QS21 in a liposomal formulation. In one embodiment, the adjuvant system includes 3D-MPL and QS21. For example, in one embodiment, the adjuvant contains 3D-MPL and QS21 in a liposomal formulation. Optionally, the adjuvant system also contains cholesterol. In one specific embodiment, the adjuvant includes QS21 and cholesterol. Optionally, the adjuvant system contains 1, 2-Dioleoyl-sn-Glycero-3-phosphocholine (DOPC). For example, in one specific adjuvant system contains cholesterol, DOPC, 3D-MPL and QS21.

In one specific example, the immunogenic composition includes an adjuvant formulated in a dose that includes: from about 0.1 to about 0.5 mg cholesterol; from about 0.25 to about 2 mg DOPC; from about 10 μg to about 100 μg 3D-MPL; and from about 10 μg to about 100 μg QS21. In another specific example, the immunogenic composition includes an adjuvant formulated in a dose that includes: from about 0.1 to about 0.5 mg cholesterol; from about 0.25 to about 2 mg DOPC; from about 10 μg to about 70 μg 3D-MPL; and from about 10 μg to about 70 μg QS21. In one specific formulation, the adjuvant is formulated in a single dose that contains: about 0.25 mg cholesterol; about 1.0 mg DOPC; about 50 μg 3D-MPL; and about 50 μg QS21. In other embodiments, the immunogenic composition is formulated with a fractional dose (that is a dose, which is a fraction of the preceding single dose formulations, such as one half of the preceding quantity of components (cholesterol, DOPC, 3D-MPL and QS21), ¼ of the preceding quantity of components, or another fractional dose (e.g., ⅓, ⅙, etc.) of the preceding quantity of components.

In one embodiment, the immunogenic compositions according to the invention include an adjuvant containing combinations of lipopolysaccharide and Quillaja saponins that have been disclosed previously, for example in EP0671948. This patent demonstrated a strong synergy when a lipopolysaccharide (3D-MPL) was combined with a Quillaja saponin (QS21).

The adjuvant may further comprise immunostimulatory oligonucleotides (for example, CpG) or a carrier.

A particularly suitable saponin for use in the present invention is Quil A and its derivatives. Quil A is a saponin preparation isolated from the South American tree *Quillaja Saponaria* Molina and was first described by Dalsgaard et al. in 1974 ("Saponin adjuvants", Archiv. für die gesamte Virusforschung, Vol. 44, Springer Verlag, Berlin, p 243-254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS21 is a natural saponin derived from the bark of *Quillaja saponaria* Molina, which induces CD8+ cytotoxic T cells (CTLs), Th1 cells and a predominant IgG2a antibody response and is a preferred saponin in the context of the present invention.

When the adjuvant comprises an immunologically active saponin fraction presented in the form of a liposome, the adjuvant may further comprise a sterol. Suitably the sterol is provided at a ratio of saponin:sterol of from 1:1 to 1:100 w/w, such as from 1:1 to 1:10 w/w; or 1:1 to 1:5 w/w.

In a specific embodiment, QS21 is provided in its less reactogenic composition where it is quenched with an exogenous sterol, such as cholesterol for example. Several particular forms of less reactogenic compositions wherein QS21 is quenched with an exogenous cholesterol exist. In a specific embodiment, the saponin/sterol is in the form of a liposome structure (WO 96/33739, Example 1). In this embodiment the liposomes suitably contain a neutral lipid, for example phosphatidylcholine, which is suitably non-crystalline at room temperature, for example eggyolk phosphatidylcholine, dioleoyl phosphatidylcholine (DOPC) or dilauryl phosphatidylcholine. The liposomes may also contain a charged lipid which increases the stability of the lipsome-QS21 structure for liposomes composed of saturated lipids. In these cases the amount of charged lipid is suitably 1-20% w/w, preferably 5-10%. The ratio of sterol to phospholipid is 1-50% (mol/mol), suitably 20-25%.

Suitable sterols include β-sitosterol, stigmasterol, ergosterol, ergocalciferol and cholesterol. In one particular embodiment, the adjuvant composition comprises cholesterol as sterol. These sterols are well known in the art, for example cholesterol is disclosed in the Merck Index, 11th Edn., page 341, as a naturally occurring sterol found in animal fat.

Where the active saponin fraction is QS21, the ratio of QS21: sterol will typically be in the order of 1:100 to 1:1 (w/w), suitably between 1:10 to 1:1 (w/w), and preferably 1:5 to 1:1 (w/w). Suitably excess sterol is present, the ratio of QS21:sterol being at least 1:2 (w/w). In one embodiment, the ratio of QS21:sterol is 1:5 (w/w). The sterol is suitably cholesterol.

In one embodiment, the invention provides a dose of an immunogenic composition comprising immunologically active saponin, preferably QS21, at a level of about 1-about 70 μg per dose, for example at an amount of about 50 μg.

In one embodiment, the invention provides a dose of an immunogenic composition comprising immunologically active saponin, preferably QS21, at a level of 60 μg or less, for example between 1 and 60 μg. In one embodiment, the dose of the immunogenic composition comprises QS21 at a level of approximately around 50 μg, for example between 45 and 55 μg, suitably between 46-54 μg or between 47 and 53 μg or between 48 and 52 μg or between 49 and 51 μg, or 50 μg.

In another embodiment the dose of the immunogenic composition comprises QS21 at a level of around 25 μg, for example between 20-30 μg, suitably between 21-29 μg or between 22 and 28 μg or between 23 and 27 μg or between 24 and 26 μg, or 25 μg.

In another embodiment, the dose of the immunogenic composition comprises QS21 at a level of around 10 μg per, for example between 5 and 15 μg, suitably between 6 and 14 μg, for example between 7 and 13 μg or between 8 and 12 μg or between 9 and 11 μg, or 10 μg.

Specifically, a 0.5 ml vaccine dose volume contains 25 μg or 50 μg of QS21 per dose. Specifically, a 0.5 ml vaccine dose volume contains 50 μg of QS21 per dose.

In compositions comprising a lipopolysaccharide, the lipopolysaccharide may be present at an amount of about 1-about 70 μg per dose, for example at an amount of about 50 μg.

The lipopolysaccharide may be a non-toxic derivative of lipid A, particularly monophosphoryl lipid A or more particularly 3-Deacylated monophoshoryl lipid A (3D-MPL).

3D-MPL is sold under the name MPL by GlaxoSmithKline Biologicals S.A. and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-γ (Th1) phenotype. 3D-MPL can be produced according to the methods disclosed in GB 2 220 211 A. Chemically it is a mixture of 3-deacylated monophosphoryl lipid A with 3, 4, 5 or 6 acylated chains. Preferably in the compositions of the present invention small particle 3D-MPL is used. Small particle 3D-MPL has a particle size such that it may be sterile-filtered through a 0.22 μm filter. Such preparations are described in WO 94/21292.

The invention therefore provides a dose of an immunogenic composition comprising lipopolysaccharide, preferably 3D-MPL, at a level of 75 μg or less, for example between 1 and 60 μg.

In one embodiment, the dose of the immunogenic composition comprises 3D-MPL at a level of around 50 μg, for example between 45-55 μg, suitably between 46-54 μg or between 47 and 53 μg or between 48 and 52 μg or between 49 and 51 μg, or 50 μg.

In one embodiment, the dose of the immunogenic composition comprises 3D-MPL at a level of around 25 μg, for example between 20-30 μg, suitably between 21-29 μg or between 22 and 28 μg or between 23 and 27 μg or between 24 and 26 μg, or 25 μg.

In another embodiment, the dose of the immunogenic composition comprises 3D-MPL at a level of around 10 μg, for example between 5 and 15 μg, suitably between 6 and 14 μg, for example between 7 and 13 μg or between 8 and 12 μg or between 9 and 11 μg, or 10 μg.

In one embodiment, the volume of the dose is 0.5 ml. In a further embodiment, the immunogenic composition is in a volume suitable for a dose which volume is higher than 0.5 ml, for example 0.6, 0.7, 0.8, 0.9 or 1 ml. In a further embodiment, the human dose is between 1 ml and 1.5 ml.

Specifically, a 0.5 ml vaccine dose volume contains 25 μg or 50 μg of 3D-MPL per dose. Specifically, a 0.5 ml vaccine dose volume contains 50 μg of 3D-MPL per dose.

The dose of the immunogenic composition according to any aspect of the invention suitably refers to human dose. By the term "human dose" is meant a dose which is in a volume suitable for human use. Generally this is between 0.3 and 1.5 ml. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml.

Suitable compositions of the invention are those wherein liposomes are initially prepared without MPL (as described in WO 96/33739), and MPL is then added, suitably as small particles of below 100 nm particles or particles that are susceptible to sterile filtration through a 0.22 μm membrane. The MPL is therefore not contained within the vesicle membrane (known as MPL out). Compositions where the MPL is contained within the vesicle membrane (known as MPL in) also form an aspect of the invention. The polypeptide comprising a *C. difficile* toxin A fragment and/or a *C. difficile* toxin B fragment can be contained within the vesicle membrane or contained outside the vesicle membrane.

In a specific embodiment, QS21 and 3D-MPL are present in the same final concentration per dose of the immunogenic composition i.e. the ratio of QS21:3D-MPL is 1:1. In one aspect of this embodiment, a dose of immunogenic composition comprises a final level of 25 μg of 3D-MPL and 25 μg of QS21 or 50 μg of 3D-MPL and 50 μg of QS21.

In one embodiment, the adjuvant includes an oil-in-water emulsion. In one embodiment the adjuvant comprises an oil in water emulsion, wherein the oil in water emulsion comprises a metabolisable oil, a tocol and an emulsifier. For example, the oil-in-water emulsion can include an oil phase that incorporates a metabolisable oil, and an additional oil phase component, such as a tocol. The oil-in-water emulsion may also contain an aqueous component, such as a buffered saline solution (e.g., phosphate buffered saline). In addition, the oil-in-water emulsion typically contains an emulsifier. In one embodiment, the metabolizable oil is squalene. In one embodiment, the tocol is alpha-tocopherol. In one embodiment, the emulsifier is a nonionic surfactant emulsifier (such as polyoxyethethylene sorbitan monooleate, Polysorbate® 80, TWEEN80™). In exemplary embodiments, the oil-in-water emulsion contains squalene and alpha tocopherol in a ratio which is equal or less than 1 (w/w).

The metabolisable oil in the oil-in-water emulsion may be present in an amount of 0.5-10 mg. The tocol in the oil-in-water emulsion may be present in an amount of 0.5-11 mg. The emulsifying agent may be present in an amount of 0.4-4 mg, In order for any oil in water composition to be suitable for human administration, the oil phase of the emulsion system has to comprise a metabolisable oil. The meaning of the term metabolisable oil is well known in the art. Metabolisable can be defined as 'being capable of being transformed by metabolism' (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® (caprylic/capric triglycerides made using glycerol from vegetable oil sources and medium-chain fatty acids (MCTs) from coconut or palm kernel oils) and others. A particularly suitable metabolisable oil is squalene. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use in this invention. Squalene is a metabolisable oil by virtue of the fact that it is an intermediate in the biosynthesis of cholesterol (Merck index, 10th Edition, entry no. 8619).

Suitably the metabolisable oil is present in the adjuvant composition in an amount of 0.5-10 mg, preferably 1-10, 2-10, 3-9, 4-8, 5-7, or 5-6 mg (e.g. 2-3, 5-6, or 9-10 mg), specifically about 5.35 mg or about 2.14 mg per dose.

Tocols are well known in the art and are described in EP0382271. Suitably the tocol is alpha-tocopherol or a derivative thereof such as alpha-tocopherol succinate (also known as vitamin E succinate). Said tocol is suitably present in in an amount of 0.5-11 mg, preferably 1-11, 2-10, 3-9, 4-8, 5-7, 5-6 mg (e.g. 10-11, 5-6, 2.5-3.5 or 1-3 mg). In a specific embodiment the tocol is present in an amount of about 5.94 mg or about 2.38 mg per dose.

The oil in water emulsion further comprises an emulsifying agent. The emulsifying agent may suitably be polyoxyethylene sorbitan monooleate. In a particular embodiment the emulsifying agent may be Polysorbate® 80 (Polyoxyethylene (20) sorbitan monooleate) or Tween® 80.

Said emulsifying agent is suitably present in the adjuvant composition in an amount of 0.1-5, 0.2-5, 0.3-4, 0.4-3 or 2-3 mg (e.g. 0.4-1.2, 2-3 or 4-5 mg) emulsifying agent. In a specific embodiment the emulsifying agent is present in an amount of about 0.97 mg or about 2.425 mg.

In one embodiment, the amounts of specific components present in the composition are the amounts present in a 0.5 ml human dose. In a further embodiment, the immunogenic composition is in a volume suitable for a human dose which volume is higher than 0.5 ml, for example 0.6, 0.7, 0.8, 0.9 or 1 ml. In a further embodiment, the human dose is between 1 ml and 1.5 ml.

Where the adjuvant is in a liquid form and is to be combined with a liquid form of a polypeptide composition, the adjuvant composition in a human dose will be a fraction of the intended final volume of the human dose, for example approximately half of the intended final volume of the human dose, for example a 350 μl volume for an intended human dose of 0.7 ml, or a 250 μl volume for an intended human dose of 0.5 ml. The adjuvant composition is diluted when combined with the polypeptide antigen composition to provide the final human dose of vaccine. The final volume of such dose will of course vary dependent on the initial volume of the adjuvant composition and the volume of polypeptide antigen composition added to the adjuvant composition. In an alternative embodiment, a liquid adjuvant is used to reconstitute a lyophilised polypeptide composition. In this embodiment, the human dose of the adjuvant composition is approximately equal to the final volume of the human dose. The liquid adjuvant composition is added to the vial containing the lyophilised polypeptide composition. The final human dose can vary between 0.5 and 1.5 ml.

The method of producing oil-in-water emulsions is well known to the person skilled in the art. Commonly, the method comprises mixing the tocol-containing oil phase with a surfactant such as a PBS/polyoxyethylene sorbitan monooleate solution, followed by homogenisation using a homogenizer. It would be clear to a man skilled in the art that a method comprising passing the mixture twice through a syringe needle would be suitable for homogenising small volumes of liquid. Equally, the emulsification process in microfluidiser (M110S Microfluidics machine, maximum of 50 passes, for a period of 2 minutes at maximum pressure input of 6 bar (output pressure of about 850 bar)) could be adapted by the man skilled in the art to produce smaller or larger volumes of emulsion. The adaptation could be achieved by routine experimentation comprising the measurement of the resultant emulsion until a preparation was achieved with oil droplets of the required diameter.

In an oil in water emulsion, the oil and emulsifier should be in an aqueous carrier. The aqueous carrier may be, for example, phosphate buffered saline.

Preferably the oil-in-water emulsion systems of the present invention have a small oil droplet size in the sub-micron range. Suitably the droplet sizes will be in the range 120 to 750 nm, more preferably sizes from 120 to 600 nm in diameter. Most preferably the oil-in water emulsion contains oil droplets of which at least 70% by intensity are less than 500 nm in diameter, more preferably at least 80% by intensity are less than 300 nm in diameter, more preferably at least 90% by intensity are in the range of 120 to 200 nm in diameter.

In one embodiment, the immunogenic composition is not 3 μg or 10 μg of any of SEQ ID Nos. 1 to 7 combined with an adjuvant comprising an oil in water emulsion having 0.125 mL SB62 emulsion (Total volume), 5.35 mg squalene, 5.94 mg DL-α-tocopherol and 2.425 mg polysorbate 80 per 0.5 ml dose. In one embodiment, the immunogenic composition is not 3 μg or 10 μg of any of SEQ ID Nos. 1 to 7 combined with an adjuvant comprising an oil in water emulsion 5.35 mg squalene, 5.94 mg DL-α-tocopherol and 2.425 mg polysorbate 80 per 0.5 ml dose. In one embodiment, the immunogenic composition does not contain an adjuvant comprising a oil in water emulsion having squalene, DL-α-tocopherol and polysorbate 80.

Immunogenic Compositions and Vaccines of the Invention

In one embodiment the immunogenic composition has a volume of 0.5 to 1.5 ml.

In one embodiment the immunogenic composition further comprises additional antigens. In one embodiment the additional antigens are antigens derived from a bacterium selected from the group consisting of *S. pneumoniae, H. influenzae, N. meningitidis, E. coli, M. catarrhalis, Clostridium tetani* (tetanus), *Corynebacterium diphtheria* (*diphtheria*), *Bordetella pertussis* (pertussis), *S. epidermidis, enterococci, S. aureus*, and *Pseudomonas aeruginosa*. In a further embodiment the immunogenic composition of the invention may comprise further antigens from *C. difficile* for example the S-layer proteins (WO01/73030). Optionally the immunogenic composition further comprises a saccharide from *C. difficile*.

There is further provided a vaccine comprising an immunogenic composition of the invention and a pharmaceutically acceptable excipient.

The vaccine preparations containing immunogenic compositions of the present invention may be used to protect a mammal susceptible to *C. difficile* infection or treat a mammal with a *C. difficile* infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Although the vaccine of the invention may be administered as a single dose, components thereof may also be co-administered together at the same time or at different times (for instance pneumococcal saccharide conjugates could be administered separately, at the same time or 1-2 weeks after the administration of the any bacterial protein component of the vaccine for coordination of the immune responses with respect to each other). In addition to a single route of administration, 2 different routes of administration may be used. For example, saccharides or saccharide conjugates may be administered intramuscularly (IM) or intradermally (ID) and bacterial proteins may be administered intranasally (IN) or intradermally (ID). In addition, the vaccines of the invention may be administered IM for priming doses and IN for booster doses.

The content of toxins in the vaccine will typically be in the range 1-250 μg, preferably 5-50 μg, most typically in the range 5-25 μg. Following an initial vaccination, subjects may receive one or several booster immunizations adequately spaced. Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

In one aspect of the invention is provided a vaccine kit, comprising a vial containing an immunogenic composition of the invention, optionally in lyophilised form, and further comprising a vial containing an adjuvant as described herein. It is envisioned that in this aspect of the invention, the adjuvant will be used to reconstitute the lyophilised immunogenic composition.

A further aspect of the invention is a method of preventing or treating *C. difficile* infection comprising administering to the host an immunoprotective dose of the immunogenic composition or vaccine or kit of the invention. In one embodiment there is provided a method of preventing or treating primary and/or recurrence episodes of *C. difficile* infection comprising administering to the host an immunoprotective dose of the immunogenic composition or vaccine or kit of the invention.

In one embodiment of the invention there is provided an immunogenic composition or vaccine of the invention for use in the treatment or prevention of *C. difficile* disease. In a further embodiment of the invention there is provided an immunogenic composition or vaccine of the invention for use in the treatment or prevention of disease caused by a strain of *C. difficile* selected from the group consisting of 078, 019, 023, 027, 033, 034, 036, 045, 058, 059, 063, 066, 075, 078, 080, 111, 112, 203, 250 and 571. Preferably the strain is strain 078.

In a further aspect of the invention there is provided a use of an immunogenic composition or vaccine of the invention in the preparation of a medicament for the prevention or treatment of *C. difficile* disease. In a further embodiment the disease is a disease caused by a strain of *C. difficile* selected from the group consisting of 078, 019, 023, 027, 033, 034, 036, 045, 058, 059, 063, 066, 075, 078, 080, 111, 112, 203, 250 and 571. Preferably the strain is strain 078.

In a further aspect of the invention there is provided a method of preventing or treating *C. difficile* disease comprising administering the immunogenic composition of the invention or the vaccine of the invention to a mammalian subject such as a human subject. In a further embodiment the disease is a disease caused by a strain of *C. difficile* selected from the group consisting of 078, 019, 023, 027, 033, 034, 036, 045, 058, 059, 063, 066, 075, 078, 080, 111, 112, 203, 250 and 571. Preferably the strain is strain 078.

General

Around" or "approximately" are defined as within 10% more or less of the given figure for the purposes of the invention.

The terms "comprising", "comprise" and "comprises" herein are intended by the inventors to be optionally substitutable with the terms "consisting of", "consist of" and "consists of", respectively, in every instance. The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example."

The amino acid numbering used herein is derived from the sequences for CDTa, CDTb, Toxin A and Toxin B presented herein as SEQ ID NO: 1, SEQ ID NO: 3, SEQ ID NO: 31 and SEQ ID NO: 32 which are to be considered as reference sequences for these proteins.

Embodiments herein relating to "vaccine compositions" of the invention are also applicable to embodiments relating to "immunogenic compositions" of the invention, and vice versa. Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, may be approximate.

All references or patent applications cited within this patent specification are incorporated by reference herein in their entirety.

In order that this invention may be better understood, the following examples are set forth. These examples are for purposes of illustration only, and are not to be construed as limiting the scope of the invention in any manner.

EXAMPLES

The AS01B adjuvant referred to is an adjuvant having 50 μg QS21 presented in the form of a liposome, 50 μg 3D-MPL, 0.25 mg cholesterol and 1.0 mg DOPC per 0.5 ml dose. A dose of 50 μl suitable for immunizing mice contains 5 μg QS21, 5 μg 3D-MPL, 0.025 mg cholesterol and 0.1 mg DOPC.

Example 1: Design of Binary Toxin Antigens

The Binary Toxin (other name: ADP-ribosyltransferase toxin) is composed by two components: the enzymatic component, named CDTa and the transport and binding component, named CDTb.

Based on literature data and the known 3D structure of CDTa (*J. Biol. Chem.* 2009, vol. 284: 28713-28719), this protein could be divided into two domains. The N-terminal domain binds to CDTb and the C-terminal domain contains the enzymatic activity. Both domains are linked by a flexible peptide.

Based on literature data and information available for other B components of other bacterial binary toxins, CDTb could be divided into five domains. The first one is the prodomain, its cleavage by an enzyme having a chymotrypsin activity allows the heptamerization of the mature protein. The second domain allows the binding to CDTa. The third and fourth ones are involved in the oligomerisation and membrane insertion. Finally, the last domain is the host cell receptor binding domain.

Example 1a: Design of CDTa Antigens

In order to be allowed to work with CDTa and CDTb together, CDTa must be inactivated. Two possibilities of inactivation were evaluated. The first one is the design of CDTa mutants that abolish the enzymatic activity and the second one is the use of the N-terminal domain of CDTa alone. This latter domain allows the binding to CDTb and does not contain residue involved in the enzymatic activity.

The first set of mutants were designed based on literature information (*Infection & Immunity,* 2001, vol. 69: 6004-6011). Authors demonstrated that CDTa mutant proteins E428Q, E430Q, S388A and R345K have a significant reduced activity. Based on data shown in the publication, two mutations were preferred amongst the four: CDTa mutant E428Q and E430Q. In the publication, these mutants abolish completely the CDTa enzymatic activity. In order to rank these mutants, some structural analyses were performed for these residues: surface-accessibility of the residues glutamate 428 (E428) and glutamate 430 (E430), effect of their mutations on the surrounding 3D structure. Based on these analyses, the CDTa mutant E428Q was chosen as preferred mutation and the CDTa mutant E430Q was selected as second choice. A double mutant E428Q, E430Q was also generated in order to be sure that the enzymatic activity was abolished.

A second set of mutants was designed because the first cytotoxicity results, obtained with the first set of mutants, were not convincing.

In this second set, a CDTa mutant containing 7 mutations (including the two mutations already described) was designed. All these mutations were designed based on literature information (available for CDTa or its *Clostridium perfringens* homologs Ia) and 3D structure analysis. All mutated residues are located around the catalytic site of CDTa. These residues have been modified in order to avoid ligand or water molecule binding. This CDTa "super mutant" contains the mutations R345A, Q350A, N385A, R402A, S388F, E428Q and E430Q.

Based on this "super mutated" CDTa, two other CDTa mutated variants were evaluated in order to eliminate E428Q and E430Q mutations (construct C108 contains the E430Q mutation but not the mutation E428Q, construct C107 does not contain both mutations).

CDTa Nterminal Domain Alone

It was described in the literature (*Infection & Immunity,* 2001, vol. 69: 6004-6011) that the $CDTa^{1-240}$ is the minimal CDTa fragment that still allows a binding to Ib (B component of binary toxin of *Clostridium perfringens*). This fragment will be tested in the lab but based on known 3D structure, it was suggested that this domain will probably not be optimal in term of correct folding of this domain of CDTa.

Antigen design was performed based on the known 3D structure (Protein Data Bank accession number: 2WN4, *J. Biol. Chem.,* 2009, vol. 284: 28713-28719) to improve the expression and folding of an isolated CDTa N-terminal domain. On the 3D structure, a linker peptide of eight amino acids allows the separation between the N- and C-terminal domains of CDTa. Two isolated CDTa N-terminal domains were designed, the first one contains this flexible peptide and the second one not.

CDTa: Sequences Summary

A summary of all CDTa sequences is presented in table 1.

TABLE 1

| Name | Length (aa)* | Location | Comments |
|---|---|---|---|
| CDTa | 463 | 1-463 | Full length of CDTa coming from strain R20291 |
| CDTa' | 421 | 44-463 | CDTa without signal peptide (C34) |
| CDTa_E428Q | 421 | 44-463 | CDTa' with mutation of $Glu^{428}$ into Gln (C44) |
| CDTa_E430Q | 421 | 44-463 | CDTa' with mutation of $Glu^{430}$ into Gln (C54) |
| CDTa_E428 430Q | 421 | 44-463 | CDTa' with the two mutations $Glu^{428}$ into Gln and $Glu^{430}$ into Gln (C67) |
| CDTa_7mutations | 421 | 44-463 | CDTa' containing 7 mutated amino acids (C69) |
| CDTa_N_litt | 198 | 44-240 | Minimum CDTa N-terminal domain that still allows binding to lb (C51) |
| CDTa_NADlink | 226 | 44-268 | CDTa N-terminal domain based on antigen design work (C49) |
| CDTa_NAD | 218 | 44-260 | CDTa N-terminal domain based on antigen design work (C50) |

*Length contains additional N-terminal Methionine but not the His-tag

Example 1b: Design of CDTb Antigens

CDTb Mature

In order to avoid the chymotrypsin activation step in the CDTb process, it was tried to express only the mature CDTb protein (without its signal peptide and prodomain).

In the literature (*Protein Expression and Purification,* 2010, vol. 74: 42-48), the mature CDTb was described as starting at Leucine 210. This mature CDTb was named CDTb". After in house experimental data, it seems that the activated CDTb starts at Serine 212. This result was supported by analysis of a 3D modelised structure of CDTb. This model was built using SwissModel (*Bioinformatics,* 2006, vol. 22: 195-201). The template used for the homology modeling was the B component of *Bacillus anthracis*, named Protective Antigen or PA (Protein Data Bank accession number: 3TEW).

CDTb Receptor-Binding Domain Alone

Given the fact that a fusion containing only the receptor-binding domains of Toxin A and B is sufficient to induce neutralizing antibodies, it was decided to produce and evaluate the CDTb receptor-binding domain alone.

The 3D structure model obtained for CDTb is accurate for the four first domains of CDTb but not for the receptor-binding domain (these domains of CDTb and PA are too different). To design constructs expressing this domain alone, the C-terminal part of the fourth domain was analysed on the 3D structure model in order to decide where the last domain will start. Two versions of the CDTb-receptor binding domain were designed. In the first one, this domain starts just after the modelised 3D structure of the fourth domain. In this version, the CDTb-receptor-binding domain will probably have a long flexible peptide in its N-terminal part. The second version starts where the 2D predicted structures performed on the C-terminal part of CDTb (predictions done using Psipred program, *Bioinformatics,* 2000, vol. 16: 404-405) become more compacts after a lack of predicted secondary structures. This could indicate the beginning of a new structural domain. In this second version, no flexible peptide is present at the N-terminal part of the isolated CDTb receptor-binding domain.

CDTb $Ca^{2+}$ Binding Motif Mutation

Following literature information, mutations in the $Ca^{2+}$ binding domain of the B component of Iota toxin of *Clostridium perfringens* (Ib) abolish the binding with the A component of this binary toxin (Ia). These mutations could be very interesting in the case of a vaccine composition containing a mixture of mature CDTb protein and a wild type CDTa protein. Using multiple protein sequence alignment, these mutations were located on the CDTb sequence and mutated. It concerns residues $Asp^{220}$, $Asp^{222}$ and $Asp^{224}$. They were mutated into Ala residues.

CDTb Prodomain

In order to try to decrease the degradation issues observed with C55 in gel, some co-expression tests were evaluated. The working hypothesis of doing that is to improve the folding of the mature CDTb.

Two limits of prodomain were proposed. The first one starts at residue 43 of CDTb (after the signal peptide cleavage) and finishes at residue $Met^{211}$ (given that the experimentally determined first residue of the mature CDTb is $Ser^{212}$). The second prodomain was designed based on the predicted 3D structure of CDTb. The linker existing between the prodomain and the first structural domain of the mature CDTb protein is removed in this construct.

CDTb: Sequence Summary

A summary of all CDTb sequences is presented in table 2.

TABLE 2

| Name | Length (aa)* | Location | Comments |
|---|---|---|---|
| CDTb | 876 | 1-876 | Full length of CDTb coming from strain R20291 |
| CDTb' | 835 | 43-876 | CDTb without signal peptide (C38) |
| CDTb" | 668 | 210-876 | CDTb without signal peptide and prodomain as defined in the literature |
| CDTb"_xp data | 666 | 212-876 | CDTb without signal peptide and prodomain, as demonstrated by in house experimental results (C55) |
| CDTbClg | 258 | 620-876 | CDTb receptor-binding domain containing natural flexible peptide in its N-terminal part, based on antigen design work (C52) |
| CDTbCsh | 242 | 636-876 | CDTb receptor-binding domain, based on antigen design work (C53) |
| CDTb Ca2+ mutated | 666 | 212-876 | Mature CDTb (without signal peptide and without prodomain) containing 3 mutations D220A, D222A and D224A (C97) |
| CDTbprodomainLg | 170 | 43-211 | CDTb prodomain (C58) |
| CDTbprodomainSh | 145 | 43-186 | CDTb prodomain without the linker existing between the prodomain and the first structural domain of mature CDTb (C59) |

*Length contains additional N-terminal Methionine but not the His-tag

Example 1c: Design of CDTa-CDTb Fusions

Background Information

The aim of these constructs is to obtain both components of the Binary Toxin into one process.

A lot of different kinds of fusions could be designed but, as proof of concept, the first fusion evaluated is the combination of CDTa N-terminal domain (named CDTaNADlink and CDTaNAD) with CDTb receptor-binding domain (named CDTbCsh and CDTbClg).

Fusion CDTaNterm-CDTb Receptor-Binding Domain Alone

Without additional experimental data on each partner of the fusion, all possible combinations were initiated but always with the CDTa domain as first partner of the fusion.

In these fusions, the CDTaNADlink and the CDTaNAD domains have two and one residues less than the designed isolated domains, respectively. These CDTa additional amino acids were kept in the isolated designs in order to avoid potential issues during the expression process.

A summary of all CDTa-CDTb fusion sequences is presented in table 3.

TABLE 3

| Name | Length (aa)* | Location CDTa | Location CDTb |
|---|---|---|---|
| CDTaNADlink-CDTbCsh (C61) | 465 | 44-266 | 636-876 |
| CDTaNAD-CDTbCsh (C63) | 458 | 44-259 | 636-876 |
| CDTaNADlink-CDTbClg (C60) | 481 | 44-266 | 620-876 |
| CDTaNAD-CDTbClg (C62) | 474 | 44-259 | 620-876 |

*Length contains additional N-terminal Methionine but not the His-tag

Example 1d: Design of ToxA-ToxB-CDTb Receptor-Binding Domain Fusion

The objective of this fusion is the combination of receptor-binding domains of the three major toxins of *Clostridium difficile* into one construct.

Given the fact that F2 and CDTb receptor-binding domains are not supposed to adopt the same fold, a linker/spacer must be used between the two partners of the fusion in order to allow a correct independent folding of them. Two fusions were designed.

In the first one (named F2_CDTbCIg), the long designed version of the receptor-binding domain is fused at the C-terminal part of F2. In this version, the long flexible N-terminal peptide of CDTb receptor-binding domain will function as spacer.

In the second fusion (named F2_GG_NVCDTbCsh), the short designed version of the receptor-binding domain is fused at the C-terminal part of F2. In order to allow a correct folding of the two partners, the length of the linker created in this fusion must be increased. In order to do that, the CDTb-receptor binding domain was extended with two natural residues, moreover two exogenous Glycines were added between F2 and the longer version of CDTbCsh.

A summary of all F2-CDTb fusion sequences is presented in table 4.

TABLE 4

| Name | Length (aa)* | Location F2 | Location CDTb | Comments |
|---|---|---|---|---|
| F2_CDTbClg | 1223 | ToxA: 2121-2686 ToxB: 1968-2366 | 620-876 | |
| F2_GG_NVCDTbCsh | 1211 | ToxA: 2121-2686 ToxB: 1968-2366 | 634-876 | Two exogenous Gly residues added as spacer between the two partners of the fusion |

*Length contains additional N-terminal Methionine but not the His-tag

Example 2: Cloning, Expression and Purification of CdtA Protein

Expression Plasmid and Recombinant Strain: CdtA Full Length

Genes encoding the protein of full length without signal peptide of CdtA with and without mutations (see tables below) and a His tag in C-term were cloned into the pET24b(+) expression vector (Novagen) using the NdeI/XhoI restriction sites using standard procedures. Final constructs were generated by the transformation of *E. coli* strain HMS174 (DE3) or BLR (DE3) pLysS (C34) with each recombinant expression vector separately according to standard method with CaCl2-treated cells (Hanahan D. <<Plasmid transformation by Simanis.>> In Glover, D. M. (Ed), DNA cloning. IRL Press London. (1985): p. 109-135.).

| CdtA<br>C number | |
|---|---|
| C34 | CdtA (aa44-463) |
| C44 | CdtA (aa44-463) mut. E428Q |
| C49 | CdtA linker (44-268) |
| C50 | CdtA WO linker (44-260) |
| C54 | CdtA (aa44-463) mut. E430Q |
| C67 | CdtA (aa44-463) mut. E428Q-E430Q |
| C68 | CdtA (aa44-463) mut. R345A-Q350A-N385A-R402A-E428Q-E430Q |
| C69 | CdtA (aa44-463) mut. R345A-Q350A-N385A-R402A-S388F-E428Q-E430Q |
| C107 | CdtA (aa44-463) mut. R345A-Q350A-N385A-R402A-S388F |
| C108 | CdtA (aa44-463) mut. R345A-Q350A-N385A-R402A-S388F-E430Q |
| C110 | CdtA (aa44-463) mut. R345A-Q350A-N385A-R402A-S388F-E428Q |

Host Strain:

HMS 174 (DE3). HMS174 strains provide the recA mutation in a K-12 background. Strains having the designation (DE3) are lysogenic for a λ prophage that contains an IPTG inducible T7 RNA polymerase. λ DE3 lysogens are designed for protein expression from pET vectors Genotype: $F^-$ recA1 hsdR($r_{K12}^-m_{K12}^+$) ($Rif^R$).

BLR(DE3) pLysS. BLR is a recA derivative of BL21. Strains having the designation (DE3) are lysogenic for a λ prophage that contains an IPTG inducible T7 RNA polymerase. λ DE3 lysogens are designed for protein expression from pET vectors This strain is also deficient in the Ion and ompT proteases, pLysS strains express T7 lysozyme which further suppress basal expression of the T7 RNA polymerase prior to induction.

Genotype: *E. coli* BLR::DE3 strain, $F^-$ ompT $hsdS_B(r_B^- m_B^-)$ gal dcm (DE3) Δ(srl-recA)306::Tn10 pLysS ($Cam^R$, $Tet^R$).

Expression of the Recombinant Proteins:

*E. coli* transformants were stripped from agar plate and used to inoculate 200 ml of LBT broth ±1% (w/v) glucose+kanamycin (50 μg/ml) to obtain O.D.600 nm between 0.1-0.2. Cultures were incubated overnight at 37° C., 250 RPM.

Each overnight culture were diluted to 1:20 in 500 ml of LBT medium containing kanamycin (50 μg/ml) and grown at 37° C. at a stirring speed of 250 rpm until O.D.620 reached 0.5/0.6.

At O.D.600 nm around 0.6, the cultures were cooled down before inducing the expression of the recombinant protein by addition of 1 mM isopropyl β-D-1-thiogalactopyranoside (IPTG; EMD Chemicals Inc., catalogue number: 5815) and incubated overnight at 23° C., 250 RPM.

After overnight induction (around 16 hours), $O.D._{600nm}$ were evaluated after induction and culture were centrifuged at 14 000 RPM for 15 minutes and pellets were frozen at −20° C. separately.

Expression Plasmid and Recombinant Strain: CdtA-N-Term

Genes encoding protein of N-terminal, without signal peptide of CdtA (see tables below) and a His tag in C-term were cloned into the pET24b(+) expression vector (Novagen) using the NdeI/XhoI restriction sites using standard procedures. Final constructs were generated by the transformation of *E. coli* strain HMS174 (DE3) with each recombinant expression vectors separately according to standard method with CaCl2-treated cells (Hanahan D. <<Plasmid transformation by Simanis.>> In Glover, D. M. (Ed), DNA cloning. IRL Press London. (1985): p. 109-135.).

| CdtA N-term | |
|---|---|
| C number | |
| C49 | CdtA linker (44-268) |
| C50 | CdtA WO linker (44-260) |

Host Strain:

HMS 174 (DE3). HMS174 strains provide the recA mutation in a K-12 background. Strains having the designation (DE3) are lysogenic for a λ prophage that contains an IPTG inducible T7 RNA polymerase. λ DE3 lysogens are designed for protein expression from pET vectors Genotype: $F^-$ recA1 hsdR($r_{K12}^-m_{K12}^+$) ($Rif^R$).

Expression of the Recombinant Proteins:

*E. coli* transformants were stripped from agar plate and used to inoculate 200 ml of LBT broth ±1% (w/v) glucose+kanamycin (50 μg/ml) to obtain O.D.600 nm between 0.1-0.2. Cultures were incubated overnight at 37° C., 250 RPM.

This overnight culture was diluted to 1:20 in 500 ml of LBT medium containing kanamycin (50 μg/ml) and grown at 37° C. at a stirring speed of 250 rpm until O.D.620 reached 0.5/0.6.

At O.D.600 nm around 0.6, the culture was cooled down before inducing the expression of the recombinant protein by addition of 1 mM isopropyl β-D-1-thiogalactopyranoside (IPTG; EMD Chemicals Inc., catalogue number: 5815) and incubated overnight at 23° C., 250 RPM.

After overnight induction (around 16 hours), $O.D._{600nm}$ was evaluated after induction and culture was centrifuged at 14 000 RPM for 15 minutes and pellets were frozen at −20° C. separately.

Purification

The following procedure was used to purify constructs C34, C44, C49, C50, C54, C67, C69, C107 and C110.

The bacterial pellets were re-suspended in 20 mM or 50 mM bicine buffers (pH 7.5 or pH 8.0), containing 500 mM NaCl, 0 mM or 5 mM TCEP (Thermo Scientific Pierce, (2-carboxyethyl)phosphine hydrochloride) and a mixture of protease inhibitors (Complete, Roche, without EDTA). Bacteria were lysed using a French Press system 3×20 000 PSI. Soluble (supernatant) and insoluble (pellet) components were separated by centrifugation at 20 000 g for 30 min at 4° C.

The 6-His tagged-proteins were purified under native conditions on IMAC. The soluble components were loaded on a 5 ml GE Histrap column (GE) pre-equilibrated with the same buffer used to bacterial re-suspension. After loading on the column, the column was washed with a 20 mM or 50 mM bicine buffer (pH7.5 or pH8.0), containing 500 mM NaCl, 10 mM imidazole, 5 mM TCEP. Elution was performed using a 50 mM bicine buffer pH7.6, 500 mM NaCl, 1 mM TCEP and imidazole (250 mM or 500 mM).

After desalting (BIORAD Bio-Gel P6 Desalting) and concentration (Amicon Ultra 10 kDa) steps, the product was loaded on SEC chromatography (SUPERDEX™ 75 or 200) in 20 mM or 50 mM bicine buffer (pH7.5 or pH8.0), 150 mM NaCl, 1 mM TCEP, for further purification step.

Fractions containing Cdta antigen were selected on the basis of purity by SDS-PAGE. Protein concentration was determined using Lowry RC/DC Protein Assay of BioRad. The purified bulk was sterile-filtered on 0.22 μm and stored at −80° C.

Example 4: Cloning, Expression and Purification of *C. difficile* CdtB Protein

Expression Plasmid and Recombinant Strain: CdtB Full Length.

Genes encoding the truncated protein of CdtB without signal peptide (Pro-CdtB') and a His tag in C-term were cloned into the pGEX-6p1 expression vector (GE Healthcare) using the BamHI/XhoI restriction sites using standard procedures. This vector included GST (Gluthathione-S-transferase) as fusion partner in N-terminal of either CdtB' (GST-Pro-Cdtb'). The final construct was generated by the transformation of *E. coli* strain BL21 (DE3) with the recombinant expression vector according to standard method with CaCl2-treated cells (Hanahan D. <<Plasmid transformation by Simanis.>> In Glover, D. M. (Ed), DNA cloning. IRL Press London. (1985): p. 109-135.).

Genes encoding the truncated protein of CdtB without signal peptide (Pro-CdtB': C38) and without signal peptide and prodomain (CdtB'': C40 or C55) and a His tag in C-term were cloned into the pET24b(+) expression vector (Novagen) using the NdeI/XhoI restriction sites using standard procedures. Final constructs were generated by the transformation of *E. coli* B834 (DE3) modified strain for C55 and BL21(DE3) for C38 and C40 with the appropriate recombinant expression vectors according to standard method with CaCl2-treated cells (Hanahan D. <<Plasmid transformation by Simanis.>> In Glover, D. M. (Ed), DNA cloning. IRL Press London. (1985): p. 109-135.).

| CdtB C number | |
|---|---|
| C37 | CdtB' Δ signal sequence (aa43-876) + GST N-term |
| C38 | CdtB' Δ signal sequence (aa43-876) |
| C40 | CdtB'' Δ signal sequence and prodomain (aa210-876) |
| C55 | CdtB Δ prodomain (aa. 212-876) |

Host Strain

BL21(DE3). BL21(DE3) is a non-methionine auxotroph derivative of B834. Strains having the designation (DE3) are lysogenic for a λ prophage that contains an IPTG inducible T7 RNA polymerase. λ DE3 lysogens are designed for protein expression from pET vectors This strain is also deficient in the Ion and ompT proteases.

Genotype: *E. coli* BL21::DE3 strain, $F^-$ ompT $hsdS_B(r_B^- m_B^-)$ gal dcm (DE3).

B834 is the parental strain for BL21. These protease-deficient hosts are methionine auxotrophs. λ DE3 lysogens are designed for protein expression from pET vectors This strain is also deficient in the Ion and ompT proteases.

Modification: Including PGL gene to avoid phosphogluconoylation in the biotin locus (Strain is auxotroph for biotin).

Genotype: B834::DE3 strain, F-ompT hsdSB(rB-mB-) gal dcm met (DE3)

Modification: Δ(bioA-bioD)::PGL

Expression of the Recombinant Proteins:

*E. coli* transformants were stripped from agar plate and used to inoculate 200 ml of LBT broth ±1% (w/v) glucose+/−kanamycin (50 μg/ml) or ampicillin (100 μg/ml) to obtain $O.D._{600nm}$ between 0.1-0.2. Cultures were incubated overnight at 37° C., 250 RPM.

Overnight culture were diluted to 1:20 in 500 ml of LBT medium containing +/−kanamycin (50 μg/ml) or ampicillin (100 μg/ml) and grown at 37° C. at a stirring speed of 250 rpm until $O.D._{620}$ reached 0.5/0.6.

At an O.D. at 600 nm of around 0.6, cultures were cooled down before inducing the expression of the recombinant protein by addition of 1 mM isopropyl β-D-1-thiogalactopyranoside (IPTG; EMD Chemicals Inc., catalogue number: 5815) and incubated overnight at 23° C., 250 RPM.

After the overnight inductions (around 16 hours), O.D. at 600 nm were evaluated after induction and cultures were centrifuged at 14 000 RPM for 15 minutes and pellets were frozen at −20° C. separately.

Expression Plasmid and Recombinant Strain.

Genes encoding the truncated protein of CdtB without prodomain CdtB mature, Knock-out of Ca++ binding site (inhibit binding of CdtA to CdtB) and a His tag in C-term was cloned into the pET24b(+) expression vector (Novagen) using the NdeI/XhoI restriction sites using standard procedures. The final construct was generated by the transformation of *E. coli* B834 (DE3) modified strain with the recombinant expression vector according to standard method with CaCl2-treated cells (Hanahan D. <<Plasmid transformation by Simanis.>> In Glover, D. M. (Ed), DNA cloning. IRL Press London. (1985): p. 109-135.).

| CdtB Ca++ binding domain knock-out | |
|---|---|
| C number | |
| C97 | CdtB mature mut Asp 220-222-224 Ala (aa. 212-876) |

Host Strain

B834 is the parental strain for BL21. These protease-deficient hosts are methionine auxotrophs. λ DE3 lysogens are designed for protein expression from pET vectors This strain is also deficient in the Ion and ompT proteases.

Modification: Including PGL gene to avoid phosphogluconoylation in the biotin locus (Strain is auxotroph for biotin).

Genotype: B834::DE3 strain, F-ompT hsdSB(rB-mB-) gal dcm met (DE3)

Modification: Δ(bioA-bioD)::PGL

Expression of the Recombinant Proteins:

A *E. coli* transformant was stripped from agar plate and used to inoculate 200 ml of LBT broth ±1% (w/v) glucose+ kanamycin (50 μg/ml) to obtain $O.D._{600nm}$ between 0.1-0.2. Cultures were incubated overnight at 37° C., 250 RPM.

This overnight culture was diluted to 1:20 in 500 ml of LBT medium containing kanamycin (50 μg/ml) and grown at 37° C. at a stirring speed of 250 rpm until $O.D._{620}$ reached 0.5/0.6.

At an O.D. at 600 nm of around 0.6, the culture was cooled down before inducing the expression of the recombinant protein by addition of 1 mM isopropyl β-D-1-thiogalactopyranoside (IPTG; EMD Chemicals Inc., catalogue number: 5815) and incubated overnight at 23° C., 250 RPM.

After the overnight induction (around 16 hours), O.D. at 600 nm was evaluated after induction and culture was centrifuged at 14 000 RPM for 15 minutes and pellets were frozen at −20° C. separately.

Purification

C37

The bacterial pellet was re-suspended in 50 mM bicine buffer (pH 8.0) containing 500 mM NaCl, 5 mM TCEP (Thermo Scientific Pierce, (2-carboxyethyl)phosphine hydrochloride) and a mixture of protease inhibitor (Complete, Roche). Bacteria were lysed using a French Press system 3×20 000 PSI. Soluble (supernatant) and insoluble (pellet) components were separated by centrifugation at 20 000 g for 30 min at 4° C.

The 6-His tagged-protein was purified under native conditions on IMAC. The soluble components were loaded on a 5 ml GE Histrap column (GE) pre-equilibrated with the same buffer used to bacterial re-suspension. After loading on the column, the column was washed with a 50 mM bicine buffer pH8.0, containing 150 mM NaCl, 25 mM imidazole, 1 mM TCEP. Elution was performed using a 50 mM bicine buffer pH8.0 containing 150 mM NaCl, 250 mM imidazole, 1 mM TCEP.

After desalting step (BIORAD Bio-Gel P6 Desalting) in 50 mM bicine buffer pH8.0 containing 150 mM NaCl and 1 mM TCEP, the product was treated (overnight at 4° C.) with PreScission protease (GE-Healthcare) in order to cleave the GST tag. After overnight treatment, 0.2% Tween 20 was added to the digestion mixture.

Then the protein was passed through a GST affinity column (GE GSTrap FF) pre-equilibrated with buffer 50 mM bicine buffer pH8.0 containing 150 mM NaCl, 1 mM TCEP, 0.2% tween20 and 20 mM reduced glutation, in order to remove the cleaved tag, un-cleaved fusion protein and the PreScission protease.

The GST-free protein was collected in the flow through and loaded again on a 5 ml GE Histrap column (GE) pre-equilibrated with 50 mM bicine buffer pH8.0 containing 150 mM NaCl, 1 mM TCEP, 0.2% tween20. After loading on the column, the column was washed with a 50 mM bicine buffer pH8.0, containing 150 mM NaCl, 0.2% tween20, 1 mM TCEP and 10 mM imidazole. Elution was performed using a 50 mM bicine buffer pH8.0 containing 150 mM NaCl, 0.2% tween20, 1 mM TCEP and 500 mM imidazole.

After desalting step (BIORAD Bio-Gel P6 Desalting) in 50 mM bicine buffer pH8.0 containing 150 mM NaCl, 1 mM TCEP and 0.2% tween 20, the product was treated with α-chymotrypsin (from bovine pancreas—Sigma), followed by trypsin inhibitor treatment (from egg white—Sigma). The complete activation of Cdtb by chymotrypsin was monitored by SDS-PAGE.

The fully activated product was loaded on SEC chromatography (SUPERDEX™ 75) in 50 mM bicine buffer pH8.0 containing 300 mM NaCl, 1 mM TCEP. Fractions containing CdtB antigen were selected on the basis of purity by SDS-PAGE. Protein concentration was determined using Lowry RC/DC Protein Assay of BioRad. The purified bulk was sterile-filtered on 0.22 μm and stored at −80° C.

C38

The bacterial pellet was re-suspended in 50 mM bicine buffer (pH 8.0) containing 150 mM NaCl, 5 mM TCEP (Thermo Scientific Pierce, (2-carboxyethyl)phosphine hydrochloride), 0.4% empigen and a mixture of protease inhibitor (Complete, Roche). Bacteria were lysed using a French Press system 3×20 000 PSI. Soluble (supernatant) and insoluble (pellet) components were separated by centrifugation at 20 000 g for 30 min at 4° C.

The 6-His tagged-protein was purified under native conditions on IMAC. The soluble components were loaded on a 5 ml GE Histrap column (GE) pre-equilibrated with 50 mM bicine buffer (pH 8.0) containing 150 mM NaCl, 1 mM TCEP (Thermo Scientific Pierce, (2-carboxyethyl)phosphine hydrochloride) and 0.15% empigen. After loading on the column, the column was washed with a 50 mM bicine buffer pH8.0, containing 150 mM NaCl, 20 mM imidazole, 1 mM TCEP and 0.2% tween 20. Elution was performed using a 50 mM bicine buffer pH8.0 containing 150 mM NaCl, 500 mM imidazole, 1 mM TCEP and 0.2% tween 20.

After desalting step (BIORAD Bio-Gel P6 Desalting) in 50 mM bicine buffer pH8.0 containing 150 mM NaCl, 1 mM TCEP and 0.2% tween 20, the product was treated with α-chymotrypsin (from bovine pancreas—Sigma), followed by trypsin inhibitor treatment (from egg white—Sigma). The complete activation of Cdb by chymotrypsin was monitored by SDS-PAGE.

The fully activated product was loaded on SEC chromatography (SUPERDEX™ 75) in 50 mM bicine buffer pH8.0, 300 mM NaCl, 1 mM TCEP. Fractions containing Cdtb protein were selected on the basis of purity by SDS-PAGE and loaded again on a 5 ml GE Histrap column (GE) pre-equilibrated with 50 mM bicine buffer (pH 8.0) containing 300 mM NaCl, 1 mM TCEP. After loading on the column, the column was washed with a 50 mM bicine buffer pH8.0, containing 300 mM NaCl, 10 mM imidazole, 1 mM TCEP. Elution was performed using a 50 mM bicine buffer pH8.0 containing 300 mM NaCl, 500 mM imidazole, 1 mM TCEP.

After desalting step (BIORAD Bio-Gel P6 Desalting) in 50 mM bicine buffer pH8.0 containing 300 mM NaCl, 1 mM TCEP the protein concentration was determined using Lowry RC/DC Protein Assay of BioRad. The purified bulk was sterile-filtered on 0.22 μm and stored at −80° C.

C40

The bacterial pellet was re-suspended in 20 mM bicine buffer (pH 8.0) containing 500 mM NaCl, 5 mM$CaCl_2$ and a mixture of protease inhibitor (Complete, Roche). Bacteria were lysed using a French Press system 3×20 000 PSI. Soluble (supernatant) and insoluble (pellet) components were separated by centrifugation at 20 000 g for 30 min at 4° C.

The 6-His tagged-protein was purified under native conditions on IMAC. The soluble components were loaded on a 1 ml GE Histrap column (GE) pre-equilibrated with 20 mM bicine buffer (pH 8.0) containing 500 mM NaCl, 5 mM$CaCl_2$. After loading on the column, the column was washed with a 20 mM bicine buffer pH8.0, containing 500 mM NaCl, 5 mM $CaCl_2$ and 5 mM imidazole. Elution was performed using a 20 mM bicine buffer pH8.0 containing 150 mM NaCl, 5 mM $CaCl_2$ and 250 mM imidazole.

After desalting step (BIORAD Bio-Gel P6 Desalting) in 20 mM bicine buffer pH8.0 containing 150 mM NaCl, 1 mM TCEP the product was loaded on SEC chromatography (SUPERDEX™ 75) in the same buffer. Fractions containing Cdtb antigen were selected on the basis of purity by SDS-PAGE. Protein concentration was determined using Lowry RC/DC Protein Assay of BioRad. The purified bulk was sterile-filtered on 0.22 μm and stored at −80° C.

C55

The bacterial pellet was re-suspended in 50 mM bicine buffer (pH 8.0) containing 150 mM NaCl, 5 mM TCEP (Thermo Scientific Pierce, (2-carboxyethyl) phosphine hydrochloride), 0.4% empigen and a mixture of protease inhibitors (Complete, Roche). Bacteria were lysed using a French Press system 3×20 000 PSI. Soluble (supernatant) and insoluble (pellet) components were separated by centrifugation at 20 000 g for 30 min at 4° C.

The 6-His tagged-protein was purified under native conditions on IMAC. The soluble components were loaded on a 5 ml GE Histrap column (GE) pre-equilibrated with 50 mM bicine buffer (pH 8.0) containing 150 mM NaCl, 0.15% empigen, 1 mM TCEP. After loading on the column, the column was washed with a 50 mM bicine buffer pH8.0, containing 150 mM NaCl, 0.2% tween 20, 20 mM imidazole and 1 mM TCEP. Elution was performed using a 50 mM bicine buffer pH8.0 containing 150 mM NaCl, 0.2% tween 20, 500 mM imidazole and 1 mM TCEP.

After desalting step (BIORAD Bio-Gel P6 Desalting) in 50 mM bicine buffer pH8.0 containing 300 mM NaCl, 1 mM TCEP the product was loaded on SEC chromatography (SUPERDEX™ 75) in the same buffer. Fractions containing Cdtb antigen were selected on the basis of purity by SDS-PAGE. Protein concentration was determined using Lowry RC/DC Protein Assay of BioRad. The purified bulk was sterile-filtered on 0.22 μm and stored at −80° C.

Expression of the Recombinant Proteins: CdtB Receptor Binding Domain:

Expression Plasmid and Recombinant Strain.

Genes encoding the truncated protein of CdtB only recptor binding domain (C52-C53) and a His tag in C-term was cloned into the pET24b(+) expression vector (Novagen) using the NdeI/XhoI restriction sites using standard procedures. The final constructs were generated by the transformation of *E. coli* B834 (DE3) modified strain with the recombinant expression vector according to standard method with CaCl2-treated cells (Hanahan D. <<Plasmid transformation by Simanis.>> In Glover, D. M. (Ed), DNA cloning. IRL Press London. (1985): p. 109-135.).

Host Strain

B834 is the parental strain for BL21. These protease-deficient hosts are methionine auxotrophs. λ DE3 lysogens are designed for protein expression from pET vectors This strain is also deficient in the Ion and ompT proteases.

Modification: Including PGL gene to avoid phosphogluconoylation in the biotin locus (Strain is auxotroph for biotin).

Genotype: B834::DE3 strain, F-ompT hsdSB(rB-mB-) gal dcm met (DE3)

Modification: Δ(bioA-bioD)::PGL

| CdtB Rec. Bdng domain | |
|---|---|
| C number | |
| C52 | CdtB receptor binding domain long (aa. 620-876) |
| C53 | CdtB receptor binding domain short (aa. 636-876) |

Expression of the Recombinant Proteins:

A *E. coli* transformants were stripped from agar plate and used to inoculate 200 ml of LBT broth ±1% (w/v) glucose+ kanamycin (50 μg/ml) to obtain $O.D._{600nm}$ between 0.1-0.2. Cultures were incubated overnight at 37° C., 250 RPM.

These overnight cultures were diluted to 1:20 in 500 ml of LBT medium containing kanamycin (50 μg/ml) and grown at 37° C. at a stirring speed of 250 rpm until $O.D._{620}$ reached 0.5/0.6.

At an O.D. at 600 nm of around 0.6, the cultures were cooled down before inducing the expression of the recombinant protein by addition of 1 mM isopropyl β-D-1-thiogalactopyranoside (IPTG; EMD Chemicals Inc., catalogue number: 5815) and incubated overnight at 23° C., 250 RPM.

After the overnight inductions (around 16 hours), O.D. at 600 nm were evaluated after induction and cultures were centrifuged at 14 000 RPM for 15 minutes and pellets were frozen at −20° C. separately.

Purification

C52 and C53

The bacterial pellets were re-suspended in 50 mM bicine buffer pH 8.0, containing 500 mM NaCl and a mixture of protease inhibitors (Complete, Roche, without EDTA). Bacteria were lysed using a French Press system 3×20 000 PSI. Soluble (supernatant) and insoluble (pellet) components were separated by centrifugation at 20 000 g for 30 min at 4° C.

The 6-His tagged-proteins were purified under native conditions on IMAC. The soluble components were loaded on a 5 ml GE Histrap column (GE) pre-equilibrated with the same buffer used to bacterial re-suspension. After loading on the column, the column was washed with a 20 mM bicine buffer pH7.5 containing 500 mM NaCl, 25 mM imidazole. Elution was performed using a 50 mM bicine buffer pH7.5, 500 mM NaCl, and 250 mM imidazole.

After desalting (BIORAD Bio-Gel P6 Desalting) and concentration (Amicon Ultra 10 kDa) steps, the product was loaded on SEC chromatography (SUPERDEX™ 75) in 20 mM buffer pH7.5, 150 mM NaCl.

Fractions containing Cdtb antigen were selected on the basis of purity by SDS-PAGE. Protein concentration was determined using Lowry RC/DC Protein Assay of BioRad. The purified bulk was sterile-filtered on 0.22 μm and stored at −80° C.

Example 6: Cloning, Expression and Purification of *C. difficile* CdtA N-Term and CdtB Receptor Binding Domain Fusion Proteins Expression Plasmid and Recombinant Strain.

Genes encoding the fusion protein of CdtA N-term (C49 or C50) with CdtB receptor binding domain protein long or short version (C61 or C62) and a His tag in C-term were cloned into the pET24b(+) expression vector (Novagen) using the NdeI/XhoI restriction sites using standard procedures. The final constructs were generated by the transformation of *E. coli* B834 (DE3) modified strain with the appropriate recombinant expression vector according to standard method with CaCl2-treated cells (Hanahan D. <<Plasmid transformation by Simanis.>> In Glover, D. M. (Ed), DNA cloning. IRL Press London. (1985): p. 109-135.).

| Fusion CdtA N-term/CdtB-receptor binding domain | |
|---|---|
| C number | |
| C61 | CdtA N-term link (aa. 44-268)-CdtB RBD short (aa. 636-876) |
| C62 | CdtA N-term (aa. 44-260)-CdtB RBD long (aa. 621-876) |

Host Strain

Genotype: *E. coli* BL21::DE3 strain, $F^-$ ompT $hsdS_B(r_B^- m_B^-)$ gal dcm (DE3).

B834 is the parental strain for BL21. These protease-deficient hosts are methionine auxotrophs. λ DE3 lysogens are designed for protein expression from pET vectors This strain is also deficient in the Ion and ompT proteases.

Modification: Including PGL gene to avoid phosphoglu-conoylation in the biotin locus (Strain is auxotroph for biotin).

[016] Genotype: B834::DE3 strain, F-ompT hsdSB(rB-mB-) gal dcm met (DE3)

Modification: Δ(bioA-bioD)::PGL

Expression of the Recombinant Proteins:

*E. coli* transformants were stripped from each agar plate and used to inoculate 200 ml of LBT broth ±1% (w/v) glucose+kanamycin (50 μg/ml) to obtain O.D.$_{600nm}$ between 0.1-0.2. Cultures were incubated overnight at 37° C., 250 RPM.

These overnight cultures were diluted to 1:20 in 500 ml of LBT medium containing kanamycin (50 μg/ml) and grown at 37° C. at a stirring speed of 250 rpm until O.D.$_{620}$ reached 0.5/0.6.

At an O.D. at 600 nm of around 0.6, the cultures were cooled down before inducing the expression of the recombinant protein by addition of 1 mM isopropyl β-D-1-thio-galactopyranoside (IPTG; EMD Chemicals Inc., catalogue number: 5815) and incubated overnight at 23° C., 250 RPM.

After the overnight induction (around 16 hours), O.D. at 600 nm was evaluated after induction and culture was centrifuged at 14 000 RPM for 15 minutes and pellets were frozen at −20° C. separately.

Purification

C61

The bacterial pellet was re-suspended in 50 mM bicine buffer (pH 8.0) containing 300 mM NaCl, 5 mM TCEP (Thermo Scientific Pierce, (2-carboxyethyl) phosphine hydrochloride), 0.4% empigen and a mixture of protease inhibitors (Complete, Roche). Bacteria were lysed using a French Press system 3×20 000 PSI. Soluble (supernatant) and insoluble (pellet) components were separated by centrifugation at 20 000 g for 30 min at 4° C.

The 6-His tagged-protein was purified under native conditions on IMAC. The soluble components were loaded on a 5 ml GE Histrap column (GE) pre-equilibrated with 50 mM bicine buffer (pH 8.0) containing 300 mM NaCl, 0.15% empigen, 1 mM TCEP. After loading on the column, the column was washed with a 50 mM bicine buffer pH8.0, containing 300 mM NaCl, 0.2% tween 20, 25 mM imidazole and 1 mM TCEP. Elution was performed using a 50 mM bicine buffer pH8.0 containing 150 mM NaCl, 0.2% tween 20, 500 mM imidazole and 1 mM TCEP.

After desalting step (BIORAD Bio-Gel P6 Desalting) in 50 mM bicine buffer pH8.0 containing 300 mM NaCl, 1 mM TCEP the product was loaded on SEC chromatography (SUPERDEX™ 200) in the same buffer. Fractions containing the recombinant antigen were selected on the basis of purity by SDS-PAGE. Protein concentration was determined using Lowry RC/DC Protein Assay of BioRad. The purified bulk was sterile-filtered on 0.22 μm and stored at −80° C.

Example 7: Cloning and Expression of *C. difficile* CdtB Mature Co-Expressed (C55) with Prodomain of CdtB C58

Expression Plasmid and Recombinant Strain.

Genes encoding protein pro domain of CdtB without His tag was cloned into the pET21b(+) expression vector (Novagen) using the NdeI/XhoI restriction sites using standard procedures. The final construct was generated by the transformation of *E. coli* B834 (DE3) modified strain with the recombinant expression vector of prodomain CdtB and CdtB mature protein C55—information about cloning of C55 see example 3 according to standard method with CaCl2-treated cells (Hanahan D. <<Plasmid transformation by Simanis.>> In Glover, D. M. (Ed), DNA cloning. IRL Press London. (1985): p. 109-135.).

| Pro domain of CdtB alone | |
|---|---|
| C number | |
| C58 | Pro-domaine CdtB long (aa. 43-211) |

Host Strain

B834 is the parental strain for BL21. These protease-deficient hosts are methionine auxotrophs. λ DE3 lysogens are designed for protein expression from pET vectors This strain is also deficient in the Ion and ompT proteases.

Modification: Including PGL gene to avoid phosphoglu-conoylation in the biotin locus (Strain is auxotroph for biotin).

[016] Genotype: B834::DE3 strain, F-ompT hsdSB(rB-mB-) gal dcm met (DE3)

Modification: Δ(bioA-bioD)::PGL

Expression of the Recombinant Proteins:

A *E. coli* transformant was stripped from agar plate and used to inoculate 200 ml of LBT broth ±1% (w/v) glucose+kanamycin (50 μg/ml) and ampicillin (100 μg/ml) to obtain O.D.$_{600nm}$ between 0.1-0.2. Culture was incubated overnight at 37° C., 250 RPM.

This overnight culture was diluted to 1:20 in 500 ml of LBT medium containing kanamycin (50 μg/ml) and ampicillin (100 μg/ml) and grown at 37° C. at a stirring speed of 250 rpm until O.D.$_{620}$ reached 0.5/0.6.

At an O.D. at 600 nm of around 0.6, the culture was cooled down before inducing the expression of the recombinant protein by addition of 1 mM isopropyl β-D-1-thio-galactopyranoside (IPTG; EMD Chemicals Inc., catalogue number: 5815) and incubated overnight at 23° C., 250 RPM.

After the overnight induction (around 16 hours), O.D. at 600 nm was evaluated after induction and culture was centrifuged at 14 000 RPM for 15 minutes and pellets were frozen at −20° C. separately.

Purification same as C55 produced alone

Example 8: Molecular Weight Evaluation of CdtA, CdtB and CdtA-CdtB Fusion Constructions Analytical ultracentrifugation was used to determine the homogeneity and size distribution in solution of the different species within a protein sample by measuring the rate at which molecules move in response to a centrifugal force. This is based on the calculation of the coefficients of sedimentation of the different species that are obtained by sedimentation velocity experiment, which depend on their molecular shape and mass.

1. Protein samples are spun in a Beckman-Coulter ProteomeLab XL-1 analytical ultracentrifuge at 8000 RPM, 25000 RPM or 42000 RPM depending of the target protein size, after the AN-60Ti rotor had been equilibrated to 15° C.

2. For data collection, scans were recorded at 280 nm every 5 minutes.

3. Data analysis was performed using the program SEDFIT for determination of the C(S) distribution. Determination of the partial specific volume of the proteins was performed with the SEDNTERP software from their amino acid sequence. Sednterp was also used to determine the viscosity and the density of the buffer.

4. Determination of the molecular weight of the different species has been determined from the C(S) distribution plot (concentration vs sedimentation coefficient), considering that it's a better representation of the raw data than the C(M) distribution (concentration vs molecular weight) to characterize the size distribution of a mixture.

FIGS. 1*a* to 1*h* describe the size distribution of the different CdtA. CdtB and CdtA-CdtB fusion constructions as determined by sedimentation velocity analytical ultracentrifugation.

Figure 1B:
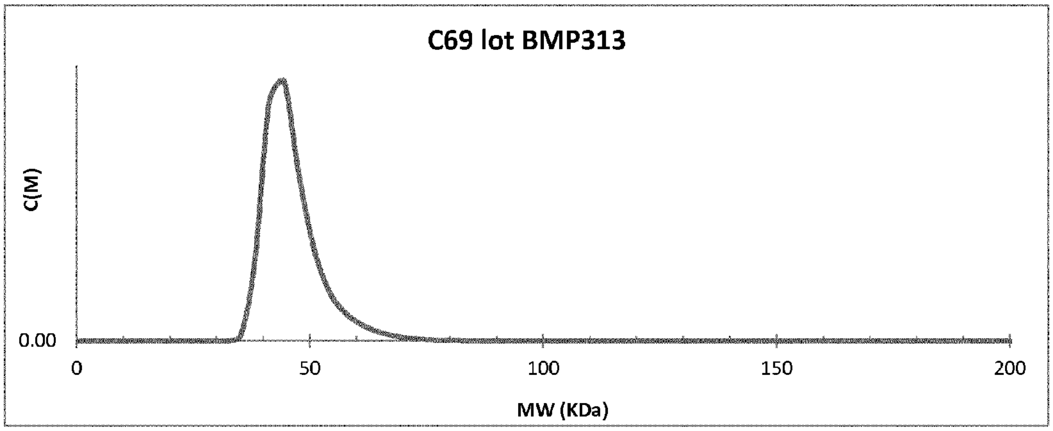
FIG. 1*b*: AUC of C69 CdtA (aa44-463) mut. R345A-Q350A-N385A-R402A-S388F-E428Q-E430Q
Figure 1C:
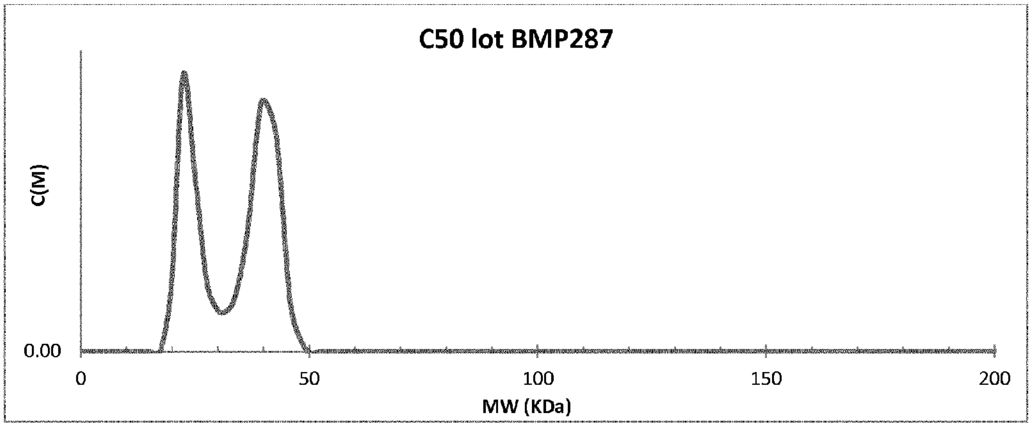
FIG. 1*c*: AUC of C50 (CdtA N-term without linker (aa44-260)

The calculated molecular weight of the main species for C67 and C69 mutated full length CdtA protein may correspond with a monomer, while the C50 truncated CdtA N-terminal construction is present in solution as a mix of monomer and dimer (FIGS. 1*a*, 1*b* and 1*c*).

Figure 1D:
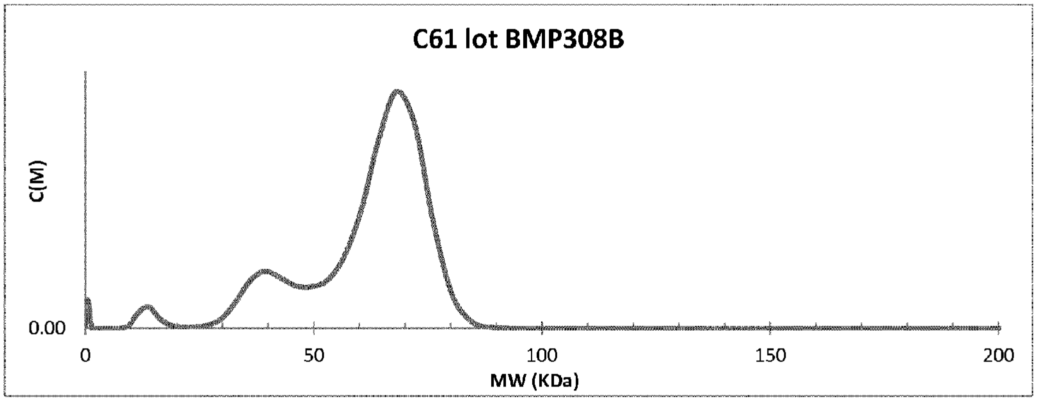
FIG. 1*d*: AUC of C61 (fusion CdtA N term with linker-CdtBshort)
Figure 1E:
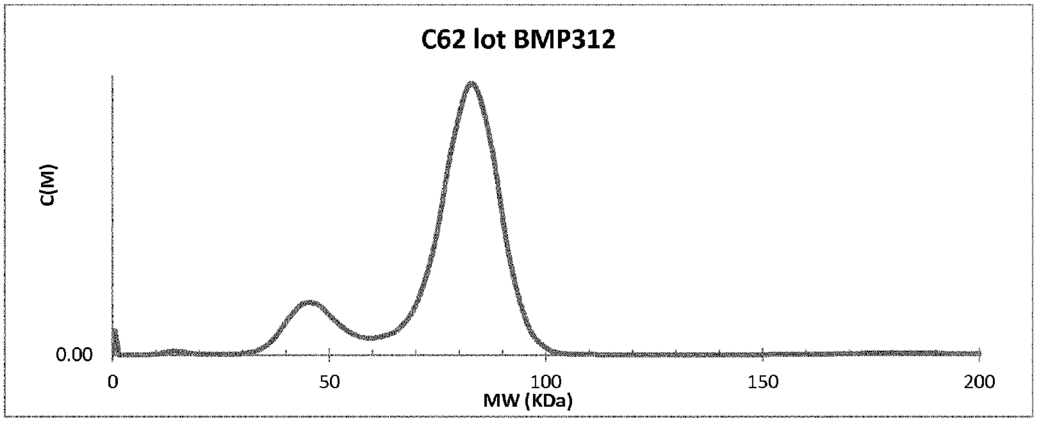
FIG. 1*e*: AUC of C62 (fusion CdtA N term without linker-CdtBlong)

Both C61 and C62 fusions of CdtA-CdtB are mainly dimeric, with a minor proportion of monomer (FIGS. 1*d* and 1*e*).

Figure 1F:
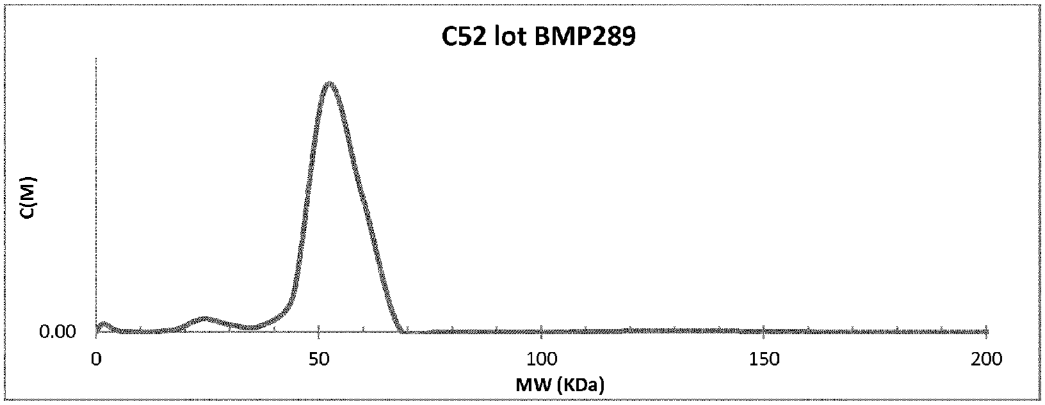
FIG. 1*f*: AUC of C52 (CdtB long)
Figure 1G:
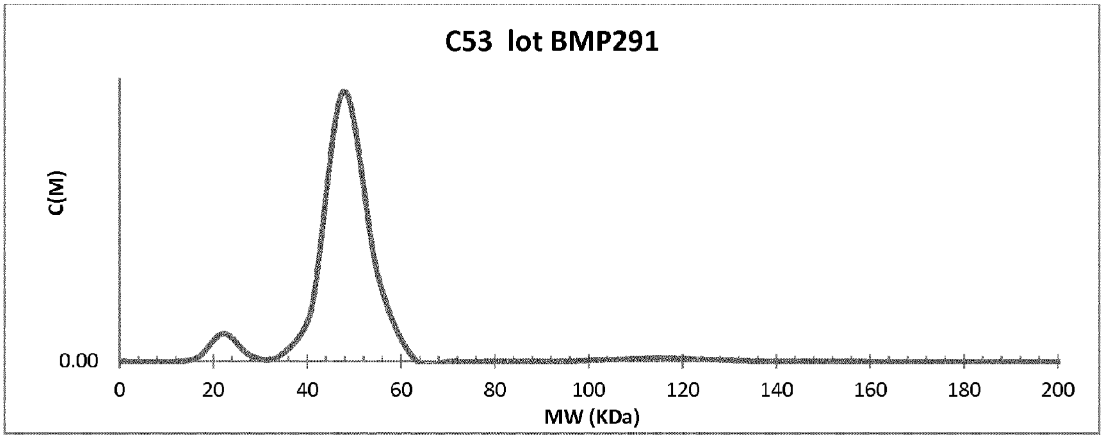
FIG. 1*g*: AUC of C53 (CdtB short)

Constructions of the CdtB receptor binding domain C52 and C52 are mainly dimeric with presence of small amount of monomer (FIGS. 1*f* and 1*g*).

Figure 1H:
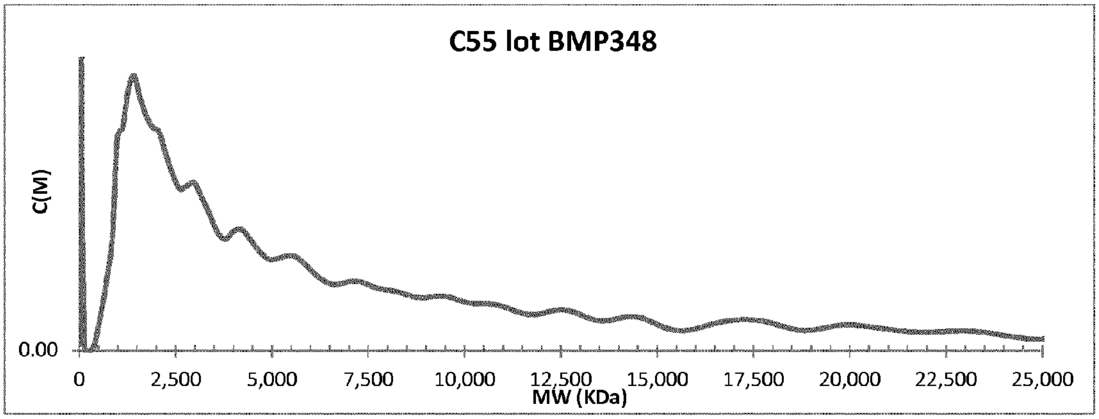
FIG. 1*h*: AUC of C55 CdtB Δ prodomain (aa. 212-876)

Full length CdtB without prodomain C55 is highly aggregated after purification, presenting a heterogeneous size distribution by AUC (FIG. 1*h*).

Example 9: SDS PAGE Profile of CdtA, CdtB and CdtA-CdtB Fusion Constructions after Purification Purified proteins from each construction were separated on denaturing and reducing SDS PAGE in order to assess the sequence integrity.

Figure 2A:
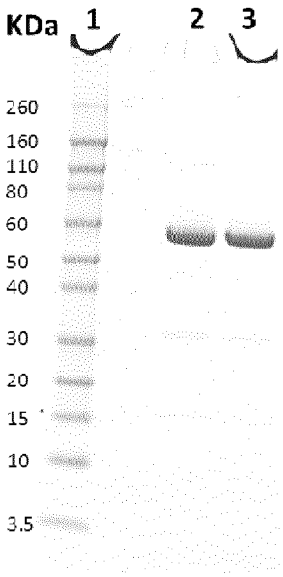
FIG. 2*a*: SDS PAGE of purified CdtA-CdtB fusion constructions. Lane 1: Molecular weight marker Novex sharp prestained. Lane 2: 5 μg of C61 CdtA N-term link (aa. 44-268)-CdtB RBD short (aa. 636-876). Lane 3: 5 μg of C62 CdtA N-term (aa. 44-260)-CdtB RBD long (aa. 621-876).
Figure 2B:
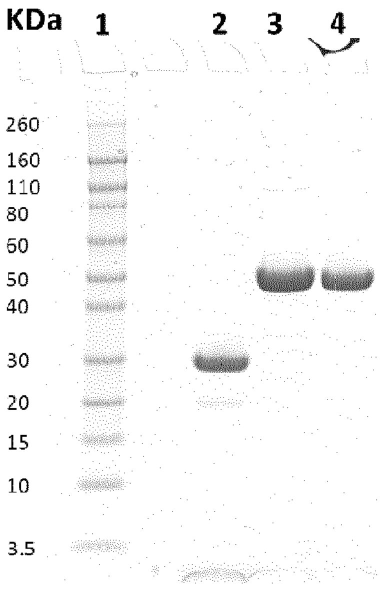
FIG. 2*b*: SDS PAGE of purified CdtA constructions. Lane 1: Molecular weight marker Novex sharp prestained. Lane 2: 5 μg of C50 CdtA WO linker (44-260). Lane 3: 5 μg of C67 CdtA full length (aa44-463) mut. E428Q-E430Q. Lane 4: 5 μg of C69 CdtA full length (aa44-463) mut. R345A-Q350A-N385A-R402A-S388F-E428Q-E430Q.

FIG. 2*a* shows that CdtA-CdtB fusion constructions C61 and C62 are present in majority at the expected molecular weight. Same observations are made for CdtA constructions on FIG. 2*b*.

Figure 2C:
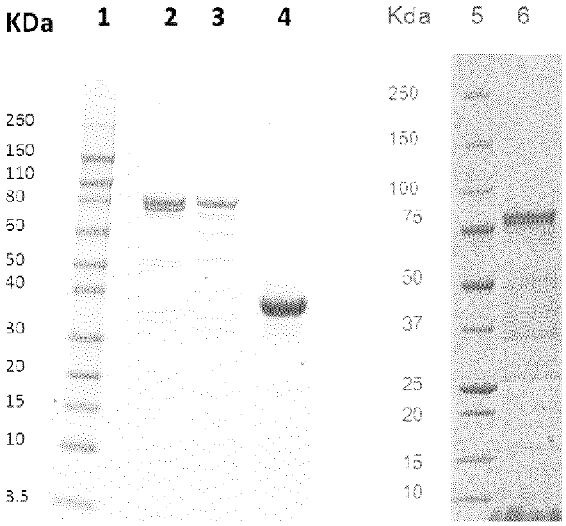
FIG. 2*c*: SDS PAGE of purified CdtB constructions. Lane 1: Molecular weight marker Novex sharp prestained. Lane 2: 5 μg of C37 CdtB' Δsignal sequence (aa43-876)+GST N-term after removal of the N-term GST and activation by prodomain cleavage with chymotrypsin. Lane 3: 5 μg of C55 CdtB Δ prodomain (aa. 212-876). Lane 4: 5 μg of C52 CdtB receptor binding domain long (aa. 621-876). Lane 5: Molecular weight marker. Lane 6: 5 μg of C38 CdtB' Δsignal sequence (aa43-876).

It is shown on FIG. 2*c* that chymotrypsin activation of C37 CdtB (aa. 43-876) construction results in the truncation of the prodomain for the obtention of a protein (lane 2) at a molecular weight comparable to the mature CdtB represented at the lane 3 by C55 (aa. 212-876). SDS PAGE profile of C55 contains significant amount of secondary products that couldn't be separated from the complete protein, which is coherent with the highly aggregated profile observed by AUC on FIG. 2*h*.

CdtB expressed with prodomain C38 (aa. 43-876) was purified as a an heterogeneous preparation composed at the majority of a doublet of the expected molecular weight containing a significant amount of secondary products.

Example 9: Immunisation of Mice with *C. difficile* CdtA and CdtB Sub-Units Proteins in a AS01B Formulation Mice Immunisation Groups of 25 female Balb/C mice were immunized IM at days 0, 14 and 28 with 5 μg of full CdtA and CdtB binary toxin purified sub-units. These antigens were injected in an AS01B formulation.

Figure 3:
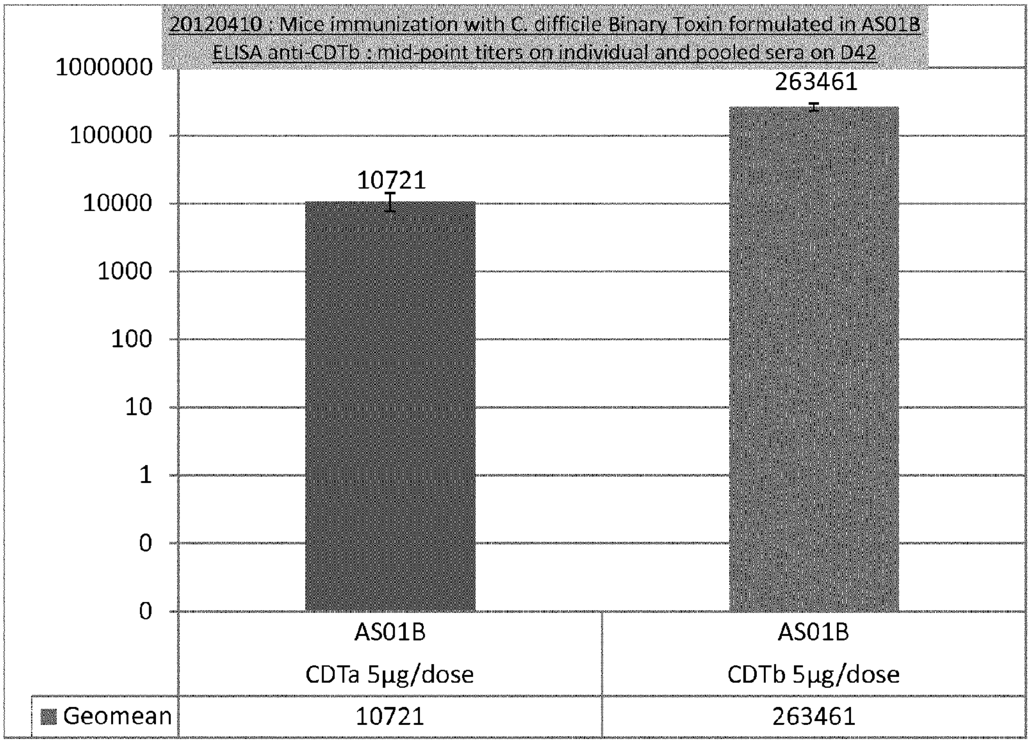
FIG. 3—Graph showing anti-CDTb immunogenicity in mice immunised with *C. difficile* Binary Toxin component A or *C. difficile* Binary Toxin component B, in both cases formulated with adjuvant FIG. 4—Graph showing anti-CDTa immunogenicity in mice immunised with *C. difficile* Binary Toxin component A or *C. difficile* Binary Toxin component B, in both cases formulated with adjuvant FIG. 5—Cytotoxicity inhibition titres in HCT116 cells from mice immunised with *C. difficile* Binary Toxin component A or *C. difficile* Binary Toxin component B, in both cases formulated with adjuvant FIG. 6—Cytotoxicity inhibition titres in HT29 cells from mice immunised with *C. difficile* Binary Toxin component A or *C. difficile* Binary Toxin component B, in both cases formulated with adjuvant FIG. 7—Graph showing anti-CDTb immunogenicity in mice immunised with *C. difficile* Cdtb (activated or non activated, with and without F2 fusion comprising fragments from Toxin A and Toxin B) formulated with adjuvant FIG. 8—Graph showing anti-Tox A immunogenicity in mice immunised with *C. difficile* Cdtb (activated or non activated, with and without F2 fusion comprising fragments from Toxin A and Toxin B) formulated with adjuvant FIG. 9—Graph showing anti-Tox B immunogenicity in mice immunised with *C. difficile* Cdtb (activated or non activated, with and without F2 fusion comprising fragments from Toxin A and Toxin B) formulated with adjuvant FIG. 10—Tox A cytotoxicity inhibition titres in HT29 cells from mice immunised with *C. difficile* Cdtb (activated or non activated, with and without F2 fusion comprising fragments from Toxin A and Toxin B) formulated with adjuvant FIG. 11—Tox B cytotoxicity inhibition titres in HCT116 cells from mice immunised with *C. difficile* Cdtb (activated or non activated, with and without F2 fusion comprising fragments from Toxin A and Toxin B) formulated with adjuvant FIG. 12—Binary Toxin cytotoxicity inhibition titres in HT29 cells from mice immunised with *C. difficile* Binary Toxin component A or *C. difficile* Binary Toxin component B, in both cases formulated with adjuvant FIG. 13—Graph showing anti-CDTb immunogenicity in mice immunized with different binary toxin vaccine candidates (CdtA/CdtB) combined with F2 at 6 μg/dose in an adjuvant formulation FIG. 14—Graph showing anti-CDTa immunogenicity in mice immunized with different binary toxin vaccine candidates (CdtA/CdtB) combined with F2 at 6 μg/dose in an adjuvant formulation FIG. 15—Graph showing anti-Tox B immunogenicity in mice immunized with different binary toxin vaccine candidates (CdtA/CdtB) combined with F2 at 6 μg/dose in an adjuvant formulation FIG. 16—Graph showing anti-Tox A immunogenicity in mice immunized with different binary toxin vaccine candidates (CdtA/CdtB) combined with F2 at 6 μg/dose in an adjuvant formulation FIG. 17—Binary Toxin cytotoxicity inhibition titres in HCT116 cells from mice immunised with different binary toxin vaccine candidates (CdtA/CdtB) combined with F2 at 6 μg/dose in an adjuvant formulation FIG. 18—Binary Toxin cytotoxicity inhibition titres in HT29 cells from mice immunised with different binary toxin vaccine candidates (CdtA/CdtB) combined with F2 at 6 μg/dose in an adjuvant formulation FIG. 19—Tox A cytotoxicity inhibition titres in HT29 cells from mice immunised with different binary toxin vaccine candidates (CdtA/CdtB) combined with F2 at 6 μg/dose in an adjuvant formulation FIG. 20—Tox B cytotoxicity inhibition titres in HCT116 cells from mice immunised with different binary toxin vaccine candidates (CdtA/CdtB) combined with F2 at 6 μg/dose in an adjuvant formulation FIG. 21—Graph showing anti-CDTb immunogenicity in mice immunized with different binary toxin vaccine candidates (CdtA/CdtB) combined with F2 at 2 μg/dose in an adjuvant formulation FIG. 22—Graph showing anti-CDTa immunogenicity in mice immunized with different binary toxin vaccine candidates (CdtA/CdtB) combined with F2 at 2 μg/dose in an adjuvant formulation FIG. 23—Graph showing anti-Tox B immunogenicity in mice immunized with different binary toxin vaccine candidates (CdtA/CdtB) combined with F2 at 2 μg/dose in an adjuvant formulation FIG. 24—Graph showing anti-Tox A immunogenicity in mice immunized with different binary toxin vaccine candidates (CdtA/CdtB) combined with F2 at 2 μg/dose in an adjuvant formulation FIG. 25—Binary Toxin cytotoxicity inhibition titres in HCT116 cells from mice immunised with different binary toxin vaccine candidates (CdtA/CdtB) combined with F2 at 2 μg/dose in an adjuvant formulation FIG. 26—Binary Toxin cytotoxicity inhibition titres in HT29 cells from mice immunised with different binary toxin vaccine candidates (CdtA/CdtB) combined with F2 at 2 μg/dose in an adjuvant formulation FIG. 27—Tox A cytotoxicity inhibition titres in HT29 cells from mice immunised with different binary toxin vaccine candidates (CdtA/CdtB) combined with F2 at 2 μg/dose in an adjuvant formulation FIG. 28—Tox B cytotoxicity inhibition titres in HCT116 cells from mice immunised with different binary toxin vaccine candidates (CdtA/CdtB) combined with F2 at 2 μg/dose in an adjuvant formulation FIG. 29—Graph showing anti-CDTb immunogenicity in mice immunized with different binary toxin vaccine candidates (CdtA/CdtB) combined with F2 at 10 μg/dose in a non-adjuvanted formulation FIG. 30—Graph showing anti-CDTa immunogenicity in mice immunized with different binary toxin vaccine candidates (CdtA/CdtB) combined with F2 at 10 μg/dose in a non-adjuvanted formulation FIG. 31—Graph showing anti-Tox B immunogenicity in mice immunized with different binary toxin vaccine candidates (CdtA/CdtB) combined with F2 at 10 μg/dose in a non-adjuvanted formulation FIG. 32—Graph showing anti-Tox A immunogenicity in mice immunized with different binary toxin vaccine candidates (CdtA/CdtB) combined with F2 at 10 μg/dose in a non-adjuvanted formulation FIG. 33—Binary Toxin cytotoxicity inhibition titres in HCT116 cells from mice immunised with different binary toxin vaccine candidates (CdtA/CdtB) combined with F2 at 10 μg/dose in a non-adjuvanted formulation FIG. 34—Binary Toxin cytotoxicity inhibition titres in HT29 cells from mice immunised with different binary toxin vaccine candidates (CdtA/CdtB) combined with F2 at 10 μg/dose in a non-adjuvanted formulation FIG. 35—Tox A cytotoxicity inhibition titres in HT29 cells from mice immunised with different binary toxin vaccine candidates (CdtA/CdtB) combined with F2 at 10 μg/dose in a non-adjuvanted formulation FIG. 36—Tox B cytotoxicity inhibition titres in HCT116 cells from mice immunised with different binary toxin vaccine candidates (CdtA/CdtB) combined with F2 at 10 μg/dose in a non-adjuvanted formulation
Figure 4:
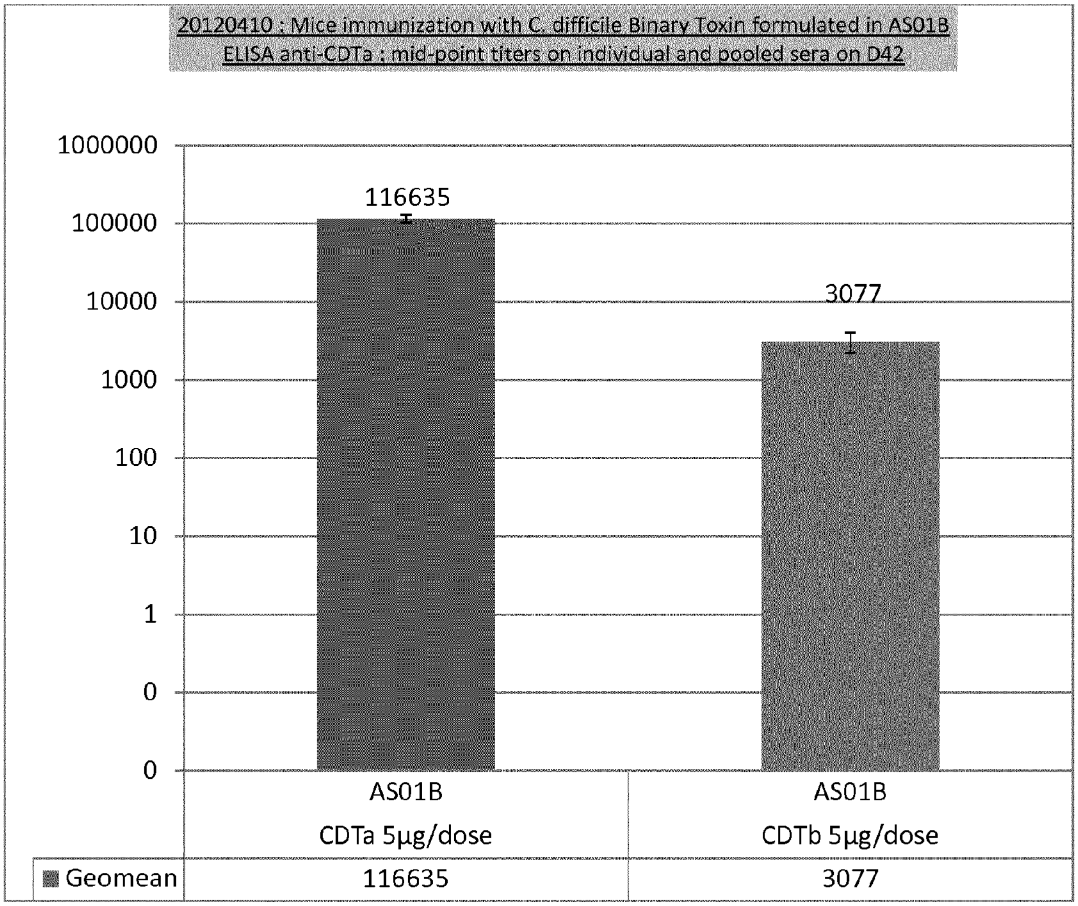

Anti-CdtA and anti-CdtB ELISA titers were determined in individual sera collected at day 42 (Post III 14). Results are shown in FIGS. 3-4.

Figure 5:
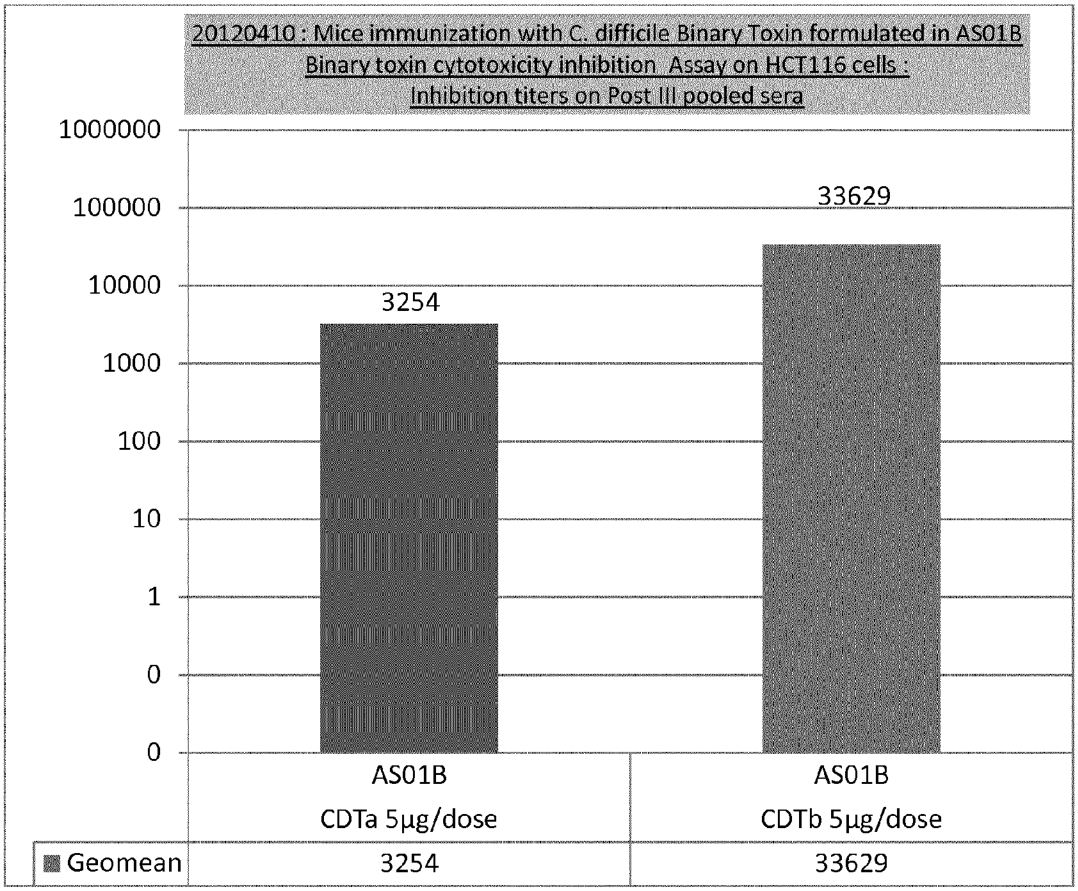
Figure 6:
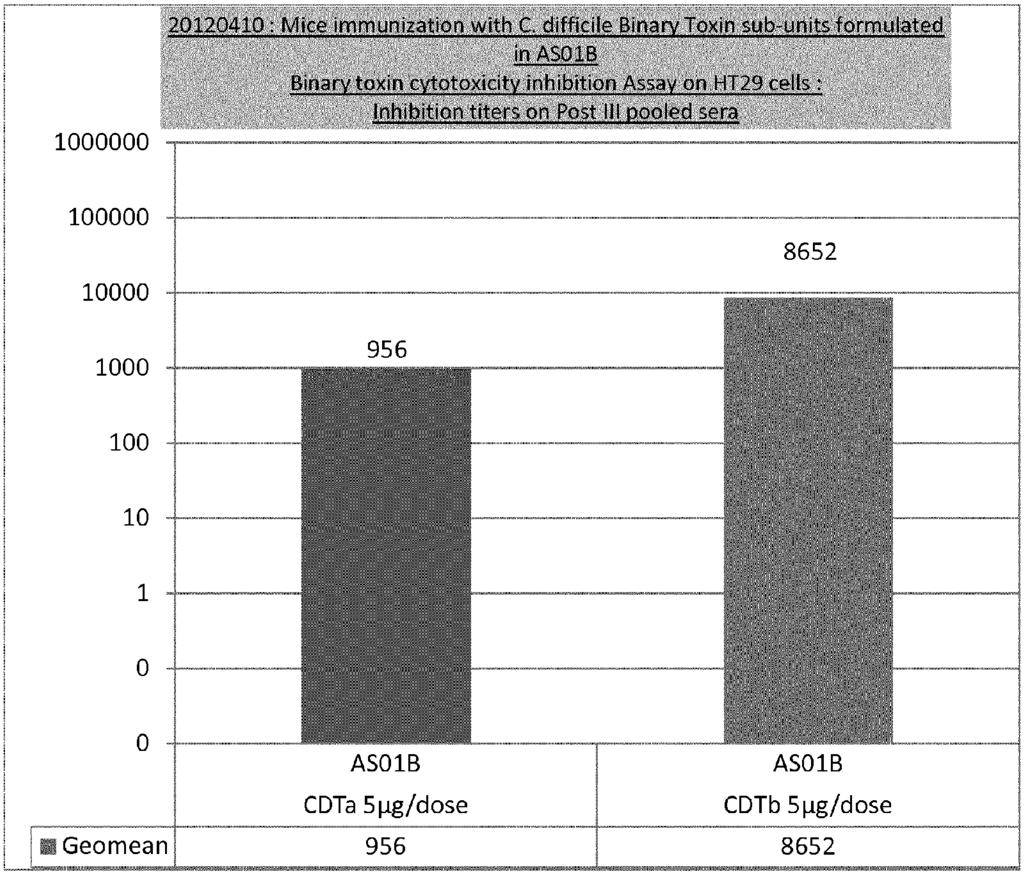

A binary toxin cytotoxicity inhibition assay was also performed on pooled Post III sera (day42). Results are shown in FIGS. 5-6

Anti-CdtA and Anti-CdtB ELISA Response: Protocol

Full CdtA (C34) or full CdtB (C37)sub-units were coated at 1 μg/ml (for CdtA) or 2 μg/ml (for CdtB) in phosphate buffered saline (PBS) on high-binding microtitre plates (Nunc MAXISORP™), overnight at 4° C. The plates were blocked with PBS-BSA 1% for 30 min at RT with agitation. The mice anti-sera are prediluted 1/500 in PBS-BSA0.2%-TWEEN™ 0.05%. and then, further twofold dilutions were made in microplates and incubated at RT for min. After washing, bound mouse antibody was detected using Jackson ImmunoLaboratories Inc. peroxidase-conjugated Anti-Mouse (ref: 110-035-003) diluted 1:5000 in PBS-BSA0.2%-tween 0.05%. The detection antibodies were incubated for 30 min. at room temperature (RT) with agitation. The color was developed using 4 mg O-phenylenediamine (OPD)+5 μl $H_2O_2$ per 10 ml pH 4.5 0.1M citrate buffer for 15 minutes in the dark at room temperature. The reaction was stopped with 50 μl HCl, and the optical density (OD) was read at 490 nm relative to 620 nm.

The level of anti-CdtA or anti-CdtB antibodies are expressed in mid-point titers. A GMT was calculated for the 25 samples in each treatment group.

Binary Toxin Cytotoxicity Inhibition Assay

Human colonic eptithelial cells (HT29 or HCT-116 cells) were cultured at 37° C. with 5% $CO_2$ in DMEM +10% fetal bovine serum +1% glutamine +1% antibiotics (penicillin-streptomycin-amphotericin) and were seeded in 96-well black tissue culture plates (Greiner Bio-one, Ref: 655090) at a density of $4.10^4$ cells/well for HT29 and $1.10^4$ cells/well for HCT116. After 24 h, the cell media was removed from the wells.

The mice anti-sera were prediluted 1:50 in cell media and then, further three-fold dilutions were made in microplate (NUNC, Ref: 163320). 50 μl of serial dilutions of mice pooled antisera were added to the black plates. 50 μl of a mix of CdtA (25 ng/ml) and chemotrypsin-activated CdtB (75 ng/ml) were then added and the black plates incubated at 37° C. with 5% $CO_2$ for 6 days.

After 6 days, the mix of antisera and toxin were removed from the wells and 100 μl of Hoescht stain (BD Pharmingen, Ref: 561908) diluted 1:500 in phosphate buffer saline (PBS) was added in each well for 2 hours in the dark at room temperature.

After coloration, the Hoescht stain was removed from the wells and the cells fluorescence cells was measured using an Axiovision microscope.

The surface covered by fluorescent staining was determined in each well and cytotoxicity inhibition titers were defined as the reciprocal dilution inducing a 50% inhibition of the fluorescent signal.

Example 10: Immunisation of Mice with *C. difficile* CdtB Chemotrypsin-Activated or not, Mixed with F2 or not, Formulated in AS01B Mice Immunisation Groups of 25 female Balb/C mice were immunized IM at days 0, 14 and 28 with 5 μg of CdtB binary toxin purified sub-unit chemotrypsin-activated or not, mixed with 5 μg of F2 or not. These antigens were injected in an AS01B formulation.

Figure 7:
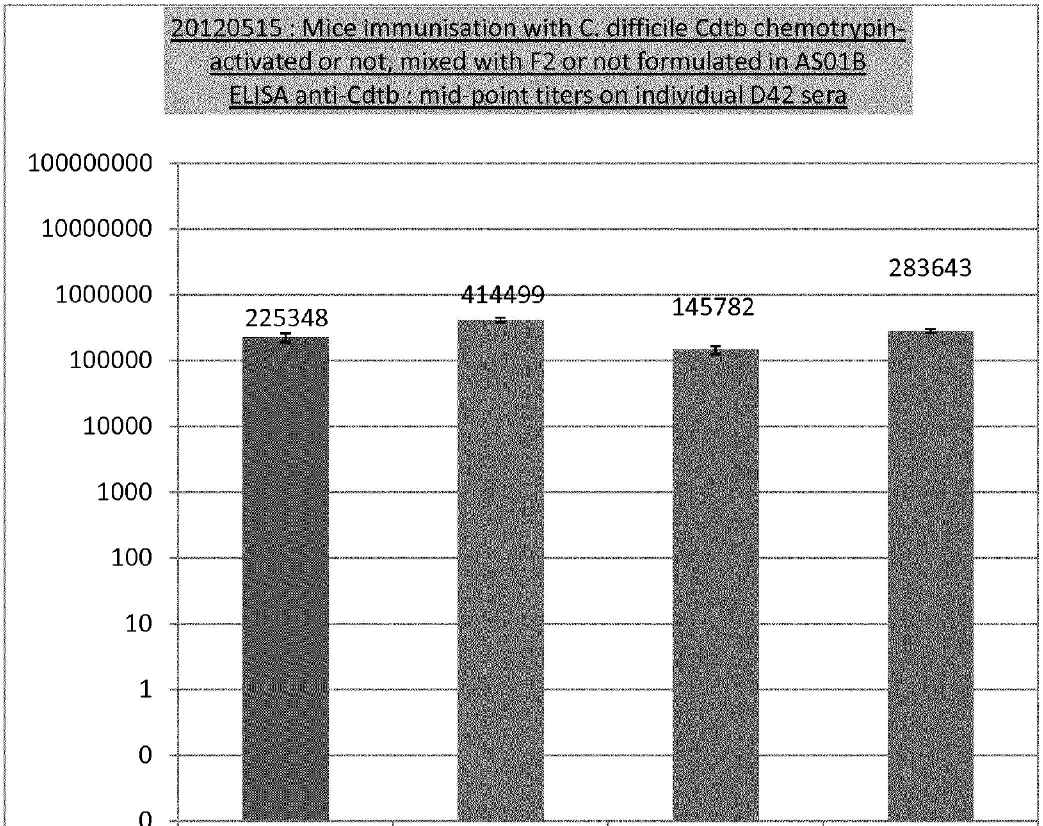
Figure 8:
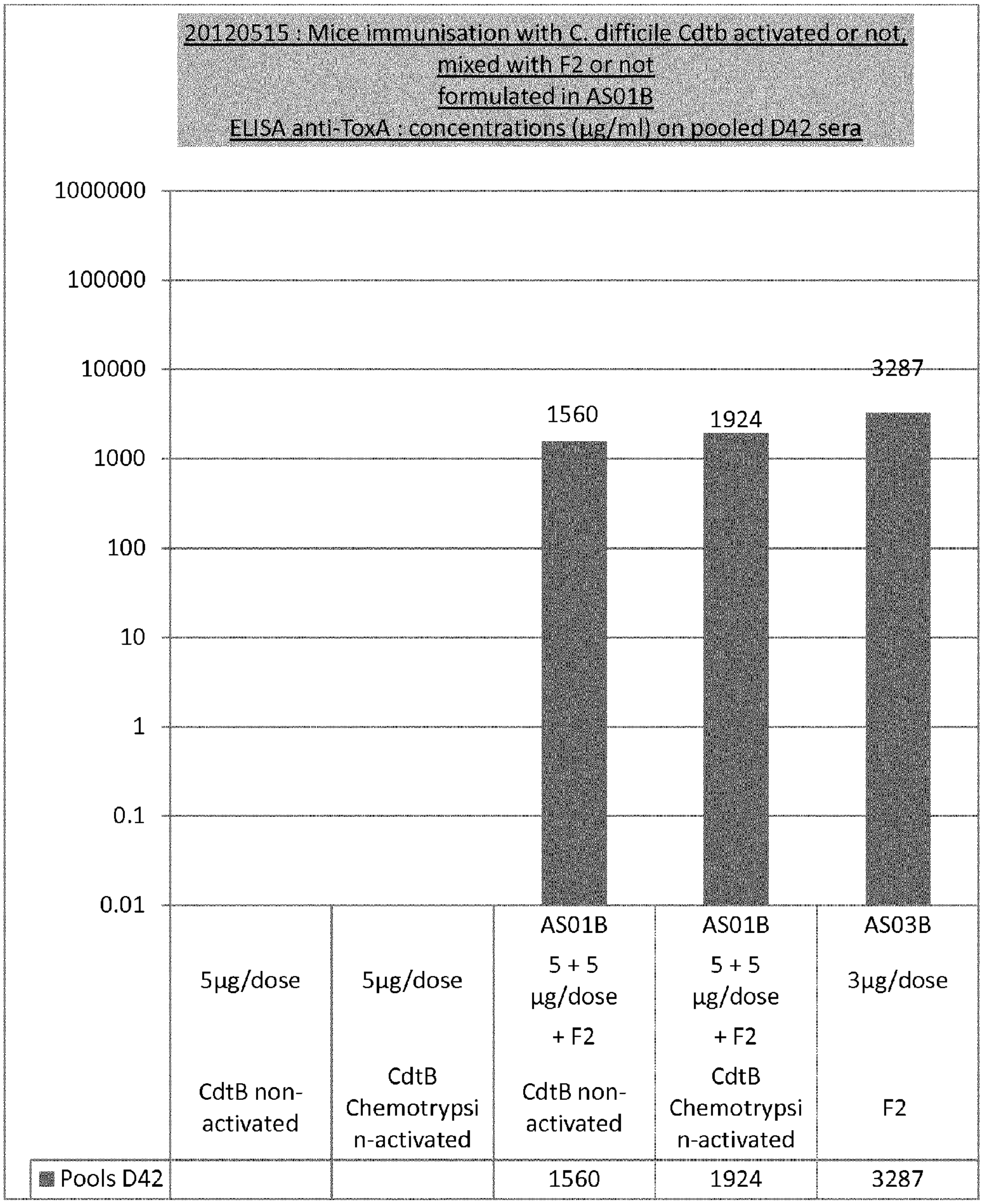
Figure 9:
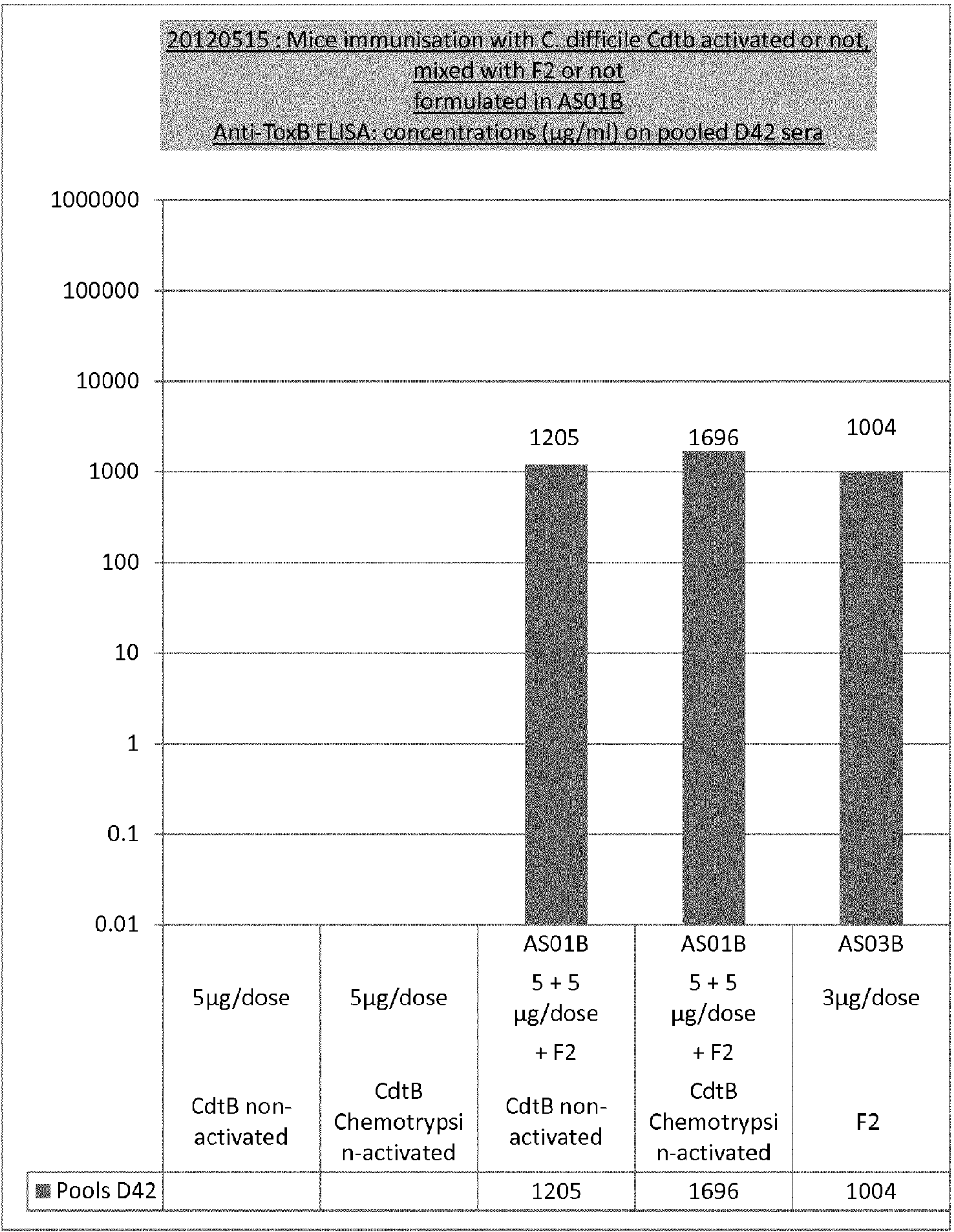

Anti-CdtB, anti-ToxA and anti-ToxB ELISA titers were determined in individual sera collected at day 42 (Post III 14). Results are shown in FIGS. 7-9.

Figure 10:
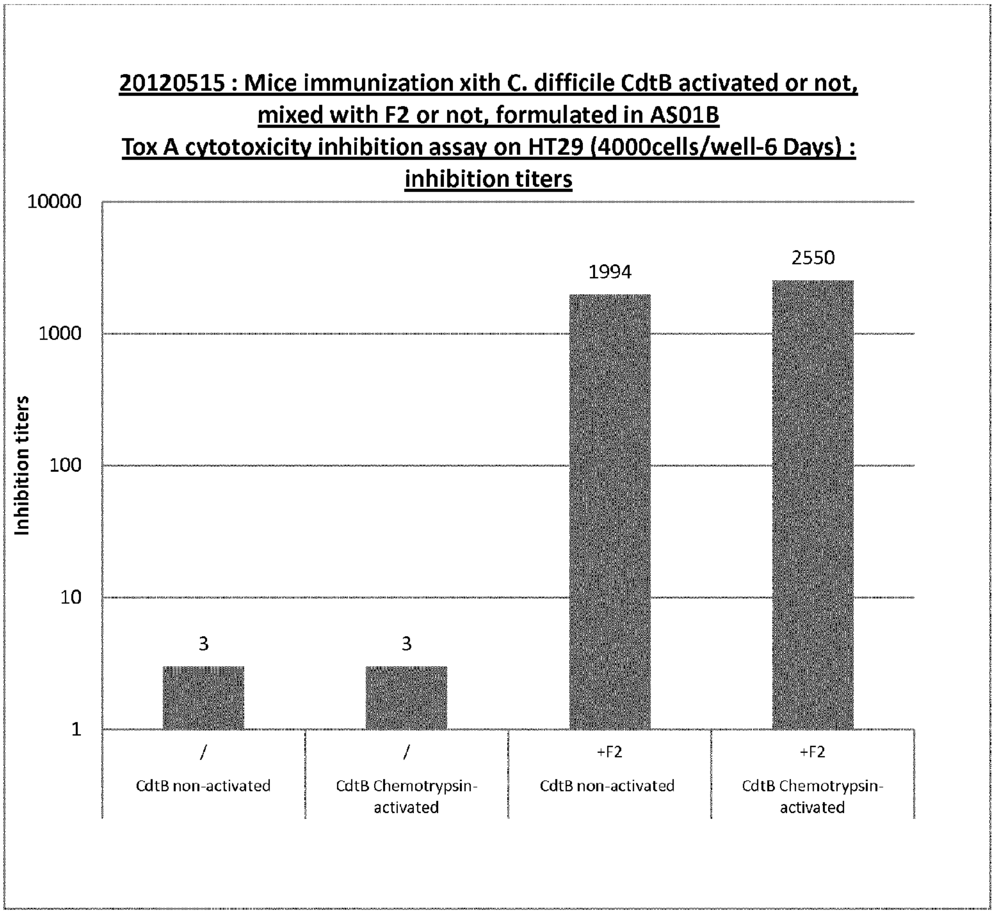
Figure 11:
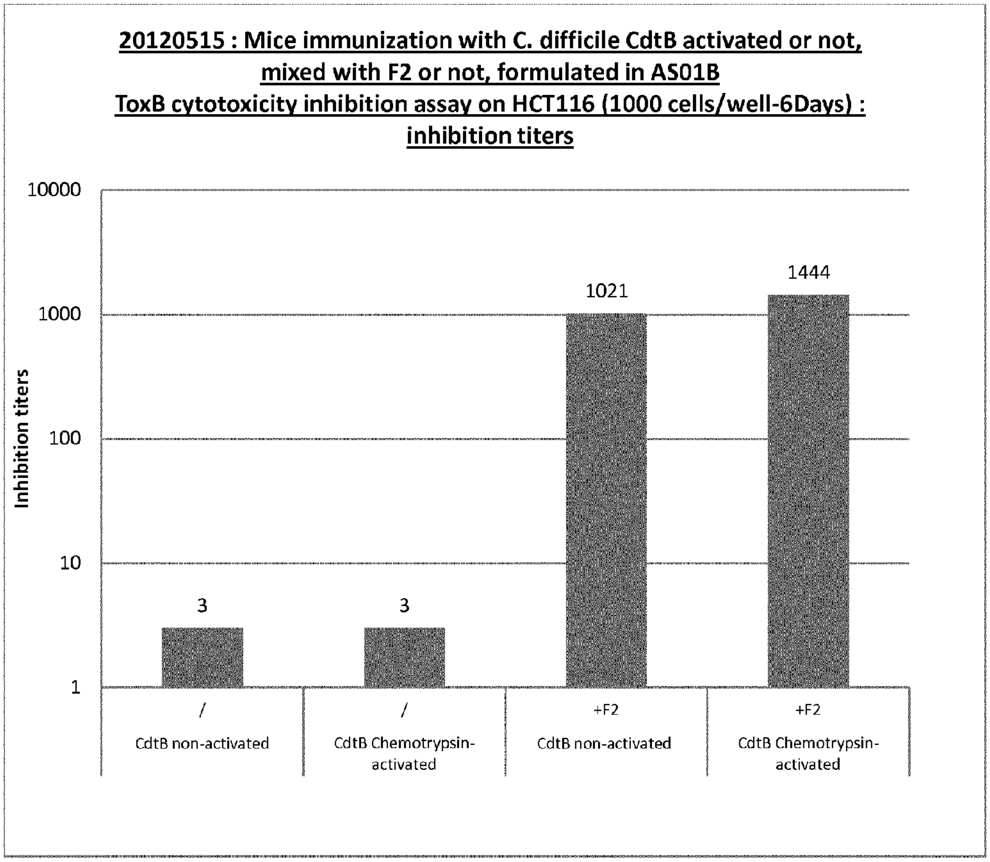
Figure 12:
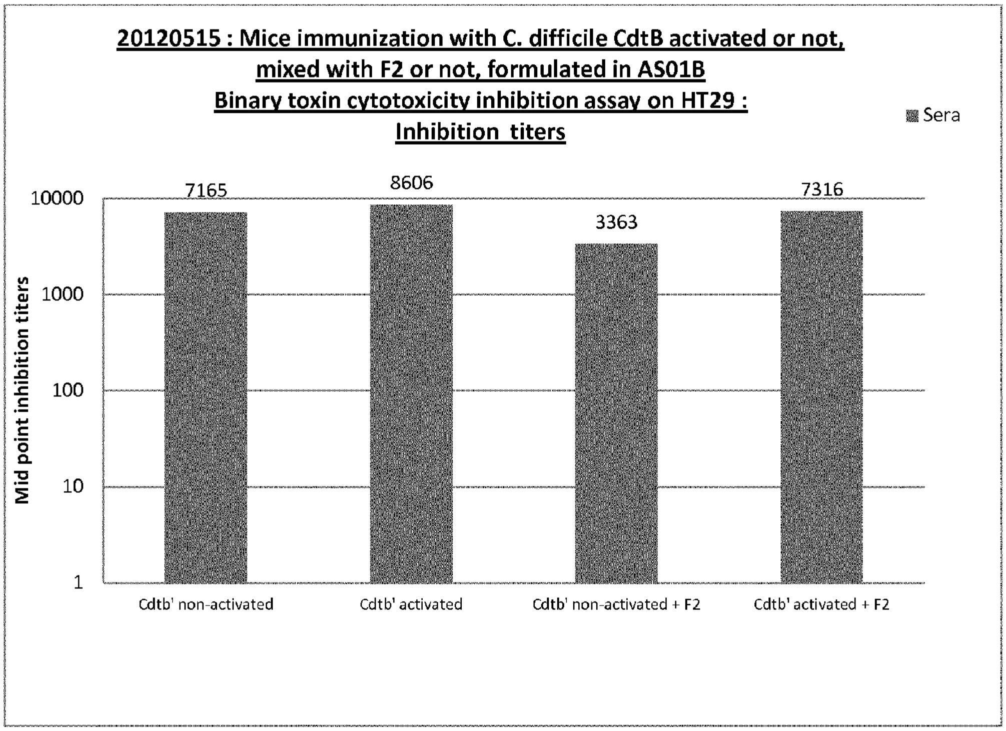
Figure 13:
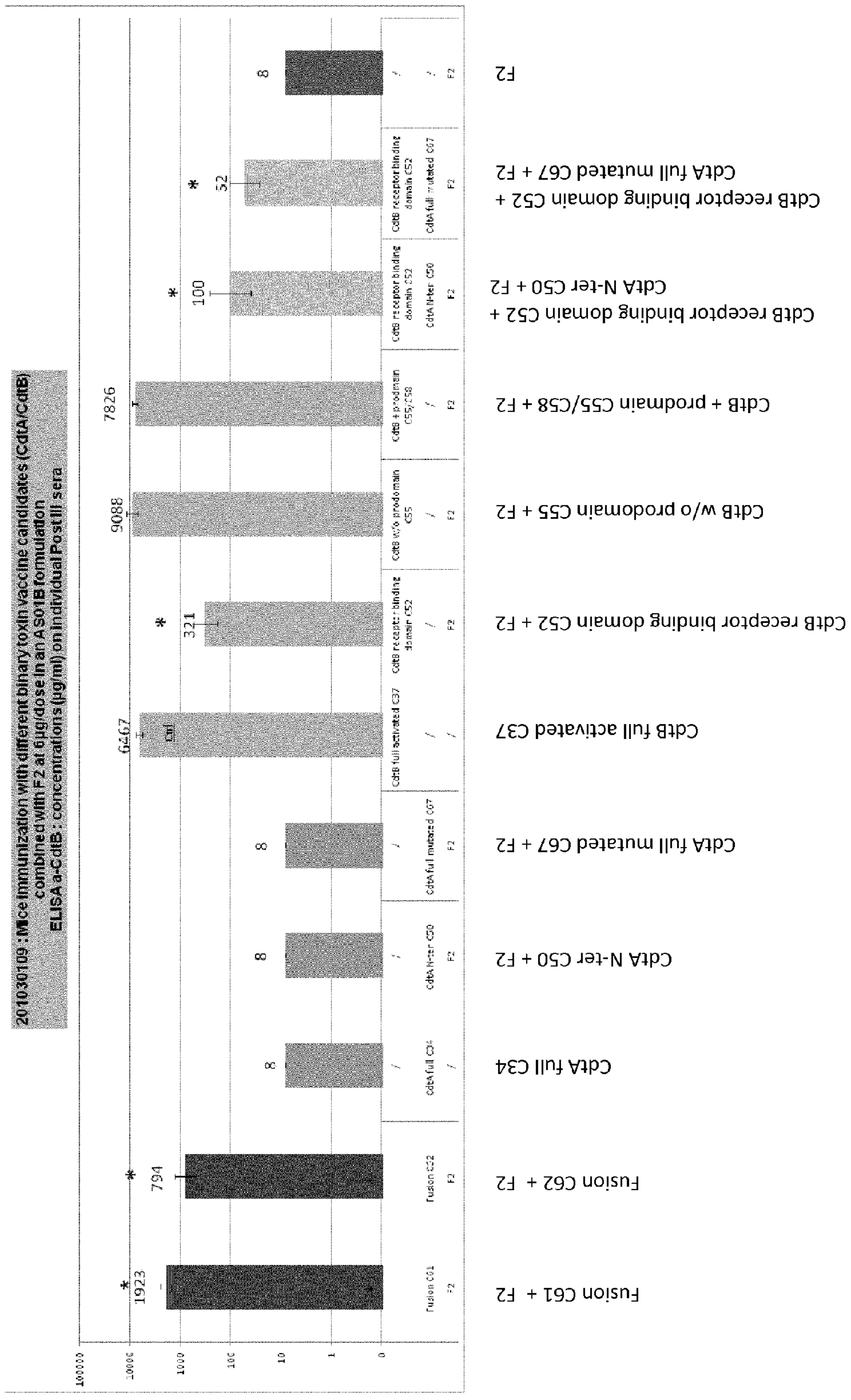
Figure 14:
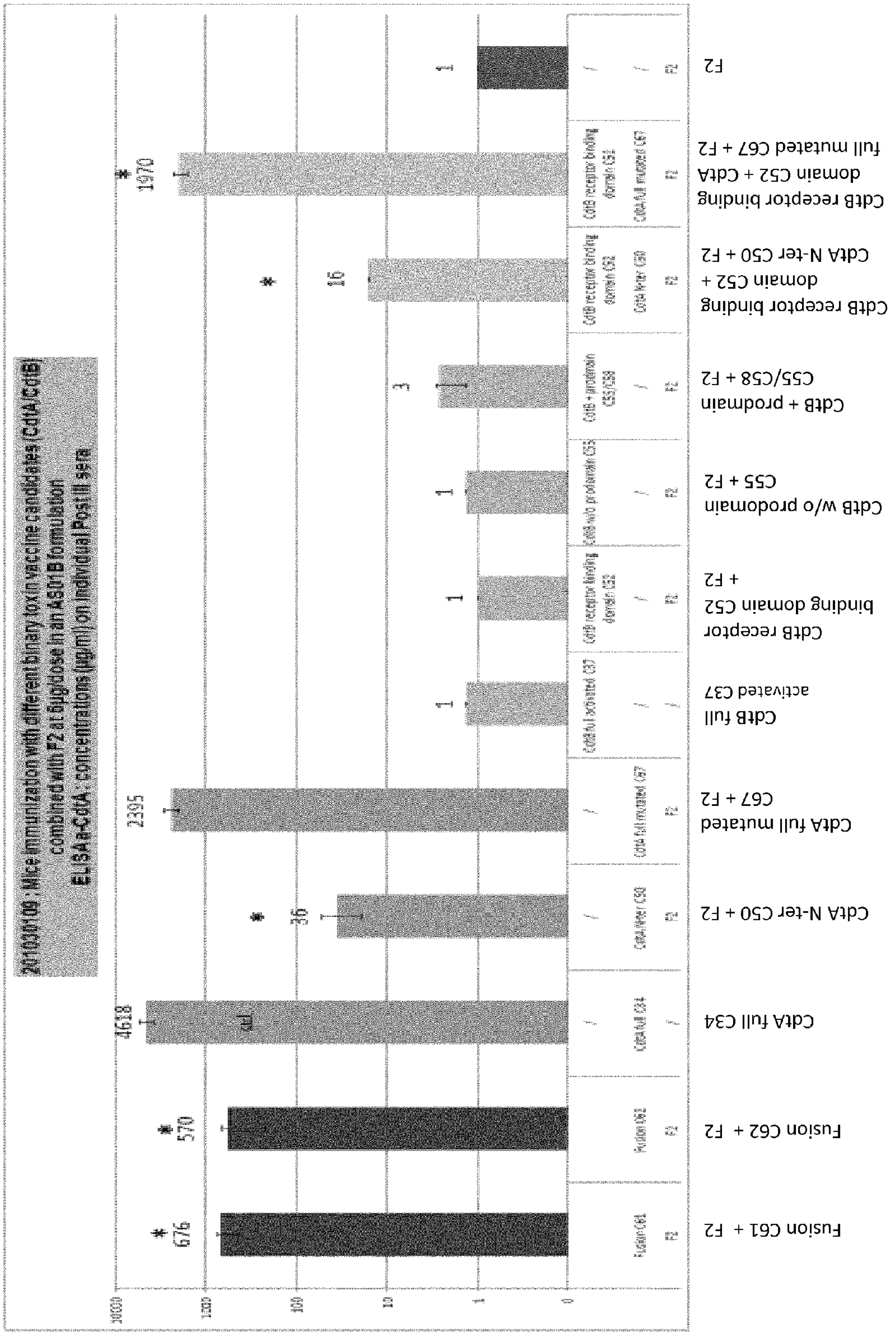
Figure 15:
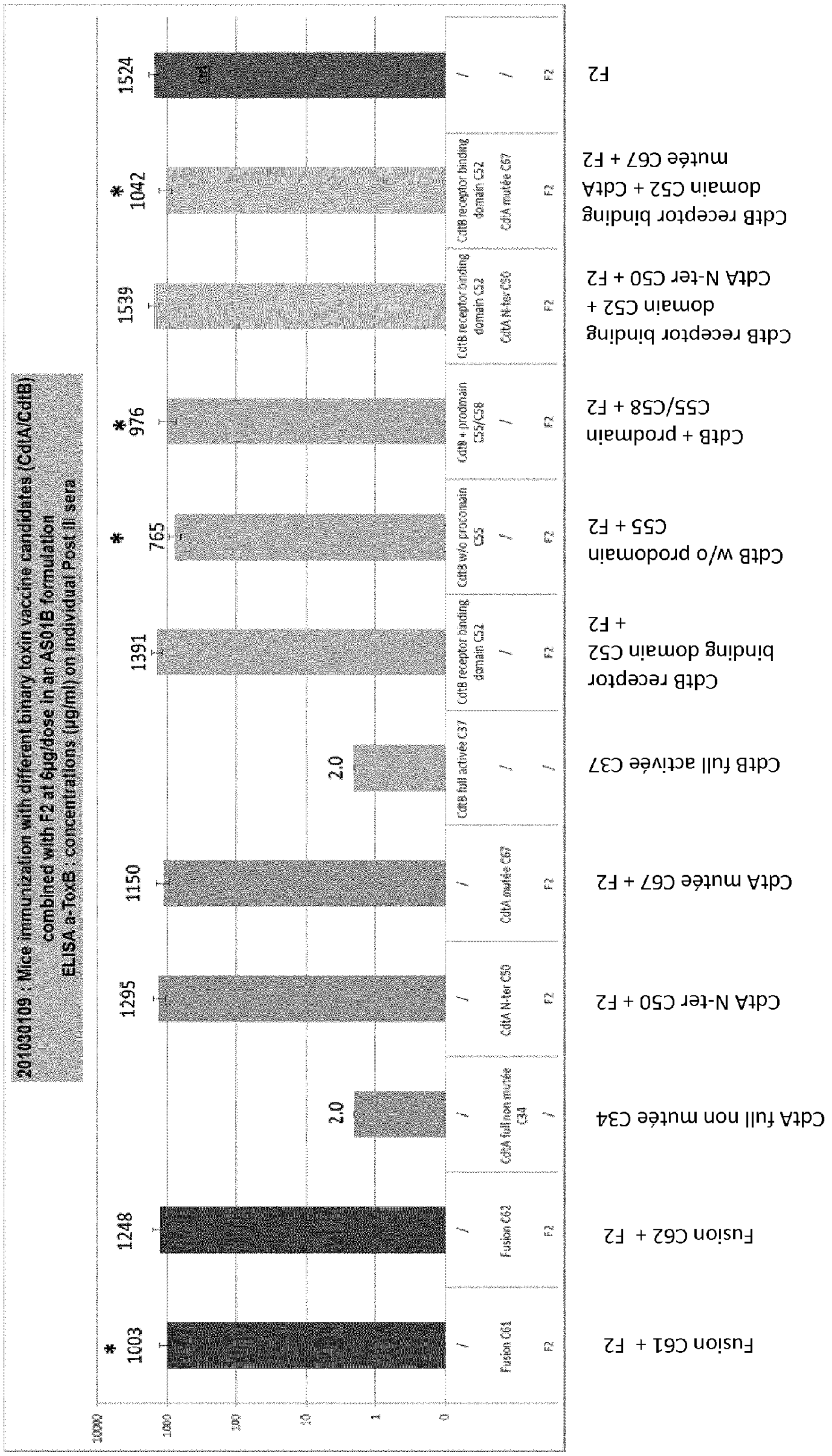
Figure 16:
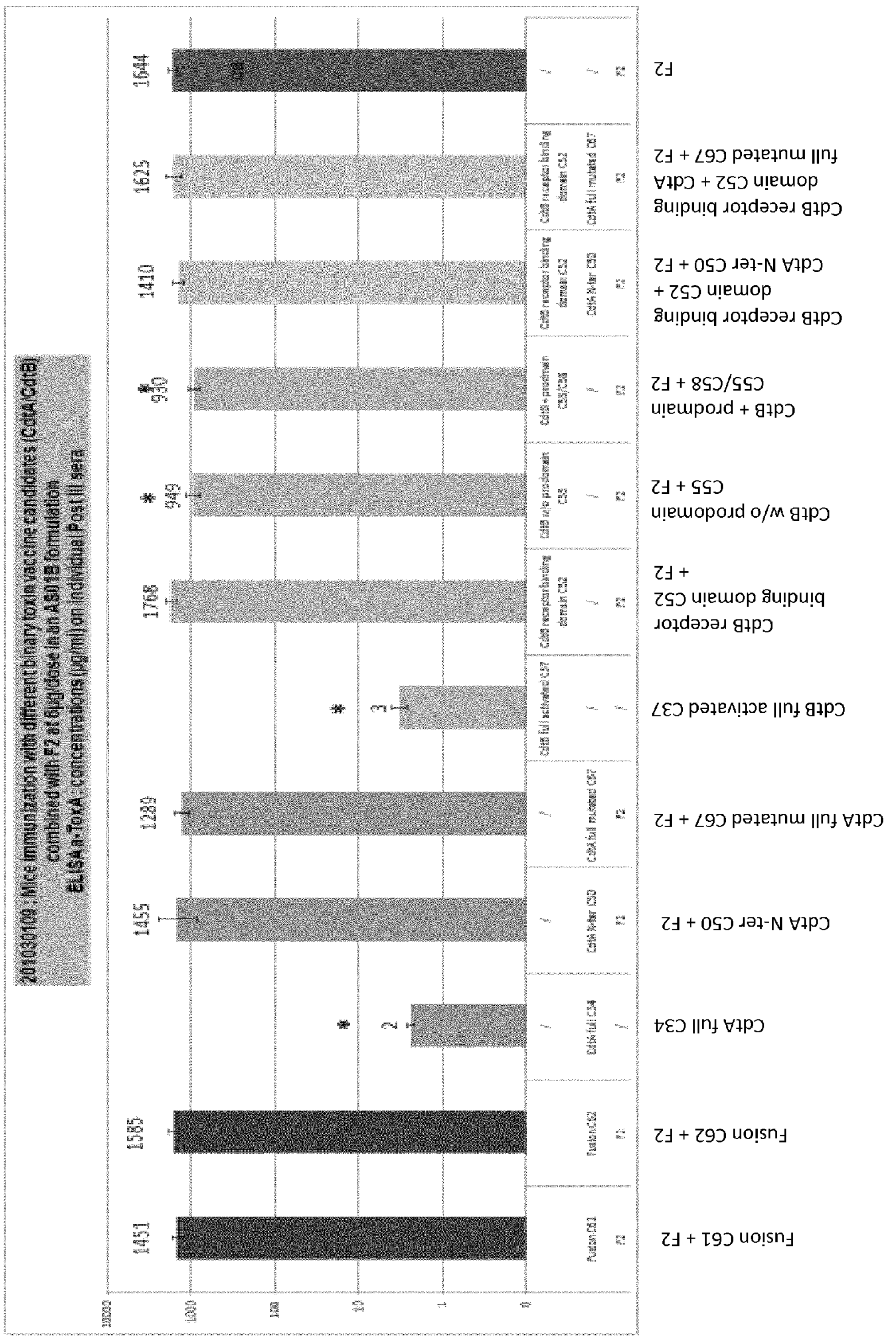
Figure 17:
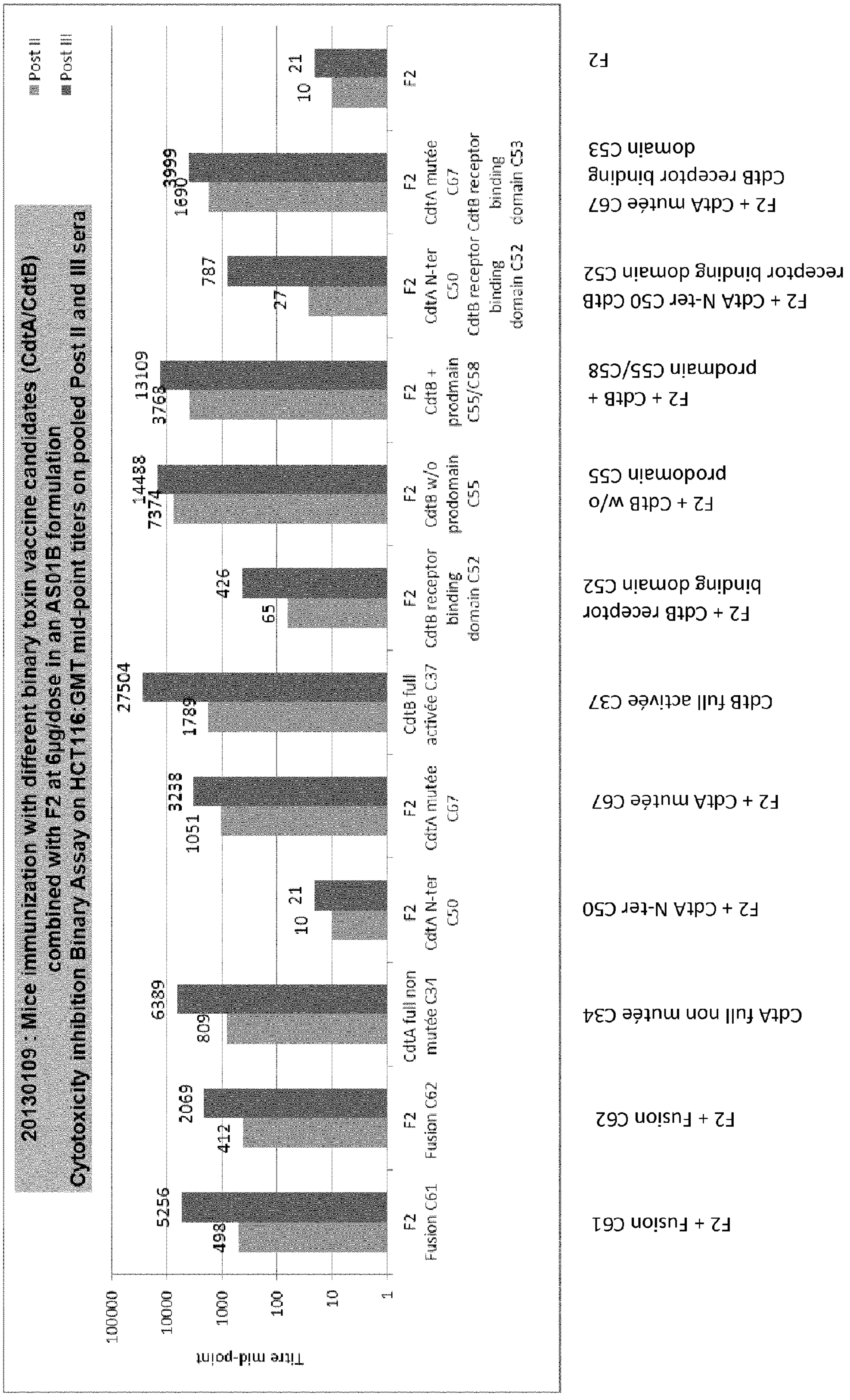
Figure 18:
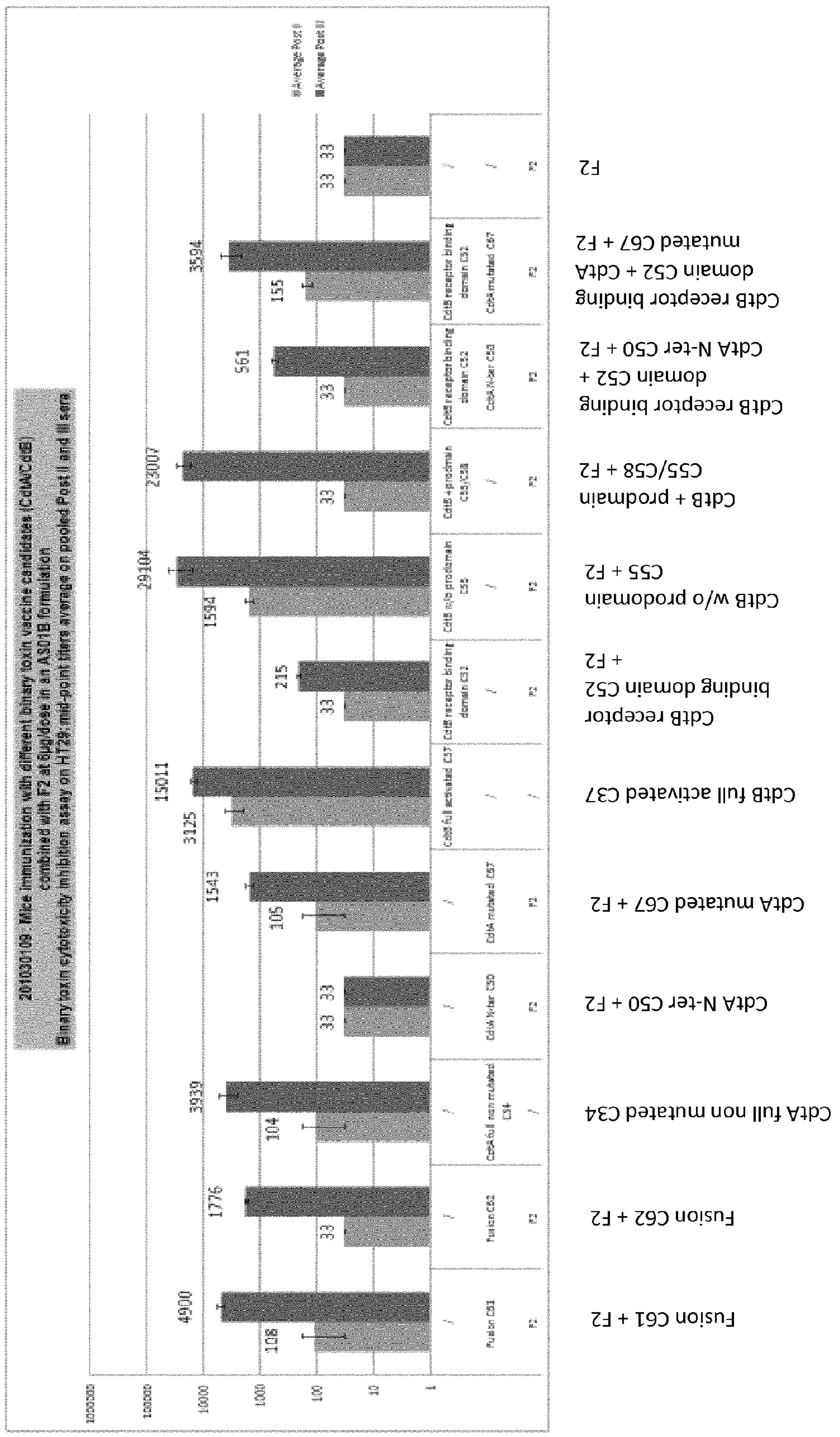
Figure 19:
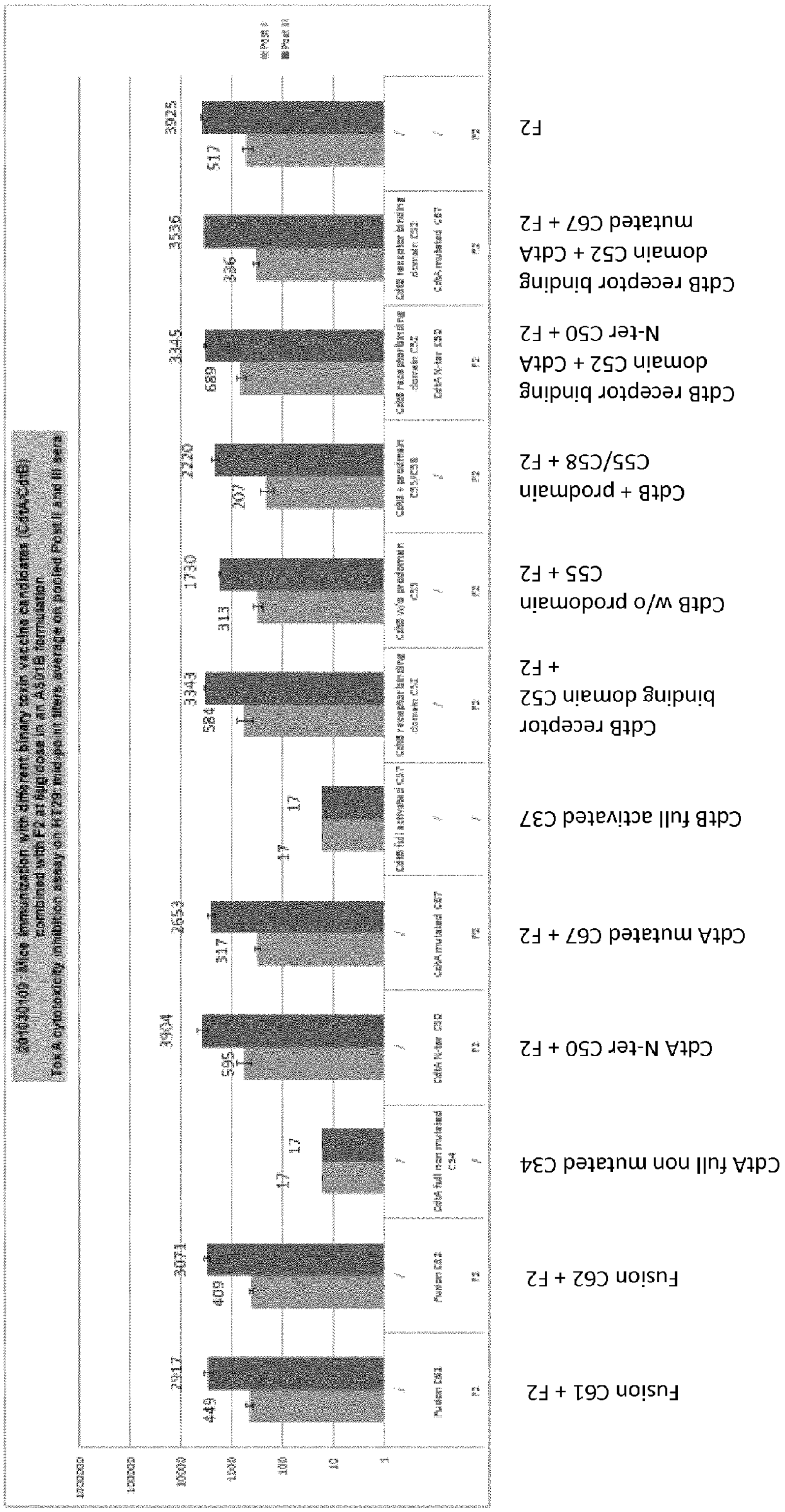
Figure 20:
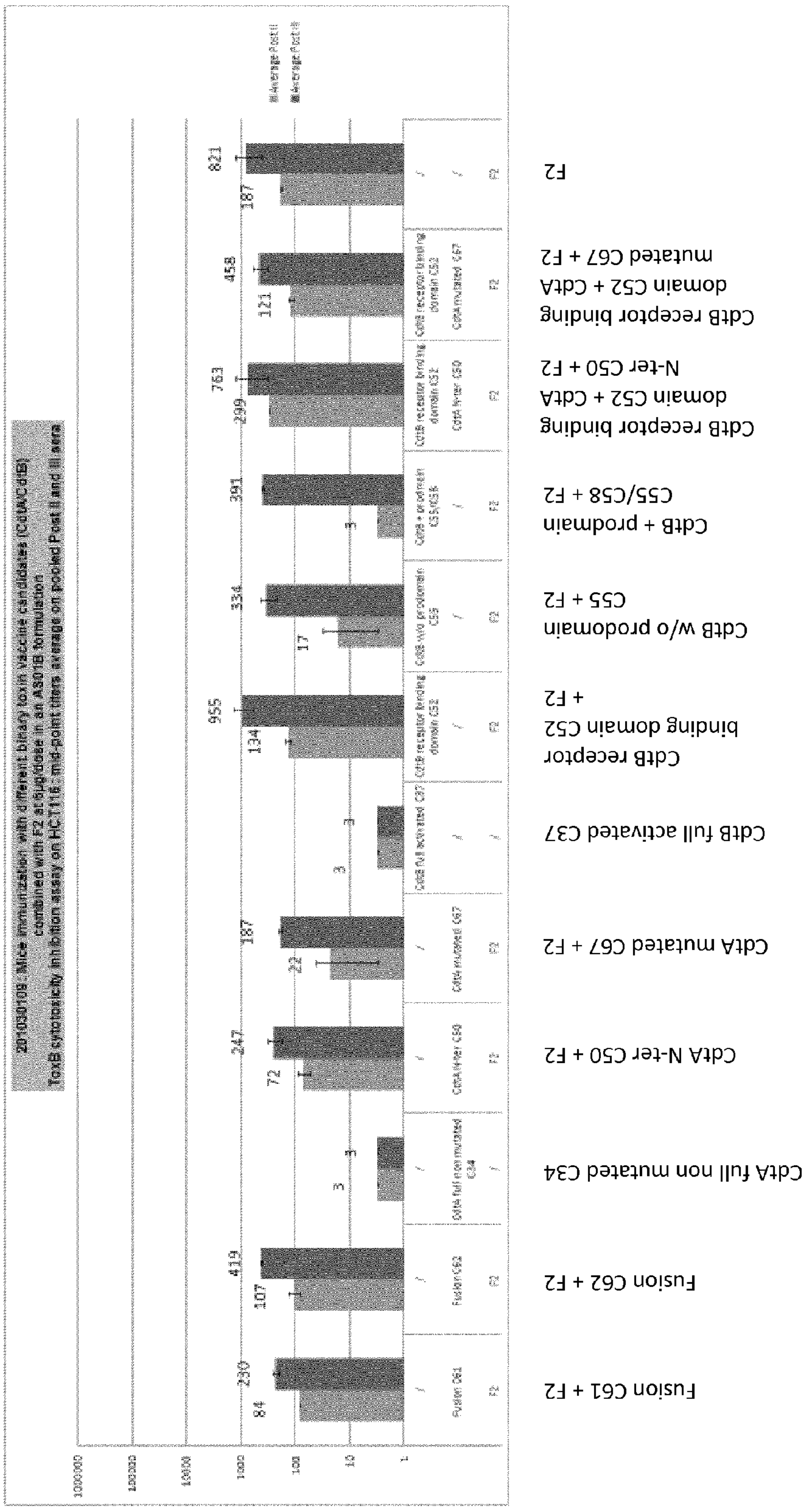
Figure 21:
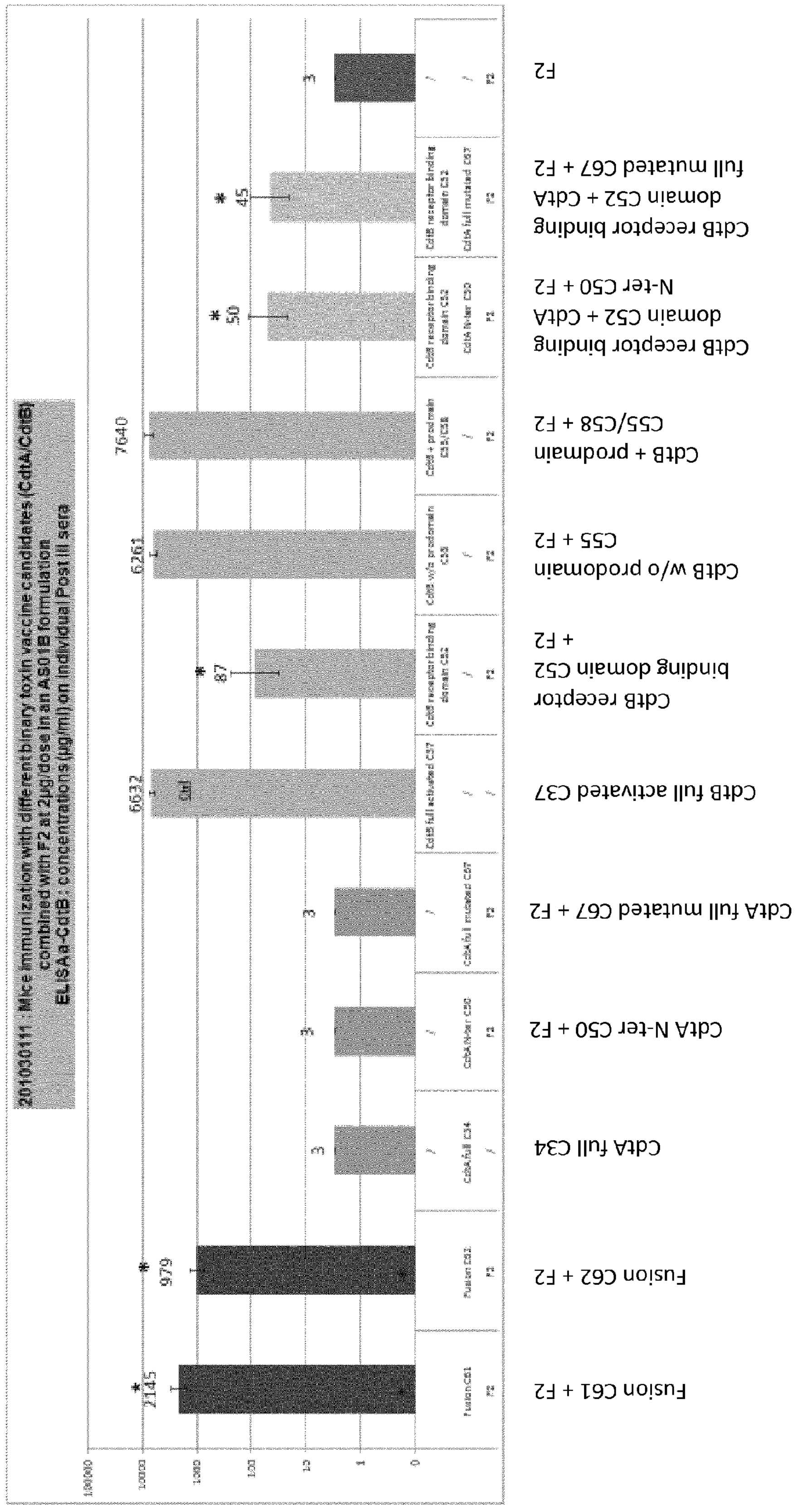
Figure 22:
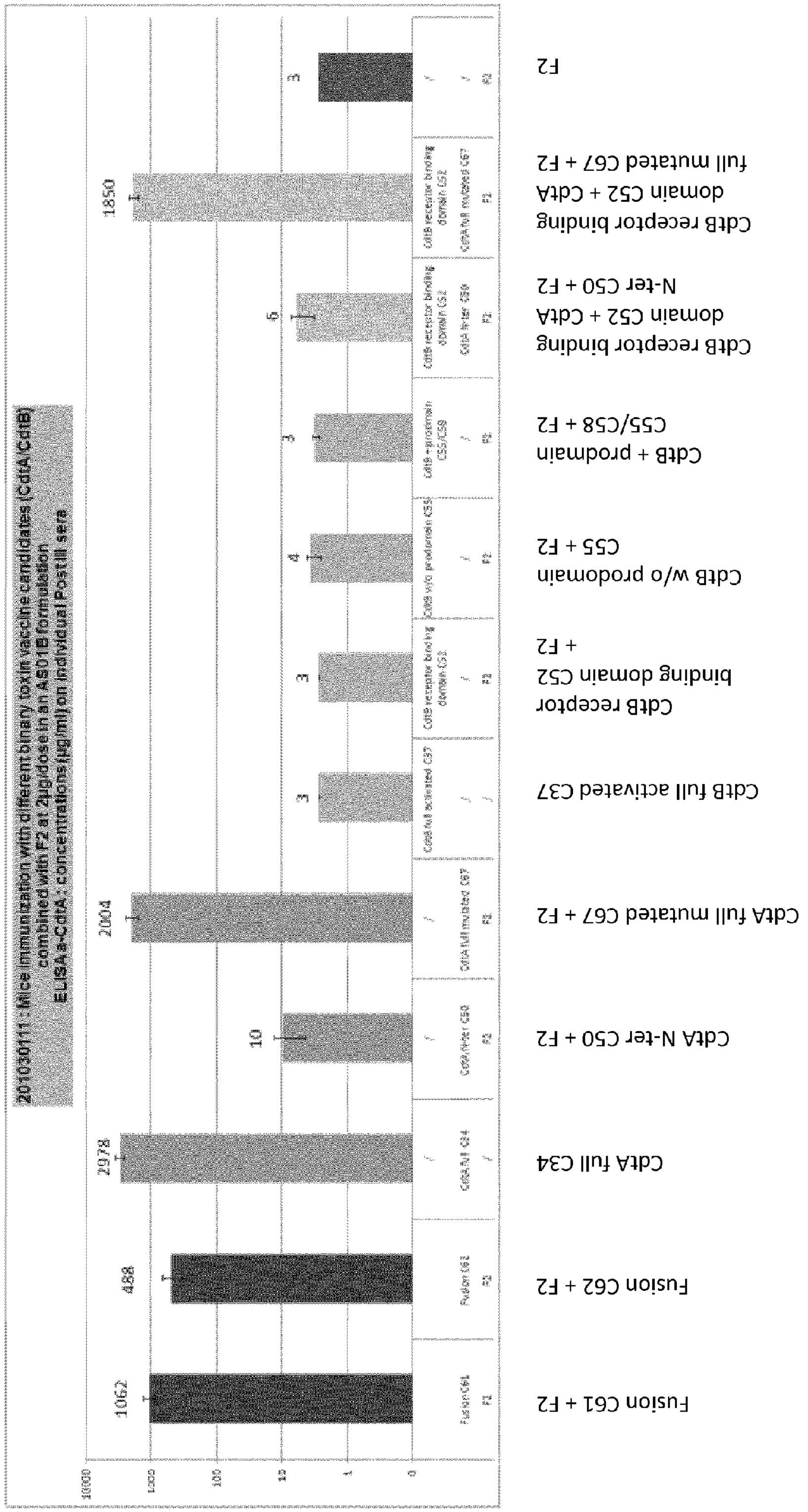
Figure 23:
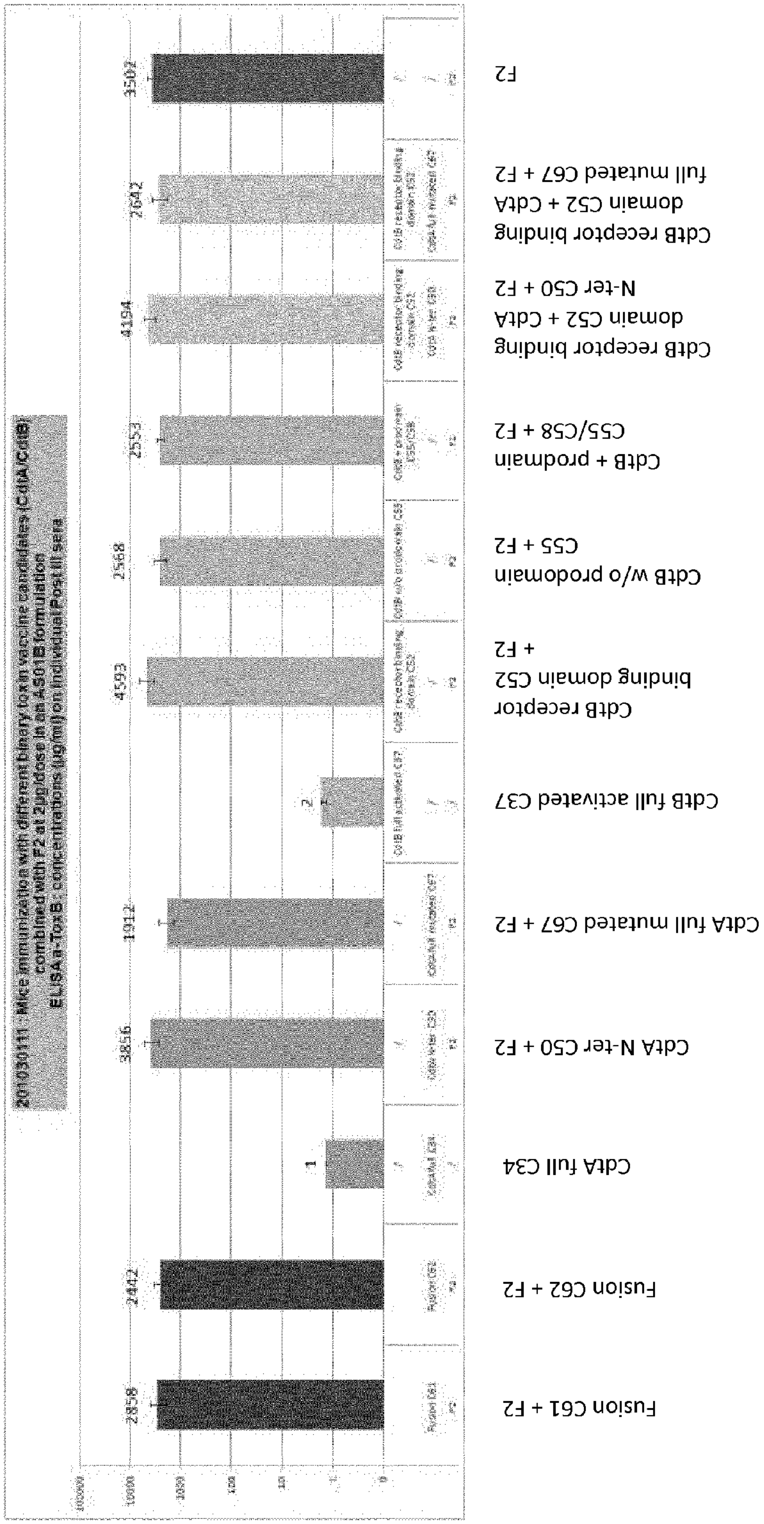
Figure 24:
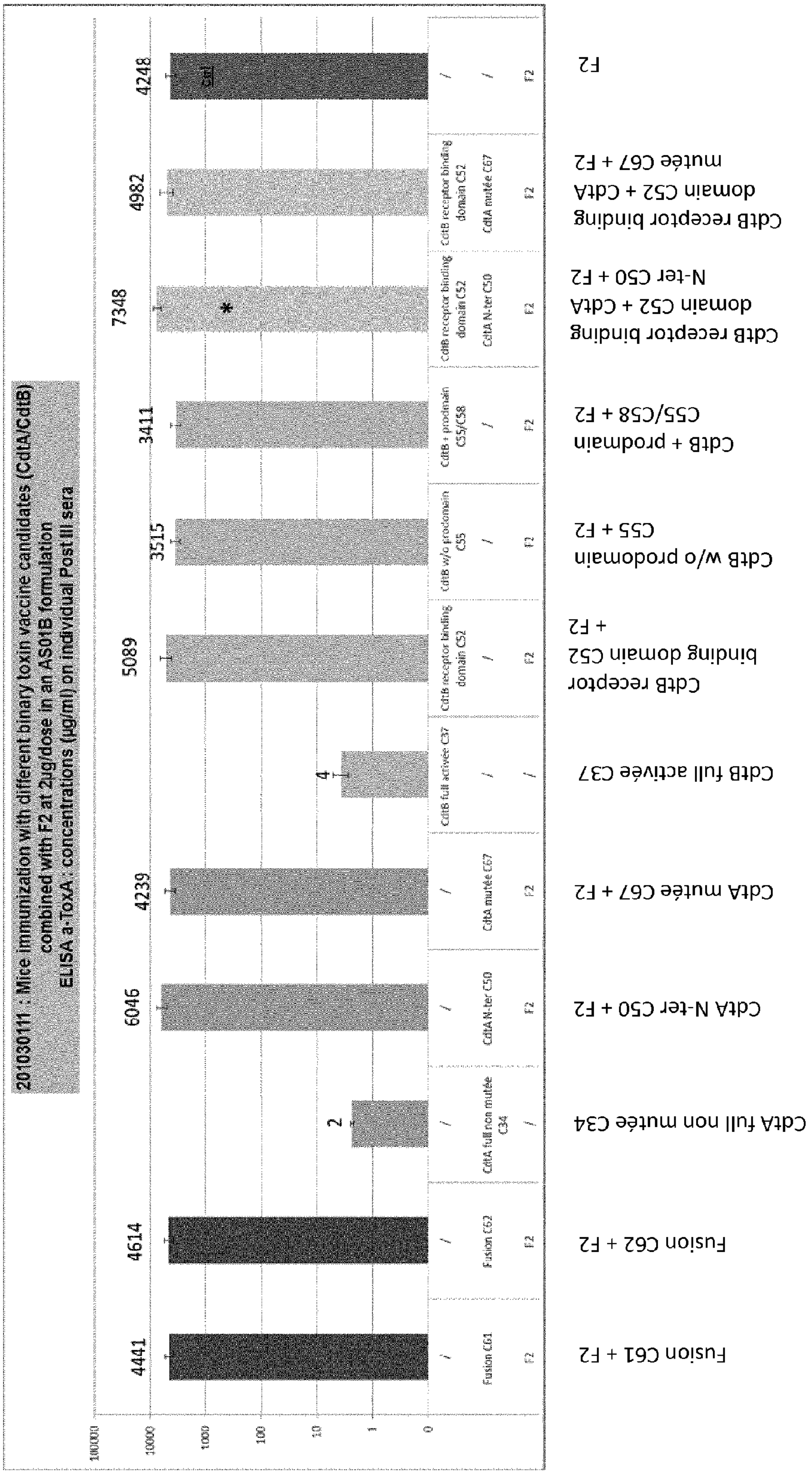
Figure 25:
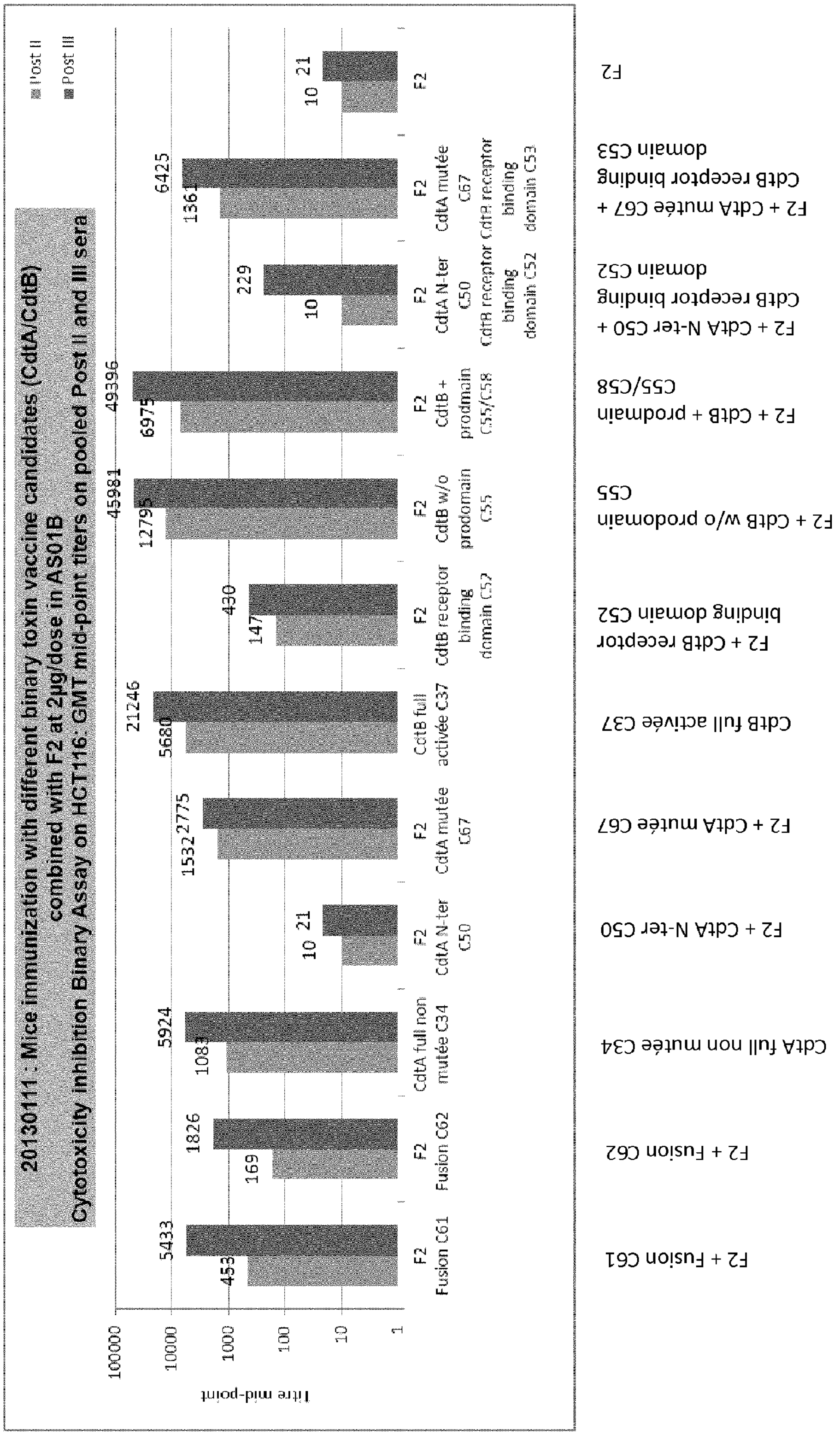
Figure 26:
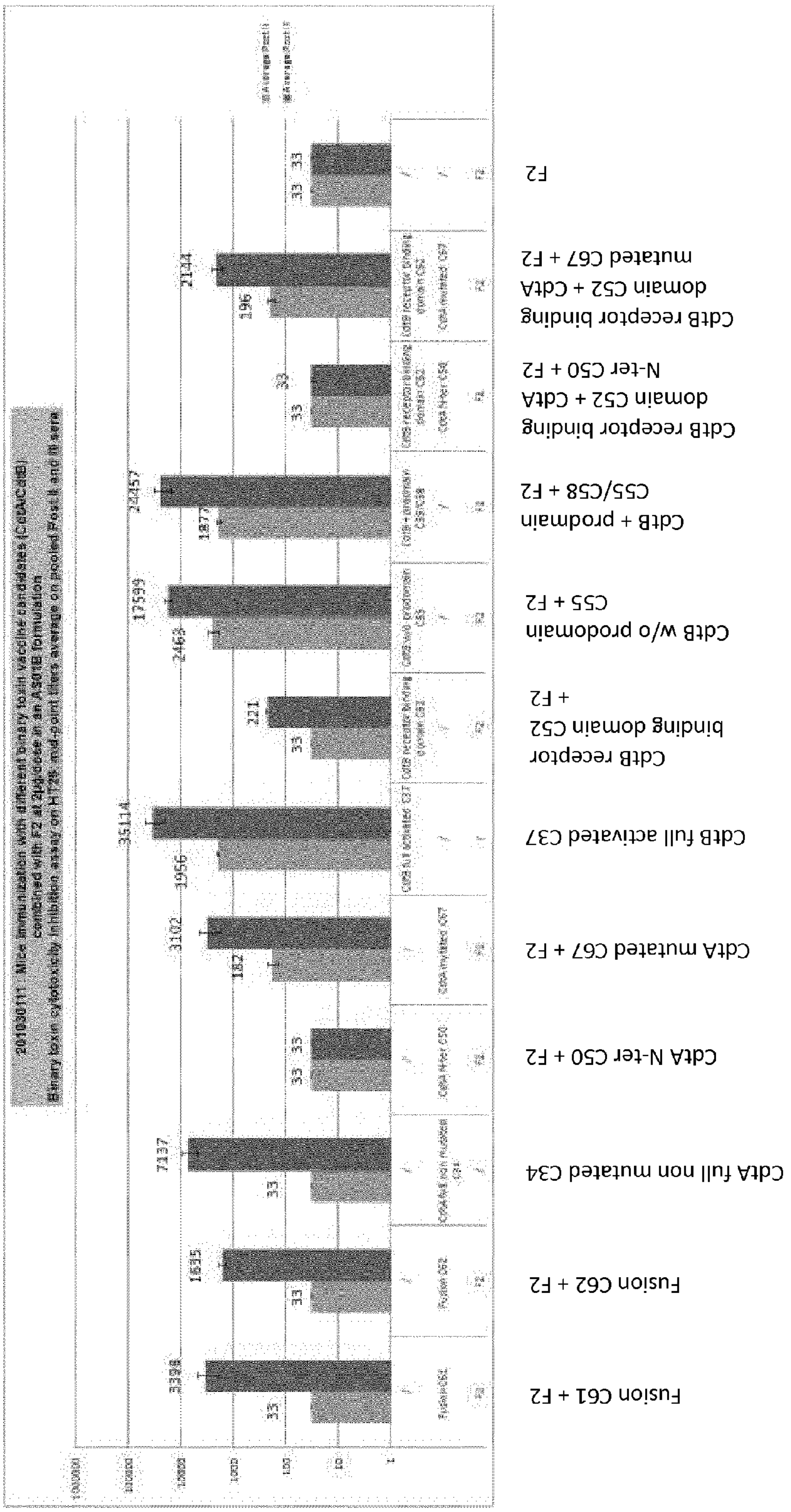
Figure 27:
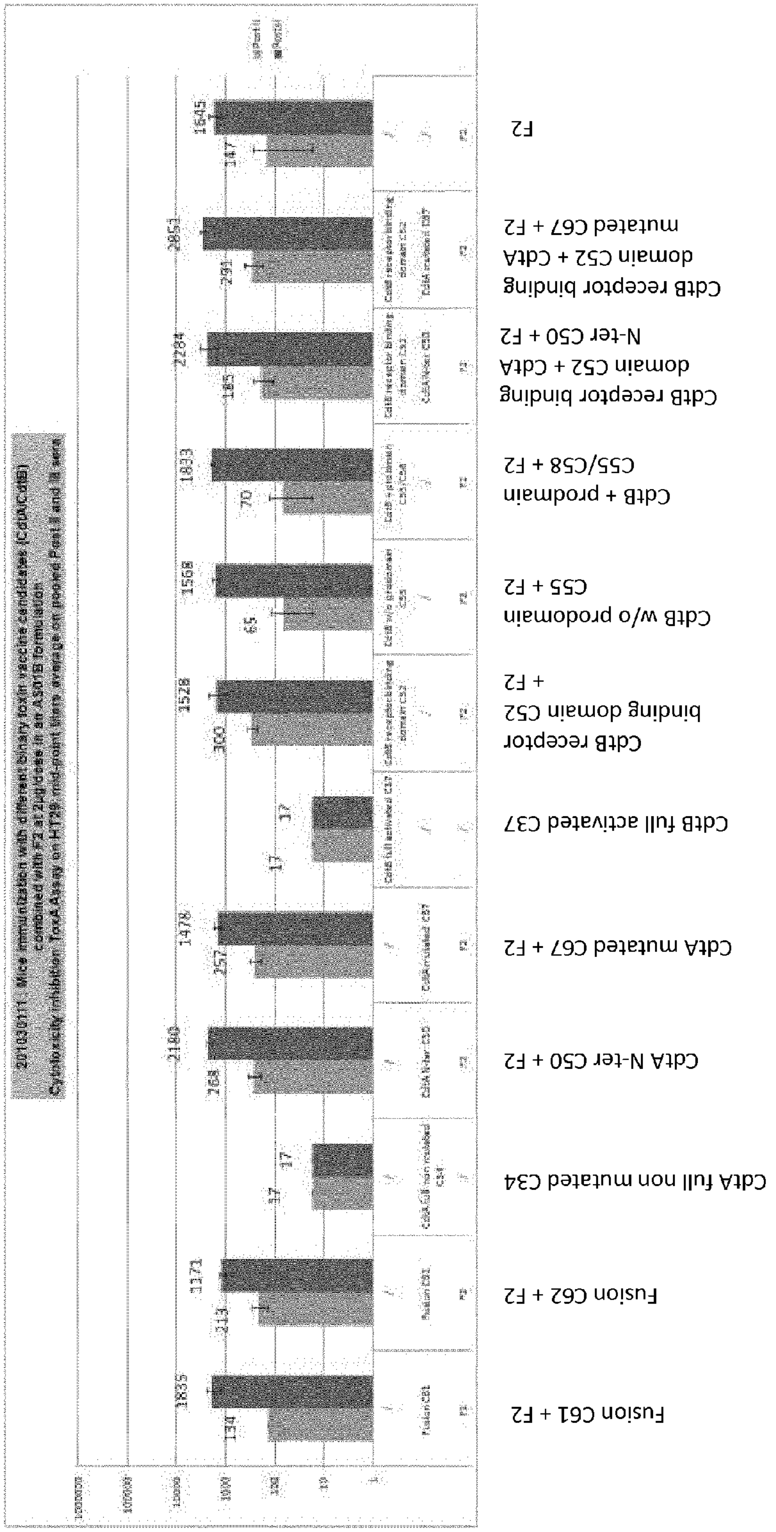
Figure 28:
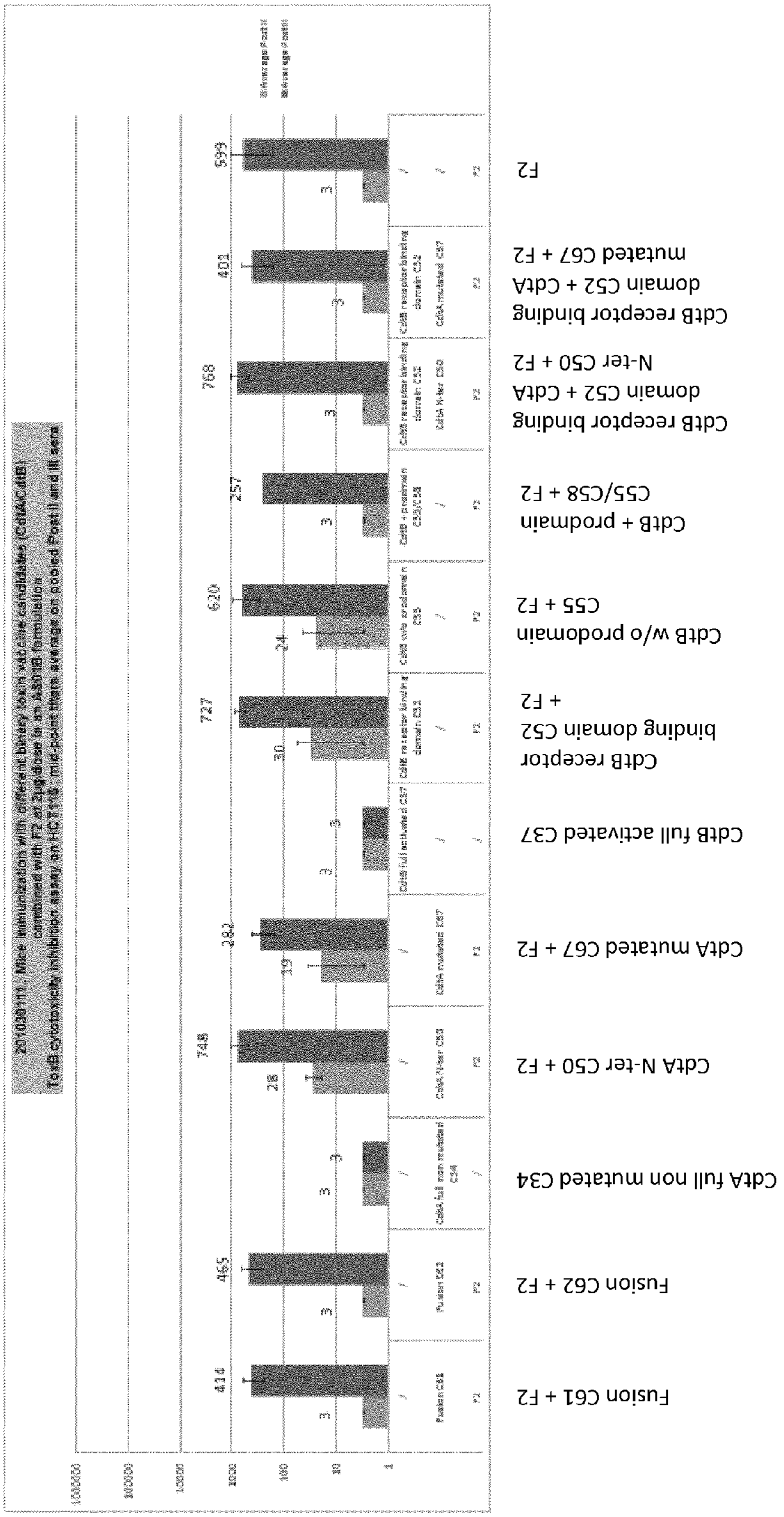
Figure 29:
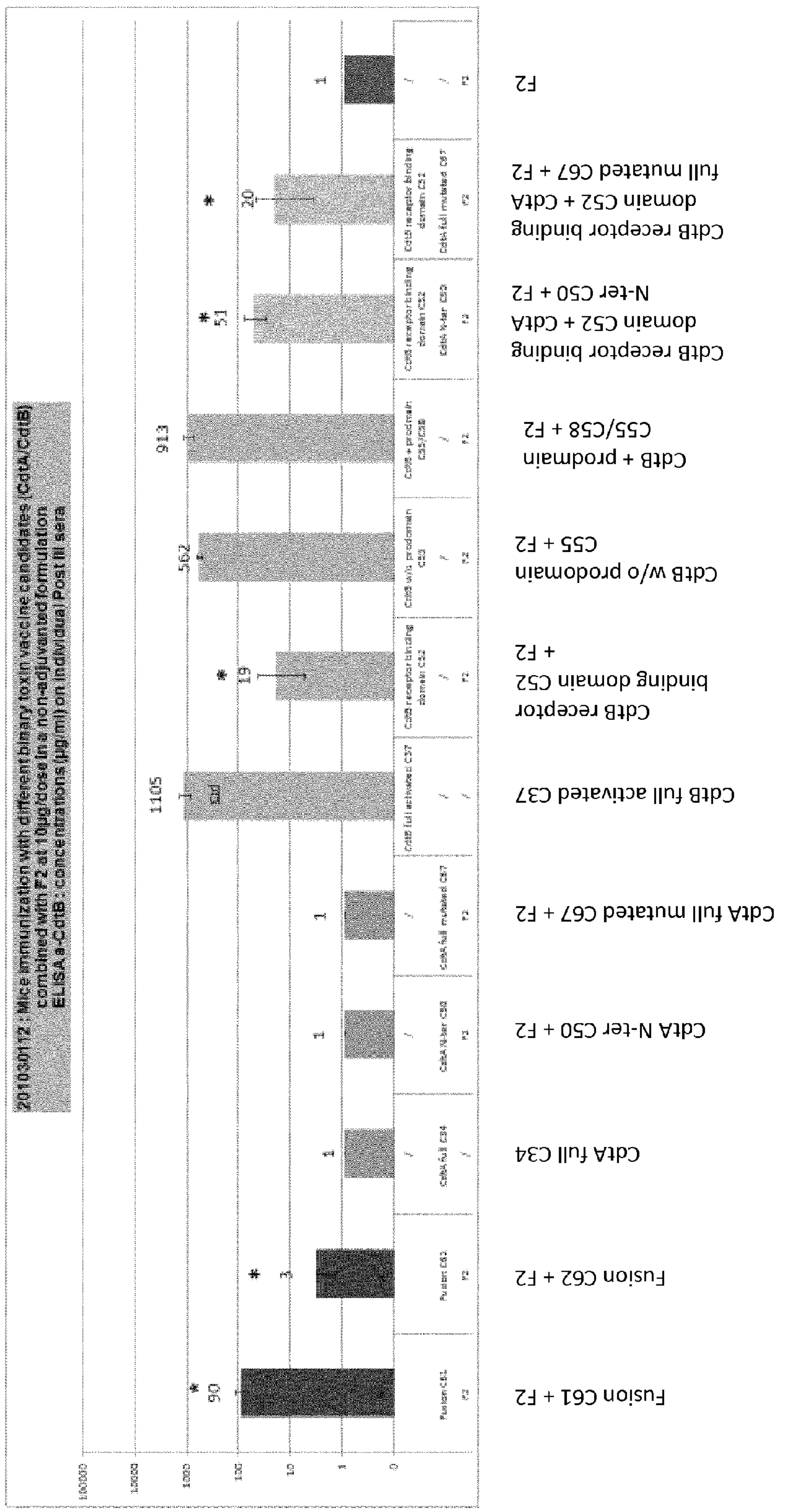
Figure 30:
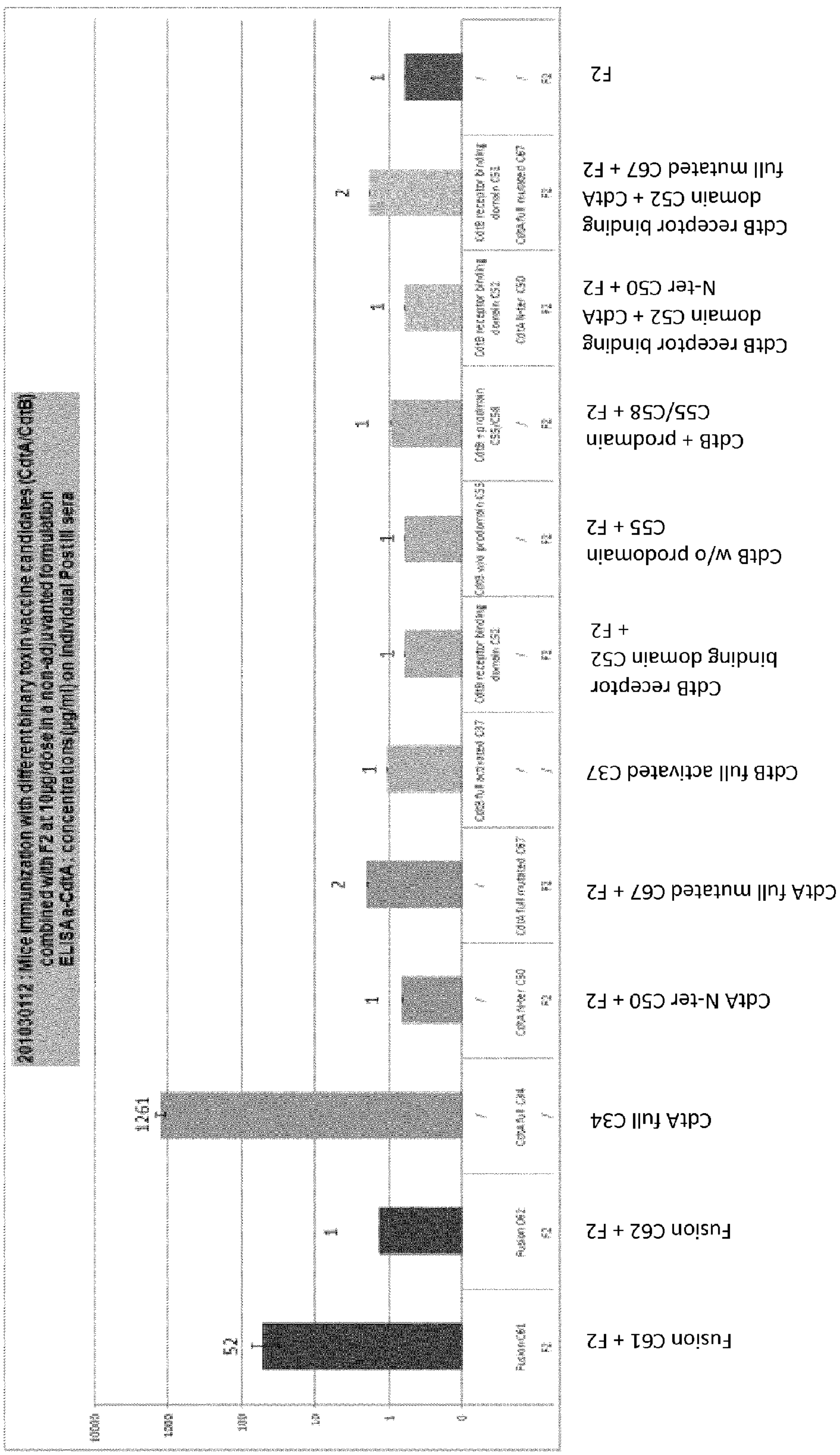
Figure 31:
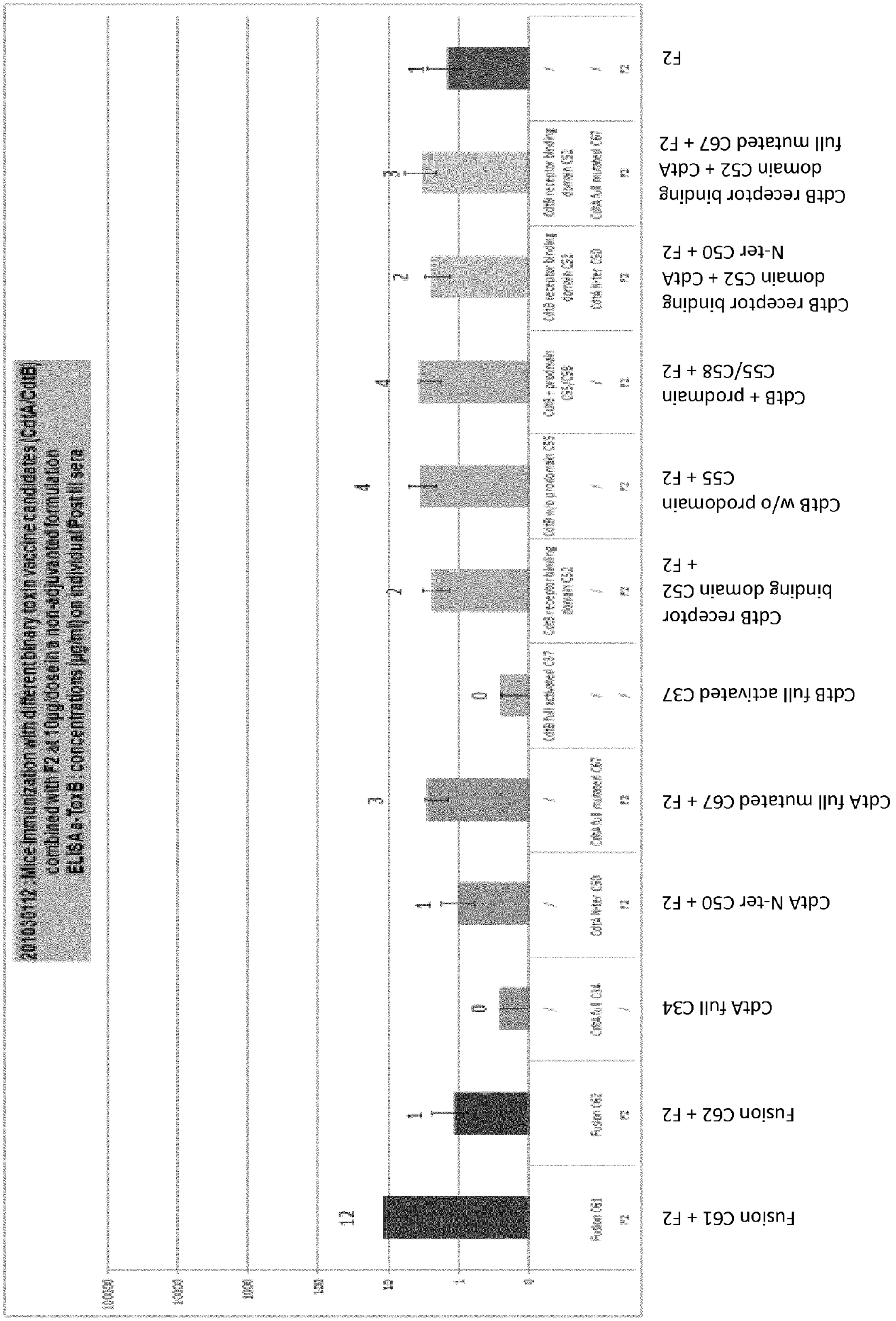
Figure 32:
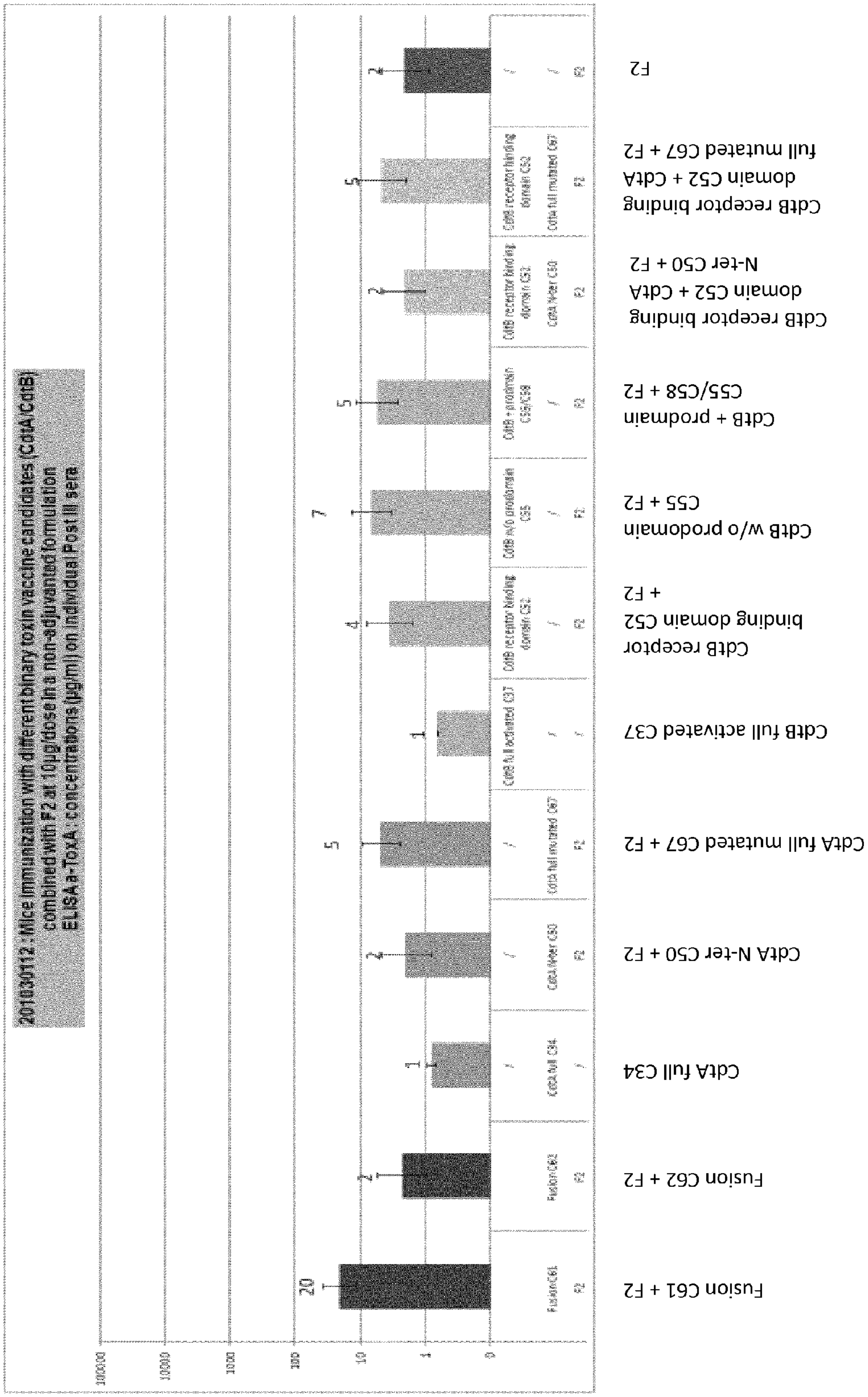
Figure 33:
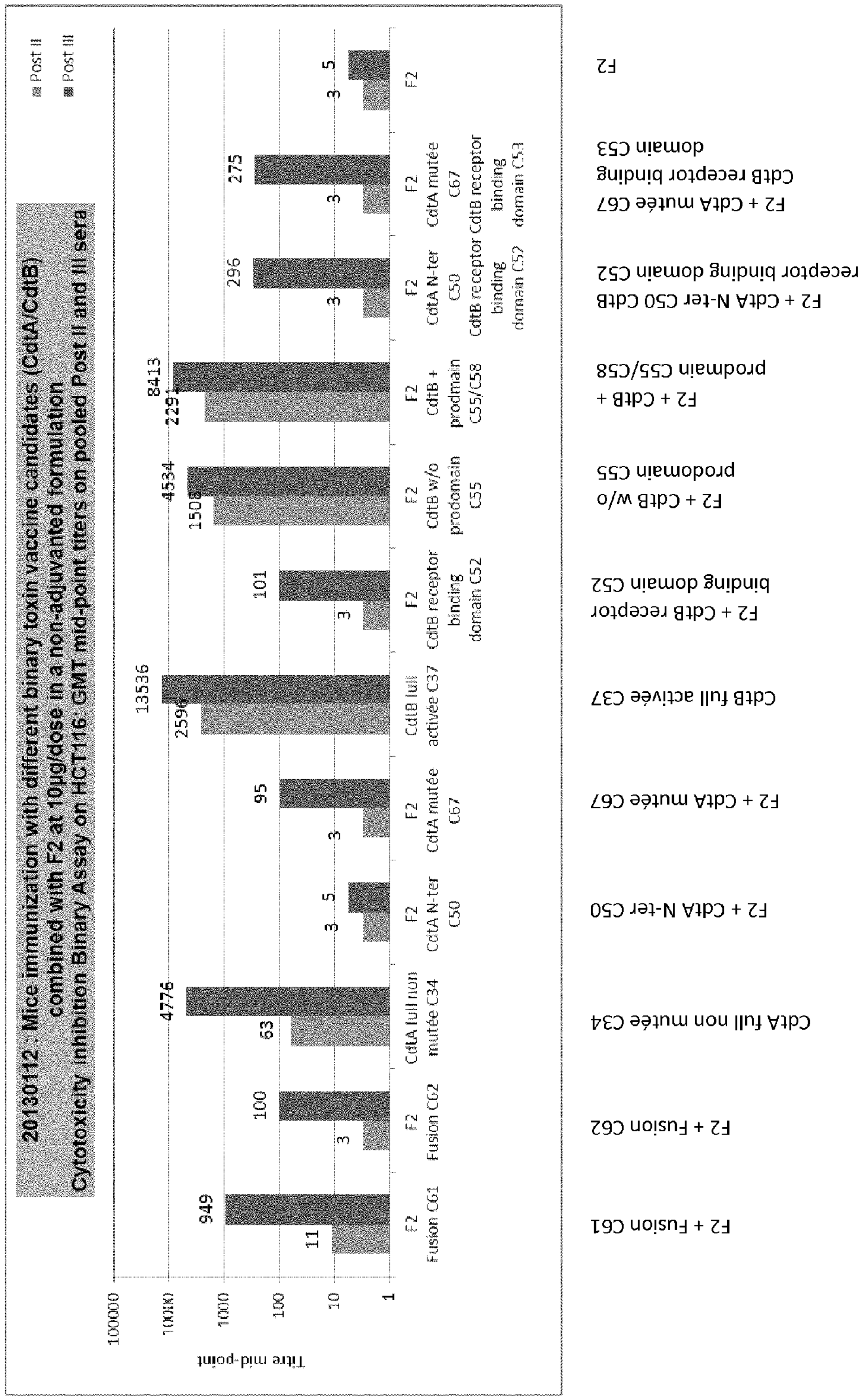
Figure 34:
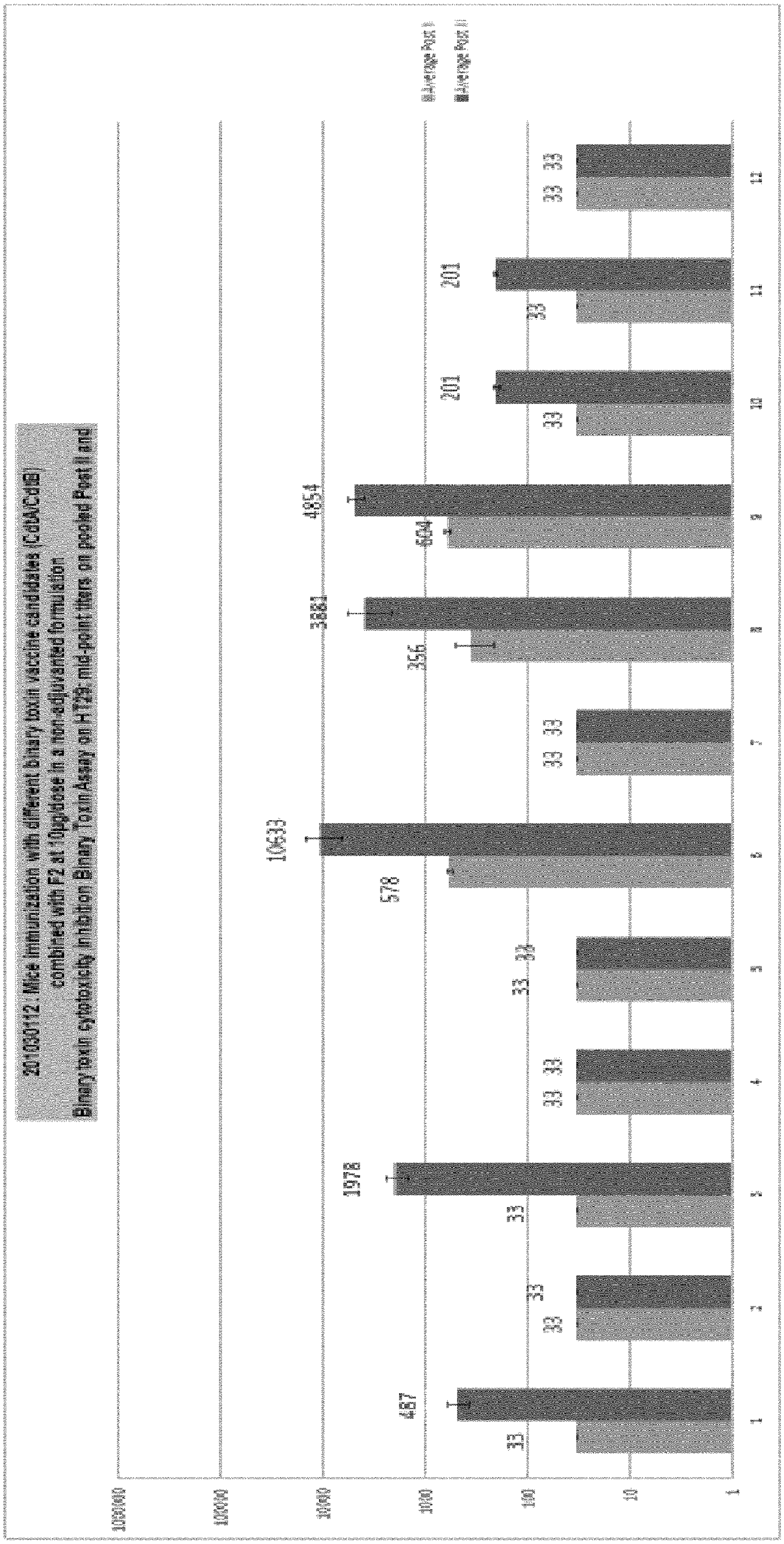
Figure 35:
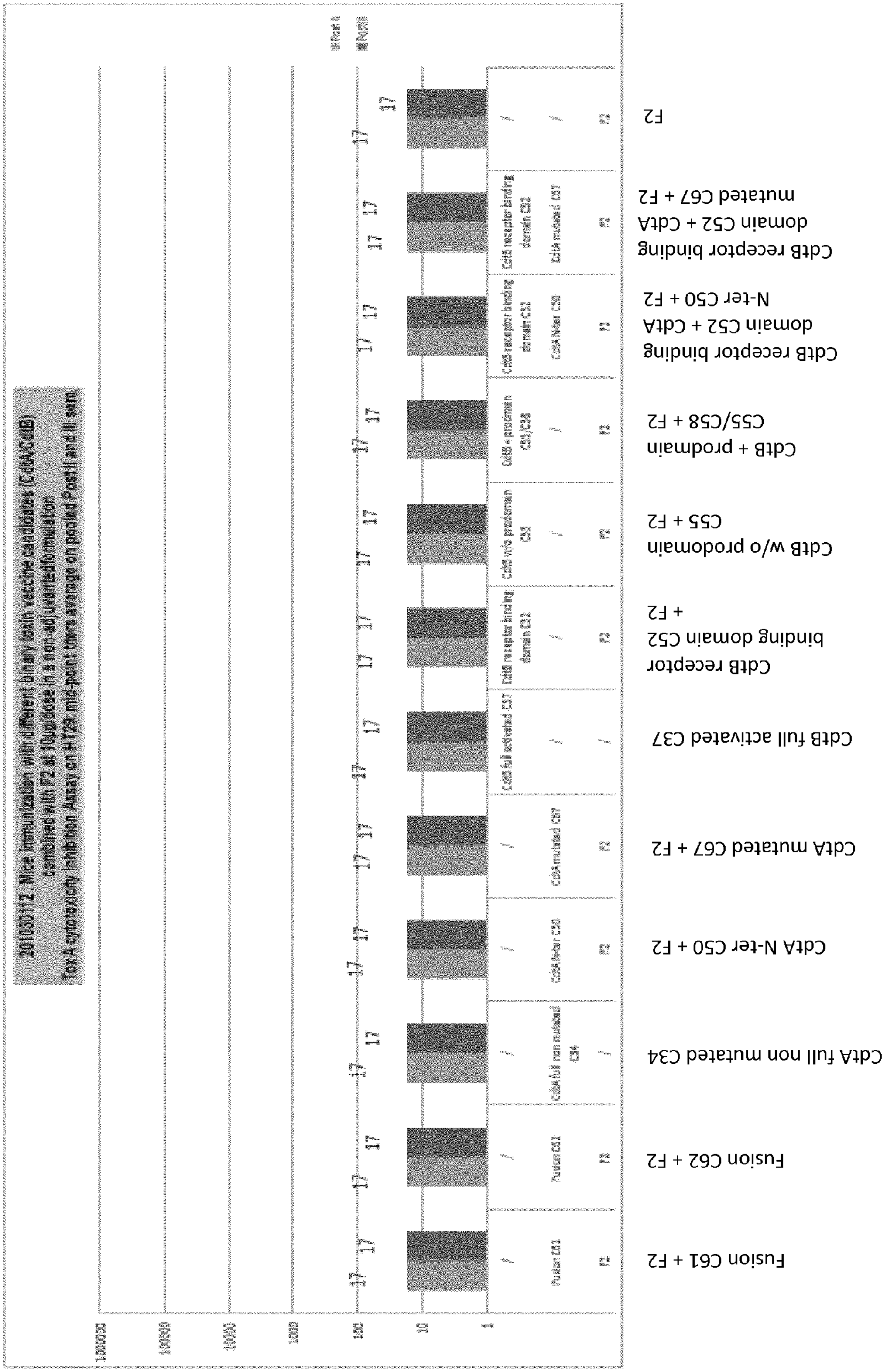
Figure 36:
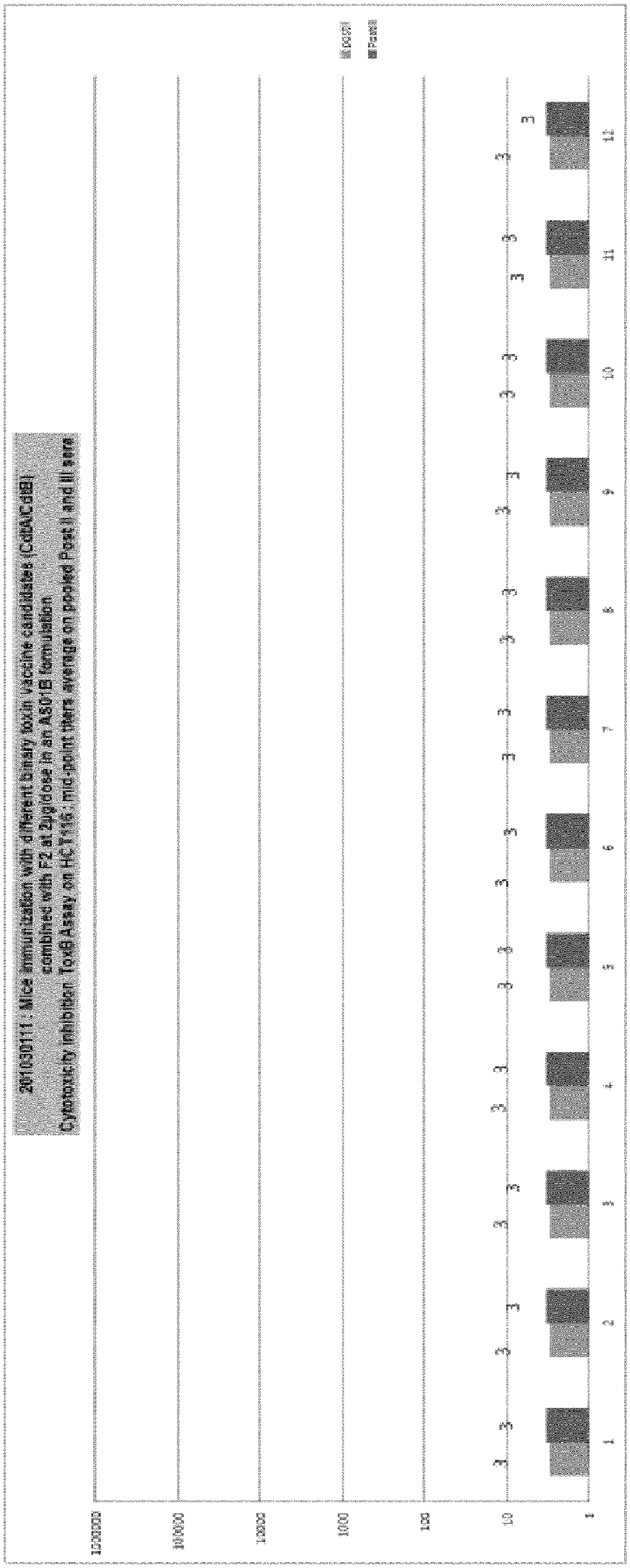

A binary toxin, ToxA and ToxB cytotoxicity inhibition assay was also performed on pooled Post III sera (day42). Results are shown in FIGS. 10-12.

Anti-CdtB, Anti-ToxA and Anti-ToxB ELISA Response: Protocol

Full CdtB (C37)sub-unit, F2 Cter ToxA and F2 Cter ToxB were coated at 0.5 μg/ml (for CdtB), 2 μg/ml (for ToxA F2 Cter) and 1 μg/ml (for ToxB F2 Cter) in phosphate buffered saline (PBS) on high-binding microtitre plates (Nunc MAXISORP™), overnight at 4° C. The plates were blocked with PBS-BSA 1% for 30 min at RT with agitation. The mice anti-sera are prediluted 1/500 in PBS-BSA0.2%-TWEEN™ 0.05%. and then, further twofold dilutions were made in microplates and incubated at RT for 30 min. After washing, bound mouse antibody was detected using Jackson ImmunoLaboratories Inc. peroxidase-conjugated Anti-Mouse (ref: 110-035-003) diluted 1:5000 in PBS-BSA0.2%-tween 0.05%. The detection antibodies were incubated for 30 min. at room temperature (RT) with agitation. The color was developed using 4 mg 0-phenylenediamine (OPD)+5 μl $H_2O_2$ per 10 ml pH 4.5 0.1M citrate buffer for 15 minutes in the dark at room temperature. The reaction was stopped with 50 μl HCl, and the optical density (OD) was read at 490 nm relative to 620 nm.

The level of anti-CdtB antibodies are expressed in mid-point titers.

The level of anti-F2Cter ToxA and F2Cter ToxB antibodies present in each individual sera is determined by comparison to a reference serum added on each plate and expressed in μg/ml.

A GMT was calculated for the 25 samples in each treatment group.

Binary Toxin, ToxA and ToxB Cytotoxicity Inhibition Assay

Human colonic eptithelial cells (HT29 or HCT-116 cells) were cultured at 37° C. with 5% $CO_2$ in DMEM +10% fetal bovine serum +1% glutamine +1% antibiotics (penicillin-streptomycin-amphotericin) and were seeded in 96-well black tissue culture plates (Greiner Bio-one, Ref: 655090) at a density of $4.10^4$ cells/well for HT29 and $1.10^4$ cells/well for HCT116.

After 24 h, the cell media was removed from the wells.

The mice anti-sera were prediluted 1:5 for g1 (CdtB non-activated) and g2 (CdtB activated) and 1:20 for g3 (CdtB non-activated+F2) and g4 (Cdtb activated+F2) in cell media, for ToxA inhibition cytotoxicity assay, 1:10 for ToxB inhibition cytotoxicity assay and 1:50 for binary toxin inhibition assay. Then, further three-fold dilutions were made in microplate (NUNC, Ref: 163320). 50 μl of serial dilutions of mice pooled antisera were added to the black plates. 50 μl of ToxA (0.01 μg/ml) on HT29, ToxB (0.022 μg/ml) on HCT116 and a mix of CdtA (25 ng/ml) and chemotrypsin-activated CdtB (75 ng/ml) on HT29 and HCT116 were then added in the black plates and incubated at 37° C. with 5% $CO_2$ for 6 days.

After 6 days, the mix of antisera and toxin were removed from the wells and 100 μl of Hoescht stain (BD Pharmingen, Ref: 561908) diluted 1:500 in phosphate buffer saline (PBS) was added in each well for 2 hours in the dark at room temperature.

After coloration, the Hoescht stain was removed from the wells and the cells fluorescence cells was measured using an Axiovision microscope.

The surface covered by fluorescent staining was determined in each well and cytotoxicity inhibition titers were defined as the reciprocal dilution inducing a 50% inhibition of the fluorescent signal.

Example 11: Immunisation of Mice with Different Binary Toxin Vaccine Candidates (CdtA/CdtB) Combined with F2 at 6 μg/Dose in an AS01B Formulation Mice Immunisation Groups of 20 female Balb/C mice were immunized IM at days 0, 14 and 28 with 6 μg of CdtA-CdtB fusion (C61 and C62), or 3 μg of CdtA (C34, C50 or C67) and/or 3 μg of CdtB (C37, C52, C55 or C55/C58) mixed or not with 6 μg of F2. These antigens were injected in an AS01B formulation.

Anti-CdtA, anti-CdtB, anti-ToxA and anti-ToxB ELISA titers were determined in individual sera collected at day 42 (Post III 14). Results are shown in FIGS. 13-16.

A binary toxin, ToxA and ToxB cytotoxicity inhibition assay was also performed on pooled Post III sera (day42). Results are shown in FIGS. 17-20.

Anti-CdtA, Anti-CdtB, Anti-ToxA F2Cter and Anti-ToxB F2 Cter ELISA Response: Protocol CdtA mut E428Q (C44), Full CdtB (C37)sub-units, F2 Cter ToxA and F2 Cter ToxB were coated at 1 μg/ml (for CdtA), 0.5 μg/ml (for CdtB), 2 μg/ml (for ToxA F2 Cter) and 1 μg/ml (for ToxB F2 Cter) in phosphate buffered saline (PBS) on high-binding microtitre plates (Nunc MAXISORP™), overnight at 4° C. The plates were blocked with PBS-BSA 1% for 30 min at RT with agitation. The mice anti-sera were prediluted 1:100 (for CdtA, CdtB, ToxB) or 1:200 (for ToxA) for Post II and 1:500 (for CdtA and ToxA), 1:500 or 1:2000 (for CdtB) and 1:250 (for ToxB) for Post III in PBS-BSA0.2%-TWEEN™ 0.05%. Then, further twofold dilutions were made in microplates and incubated at RT for 30 min. After washing, bound mouse antibody was detected using Jackson ImmunoLaboratories Inc. peroxidase-conjugated Anti-Mouse (ref: 110-035-003) diluted 1:5000 in PBS-BSA0.2%-tween 0.05%. The detection antibodies were incubated for 30 min. at room temperature (RT) with agitation. The color was developed using 4 mg O-phenylenediamine (OPD)+5 μl $H_2O_2$ per 10 ml pH 4.5 0.1M citrate buffer for 15 minutes in the dark at room temperature. The reaction was stopped with 50 μl HCl, and the optical density (OD) was read at 490 nm relative to 620 nm.

The level of anti-CdtA, anti-CdtB, anti-F2Cter ToxA and F2Cter ToxB antibodies present in each individual sera is determined by comparison to a reference serum added on each plate and expressed in μg/ml. A GMT was calculated for the 20 samples in each treatment group.

Binary Toxin, ToxA and ToxB Cytotoxicity Inhibition Assay

Human colonic eptithelial cells (HT29 or HCT-116 cells) were cultured at 37° C. with 5% $CO_2$ in DMEM +10% fetal bovine serum +1% glutamine +1% antibiotics (penicillin-streptomycin-amphotericin) and were seeded in 96-well black tissue culture plates (Greiner Bio-one, Ref: 655090) at a density of $4.10^4$ cells/well for HT29 and $1.10^4$ cells/well for HCT116. After 24 h, the cell media was removed from the wells.

The mice anti-sera were prediluted 1:50 in cell media, for ToxA inhibition cytotoxicity assay, 1:10 for ToxB inhibition cytotoxicity assay, 1:50 for binary toxin inhibition assay on HT29 and 1:30 (for Post II) and 1:30 or 1:100 (for Post III) for binary toxin inhibition assay on HCT116. Then, further three-fold dilutions were made in microplate (NUNC, Ref: 163320). 50 μl of serial dilutions of mice pooled antisera were added to the black plates. 50 μl of ToxA (0.025 μg/ml) on HT29, ToxB (0.6 μg/ml) on HCT116 and a mix of CdtA (25 ng/ml) and chemotrypsin-activated CdtB (75 ng/ml) on HT29 and HCT116 were then added in the black plates and incubated at 37° C. with 5% $CO_2$ for 6 days.

After 6 days, the mix of antisera and toxin were removed from the wells and 100 μl of Hoescht stain (BD Pharmingen, Ref: 561908) diluted 1:500 in phosphate buffer saline (PBS) was added in each well for 2 hours in the dark at room temperature.

After coloration, the Hoescht stain was removed from the wells and the cells fluorescence cells was measured using an Axiovision microscope.

The surface covered by fluorescent staining was determined in each well and cytotoxicity inhibition titers were defined as the reciprocal dilution inducing a 50% inhibition of the fluorescent signal.

Example 12: Immunisation of Mice with Different Binary Toxin Vaccine Candidates (CdtA/CdtB) Combined with F2 at 2 m/Dose in an AS01B Formulation Mice Immunisation Groups of 20 female Balb/C mice were immunized IM at days 0, 14 and 28 with 2 μg of CdtA-CdtB fusion (C61 and C62), or 1 μg of CdtA (C34, C50 or C67) and/or 1 μg of CdtB (C37, C52, C55 or C55/C58) mixed or not with 2 μg of F2. These antigens were injected in an AS01B formulation.

Anti-CdtA, anti-CdtB, anti-ToxA and anti-ToxB ELISA titers were determined in individual sera collected at day 42 (Post III 14). Results are shown in FIGS. 21-24.

A binary toxin, ToxA and ToxB cytotoxicity inhibition assay was also performed on pooled Post III sera (day42). Results are shown in FIGS. 25-28.

Anti-CdtA, Anti-CdtB, Anti-ToxA and Anti-ToxB ELISA Response: Protocol

CdtA mut E428Q (C44), Full CdtB (C37)sub-units, F2 Cter ToxA and F2 Cter ToxB were coated at 1 μg/ml (for CdtA), 0.5 μg/ml (for CdtB), 2 μg/ml (for ToxA F2 Cter) and 1 μg/ml (for ToxB F2 Cter) in phosphate buffered saline (PBS) on high-binding microtitre plates (Nunc MAXISORP™), overnight at 4° C. The plates were blocked with PBS-BSA 1% for 30 min at RT with agitation. The mice anti-sera were prediluted 1:100 (for CdtB, ToxA, ToxB) and 1:100 or 1:250 (for CdtA) for Post II and 1:500 for Post III in PBS-BSA0.2%-TWEEN™ 0.05%. Then, further twofold dilutions were made in microplates and incubated at RT for 30 min. After washing, bound mouse antibody was detected using Jackson ImmunoLaboratories Inc. peroxidase-conjugated Anti-Mouse (ref: 110-035-003) diluted 1:5000 in PBS-BSA0.2%-tween 0.05%. The detection antibodies were incubated for 30 min. at room temperature (RT) with agitation. The color was developed.

Example 13: Immunisation of Mice with Different Binary Toxin Vaccine Candidates (CdtA/CdtB) Combined with F2 at 10 μg/Dose in a Non-Adjuvanted Formulation Mice Immunisation Groups of 20 female Balb/C mice were immunized IM at days 0, 14 and 28 with 10 μg of CdtA-CdtB fusion (C61 and C62), or 5 μg of CdtA (C34, C50 or C67) and/or 5 μg of CdtB (C37, C52, C55 or C55/C58) mixed or not with 10 μg of F2. These antigens were injected in a non-adjuvanted formulation.

Anti-CdtA, anti-CdtB, anti-ToxA and anti-ToxB ELISA titers were determined in individual sera collected at day 42 (Post III 14). Results are shown in FIGS. 29-32.

A binary toxin, ToxA and ToxB cytotoxicity inhibition assay was also performed on pooled Post III sera (day42). Results are shown in FIGS. 33-36.

Anti-CdtA, Anti-CdtB, Anti-ToxA and Anti-ToxB ELISA Response: Protocol

CdtA mut E428Q (C44), Full CdtB (C37)sub-units, F2 Cter ToxA and F2 Cter ToxB were coated at 1 μg/ml (for CdtA), 0.5 μg/ml (for CdtB), 2 μg/ml (for F2 Cter ToxA) and 1 μg/ml (for F2 Cter ToxB) in phosphate buffered saline (PBS) on high-binding microtitre plates (Nunc MAXISORP™), overnight at 4° C. The plates were blocked with PBS-BSA 1% for 30 min at RT with agitation. The mice anti-sera were prediluted 1:100 (for CdtA, CdtB, ToxA, ToxB) for Post II and 1:100 (for CdtA, ToxA, ToxB), 1:100 or 1:200 (for CdtB) for Post III in PBS-BSA0.2%-TWEEN™ 0.05%. Then, further twofold dilutions were made in microplates and incubated at RT for 30 min. After washing, bound mouse antibody was detected using Jackson ImmunoLaboratories Inc. peroxidase-conjugated Anti-Mouse (ref: 110-035-003) diluted 1:5000 in PBS-BSA0.2%-tween 0.05%. The detection antibodies were incubated for 30 min. at room temperature (RT) with agitation. The color was developed using 4 mg 0-phenylenediamine (OPD)+5 μl $H_2O_2$ per 10 ml pH 4.5 0.1M citrate buffer for 15 minutes in the dark at room temperature. The reaction was stopped with 50 μl HCl, and the optical density (OD) was read at 490 nm relative to 620 nm.

A GMT was calculated for the 20 samples in each treatment group.

Binary Toxin, ToxA and ToxB Cytotoxicity Inhibition Assay: Protocol

Human colonic eptithelial cells (HT29 or HCT-116 cells) were cultured at 37° C. with 5% $CO_2$ in DMEM +10% fetal bovine serum +1% glutamine +1% antibiotics (penicillin-streptomycin-amphotericin) and were seeded in 96-well black tissue culture plates (Greiner Bio-one, Ref: 655090) at a density of $4.10^4$ cells/well for HT29 and $1.10^4$ cells/well for HCT116.

After 24 h, the cell media was removed from the wells.

The mice anti-sera were prediluted 1:50 in cell media, for ToxA inhibition cytotoxicity assay, 1:10 for ToxB inhibition cytotoxicity assay, 1:50 for binary toxin inhibition assay on HT29 and 1:30 (for Post II) and 1:30 or 1:100 (for Post III) for binary toxin inhibition assay on HCT116. Then, further three-fold dilutions were made in microplate (NUNC, Ref: 163320). 50 μl of serial dilutions of mice pooled antisera were added to the black plates. 50 μl of ToxA (0.025 μg/ml) on HT29, ToxB (0.6 μg/ml) on HCT116 and a mix of CdtA (25 ng/ml) and chemotrypsin-activated CdtB (75 ng/ml) on HT29 and HCT116 were then added in the black plates and incubated at 37° C. with 5% $CO_2$ for 6 days.

After 6 days, the mix of antisera and toxin were removed from the wells and 100 μl of Hoescht stain (BD Pharmingen, Ref: 561908) diluted 1:500 in phosphate buffer saline (PBS) was added in each well for 2 hours in the dark at room temperature.

After coloration, the Hoescht stain was removed from the wells and the cells fluorescence cells was measured using an Axiovision microscope.

The surface covered by fluorescent staining was determined in each well and cytotoxicity inhibition titers were defined as the reciprocal dilution inducing a 50% inhibition of the fluorescent signal.

Example 14: Cloning and Expression of *C. difficile* F2 and CdtB Receptor Binding Domain Fusion Proteins Expression Plasmid and Recombinant Strain.

Genes encoding the fusion protein of F2 protein with CdtB receptor binding domain protein long or short version (C64 and C65) and a His tag in C-term were cloned into the pET24b(+) expression vector (Novagen) using the NdeI/XhoI restriction sites using standard procedures.

| Fusion F2/CdtB-receptor binding domain | |
|---|---|
| C number | |
| C64 | CdtA N-term (aa. 44-260)-CdtB RBD long (aa. 621-876) |
| C65 | F2-CdtB RBD short (aa. 636-876) |

Sequence Summary (Table A)

| Description | Construct reference | Amino acid sequence | Polynucleotide sequence |
|---|---|---|---|
| CDTa full length (strain R20291) | N/A | SEQ. I.D. NO: 1 | SEQ. I.D. NO: 2 |
| CDTb full length (strain R20291) | N/A | SEQ. I.D. NO: 3 | SEQ. I.D. NO: 4 |
| CDTa without signal peptide | C34 | SEQ. I.D. NO: 5 | SEQ. I.D. NO: 6 |
| CDTb' (minus signal peptide) ligated to Glutathione-S-transferase protein. (GST underlined) | C37 | SEQ. I.D. NO: 7 | SEQ. I.D. NO: 8 |
| CDTb" (minus pro-domain and signal peptide) | C40 | SEQ. I.D. NO: 9 | N/A |
| CDTa mutation E428Q | C44 | SEQ. I.D. NO: 10 | SEQ. I.D. NO: 11 |
| CDTa mutation E430Q | C54 | SEQ. I.D. NO: 12 | N/A |
| CDTa N terminal domain (residue 44 to residue 240) | Gülke et al 2001 | SEQ. I.D. NO: 13 | N/A |
| CDTa without signal peptide, with a linker between the N-term domain and the C-term domain (containing the enzymatic activity). This construct covers the fragment from amino acid 44 to aa 268. | C49 | SEQ. I.D. NO: 14 | N/A |
| CDTa without signal peptide or linker. This construct covers the fragment from aa 44 to aa 260. | C50 | SEQ. I.D. NO: 15 | |
| CDTb minus signal peptide (CDTb') | C38 | SEQ ID NO: 16 | SEQ ID NO: 17 |
| Fusion 1 | F1 | SEQ ID NO: 18 | |
| Fusion 2 | F2 | SEQ ID NO: 19 | |
| Fusion 3 | F3 | SEQ ID NO: 20 | |
| Fusion 4 | F4 | SEQ ID NO: 21 | |
| Fusion 5 | F5 | SEQ ID NO: 22 | |
| Fusion F54 Gly | N/A | SEQ ID NO: 24 | SEQ ID NO: 23 |
| Fusion F54 New | N/A | SEQ ID NO: 26 | SEQ ID NO: 25 |
| Fusion F5 ToxB | N/A | SEQ ID NO: 28 | SEQ ID NO: 27 |
| Fusion F52 New | N/A | SEQ ID NO: 30 | SEQ ID NO: 29 |
| Toxin A | N/A | SEQ ID NO: 31 | |
| Toxin B | N/A | SEQ ID NO: 32 | |
| CDTb" (minus pro-domain and signal peptide) ligated to Glutathione-S-transferase protein. | C39 | SEQ ID NO: 33 | N/A |
| CdtB receptor binding domain with linker in N-term of sequence, from aa 620-876 | C52 | SEQ ID NO: 34 | SEQ ID NO: 35 |
| CdtB receptor binding domain without linker in N-term of sequence, from aa 636-876 | C53 | SEQ ID NO: 36 | SEQ ID NO: 37 |
| CDTb with prodomain removed (CDTb", aa212-876) | C55 | SEQ ID NO: 51 | |
| CDTb prodomain sequence (long, aa43-211) | C58 | SEQ ID NO: 38 | N/A |
| CDTb prodomain sequence (short, aa43-186) | C59 | SEQ ID NO: 39 | N/A |
| Fusion CDTa N-term with linker (aa44-268) to CDTb receptor binding domain with linker in N term of sequence (aa621-876) | C60 | SEQ ID NO: 40 | N/A |
| Fusion CDTa N-term with linker (aa44-268) to CDTb receptor binding domain without linker in N term of sequence (aa636-876) | C61 | SEQ ID NO: 41 | N/A |
| Fusion CDTa N-term without linker (aa44-260) to CDTb receptor binding domain with linker in N term of sequence (aa621-876) | C62 | SEQ ID NO: 42 | N/A |

-continued

Sequence Summary (Table A)

| Description | Construct reference | Amino acid sequence | Polynucleotide sequence |
|---|---|---|---|
| Fusion CDTa N-term without linker (aa44-260) to CDTb receptor binding domain without linker in N term of sequence (aa636-876) | C63 | SEQ ID NO: 43 | N/A |
| Fusion F2-CDTb receptor binding domain with linker in N term of sequence (aa621-876) | C64 | SEQ ID NO: 44 | N/A |
| Fusion of F2 to CDTb receptor binding domain without linker in N term of sequence (aa636-876) with 2 heterogeneous Gly residues between F2 and CTDb sequences | C65 | SEQ ID NO: 45 | N/A |
| CDTa without signal peptide, with two mutations (E428Q, E430Q, aa 44-463). | C67 | SEQ ID NO: 46 | SEQ ID NO: 47 |
| CDTa without signal peptide, with seven mutations (R345A, Q350A, N385A, R402A, S388F, E428Q, E430Q, aa 44-463). | C69 | SEQ ID NO: 48 | SEQ ID NO: 49 |
| CDTb without signal sequence and prodomain (mature fragment based on MS data) with Ca2+ binding motif mutation (aa212-876, mut Asp-9-11-13 Ala) | C97 | SEQ ID NO: 50 | N/A |
| CDTa without signal peptide, with five mutations (R345A, Q350A, N385A, R402A, S388F, aa 44-463). | C107 | SEQ ID NO: 52 | SEQ ID NO: 53 |
| CDTa without signal peptide, with six mutations (R345A, Q350A, N385A, R402A, S388F, E430Q, aa 44-463). | C108 | SEQ ID NO: 54 | SEQ ID NO: 55 |
| CdtA without signal peptide, with six mutations (R345A-Q350A-N385A-R402A-S388F-E428Q, aa 44-463). | C110 | SEQ ID NO: 56 | N/A |

SEQUENCE LISTING

SEQ ID 1

- CDTa full length polypeptide sequence
MKKFRKHKRISNCISILLILYLTLGGLLPNNIYAQDLQSYSEKVCNTTYKAPIERPEDFLKDKE

KAKEWERKEAERIEQKLERSEKEALESYKKDSVEISKYSQTRNYFYDYQIEANSREKEYKEL

RNAISKNKIDKPMYVYYFESPEKFAFNKVIRTENQNEISLEKFNEFKETIQNKLFKQDGFKDIS

LYEPGKGDEKPTPLLMHLKLPRNTGMLPYTNTNNVSTLIEQGYSIKIDKIVRIVIDGKHYIKAE

ASVVSSLDFKDDVSKGDSWGKANYNDWSNKLTPNELADVNDYMRGGYTAINNYLISNGPV

NNPNPELDSKITNIENALKREPIPTNLTVYRRSGPQEFGLTLTSPEYDFNKLENIDAFKSKWE

GQALSYPNFISTSIGSVNMSAFAKRKIVLRITIPKGSPGAYLSAIPGYAGEYEVLLNHGSKFKI

NKIDSYKDGTITKLIVDATLIP

SEQ ID 2

- CDTa full length polynucleotide sequence
ATGAAAAAATTTAGGAAACATAAAAGGATTAGTAATTGTATATCTATATTGTTGATATTAT

ATCTAACTTTAGGTGGTTTGTTACCTAATAACATTTATGCACAAGACTTACAAAGCTATA

GTGAAAAAGTTTGCAATACTACTTACAAGGCTCCTATAGAAAGACCAGAAGATTTTCTTA

AAGATAAAGAAAAGGCTAAAGAATGGGAAAGAAAAGAAGCAGAAAGAATAGAGCAAAAA

CTTGAAAGATCTGAAAAAGAAGCATTAGAATCATATAAAAAAGATTCTGTAGAAATAAGT

AAATATTCTCAGACAAGAAATTATTTTTATGATTATCAAATAGAAGCAAATTCTCGAGAAA

AAGAATATAAAGAACTTCGAAATGCTATATCAAAAAATAAAATAGATAAACCTATGTATGT

CTATTATTTTGAATCTCCAGAAAAATTTGCATTTAATAAAGTAATAAGAACAGAAAATCAA

-continued

AACGAAATTTCATTAGAAAAATTTAATGAGTTTAAAGAAACTATACAAAACAAATTATTTA

AGCAAGATGGATTTAAAGATATTTCTTTATATGAACCTGGAAAAGGTGATGAAAAACCTA

CACCATTACTTATGCACTTAAAATTACCTAGAAATACTGGTATGTTACCATATACAAATAC

TAACAATGTAAGTACATTAATAGAGCAAGGATATAGTATAAAAATAGATAAAATTGTTCGT

ATAGTTATAGATGGGAAGCACTATATTAAAGCAGAAGCATCTGTTGTAAGTAGTCTTGAT

TTTAAAGATGATGTAAGTAAGGGGGATTCTTGGGGTAAAGCAAATTATAATGATTGGAG

TAATAAATTAACACCTAATGAACTTGCTGATGTAAATGATTATATGCGTGGAGGATATAC

TGCAATTAATAATTATTTAATATCAAATGGTCCAGTAAATAATCCTAACCCAGAATTAGAT

TCTAAAATCACAAACATTGAAAATGCATTAAAACGTGAACCTATTCCAACTAATTTAACTG

TATATAGAAGATCTGGTCCTCAAGAATTTGGTTTAACTCTTACTTCCCCTGAATATGATTT

TAACAAACTAGAAAATATAGATGCTTTTAAATCAAAATGGGAAGGACAAGCACTGTCTTA

TCCAAACTTTATTAGTACTAGTATTGGTAGTGTGAATATGAGTGCATTTGCTAAAAGAAA

AATAGTACTACGTATAACTATACCTAAAGGTTCTCCTGGAGCTTATCTATCAGCTATTCC

AGGTTATGCAGGTGAATATGAAGTGCTTTTAAATCATGGAAGCAAATTTAAAATCAATAA

AATTGATTCTTACAAAGATGGTACTATAACAAAATTAATTGTTGATGCAACATTGATACCT

TAA

SEQ ID 3

- CDTb full length polypeptide sequence
MKIQMRNKKVLSFLTLTAIVSQALVYPVYAQTSTSNHSNKKKEIVNEDILPNNGLMGYYFTDE

HFKDLKLMAPIKDGNLKFEEKKVDKLLDKDKSDVKSIRWTGRIIPSKDGEYTLSTDRDDVLM

QVNTESTISNTLKVNMKKGKEYKVRIELQDKNLGSIDNLSSPNLYWELDGMKKIIPEENLFLR

DYSNIEKDDPFIPNNNFFDPKLMSDWEDEDLDTDNDNIPDSYERNGYTIKDLIAVKWEDSFA

EQGYKKYVSNYLESNTAGDPYTDYEKASGSFDKAIKTEARDPLVAAYPIVGVGMEKLIISTN

EHASTDQGKTVSRATTNSKTESNTAGVSVNVGYQNGFTANVTTNYSHTTDNSTAVQDSNG

ESWNTGLSINKGESAYINANVRYYNTGTAPMYKVTPTTNLVLDGDTLSTIKAQENQIGNNLS

PGDTYPKKGLSPLALNTMDQFSSRLIPINYDQLKKLDAGKQIKLETTQVSGNFGTKNSSGQI

VTEGNSWSDYISQIDSISASIILDTENESYERRVTAKNLQDPEDKTPELTIGEAIEKAFGATKK

DGLLYFNDIPIDESCVELIFDDNTANKIKDSLKTLSDKKIYNVKLERGMNILIKTPTYFTNFDDY

NNYPSTWSNVNTTNQDGLQGSANKLNGETKIKIPMSELKPYKRYVFSGYSKDPLTSNSIIVKI

KAKEEKTDYLVPEQGYTKFSYEFETTEKDSSNIEITLIGSGTTYLDNLSITELNSTPEILDEPEV

KIPTDQEIMDAHKIYFADLNFNPSTGNTYINGMYFAPTQTNKEALDYIQKYRVEATLQYSGFK

DIGTKDKEMRNYLGDPNQPKTNYVNLRSYFTGGENIMTYKKLRIYAITPDDRELLVLSVD

SEQ ID 4

- CDTb full length polynucleotide sequence
ATGAAAATACAAATGAGGAATAAAAAGGTATTAAGTTTTTTAACACTTACAGCTATAGTTA

GTCAAGCACTAGTATATCCTGTATATGCTCAAACTAGTACAAGTAATCATTCTAATAAGA

AAAAAGAAATTGTAAATGAAGATATACTCCCAAACAATGGATTAATGGGATATTATTTCA

CAGATGAGCACTTTAAAGATTTAAAATTAATGGCACCCATAAAAGATGGTAATTTAAAAT

TTGAAGAAAAAGAAAGTAGATAAACTTCTGGATAAAGACAAATCAGATGTAAAATCTATAC

GATGGACAGGAAGAATAATTCCTTCTAAGGATGGTGAATATACATTATCAACTGATAGA

GATGATGTCTTAATGCAAGTAAATACTGAGAGTACTATATCAAATACACTTAAAGTTAATA

TGAAAAAGGGTAAAGAATATAAAGTTAGAATAGAGCTACAAGATAAAAATTTAGGTTCAA

-continued

TAGATAATTTATCATCACCTAATCTTTATTGGGAATTAGATGGTATGAAGAAAATTATACC

AGAAGAAAATTTATTCTTAAGAGATTATTCTAATATAGAAAAAGATGATCCATTTATCCCA

AATAACAATTTCTTTGACCCAAAGTTGATGTCTGATTGGGAAGACGAAGATTTGGATACA

GATAATGATAATATACCAGATTCATATGAACGAAATGGATATACTATTAAGGACTTAATT

GCAGTTAAGTGGGAAGATAGTTTTGCAGAACAAGGCTATAAGAAATATGTATCAAATTAT

TTAGAGTCAAATACTGCTGGAGATCCATATACAGATTATGAAAAAGCTTCAGGTTCTTTT

GACAAGGCTATAAAGACTGAAGCAAGAGATCCGTTAGTTGCAGCATATCCAATTGTTGG

AGTAGGTATGGAAAAATTAATTATATCTACAAATGAACATGCCTCTACTGATCAAGGTAA

AACTGTTTCCAGAGCTACTACTAACAGTAAAACTGAATCTAATACAGCTGGTGTGTCTGT

TAATGTAGGATATCAAAATGGATTCACAGCTAATGTAACTACAAATTATTCCCATACAAC

AGATAATTCAACTGCTGTTCAAGATAGTAATGGAGAATCATGGAATACTGGATTAAGTAT

AAACAAAGGAGAATCTGCATATATAAATGCAAATGTTAGATATTACAACACAGGTACTGC

ACCTATGTACAAAGTGACACCAACAACAAATTTAGTGTTAGATGGAGATACATTATCAAC

TATCAAAGCACAAGAAAATCAAATTGGCAATAATCTATCTCCTGGAGATACTTATCCCAA

AAAAGGGCTTTCACCTCTAGCTCTTAACACAATGGATCAATTTAGCTCTAGACTGATTCC

TATAAATTATGATCAATTAAAAAAATTAGATGCTGGAAAGCAAATTAAATTAGAAACAACA

CAAGTAAGTGGAAATTTTGGTACAAAAAATAGTTCTGGACAAATAGTAACAGAAGGAAAT

AGTTGGTCAGACTATATAAGTCAAATTGACAGTATTTCTGCATCTATTATATTAGATACAG

AGAATGAATCTTACGAAAGAAGAGTTACTGCTAAAAATTTACAGGATCCAGAAGATAAAA

CACCTGAACTTACAATTGGAGAAGCAATTGAAAAAGCTTTTGGCGCTACTAAAAAAGAT

GGTTTGTTATATTTTAATGATATACCAATAGATGAAAGTTGTGTTGAACTCATATTTGATG

ATAATACAGCCAATAAGATTAAAGATAGTTTAAAAACTTTGTCTGATAAAAAGATATATAA

TGTTAAACTTGAAAGAGGAATGAATATACTTATAAAAACACCAACTTACTTTACTAATTTT

GATGATTATAATAATTACCCTAGTACATGGAGTAATGTCAATACTACGAATCAAGATGGT

TTACAAGGCTCAGCAAATAAATTAAATGGTGAGACGAAGATTAAAATCCCTATGTCTGAG

CTAAAACCTTATAAACGTTATGTTTTTAGTGGATATTCAAAGGATCCTTTAACATCTAATT

CAATAATTGTAAAGATAAAAGCAAAAGAAGAGAAAACGGATTATTTGGTACCAGAACAA

GGATATACAAAATTTAGTTATGAATTTGAAACTACTGAAAAAGATTCTTCTAATATAGAGA

TAACATTAATTGGTAGTGGTACAACATACTTAGATAACTTATCTATTACAGAGCTAAATAG

TACTCCTGAAATACTTGATGAACCAGAAGTTAAAATTCCAACTGACCAAGAAATAATGGA

TGCACATAAAATATATTTTGCAGATTTAAATTTTAATCCAAGTACAGGAAATACTTATATA

AATGGTATGTATTTTGCACCAACACAAACTAATAAAGAAGCTCTCGATTATATCCAAAAA

TATAGAGTTGAAGCTACTTTACAATATTCTGGATTTAAAGATATTGGAACTAAAGATAAA

GAAATGCGTAATTATTTAGGAGATCCAAATCAGCCTAAAACTAATTATGTTAATCTTAGG

AGTTATTTTACAGGTGGAGAAAATATTATGACATACAAGAAATTAAGAATATATGCAATTA

CTCCAGACGATAGAGAGTTATTAGTTCTTAGTGTTGATTAG

SEQ ID 5

- CDTa C34 construct polypeptide sequence
MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISLE

KFNEFKETIQNKLFKQDGFKDISLYEPGKGDEKPTPLLMHLKLPRNTGMLPYTNTNNVSTLIE

QGYSIKIDKIVRIVIDGKHYIKAEASVVSSLDFKDDVSKGDSWGKANYNDWSNKLTPNELAD

-continued

VNDYMRGGYTAINNYLISNGPVNNPNPELDSKITNIENALKREPIPTNLTVYRRSGPQEFGLT

LTSPEYDFNKLENIDAFKSKWEGQALSYPNFISTSIGSVNMSAFAKRKIVLRITIPKGSPGAYL

SAIPGYAGEYEVLLNHGSKFKINKIDSYKDGTITKLIVDATLIP

SEQ ID 6

- CDTb C34 construct polynucleotide sequence
ATGGTTTGCAATACCACCTATAAAGCACCGATTGAACGTCCGGAAGATTTTCTGAAAGA

TAAAGAAAAAGCCAAAGAATGGGAACGCAAAGAAGCAGAACGTATTGAACAGAAACTG

GAACGTAGCGAAAAAGAAGCACTGGAAAGCTACAAAAAAGATAGCGTGGAAATTTCAAA

ATATAGCCAGACCCGCAATTATTTCTATGATTATCAGATTGAAGCCAATAGCCGTGAAAA

AGAATATAAAGAACTGCGCAATGCCATTAGCAAAAACAAAATTGATAAACCGATGTATGT

GTATTATTTCGAAAGTCCGGAAAAATTTGCCTTTAACAAAGTGATTCGCACCGAAAATCA

GAATGAAATTAGCCTGGAAAAATTCAATGAATTTAAAGAAACCATTCAGAATAAACTGTT

TAAACAGGATGGCTTTAAAGATATTTCACTGTATGAACCGGGTAAAGGTGATGAAAAAC

CGACACCGCTGCTGATGCATCTGAAACTGCCTCGTAATACCGGTATGCTGCCGTATAC

CAATACCAATAATGTTAGCACCCTGATTGAACAGGGCTATAGCATCAAAATTGATAAAAT

TGTGCGCATTGTGATTGATGGCAAACATTATATCAAAGCCGAAGCCAGCGTTGTTTCAA

GCCTGGATTTTAAAGATGATGTGAGCAAAGGCGATAGCTGGGGTAAAGCAAACTATAAT

GATTGGAGCAATAAACTGACCCCGAATGAACTGGCAGATGTGAATGATTATATGCGTGG

TGGTTATACCGCCATTAACAATTATCTGATTAGCAATGGTCCGGTGAATAATCCGAATCC

GGAACTGGATAGCAAAATTACCAATATTGAAAATGCCCTGAAACGCGAACCGATTCCGA

CCAATCTGACCGTTTATCGTCGTAGCGGTCCGCAAGAATTTGGTCTGACCCTGACCAGT

CCGGAATATGACTTTAACAAACTGGAAAATATTGATGCCTTTAAAAGCAAATGGGAAGG

TCAGGCACTGAGCTATCCGAACTTTATTAGCACCAGCATTGGTAGCGTTAATATGAGCG

CATTTGCCAAACGTAAAATTGTGCTGCGTATTACCATTCCGAAAGGTAGTCCGGGTGCA

TATCTGAGCGCAATTCCGGGTTATGCCGGTGAATATGAAGTTCTGCTGAATCATGGCAG

CAAATTCAAAATTAACAAAATTGATAGCTATAAAGATGGCACCATTACCAAACTGATTGT

TGATGCAACCCTGATTCCGTAA

SEQ ID 7

- CDTb C37 construct. CDTb' (minus signal peptide)
ligated to Glutathione-S-transferase protein (GST
underlined) polypeptide sequence.
MSPILGYWKIKGLVQPTRLLLEYLEEKYEEHLYERDEGDKWRNKKFELGLEFPNLPYYIDGD

VKLTQSMAIIRYIADKHNMLGGCPKERAEISMLEGAVLDIRYGVSRIAYSKDFETLKVDFLSKL

PEMLKMFEDRLCHKTYLNGDHVTHPDFMLYDALDVVLYMDPMCLDAFPKLVCFKKRIEAIP

QIDKYLKSSKYIAWPLQGWQATFGGGDHPPKSDLEVLFQGPLGSHMEIVNEDILPNNGLMG

YYFTDEHFKDLKLMAPIKDGNLKFEEKKVDKLLDKDKSDVKSIRWTGRIIPSKDGEYTLSTDR

DDVLMQVNTESTISNTLKVNMKKGKEYKVRIELQDKNLGSIDNLSSPNLYWELDGMKKIIPE

ENLFLRDYSNIEKDDPFIPNNNFFDPKLMSDWEDEDLDTDNDNIPDSYERNGYTIKDLIAVK

WEDSFAEQGYKKYVSNYLESNTAGDPYTDYEKASGSFDKAIKTEARDPLVAAYPIVGVGME

KLIISTNEHASTDQGKTVSRATTNSKTESNTAGVSVNVGYQNGFTANVTTNYSHTTDNSTA

VQDSNGESWNTGLSINKGESAYINANVRYYNTGTAPMYKVTPTTNLVLDGDTLSTIKAQEN

QIGNNLSPGDTYPKKGLSPLALNTMDQFSSRLIPINYDQLKKLDAGKQIKLETTQVSGNFGT

KNSSGQIVTEGNSWSDYISQIDSISASIILDTENESYERRVTAKNLQDPEDKTPELTIGEAIEK

-continued

AFGATKKDGLLYFNDIPIDESCVELIFDDNTANKIKDSLKTLSDKKIYNVKLERGMNILIKTPTY

FTNFDDYNNYPSTWSNVNTTNQDGLQGSANKLNGETKIKIPMSELKPYKRYVFSGYSKDPL

TSNSIIVKIKAKEEKTDYLVPEQGYTKFSYEFETTEKDSSNIEITLIGSGTTYLDNLSITELNSTP

EILDEPEVKIPTDQEIMDAHKIYFADLNFNPSTGNTYINGMYFAPTQTNKEALDYIQKYRVEA

TLQYSGFKDIGTKDKEMRNYLGDPNQPKTNYVNLRSYFTGGENIMTYKKLRIYAITPDDREL

LVLSVD

SEQ ID 8

- CDTb C37construct. CDTb' (minus pro-domain) ligated to Glutathione-
S-transferase protein (GST underlined) polynucleotide sequence.
atgtcccctatactaggttattggaaaattaagggccttgtgcaacccactcgacttcttttggaatatcttgaagaaaaatatgaag agcatttgtatgagcgcgatgaaggtgataaatggcgaaacaaaaagtttgaattgggtttggagtttcccaatcttccttattatatt gatggtgatgttaaattaacacagtctatggccatcatacgttatatagctgacaagcacaacatgttgggtggttgtccaaaagag cgtgcagagatttcaatgcttgaaggagcggttttggatattagatacggtgtttcgagaattgcatatagtaaagactttgaaactct caaagttgatttcttagcaagctacctgaaatgctgaaaatgttcgaagatcgtttatgtcataaaacatatttaaatggtgatcatgt aacccatcctgacttcatgttgtatgacgctcttgatgttgttttatacatggacccaatgtgcctggatgcgttcccaaaattagtttgttt taaaaaacgtattgaagctatcccacaaattgataagtacttaaaatccagcaagtatatagcatggcctttgcagggctggcaa gccacgtttggtggtggcgaccatcctccaaaatcggatctggaagttctgttccaggggcccctgggatcccatatggaaattgtg aatgaagatattctgccgaataatggtctgatgggatactactttaccgatgaacattttaaagatctgaaactgatggcaccgatta aagatggcaatctgaaatttgaagaaaaaaaagtggataaactgctggataaagataaaagtgatgtgaaaagcattcgttgg accggtcgtattattccgagcaaagatggtgaatacaccctgagcaccgatcgtgatgatgttctgatgcaggttaataccgaaag caccattagcaataccctgaaagtgaatatgaaaaaaggcaaagaatataaagtgcgcattgaactgcaggataaaaatctgg gtagcattgataatctgagcagcccgaatctgtattgggaactggatggtatgaaaaaaatcattccggaagaaaacctgtttctg cgcgattatagcaatattgaaaaagatgatccgtttattccgaataataactttttgatccgaaactgatgagcgattgggaagatg aagatctggataccgataatgataatattccggatagctatgaacgcaatggctataccattaaagatctgattgccgtgaaatgg gaagatagctttgcagaacagggctataagaaatatgtgagcaattatctggaaagcaataccgcaggcgatccgtataccgat tatgaaaaagcaagcggcagctttgataaagccattaaaaccgaagcacgtgatccgctggttgcagcatatccgattgttggtg ttggtatggaaaaactgattattagcaccaatgaacatgcaagcaccgatcagggtaaaaccgttagccgtgcaaccaccaata gcaaaaccgaaagcaatacagccggtgttagcgttaatgttggttatcagaatggttttaccgccaatgtgaccaccaattatagc cataccaccgataatagcaccgcagttcaggatagcaatggtgaaagctggaataccggtctgagcattaacaaaggtgaaa gcgcatatatcaatgccaatgtgcgctattataacaccggcaccgcaccgatgtataaagttaccccgaccaccaatctggttctg gatggtgataccctgagtaccattaaagcacaagaaaatcagattggcaataatctgagtccgggtgatacctatccgaaaaaa ggtctgagtccgctggcactgaataccatggatcagtttagcagccgtctgattccgattaactatgatcagctgaaaaaactggat gccggtaaacaaatcaaactggaaaccacccaggttagcggtaatttggcaccaaaaattcaagcggtcagattgttaccgaa ggtaatagctggtcagattatatcagccagattgatagcattagcgccagcattattctggatacagaaaatgaaagctatgaacg tcgtgtgaccgcaaaaaatctgcaggacccggaagataaaacaccggaactgaccattggtgaagcaattgaaaaagcattt ggtgccaccaaaaaagatggcctgctgtattttaacgatattccgattgatgaaagctgcgtggaactgatttttgatgataataccg ccaataaaatcaaagatagcctgaaaaccctgagcgacaaaaaaatctataatgtgaaactggaacgcggtatgaatattctg attaaaaccccgacctattttaccaattttgatgattataacaattatccgagcacttggagcaatgtgaataccaccaatcaggatg gtctgcagggtagcgcaaataaactgaatggtgaaaccaaaatcaaaattccgatgagcgaactgaaaccgtataaacgttat gtgtttagcggctatagcaaagatccgctgaccagcaatagcattattgtgaaaatcaaagccaaagaagaaaaaaccgattat ctggttccggaacagggttataccaaatttagctatgaatttgaaaccaccgaaaaagatagcagtaatattgaaattaccctgatt ggtagcggcaccacctatctggataatctgagtattaccgaactgaatagcacaccggaaattctggatgaaccggaagtgaaa -continued attccgaccgatcaagaaattatggatgcccataaaatctattttgccgatctgaactttaatccgagcaccggcaatacctatatta acggcatgtattttgcaccgacccagaccaataaagaagccctggattatattcagaaatatcgtgttgaagccaccctgcagtat agcggttttaaagatattggcaccaaagataaagaaatgcgtaattatctgggcgatccgaatcagccgaaaaccaattatgtta atctgcgcagctattttaccggtggcgaaaacattatgacctacaaaaaactgcgcatttatgccattacaccggatgatcgtgaa ctgctggttctgagcgttgattaa

SEQ ID 9

- CDTb C40 construct. CDTb" (minus pro-domain and signal peptide) polypeptide sequence.

LMSDWEDEDLDTDNDNIPDSYERNGYTIKDLIAVKWEDSFAEQGYKKYVSNYLESNTAGDP

YTDYEKASGSFDKAIKTEARDPLVAAYPIVGVGMEKLIISTNEHASTDQGKTVSRATTNSKTE

SNTAGVSVNVGYQNGFTANVTTNYSHTTDNSTAVQDSNGESWNTGLSINKGESAYINANV

RYYNTGTAPMYKVTPTTNLVLDGDTLSTIKAQENQIGNNLSPGDTYPKKGLSPLALNTMDQ

FSSRLIPINYDQLKKLDAGKQIKLETTQVSGNFGTKNSSGQIVTEGNSWSDYISQIDSISASIIL

DTENESYERRVTAKNLQDPEDKTPELTIGEAIEKAFGATKKDGLLYFNDIPIDESCVELIFDDN

TANKIKDSLKTLSDKKIYNVKLERGMNILIKTPTYFTNFDDYNNYPSTWSNVNTTNQDGLQG

SANKLNGETKIKIPMSELKPYKRYVFSGYSKDPLTSNSIIVKIKAKEEKTDYLVPEQGYTKFSY

EFETTEKDSSNIEITLIGSGTTYLDNLSITELNSTPEILDEPEVKIPTDQEIMDAHKIYFADLNFN

PSTGNTYINGMYFAPTQTNKEALDYIQKYRVEATLQYSGFKDIGTKDKEMRNYLGDPNQPK

TNYVNLRSYFTGGENIMTYKKLRIYAITPDDRELLVLSVD

SEQ ID 10

- C44 construct. CDTa mutation E428Q polypeptide sequence.

MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISLE

KFNEFKETIQNKLFKQDGFKDISLYEPGKGDEKPTPLLMHLKLPRNTGMLPYTNTNNVSTLIE

QGYSIKIDKIVRIVIDGKHYIKAEASVVSSLDFKDDVSKGDSWGKANYNDWSNKLTPNELAD

VNDYMRGGYTAINNYLISNGPVNNPNPELDSKITNIENALKREPIPTNLTVYRRSGPQEFGLT

LTSPEYDFNKLENIDAFKSKWEGQALSYPNFISTSIGSVNMSAFAKRKIVLRITIPKGSPGAYL

SAIPGYAGqYEVLLNHGSKFKINKIDSYKDGTITKLIVDATLIP

SEQ ID 11

- CDTa mutation E428Q polynucleotide sequence.

atggtttgcaataccacctataaagcaccgattgaacgtccggaagattttctgaaagataaagaaaaagccaaagaatggga acgcaaagaagcagaacgtattgaacagaaactggaacgtagcgaaaaagaagcactggaaagctacaaaaaagatagc gtggaaatttcaaaatatagccagacccgcaattatttctatgattatcagattgaagccaatagccgtgaaaaagaatataaaga actgcgcaatgccattagcaaaaacaaaattgataaaccgatgtatgtgtattatttcgaaagtccggaaaaatttgcctttaacaa agtgattcgcaccgaaaatcagaatgaaattagcctggaaaaattcaatgaatttaaagaaaccattcagaataaactgtttaaa caggatggctttaaagatatttcactgtatgaaccgggtaaaggtgatgaaaaaccgacaccgctgctgatgcatctgaaactgc ctcgtaataccggtatgctgccgtataccaataccaataatgttagcaccctgattgaacagggctatagcatcaaaattgataaa attgtgcgcattgtgattgatggcaaacattatatcaaagccgaagccagcgttgtttcaagcctggattttaaagatgatgtgagca aaggcgatagctggggtaaagcaaactataatgattggagcaataaactgaccccgaatgaactggcagatgtgaatgattat atgcgtggtggttataccgccattaacaattatctgattagcaatggtccggtgaataatccgaatccggaactggatagcaaaatt accaatattgaaaatgccctgaaacgcgaaccgattccgaccaatctgaccgtttatcgtcgtagcggtccgcaagaatttggtct gaccctgaccagtccggaatatgactttaacaaactggaaaatattgatgcctttaaaagcaaatgggaaggtcaggcactgag ctatccgaactttattagcaccagcattggtagcgttaatatgagcgcatttgccaaacgtaaaattgtgctgcgtattaccattccga -continued aaggtagtccgggtgcatatctgagcgcaattccgggttatgccggtCaatatgaagttctgctgaatcatggcagcaaattcaaa attaacaaaattgatagctataaagatggcaccattaccaaactgattgttgatgcaaccctgattccgtaa

SEQ ID 12

- C54 construct. CDTa mutation E430Q polypeptide sequence.

MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISLE

KFNEFKETIQNKLFKQDGFKDISLYEPGKGDEKPTPLLMHLKLPRNTGMLPYTNTNNVSTLIE

QGYSIKIDKIVRIVIDGKHYIKAEASVVSSLDFKDDVSKGDSWGKANYNDWSNKLTPNELAD

VNDYMRGGYTAINNYLISNGPVNNPNPELDSKITNIENALKREPIPTNLTVYRRSGPQEFGLT

LTSPEYDFNKLENIDAFKSKWEGQALSYPNFISTSIGSVNMSAFAKRKIVLRITIPKGSPGAYL

SAIPGYAGEYqVLLNHGSKFKINKIDSYKDGTITKLIVDATLIP

SEQ ID 13

- CDTa N terminal domain (residue 44 to residue 240) polypeptide sequence.

MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISLE

KFNEFKETIQNKLFKQDGFKDISLYEPGKGDEKPTPLLMHLKLPRNTGMLPYTNTNNVSTLIE

QGYSIKIDKI

SEQ ID 14

- C49 construct. CDTa Nterminal domain without signal peptide, with the linker existing between the N-term domain and the C-term domain (containing the enzymatic activity). This construct covers the fragment from amino acid 44 to aa 268 polypeptide sequence.

MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISLE

KFNEFKETIQNKLFKQDGFKDISLYEPGKGDEKPTPLLMHLKLPRNTGMLPYTNTNNVSTLIE

QGYSIKIDKIVRIVIDGKHYIKAEASVVSSLDFKDDVS

SEQ ID 15

- C50 construct. CDTa without signal peptide and the linker existing between the N terminal and C terminal domains of CDTa. This construct covers the fragment from aa 44 to aa 260 polypeptide sequence.

MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISLE

KFNEFKETIQNKLFKQDGFKDISLYEPGKGDEKPTPLLMHLKLPRNTGMLPYTNTNNVSTLIE

QGYSIKIDKIVRIVIDGKHYIKAEASVVSS

SEQ ID NO: 16

- Polypeptide sequence of CDTb with pro-domain removed (CDTb')

EIVNEDILPNNGLMGYYFTDEHFKDLKLMAPIKDGNLKFEEKKVDKLLDKDKSDVKSIRWTG

RIIPSKDGEYTLSTDRDDVLMQVNTESTISNTLKVNMKKGKEYKVRIELQDKNLGSIDNLSSP

NLYWELDGMKKIIPEENLFLRDYSNIEKDDPFIPNNNFFDPKLMSDWEDEDLDTDNDNIPDS

YERNGYTIKDLIAVKWEDSFAEQGYKKYVSNYLESNTAGDPYTDYEKASGSFDKAIKTEAR

DPLVAAYPIVGVGMEKLIISTNEHASTDQGKTVSRATTNSKTESNTAGVSVNVGYQNGFTA

NVTTNYSHTTDNSTAVQDSNGESWNTGLSINKGESAYINANVRYYNTGTAPMYKVTPTTNL

VLDGDTLSTIKAQENQIGNNLSPGDTYPKKGLSPLALNTMDQFSSRLIPINYDQLKKLDAGK

QIKLETTQVSGNFGTKNSSGQIVTEGNSWSDYISQIDSISASIILDTENESYERRVTAKNLQD

PEDKTPELTIGEAIEKAFGATKKDGLLYFNDIPIDESCVELIFDDNTANKIKDSLKTLSDKKIYN

-continued

VKLERGMNILIKTPTYFTNFDDYNNYPSTWSNVNTTNQDGLQGSANKLNGETKIKIPMSELK

PYKRYVFSGYSKDPLTSNSIIVKIKAKEEKTDYLVPEQGYTKFSYEFETTEKDSSNIEITLIGS

GTTYLDNLSITELNSTPEILDEPEVKIPTDQEIMDAHKIYFADLNFNPSTGNTYINGMYFAPTQ

TNKEALDYIQKYRVEATLQYSGFKDIGTKDKEMRNYLGDPNQPKTNYVNLRSYFTGGENIM

TYKKLRIYAITPDDRELLVLSVD

SEQ ID NO: 17

- Polypeptide sequence of CDTb with pro-domain removed (CDTb')

catatggaaattgtgaatgaagatattctgccgaataatggtctgatgggatactactttaccgatgaacattttaaagatctgaaac tgatggcaccgattaaagatggcaatctgaaatttgaagaaaaaaaagtggataaactgctggataaagataaaagtgatgtg aaaagcattcgttggaccggtcgtattattccgagcaaagatggtgaatacaccctgagcaccgatcgtgatgatgttctgatgca ggttaataccgaaagcaccattagcaataccctgaaagtgaatatgaaaaaggcaaagaatataaagtgcgcattgaactgc aggataaaaatctgggtagcattgataatctgagcagcccgaatctgtattgggaactggatggtatgaaaaaaatcattccgga agaaaacctgtttctgcgcgattatagcaatattgaaaaagatgatccgtttattccgaataataactttttgatccgaaactgatga gcgattgggaagatgaagatctggataccgataatgataatattccggatagctatgaacgcaatggctataccattaaagatctg attgccgtgaaatgggaagatagctttgcagaacagggctataagaaatatgtgagcaattatctggaaagcaataccgcaggc gatccgtataccgattatgaaaaagcaagcggcagctttgataaagccattaaaaccgaagcacgtgatccgctggttgcagca tatccgattgttggtgttggtatggaaaaactgattattagcaccaatgaacatgcaagcaccgatcagggtaaaaccgttagccg tgcaaccaccaatagcaaaaccgaaagcaatacagccggtgttagcgttaatgttggttatcagaatggttttaccgccaatgtga ccaccaattatagccataccaccgataatagcaccgcagttcaggatagcaatggtgaaagctggaataccggtctgagcatta acaaaggtgaaagcgcatatatcaatgccaatgtgcgctattataacaccggcaccgcaccgatgtataaagttaccccgacca ccaatctggttctggatggtgataccctgagtaccattaaagcacaagaaaatcagattggcaataatctgagtccgggtgatacc tatccgaaaaaaggtctgagtccgctggcactgaataccatggatcagtttagcagccgtctgattccgattaactatgatcagctg aaaaaactggatgccggtaaacaaatcaaactggaaaccacccaggttagcggtaattttggcaccaaaaattcaagcggtca gattgttaccgaaggtaatagctggtcagattatatcagccagattgatagcattagcgccagcattattctggatacagaaaatga aagctatgaacgtcgtgtgaccgcaaaaaatctgcaggacccggaagataaaacaccggaactgaccattggtgaagcaatt gaaaaagcatttggtgccaccaaaaaagatggcctgctgtattttaacgatattccgattgatgaaagctgcgtggaactgatttttg atgataataccgccaataaaatcaaagatagcctgaaaaccctgagcgacaaaaaaatctataatgtgaaactggaacgcgg tatgaatattctgattaaaaccccgacctattttaccaattttgatgattataacaattatccgagcacttggagcaatgtgaataccac caatcaggatggtctgcagggtagcgcaaataaactgaatggtgaaaccaaaatcaaaattccgatgagcgaactgaaaccg tataaacgttatgtgtttagcggctatagcaaagatccgctgaccagcaatagcattattgtgaaaatcaaagccaaagaagaaa aaaccgattatctggttccggaacagggttataccaaatttagctatgaatttgaaaccaccgaaaaagatagcagtaatattgaa attaccctgattggtagcggcaccacctatctggataatctgagtattaccgaactgaatagcacaccggaaattctggatgaacc ggaagtgaaaattccgaccgatcaagaaattatggatgcccataaaatctattttgccgatctgaactttaatccgagcaccggca atacctatattaacggcatgtattttgcaccgacccagaccaataaagaagccctggattatattcagaaatatcgtgttgaagcca ccctgcagtatagcggttttaaagatattggcaccaaagataaagaaatgcgtaattatctgggcgatccgaatcagccgaaaa ccaattatgttaatctgcgcagctattttaccggtggcgaaaacattatgacctacaaaaaactgcgcatttatgccattacaccgg atgatcgtgaactgctggttctgagcgttgattaa

SEQ ID NO: 18

- sequence of Fusion 1 (F1)

MGWQTIDGKKYYFNTNTAIASTGYTIINGKHFYFNTDGIMQIGVFKGPNGFEYFAPANTDAN

NIEGQAILYQNEFLTLNGKKYYFGSDSKAVTGWRIINNKKYYFNPNNAIAAIHLCTINNDKYYF

SYDGILQNGYITIERNNFYFDANNESKMVTGVFKGPNGFEYFAPANTHNNNIEGQAIVYQNK

FLTLNGKKYYFDNDSKAVTGWQTIDGKKYYFNLNTAEAATGWQTIDGKKYYFNLNTAEAAT

-continued

GWQTIDGKKYYFNTNTFIASTGYTSINGKHFYFNTDGIMQIGVFKGPNGFEYFAPANTDANN
IEGQAILYQNKFLTLNGKKYYFGSDSKAVTGLRTIDGKKYYFNTNTAVAVTGWQTINGKKYY
FNTNTSIASTGYTIISGKHFYFNTDGIMQIGVFKGPDGFEYFAPANTDANNIEGQAIRYQNRF
LYLHDNIYYFGNNSKAATGWVTIDGNRYYFEPNTAMGANGYKTIDNKNFYFRNGLPQIGVF
KGSNGFEYFAPANTDANNIEGQAIRYQNRFLHLLGKIYYFGNNSKAVTGWQTINGKVYYFM
PDTAMAAAGGLFEIDGVIYFFGVDGVKAPGFVSINDNKHYFDDSGVMKVGYTEIDGKHFYF
AENGEMQIGVFNTEDGFKYFAHHNEDLGNEEGEEISYSGILNFNNKIYYFDDSFTAVVGWK
DLEDGSKYYFDEDTAEAYIGLSLINDGQYYFNDDGIMQVGFVTINDKVFYFSDSGIIESGVQN
IDDNYFYIDDNGIVQIGVFDTSDGYKYFAPANTVNDNIYGQAVEYSGLVRVGEDVYYFGETY
TIETGWIYDMENESDKYYFNPETKKACKGINLIDDIKYYFDEKGIMRTGLISFENNNYYFNEN
GEMQFGYINIEDKMFYFGEDGVMQIGVFNTPDGFKYFAHQNTLDENFEGESINYTGWLDLD
EKRYYFTDEYIAATGSVIIDGEEYYFDPDTAQLVISE

SEQ ID NO: 19

- sequence of Fusion 2 (F2)
MGWQTIDGKKYYFNTNTAIASTGYTIINGKHFYFNTDGIMQIGVFKGPNGFEYFAPANTDAN
NIEGQAILYQNEFLTLNGKKYYFGSDSKAVTGWRIINNKKYYFNPNNAIAAIHLCTINNDKYYF
SYDGILQNGYITIERNNFYFDANNESKMVTGVFKGPNGFEYFAPANTHNNNIEGQAIVYQNK
FLTLNGKKYYFDNDSKAVTGWQTIDGKKYYFNLNTAEAATGWQTIDGKKYYFNLNTAEAAT
GWQTIDGKKYYFNTNTFIASTGYTSINGKHFYFNTDGIMQIGVFKGPNGFEYFAPANTDANN
IEGQAILYQNKFLTLNGKKYYFGSDSKAVTGLRTIDGKKYYFNTNTAVAVTGWQTINGKKYY
FNTNTSIASTGYTIISGKHFYFNTDGIMQIGVFKGPDGFEYFAPANTDANNIEGQAIRYQNRF
LYLHDNIYYFGNNSKAATGWVTIDGNRYYFEPNTAMGANGYKTIDNKNFYFRNGLPQIGVF
KGSNGFEYFAPANTDANNIEGQAIRYQNRFLHLLGKIYYFGNNSKAVTGWQTINGKVYYFM
PDTAMAAAGGLNQIGDYKYYFNSDGVMQKGFVSINDNKHYFDDSGVMKVGYTEIDGKHFY
FAENGEMQIGVFNTEDGFKYFAHHNEDLGNEEGEEISYSGILNFNNKIYYFDDSFTAVVGW
KDLEDGSKYYFDEDTAEAYIGLSLINDGQYYFNDDGIMQVGFVTINDKVFYFSDSGIIESGVQ
NIDDNYFYIDDNGIVQIGVFDTSDGYKYFAPANTVNDNIYGQAVEYSGLVRVGEDVYYFGET
YTIETGWIYDMENESDKYYFNPETKKACKGINLIDDIKYYFDEKGIMRTGLISFENNNYYFNE
NGEMQFGYINIEDKMFYFGEDGVMQIGVFNTPDGFKYFAHQNTLDENFEGESINYTGWLDL
DEKRYYFTDEYIAATGSVIIDGEEYYFDPDTAQLVISE

SEQ ID NO: 20

- sequence of Fusion 3 (F3)
MGWQTIDGKKYYFNTNTAIASTGYTIINGKHFYFNTDGIMQIGVFKGPNGFEYFAPANTDAN
NIEGQAILYQNEFLTLNGKKYYFGSDSKAVTGWRIINNKKYYFNPNNAIAAIHLCTINNDKYYF
SYDGILQNGYITIERNNFYFDANNESKMVTGVFKGPNGFEYFAPANTHNNNIEGQAIVYQNK
FLTLNGKKYYFDNDSKAVTGWQTIDGKKYYFNLNTAEAATGWQTIDGKKYYFNLNTAEAAT
GWQTIDGKKYYFNTNTFIASTGYTSINGKHFYFNTDGIMQIGVFKGPNGFEYFAPANTDANN
IEGQAILYQNKFLTLNGKKYYFGSDSKAVTGLRTIDGKKYYFNTNTAVAVTGWQTINGKKYY
FNTNTSIASTGYTIISGKHFYFNTDGIMQIGVFKGPDGFEYFAPANTDANNIEGQAIRYQNRF
LYLHDNIYYFGNNSKAATGWVTIDGNRYYFEPNTAMGANGYKTIDNKNFYFRNGLPQIGVF
KGSNGFEYFAHHNEDLGNEEGEEISYSGILNFNNKIYYFDDSFTAVVGWKDLEDGSKYYFD
EDTAEAYIGLSLINDGQYYFNDDGIMQVGFVTINDKVFYFSDSGIIESGVQNIDDNYFYIDDN -continued

GIVQIGVFDTSDGYKYFAPANTVNDNIYGQAVEYSGLVRVGEDVYYFGETYTIETGWIYDME

NESDKYYFNPETKKACKGINLIDDIKYYFDEKGIMRTGLISFENNNYYFNENGEMQFGYINIE

DKMFYFGEDGVMQIGVFNTPDGFKYFAHQNTLDENFEGESINYTGWLDLDEKRYYFTDEYI

AATGSVIIDGEEYYFDPDTAQLVISE

SEQ ID NO: 21

- sequence of Fusion 4 (F4)

MGWQTIDGKKYYFNTNTAIASTGYTIINGKHFYFNTDGIMQIGVFKGPNGFEYFAPANTDAN

NIEGQAILYQNEFLTLNGKKYYFGSDSKAVTGWRIINNKKYYFNPNNAIAAIHLCTINNDKYYF

SYDGILQNGYITIERNNFYFDANNESKMVTGVFKGPNGFEYFAPANTHNNNIEGQAIVYQNK

FLTLNGKKYYFDNDSKAVTGWQTIDGKKYYFNLNTAEAATGWQTIDGKKYYFNLNTAEAAT

GWQTIDGKKYYFNTNTFIASTGYTSINGKHFYFNTDGIMQIGVFKGPNGFEYFAPANTDANN

IEGQAILYQNKFLTLNGKKYYFGSDSKAVTGLRTIDGKKYYFNTNTAVAVTGWQTINGKKYY

FNTNTSIASTGYTIISGKHFYFNTDGIMQIGVFKGPDGFEYFAPANTDANNIEGQAIRYQNRF

LYLHDNIYYFGNNSKAATGWVTIDGNRYYFEPNTAMGANGYKTIDNKNFYFRNGLPQIGVF

KGSNGFEYFAPANTDANNIEGQAIRYQNRFLHLLGKIYYFGNNSKAVTGWQTINGKVYYFM

PDTAMAAAGGETIIDDKNYYFNQSGVLQTGVFSTEDGFKYFAPANTLDENLEGEAIDFTGKL

IIDENIYYFDDNYRGAVEWKELDGEMHYFSPETGKAFKGLNQIGDYKYYFNSDGVMQKGFV

SINDNKHYFDDSGVMKVGYTEIDGKHFYFAENGEMQIGVFNTEDGFKYFAHHNEDLGNEE

GEEISYSGILNFNNKIYYFDDSFTAVVGWKDLEDGSKYYFDEDTAEAYIGLSLINDGQYYFND

DGIMQVGFVTINDKVFYFSDSGIIESGVQNIDDNYFYIDDNGIVQIGVFDTSDGYKYFAPANT

VNDNIYGQAVEYSGLVRVGEDVYYFGETYTIETGWIYDMENESDKYYFNPETKKACKGINLI

DDIKYYFDEKGIMRTGLISFENNNYYFNENGEMQFGYINIEDKMFYFGEDGVMQIGVFNTPD

GFKYFAHQNTLDENFEGESINYTGWLDLDEKRYYFTDEYIAATGSVIIDGEEYYFDPDTAQL

VISE

SEQ ID NO: 22

- sequence of Fusion 5 (F5)

MGWQTIDGKKYYFNTNTAIASTGYTIINGKHFYFNTDGIMQIGVFKGPNGFEYFAPANTDAN

NIEGQAILYQNEFLTLNGKKYYFGSDSKAVTGWRIINNKKYYFNPNNAIAAIHLCTINNDKYYF

SYDGILQNGYITIERNNFYFDANNESKMVTGVFKGPNGFEYFAPANTHNNNIEGQAIVYQNK

FLTLNGKKYYFDNDSKAVTGWQTIDGKKYYFNLNTAEAATGWQTIDGKKYYFNLNTAEAAT

GWQTIDGKKYYFNTNTFIASTGYTSINGKHFYFNTDGIMQIGVFKGPNGFEYFAPANTDANN

IEGQAILYQNKFLTLNGKKYYFGSDSKAVTGLRTIDGKKYYFNTNTAVAVTGWQTINGKKYY

FNTNTSIASTGYTIISGKHFYFNTDGIMQIGVFKGPDGFEYFAPANTDANNIEGQAIRYQNRF

LYLHDNIYYFGNNSKAATGWVTIDGNRYYFEPNTAMGANGYKTIDNKNFYFRNGLPQIGVF

KGSNGFEYFAPANTDANNIEGQAIRYQNRFLHLLGKIYYFGNNSKAVTGWQTINGKVYYFM

PDTAMAAAGGLFEIDGVIYFFGVDGVKAPGIYGGGFVSINDNKHYFDDSGVMKVGYTEIDG

KHFYFAENGEMQIGVFNTEDGFKYFAHHNEDLGNEEGEEISYSGILNFNNKIYYFDDSFTAV

VGWKDLEDGSKYYFDEDTAEAYIGLSLINDGQYYFNDDGIMQVGFVTINDKVFYFSDSGIIE

SGVQNIDDNYFYIDDNGIVQIGVFDTSDGYKYFAPANTVNDNIYGQAVEYSGLVRVGEDVYY

FGETYTIETGWIYDMENESDKYYFNPETKKACKGINLIDDIKYYFDEKGIMRTGLISFENNNY

YFNENGEMQFGYINIEDKMFYFGEDGVMQIGVFNTPDGFKYFAHQNTLDENFEGESINYTG

WLDLDEKRYYFTDEYIAATGSVIIDGEEYYFDPDTAQLVISE

-continued

SEQ ID NO: 23

- nucleotide sequence of F54 Gly

ATGGCAACCGGTTGGCAGACCATCGATGGCAAAAAATATTATTTTAATACCAACACCGC

AATTGCAAGCACCGGCTATACCATTATCAACGGCAAACACTTTTATTTTAACACCGACG

GCATTATGCAGATTGGTGTGTTTAAAGGTCCGAACGGCTTTGAATACTTTGCACCGGCA

AATACCGATGCCAATAATATTGAAGGCCAGGCCATTCTGTATCAGAATGAATTTCTGAC

CCTGAACGGCAAAAAATACTACTTTGGCAGCGATAGCAAAGCAGTTACCGGTTGGCGC

ATCATCAACAATAAGAAATATTACTTCAACCCGAATAATGCAATTGCAGCAATTCATCTG

TGCACCATTAACAACGACAAATATTATTTCAGCTATGACGGTATTCTGCAGAATGGCTAC

ATTACCATCGAACGCAACAACTTTTATTTCGATGCCAACAACGAAAGCAAAATGGTGAC

CGGTGTTTTCAAAGGCCCTAATGGTTTTGAGTATTTCGCTCCGGCAAACACCCATAATA

ACAACATTGAAGGTCAGGCGATCGTTTATCAGAACAAATTCCTGACGCTGAATGGTAAG

AAATACTATTTCGATAATGACAGCAAAGCCGTGACCGGCTGGCAGACAATTGACGGGA

AGAAATATTACTTTAATCTGAATACCGCAGAAGCAGCAACCGGTTGGCAAACGATCGAC

GGTAAAAAGTACTACTTCAACCTGAACACAGCCGAAGCAGCCACAGGATGGCAGACTA

TTGATGGAAAAAAATACTATTTCAACACCAACACCTTTATTGCATCTACCGGTTATACCA

GCATTAACGGTAAACATTTCTACTTCAACACCGATGGTATCATGCAGATCGGCGTTTTCA

AAGGTCCAAATGGTTTCGAATACTTTGCCCCTGCCAATACAGATGCAAATAACATCGAG

GGTCAGGCAATCCTGTACCAAAACAAATTTCTGACCCTGAATGGGAAAAAATATTACTTT

GGTAGCGATTCTAAAGCCGTTACCGGTCTGCGTACCATTGATGGTAAAAAATACTACTT

TAATACGAATACAGCCGTTGCGGTTACAGGCTGGCAGACCATTAACGGGAAAAAATACT

ATTTTAACACAAATACCAGCATTGCCTCAACGGGTTATACCATTATTTCGGGTAAACACT

TCTACTTTAATACCGATGGTATTATGCAAATCGGAGTCTTTAAAGGACCTGATGGGTTCG

AATATTTTGCGCCTGCGAACACTGATGCGAACAATATCGAAGGACAGGCAATCCGCTAT

CAGAATCGCTTTCTGTATCTGCACGACAACATCTATTATTTTGGCAACAATTCAAAAGCA

GCCACCGGCTGGGTTACAATTGATGGCAACCGCTACTATTTCGAACCGAATACCGCAAT

GGGTGCAAATGGCTACAAAACCATCGATAATAAAAATTTCTATTTTCGCAACGGTCTGC

CGCAGATCGGGGTATTTAAAGGTAGCAACGGCTTCGAATACTTCGCTCCAGCGAATAC

GGACGCGAACAATATTGAGGGTCAAGCGATTCGTTATCAAAACCGTTTTCTGCATCTGC

TGGGCAAAATCTACTACTTTGGCAATAACAGTAAAGCAGTTACTGGATGGCAGACAATC

AATGGTAAAGTGTACTATTTTATGCCGGATACCGCCATGGCAGCAGCCGGTGGTCTGTT

TGAAATTGATGGCGTGATCTATTTTTTTGGTGTGGATGGTGTTAAAGCACCGGGAATAT

ACGGTGGTACCGGCTTTGTGACCGTGGGTGATGATAAATACTATTTCAATCCGATTAAC

GGTGGTGCAGCGAGCATTGGCGAAACCATCATCGATGACAAAAACTATTATTTCAACCA

GAGCGGTGTGCTGCAGACCGGTGTGTTTAGCACCGAAGATGGCTTTAAATATTTTGCG

CCAGCGAACACCCTGGATGAAAACCTGGAAGGCGAAGCGATTGATTTTACCGGCAAAC

TGATCATCGATGAAAACATCTATTACTTCGATGATAACTATCGTGGTGCGGTGGAATGG

AAAGAACTGGATGGCGAAATGCATTATTTTTCTCCGGAAACCGGTAAAGCGTTTAAAGG

CCTGAACCAGATCGGCGATTACAAATACTACTTCAACAGCGATGGCGTGATGCAGAAA

GGCTTTGTGAGCATCAACGATAACAAACACTATTTCGATGATAGCGGTGTGATGAAAGT

GGGCTATACCGAAATTGATGGCAAACATTTCTACTTCGCGGAAAACGGCGAAATGCAGA

-continued

TTGGCGTGTTCAATACCGAAGATGGTTTCAAATACTTCGCGCACCATAACGAAGATCTG

GGTAACGAAGAAGGCGAAGAAATTAGCTATAGCGGCATCCTGAACTTCAACAACAAAAT

CTACTACTTTGATGATAGCTTTACCGCGGTGGTGGGCTGGAAAGATCTGGAAGATGGC

AGCAAATATTATTTCGATGAAGATACCGCGGAAGCGTATATTGGCCTGAGCCTGATTAA

CGATGGCCAGTACTATTTTAACGATGATGGCATTATGCAGGTGGGTTTCGTGACCATTA

ATGATAAAGTGTTCTATTTCAGCGATAGCGGCATTATTGAAAGCGGCGTGCAGAACATT

GATGATAACTACTTCTACATCGATGATAACGGCATTGTGCAGATCGGCGTTTTTGATAC

CAGCGATGGCTACAAATATTTCGCACCGGCCAATACCGTGAACGATAACATTTATGGCC

AGGCGGTGGAATATAGCGGTCTGGTGCGTGTGGGCGAAGATGTGTATTATTTCGGCGA

AACCTATACCATCGAAACCGGCTGGATTTATGATATGGAAAACGAAAGCGATAAATATTA

CTTTAATCCGGAAACGAAAAAAGCGTGCAAAGGCATTAACCTGATCGATGATATCAAAT

ACTATTTTGATGAAAAAGGCATTATGCGTACCGGTCTGATTAGCTTCGAAAACAACAACT

ATTACTTCAACGAAAACGGTGAAATGCAGTTCGGCTACATCAACATCGAAGATAAAATG

TTCTACTTCGGCGAAGATGGTGTTATGCAGATTGGTGTTTTTAACACCCCGGATGGCTT

CAAATACTTTGCCCATCAGAATACCCTGGATGAAAATTTCGAAGGTGAAAGCATTAACTA

TACCGGCTGGCTGGATCTGGATGAAAAACGCTACTACTTCACCGATGAATACATTGCGG

CGACCGGCAGCGTGATTATTGATGGCGAAGAATACTACTTCGATCCGGATACCGCGCA

GCTGGTGATTAGCGAACATCATCATCATCACCAT

SEQ ID NO: 24

- amino acid of F54Gly

MATGWQTIDGKKYYFNTNTAIASTGYTIINGKHFYFNTDGIMQIGVFKGPNGFEYFAPANTD

ANNIEGQAILYQNEFLTLNGKKYYFGSDSKAVTGWRIINNKKYYFNPNNAIAAIHLCTINNDKY

YFSYDGILQNGYITIERNNFYFDANNESKMVTGVFKGPNGFEYFAPANTHNNNIEGQAIVYQ

NKFLTLNGKKYYFDNDSKAVTGWQTIDGKKYYFNLNTAEAATGWQTIDGKKYY

FNLNTAEAATGWQTIDGKKYYFNTNTFIASTGYTSINGKHFYFNTDGIMQIGVFKGPNGFEY

FAPANTDANNIEGQAILYQNKFLTLNGKKYYFGSDSKAVTGLRTIDGKKYYFNTNTAVAVTG

WQTINGKKYYFNTNTSIASTGYTIISGKHFYFNTDGIMQIGVFKGPDGFEYFAPANTDANNIE

GQAIRYQNRFLYLHDNIYYFGNNSKAATGWVTIDGNRYYFEPNTAMGANGYKT

IDNKNFYFRNGLPQIGVFKGSNGFEYFAPANTDANNIEGQAIRYQNRFLHLLGKIYYFGNNS

KAVTGWQTINGKVYYFMPDTAMAAAGGLFEIDGVIYFFGVDGVKAPGIYGGTGFVTVGDDK

YYFNPINGGAASIGETIIDDKNYYFNQSGVLQTGVFSTEDGFKYFAPANTLDENLEGEAIDFT

GKLIIDENIYYFDDNYRGAVEWKELDGEMHYFSPETGKAFKGLNQIGDYKYYFNSDGVMQK

GFVSINDNKHYFDDSGVMKVGYTEIDGKHFYFAENGEMQIGVFNTEDGFKYFAHHNEDLG

NEEGEEISYSGILNFNNKIYYFDDSFTAVVGWKDLEDGSKYYFDEDTAEAYIGLSLINDGQYY

FNDDGIMQVGFVTINDKVFYFSDSGIIESGVQNIDDNYFYIDDNGIVQIGVFDTSDGYKYFAP

ANTVNDNIYGQAVEYSGLVRVGEDVYYFGETYTIETGWIYDMENESDKYYFNPETKKACKG

INLIDDIKYYFDEKGIMRTGLISFENNNYYFNENGEMQFGYINIEDKMFYFGEDGVMQIGVFN

TPDGFKYFAHQNTLDENFEGESINYTGWLDLDEKRYYFTDEYIAATGSVIIDGEEYYFDPDT

AQLVISEHHHHHH

SEQ ID NO: 25

- nucleotide sequence of F54 New

ATGGCAACCGGTTGGCAGACCATCGATGGCAAAAAATATTATTTTAATACCAACACCGC

AATTGCAAGCACCGGCTATACCATTATCAACGGCAAACACTTTTATTTTAACACCGACG

-continued

GCATTATGCAGATTGGTGTGTTTAAAGGTCCGAACGGCTTTGAATACTTTGCACCGGCA

AATACCGATGCCAATAATATTGAAGGCCAGGCCATTCTGTATCAGAATGAATTTCTGAC

CCTGAACGGCAAAAAATACTACTTTGGCAGCGATAGCAAAGCAGTTACCGGTTGGCGC

ATCATCAACAATAAGAAATATTACTTCAACCCGAATAATGCAATTGCAGCAATTCATCTG

TGCACCATTAACAACGACAAATATTATTTCAGCTATGACGGTATTCTGCAGAATGGCTAC

ATTACCATCGAACGCAACAACTTTTATTTCGATGCCAACAACGAAAGCAAAATGGTGAC

CGGTGTTTTCAAAGGCCCTAATGGTTTTGAGTATTTCGCTCCGGCAAACACCCATAATA

ACAACATTGAAGGTCAGGCGATCGTTTATCAGAACAAATTCCTGACGCTGAATGGTAAG

AAATACTATTTCGATAATGACAGCAAAGCCGTGACCGGCTGGCAGACAATTGACGGGA

AGAAATATTACTTTAATCTGAATACCGCAGAAGCAGCAACCGGTTGGCAAACGATCGAC

GGTAAAAAGTACTACTTCAACCTGAACACAGCCGAAGCAGCCACAGGATGGCAGACTA

TTGATGGAAAAAAATACTATTTCAACACCAACACCTTTATTGCATCTACCGGTTATACCA

GCATTAACGGTAAACATTTCTACTTCAACACCGATGGTATCATGCAGATCGGCGTTTTCA

AAGGTCCAAATGGTTTCGAATACTTTGCCCCTGCCAATACAGATGCAAATAACATCGAG

GGTCAGGCAATCCTGTACCAAAACAAATTTCTGACCCTGAATGGGAAAAAATATTACTTT

GGTAGCGATTCTAAAGCCGTTACCGGTCTGCGTACCATTGATGGTAAAAAATACTACTT

TAATACGAATACAGCCGTTGCGGTTACAGGCTGGCAGACCATTAACGGGAAAAAATACT

ATTTTAACACAAATACCAGCATTGCCTCAACGGGTTATACCATTATTTCGGGTAAACACT

TCTACTTTAATACCGATGGTATTATGCAAATCGGAGTCTTTAAAGGACCTGATGGGTTCG

AATATTTTGCGCCTGCGAACACTGATGCGAACAATATCGAAGGACAGGCAATCCGCTAT

CAGAATCGCTTTCTGTATCTGCACGACAACATCTATTATTTTGGCAACAATTCAAAAGCA

GCCACCGGCTGGGTTACAATTGATGGCAACCGCTACTATTTCGAACCGAATACCGCAAT

GGGTGCAAATGGCTACAAAACCATCGATAATAAAAATTTCTATTTTCGCAACGGTCTGC

CGCAGATCGGGGTATTTAAAGGTAGCAACGGCTTCGAATACTTCGCTCCAGCGAATAC

GGACGCGAACAATATTGAGGGTCAAGCGATTCGTTATCAAAACCGTTTTCTGCATCTGC

TGGGCAAAATCTACTACTTTGGCAATAACAGTAAAGCAGTTACTGGATGGCAGACAATC

AATGGTAAAGTGTACTATTTTATGCCGGATACCGCCATGGCAGCAGCCGGTGGTCTGTT

TGAAATTGATGGCGTGATCTATTTTTTTGGTGTGGATGGTGTTAAAGCAGTTACCGGCTT

TGTGACCGTGGGTGATGATAAATACTATTTCAATCCGATTAACGGTGGTGCAGCGAGCA

TTGGCGAAACCATCATCGATGACAAAAACTATTATTTCAACCAGAGCGGTGTGCTGCAG

ACCGGTGTGTTTAGCACCGAAGATGGCTTTAAATATTTTGCGCCAGCGAACACCCTGGA

TGAAAACCTGGAAGGCGAAGCGATTGATTTTACCGGCAAACTGATCATCGATGAAAACA

TCTATTACTTCGATGATAACTATCGTGGTGCGGTGGAATGGAAAGAACTGGATGGCGAA

ATGCATTATTTTTCTCCGGAAACCGGTAAAGCGTTTAAAGGCCTGAACCAGATCGGCGA

TTACAAATACTACTTCAACAGCGATGGCGTGATGCAGAAAGGCTTTGTGAGCATCAACG

ATAACAAACACTATTTCGATGATAGCGGTGTGATGAAAGTGGGCTATACCGAAATTGAT

GGCAAACATTTCTACTTCGCGGAAAACGGCGAAATGCAGATTGGCGTGTTCAATACCGA

AGATGGTTTCAAATACTTCGCGCACCATAACGAAGATCTGGGTAACGAAGAAGGCGAA

GAAATTAGCTATAGCGGCATCCTGAACTTCAACAACAAAATCTACTACTTTGATGATAGC

TTTACCGCGGTGGTGGGCTGGAAAGATCTGGAAGATGGCAGCAAATATTATTTCGATGA

-continued

AGATACCGCGGAAGCGTATATTGGCCTGAGCCTGATTAACGATGGCCAGTACTATTTTA

ACGATGATGGCATTATGCAGGTGGGTTTCGTGACCATTAATGATAAAGTGTTCTATTTCA

GCGATAGCGGCATTATTGAAAGCGGCGTGCAGAACATTGATGATAACTACTTCTACATC

GATGATAACGGCATTGTGCAGATCGGCGTTTTTGATACCAGCGATGGCTACAAATATTT

CGCACCGGCCAATACCGTGAACGATAACATTTATGGCCAGGCGGTGGAATATAGCGGT

CTGGTGCGTGTGGGCGAAGATGTGTATTATTTCGGCGAAACCTATACCATCGAAACCG

GCTGGATTTATGATATGGAAAACGAAAGCGATAAATATTACTTTAATCCGGAAACGAAAA

AAGCGTGCAAAGGCATTAACCTGATCGATGATATCAAATACTATTTTGATGAAAAAGGCA

TTATGCGTACCGGTCTGATTAGCTTCGAAAACAACAACTATTACTTCAACGAAAACGGT

GAAATGCAGTTCGGCTACATCAACATCGAAGATAAAATGTTCTACTTCGGCGAAGATGG

TGTTATGCAGATTGGTGTTTTTAACACCCCGGATGGCTTCAAATACTTTGCCCATCAGAA

TACCCTGGATGAAAATTTCGAAGGTGAAAGCATTAACTATACCGGCTGGCTGGATCTGG

ATGAAAAACGCTACTACTTCACCGATGAATACATTGCGGCGACCGGCAGCGTGATTATT

GATGGCGAAGAATACTACTTCGATCCGGATACCGCGCAGCTGGTGATTAGCGAACATC

ATCATCATCACCAT

SEQ ID NO: 26 amino acid sequence of F54 New

MATGWQTIDGKKYYFNTNTAIASTGYTIINGKHFYFNTDGIMQIGVFKGPNGFEYFAPANTD

ANNIEGQAILYQNEFLTLNGKKYYFGSDSKAVTGWRIINNKKYYFNPNNAIAAIHLCTINNDKY

YFSYDGILQNGYITIERNNFYFDANNESKMVTGVFKGPNGFEYFAPANTHNNNIEGQAIVYQ

NKFLTLNGKKYYFDNDSKAVTGWQTIDGKKYYFNLNTAEAATGWQTIDGKKYYFNLNTAEA

ATGWQTIDGKKYYFNTNTFIASTGYTSINGKHFYFNTDGIMQIGVFKGPNGFEYFAPANTDA

NNIEGQAILYQNKFLTLNGKKYYFGSDSKAVTGLRTIDGKKYYFNTNTAVAVTGWQTINGKK

YYFNTNTSIASTGYTIISGKHFYFNTDGIMQIGVFKGPDGFEYFAPANTDANNIEGQAIRYQN

RFLYLHDNIYYFGNNSKAATGWVTIDGNRYYFEPNTAMGANGYKTIDNKNFYFRNGLPQIG

VFKGSNGFEYFAPANTDANNIEGQAIRYQNRFLHLLGKIYYFGNNSKAVTGWQTINGKVYYF

MPDTAMAAAGGLFEIDGVIYFFGVDGVKAVTGFVTVGDDKYYFNPINGGAASIGETIIDDKN

YYFNQSGVLQTGVFSTEDGFKYFAPANTLDENLEGEAIDFTGKLIIDENIYYFDDNYRGAVE

WKELDGEMHYFSPETGKAFKGLNQIGDYKYYFNSDGVMQKGFVSINDNKHYFDDSGVMK

VGYTEIDGKHFYFAENGEMQIGVFNTEDGFKYFAHHNEDLGNEEGEEISYSGILNFNNKIYY

FDDSFTAVVGWKDLEDGSKYYFDEDTAEAYIGLSLINDGQYYFNDDGIMQVGFVTINDKVFY

FSDSGIIESGVQNIDDNYFYIDDNGIVQIGVFDTSDGYKYFAPANTVNDNIYGQAVEYSGLVR

VGEDVYYFGETYTIETGWIYDMENESDKYYFNPETKKACKGINLIDDIKYYFDEKGIMRTGLI

SFENNNYYFNENGEMQFGYINIEDKMFYFGEDGVMQIGVFNTPDGFKYFAHQNTLDENFE

GESINYTGWLDLDEKRYYFTDEYIAATGSVIIDGEEYYFDPDTAQLVISEHHHHHH

SEQ ID NO: 27 nucleotide sequence of F5 ToxB

ATGGCAACCGGTTGGCAGACCATCGATGGCAAAAAATATTATTTTAATACCAACACCGC

AATTGCAAGCACCGGCTATACCATTATCAACGGCAAACACTTTTATTTTAACACCGACG

GCATTATGCAGATTGGTGTGTTTAAAGGTCCGAACGGCTTTGAATACTTTGCACCGGCA

AATACCGATGCCAATAATATTGAAGGCCAGGCCATTCTGTATCAGAATGAATTTCTGAC

CCTGAACGGCAAAAAATACTACTTTGGCAGCGATAGCAAAGCAGTTACCGGTTGGCGC

ATCATCAACAATAAGAAATATTACTTCAACCCGAATAATGCAATTGCAGCAATTCATCTG

-continued

TGCACCATTAACAACGACAAATATTATTTCAGCTATGACGGTATTCTGCAGAATGGCTAC

ATTACCATCGAACGCAACAACTTTTATTTCGATGCCAACAACGAAAGCAAAATGGTGAC

CGGTGTTTTCAAAGGCCCTAATGGTTTTGAGTATTTCGCTCCGGCAAACACCCATAATA

ACAACATTGAAGGTCAGGCGATCGTTTATCAGAACAAATTCCTGACGCTGAATGGTAAG

AAATACTATTTCGATAATGACAGCAAAGCCGTGACCGGCTGGCAGACAATTGACGGGA

AGAAATATTACTTTAATCTGAATACCGCAGAAGCAGCAACCGGTTGGCAAACGATCGAC

GGTAAAAAGTACTACTTCAACCTGAACACAGCCGAAGCAGCCACAGGATGGCAGACTA

TTGATGGAAAAAAATACTATTTCAACACCAACACCTTTATTGCATCTACCGGTTATACCA

GCATTAACGGTAAACATTTCTACTTCAACACCGATGGTATCATGCAGATCGGCGTTTTCA

AAGGTCCAAATGGTTTCGAATACTTTGCCCCTGCCAATACAGATGCAAATAACATCGAG

GGTCAGGCAATCCTGTACCAAAACAAATTTCTGACCCTGAATGGGAAAAAATATTACTTT

GGTAGCGATTCTAAAGCCGTTACCGGTCTGCGTACCATTGATGGTAAAAAATACTACTT

TAATACGAATACAGCCGTTGCGGTTACAGGCTGGCAGACCATTAACGGGAAAAAATACT

ATTTTAACACAAATACCAGCATTGCCTCAACGGGTTATACCATTATTTCGGGTAAACACT

TCTACTTTAATACCGATGGTATTATGCAAATCGGAGTCTTTAAAGGACCTGATGGGTTCG

AATATTTTGCGCCTGCGAACACTGATGCGAACAATATCGAAGGACAGGCAATCCGCTAT

CAGAATCGCTTTCTGTATCTGCACGACAACATCTATTATTTTGGCAACAATTCAAAAGCA

GCCACCGGCTGGGTTACAATTGATGGCAACCGCTACTATTTCGAACCGAATACCGCAAT

GGGTGCAAATGGCTACAAAACCATCGATAATAAAAATTTCTATTTTCGCAACGGTCTGC

CGCAGATCGGGGTATTTAAAGGTAGCAACGGCTTCGAATACTTCGCTCCAGCGAATAC

GGACGCGAACAATATTGAGGGTCAAGCGATTCGTTATCAAAACCGTTTTCTGCATCTGC

TGGGCAAAATCTACTACTTTGGCAATAACAGTAAAGCAGTTACTGGATGGCAGACAATC

AATGGTAAAGTGTACTATTTTATGCCGGATACCGCCATGGCAGCAGCCGGTGGTCTGTT

TGAAATTGATGGCGTGATCTATTTTTTTGGTGTGGATGGTGTTAAAGCAGTGAGCGGTC

TGATTTATATTAACGATAGCCTGTATTACTTTAAACCACCGGTGAATAACCTGATTACCG

GCTTTGTGACCGTGGGTGATGATAAATACTATTTCAATCCGATTAACGGTGGTGCAGCG

AGCATTGGCGAAACCATCATCGATGACAAAAACTATTATTTCAACCAGAGCGGTGTGCT

GCAGACCGGTGTGTTTAGCACCGAAGATGGCTTTAAATATTTTGCGCCAGCGAACACC

CTGGATGAAAACCTGGAAGGCGAAGCGATTGATTTTACCGGCAAACTGATCATCGATGA

AAACATCTATTACTTCGATGATAACTATCGTGGTGCGGTGGAATGGAAAGAACTGGATG

GCGAAATGCATTATTTTTCTCCGGAAACCGGTAAAGCGTTTAAAGGCCTGAACCAGATC

GGCGATTACAAATACTACTTCAACAGCGATGGCGTGATGCAGAAAGGCTTTGTGAGCAT

CAACGATAACAAACACTATTTCGATGATAGCGGTGTGATGAAAGTGGGCTATACCGAAA

TTGATGGCAAACATTTCTACTTCGCGGAAAACGGCGAAATGCAGATTGGCGTGTTCAAT

ACCGAAGATGGTTTCAAATACTTCGCGCACCATAACGAAGATCTGGGTAACGAAGAAG

GCGAAGAAATTAGCTATAGCGGCATCCTGAACTTCAACAACAAAATCTACTACTTTGATG

ATAGCTTTACCGCGGTGGTGGGCTGGAAAGATCTGGAAGATGGCAGCAAATATTATTTC

GATGAAGATACCGCGGAAGCGTATATTGGCCTGAGCCTGATTAACGATGGCCAGTACT

ATTTTAACGATGATGGCATTATGCAGGTGGGTTTCGTGACCATTAATGATAAAGTGTTCT

ATTTCAGCGATAGCGGCATTATTGAAAGCGGCGTGCAGAACATTGATGATAACTACTTC

-continued

TACATCGATGATAACGGCATTGTGCAGATCGGCGTTTTTGATACCAGCGATGGCTACAA

ATATTTCGCACCGGCCAATACCGTGAACGATAACATTTATGGCCAGGCGGTGGAATATA

GCGGTCTGGTGCGTGTGGGCGAAGATGTGTATTATTTCGGCGAAACCTATACCATCGA

AACCGGCTGGATTTATGATATGGAAAACGAAAGCGATAAATATTACTTTAATCCGGAAAC

GAAAAAAGCGTGCAAAGGCATTAACCTGATCGATGATATCAAATACTATTTTGATGAAAA

AGGCATTATGCGTACCGGTCTGATTAGCTTCGAAAACAACAACTATTACTTCAACGAAAA

CGGTGAAATGCAGTTCGGCTACATCAACATCGAAGATAAAATGTTCTACTTCGGCGAAG

ATGGTGTTATGCAGATTGGTGTTTTTAACACCCCGGATGGCTTCAAATACTTTGCCCATC

AGAATACCCTGGATGAAAATTTCGAAGGTGAAAGCATTAACTATACCGGCTGGCTGGAT

CTGGATGAAAAACGCTACTACTTCACCGATGAATACATTGCGGCGACCGGCAGCGTGA

TTATTGATGGCGAAGAATACTACTTCGATCCGGATACCGCGCAGCTGGTGATTAGCGAA

CATCATCATCATCACCAT

SEQ ID NO: 28 amino acid sequence of F5 ToxB

MATGWQTIDGKKYYFNTNTAIASTGYTIINGKHFYFNTDGIMQIGVFKGPNGFEYFAPANTD

ANNIEGQAILYQNEFLTLNGKKYYFGSDSKAVTGWRIINNKKYYFNPNNAIAAIHLCTINNDKY

YFSYDGILQNGYITIERNNFYFDANNESKMVTGVFKGPNGFEYFAPANTHNNNIEGQAIVYQ

NKFLTLNGKKYYFDNDSKAVTGWQTIDGKKYYFNLNTAEAATGWQTIDGKKYYFNLNTAEA

ATGWQTIDGKKYYFNTNTFIASTGYTSINGKHFYFNTDGIMQIGVFKGPNGFEYFAPANTDA

NNIEGQAILYQNKFLTLNGKKYYFGSDSKAVTGLRTIDGKKYYFNTNTAVAVTGWQTINGKK

YYFNTNTSIASTGYTIISGKHFYFNTDGIMQIGVFKGPDGFEYFAPANTDANNIEGQAIRYQN

RFLYLHDNIYYFGNNSKAATGWVTIDGNRYYFEPNTAMGANGYKTIDNKNFYFRNGLPQIG

VFKGSNGFEYFAPANTDANNIEGQAIRYQNRFLHLLGKIYYFGNNSKAVTGWQTINGKVYYF

MPDTAMAAAGGLFEIDGVIYFFGVDGVKAVSGLIYINDSLYYFKPPVNNLITGFVTVGDDKYY

FNPINGGAASIGETIIDDKNYYFNQSGVLQTGVFSTEDGFKYFAPANTLDENLEGEAIDFTGK

LIIDENIYYFDDNYRGAVEWKELDGEMHYFSPETGKAFKGLNQIGDYKYYFNSDGVMQKGF

VSINDNKHYFDDSGVMKVGYTEIDGKHFYFAENGEMQIGVFNTEDGFKYFAHHNEDLGNE

EGEEISYSGILNFNNKIYYFDDSFTAVVGWKDLEDGSKYYFDEDTAEAYIGLSLINDGQYYFN

DDGIMQVGFVTINDKVFYFSDSGIIESGVQNIDDNYFYIDDNGIVQIGVFDTSDGYKYFAPAN

TVNDNIYGQAVEYSGLVRVGEDVYYFGETYTIETGWIYDMENESDKYYFNPETKKACKGINL

IDDIKYYFDEKGIMRTGLISFENNNYYFNENGEMQFGYINIEDKMFYFGEDGVMQIGVFNTP

DGFKYFAHQNTLDENFEGESINYTGWLDLDEKRYYFTDEYIAATGSVIIDGEEYYFDPDTAQ

LVISEHHHHHH

SEQ ID NO: 29

- nucleotide sequence of F52 new

ATGGCAACCGGTTGGCAGACCATCGATGGCAAAAAATATTATTTTAATACCAACACCGC

AATTGCAAGCACCGGCTATACCATTATCAACGGCAAACACTTTTATTTTAACACCGACG

GCATTATGCAGATTGGTGTGTTTAAAGGTCCGAACGGCTTTGAATACTTTGCACCGGCA

AATACCGATGCCAATAATATTGAAGGCCAGGCCATTCTGTATCAGAATGAATTTCTGAC

CCTGAACGGCAAAAAATACTACTTTGGCAGCGATAGCAAAGCAGTTACCGGTTGGCGC

ATCATCAACAATAAGAAATATTACTTCAACCCGAATAATGCAATTGCAGCAATTCATCTG

TGCACCATTAACAACGACAAATATTATTTCAGCTATGACGGTATTCTGCAGAATGGCTAC

ATTACCATCGAACGCAACAACTTTTATTTCGATGCCAACAACGAAAGCAAAATGGTGAC

-continued

CGGTGTTTTCAAAGGCCCTAATGGTTTTGAGTATTTCGCTCCGGCAAACACCCATAATA

ACAACATTGAAGGTCAGGCGATCGTTTATCAGAACAAATTCCTGACGCTGAATGGTAAG

AAATACTATTTCGATAATGACAGCAAAGCCGTGACCGGCTGGCAGACAATTGACGGGA

AGAAATATTACTTTAATCTGAATACCGCAGAAGCAGCAACCGGTTGGCAAACGATCGAC

GGTAAAAAGTACTACTTCAACCTGAACACAGCCGAAGCAGCCACAGGATGGCAGACTA

TTGATGGAAAAAAATACTATTTCAACACCAACACCTTTATTGCATCTACCGGTTATACCA

GCATTAACGGTAAACATTTCTACTTCAACACCGATGGTATCATGCAGATCGGCGTTTTCA

AAGGTCCAAATGGTTTCGAATACTTTGCCCCTGCCAATACAGATGCAAATAACATCGAG

GGTCAGGCAATCCTGTACCAAAACAAATTTCTGACCCTGAATGGGAAAAAATATTACTTT

GGTAGCGATTCTAAAGCCGTTACCGGTCTGCGTACCATTGATGGTAAAAAATACTACTT

TAATACGAATACAGCCGTTGCGGTTACAGGCTGGCAGACCATTAACGGGAAAAAATACT

ATTTTAACACAAATACCAGCATTGCCTCAACGGGTTATACCATTATTTCGGGTAAACACT

TCTACTTTAATACCGATGGTATTATGCAAATCGGAGTCTTTAAAGGACCTGATGGGTTCG

AATATTTTGCGCCTGCGAACACTGATGCGAACAATATCGAAGGACAGGCAATCCGCTAT

CAGAATCGCTTTCTGTATCTGCACGACAACATCTATTATTTTGGCAACAATTCAAAAGCA

GCCACCGGCTGGGTTACAATTGATGGCAACCGCTACTATTTCGAACCGAATACCGCAAT

GGGTGCAAATGGCTACAAAACCATCGATAATAAAAATTTCTATTTTCGCAACGGTCTGC

CGCAGATCGGGGTATTTAAAGGTAGCAACGGCTTCGAATACTTCGCTCCAGCGAATAC

GGACGCGAACAATATTGAGGGTCAAGCGATTCGTTATCAAAACCGTTTTCTGCATCTGC

TGGGCAAAATCTACTACTTTGGCAATAACAGTAAAGCAGTTACTGGATGGCAGACAATC

AATGGTAAAGTGTACTATTTTATGCCGGATACCGCCATGGCAGCAGCCGGTGGTCTGTT

TGAAATTGATGGCGTGATCTATTTTTTTGGTGTGGATGGTGTTAAAGCAGTGAAAGGCC

TGAACCAGATCGGCGATTACAAATACTACTTCAACAGCGATGGCGTGATGCAGAAAGG

CTTTGTGAGCATCAACGATAACAAACACTATTTCGATGATAGCGGTGTGATGAAAGTGG

GCTATACCGAAATTGATGGCAAACATTTCTACTTCGCGGAAAACGGCGAAATGCAGATT

GGCGTGTTCAATACCGAAGATGGTTTCAAATACTTCGCGCACCATAACGAAGATCTGGG

TAACGAAGAAGGCGAAGAAATTAGCTATAGCGGCATCCTGAACTTCAACAACAAAATCT

ACTACTTTGATGATAGCTTTACCGCGGTGGTGGGCTGGAAAGATCTGGAAGATGGCAG

CAAATATTATTTCGATGAAGATACCGCGGAAGCGTATATTGGCCTGAGCCTGATTAACG

ATGGCCAGTACTATTTTAACGATGATGGCATTATGCAGGTGGGTTTCGTGACCATTAAT

GATAAAGTGTTCTATTTCAGCGATAGCGGCATTATTGAAAGCGGCGTGCAGAACATTGA

TGATAACTACTTCTACATCGATGATAACGGCATTGTGCAGATCGGCGTTTTTGATACCA

GCGATGGCTACAAATATTTCGCACCGGCCAATACCGTGAACGATAACATTTATGGCCAG

GCGGTGGAATATAGCGGTCTGGTGCGTGTGGGCGAAGATGTGTATTATTTCGGCGAAA

CCTATACCATCGAAACCGGCTGGATTTATGATATGGAAAACGAAAGCGATAAATATTACT

TTAATCCGGAAACGAAAAAAGCGTGCAAAGGCATTAACCTGATCGATGATATCAAATAC

TATTTTGATGAAAAAGGCATTATGCGTACCGGTCTGATTAGCTTCGAAAACAACAACTAT

TACTTCAACGAAAACGGTGAAATGCAGTTCGGCTACATCAACATCGAAGATAAAATGTT

CTACTTCGGCGAAGATGGTGTTATGCAGATTGGTGTTTTTAACACCCCGGATGGCTTCA

AATACTTTGCCCATCAGAATACCCTGGATGAAAATTTCGAAGGTGAAAGCATTAACTATA

-continued

CCGGCTGGCTGGATCTGGATGAAAAACGCTACTACTTCACCGATGAATACATTGCGGC

GACCGGCAGCGTGATTATTGATGGCGAAGAATACTACTTCGATCCGGATACCGCGCAG

CTGGTGATTAGCGAACATCATCATCATCACCAT

SEQ ID NO: 30

- amino acid sequence of F52 New

MATGWQTIDGKKYYFNTNTAIASTGYTIINGKHFYFNTDGIMQIGVFKGPNGFEYFAPANTD

ANNIEGQAILYQNEFLTLNGKKYYFGSDSKAVTGWRIINNKKYYFNPNNAIAAIHLCTINNDKY

YFSYDGILQNGYITIERNNFYFDANNESKMVTGVFKGPNGFEYFAPANTHNNNIEGQAIVYQ

NKFLTLNGKKYYFDNDSKAVTGWQTIDGKKYYFNLNTAEAATGWQTIDGKKYYFNLNTAEA

ATGWQTIDGKKYYFNTNTFIASTGYTSINGKHFYFNTDGIMQIGVFKGPNGFEYFAPANTDA

NNIEGQAILYQNKFLTLNGKKYYFGSDSKAVTGLRTIDGKKYYFNTNTAVAVTGWQTINGKK

YYFNTNTSIASTGYTIISGKHFYFNTDGIMQIGVFKGPDGFEYFAPANTDANNIEGQAIRYQN

RFLYLHDNIYYFGNNSKAATGWVTIDGNRYYFEPNTAMGANGYKTIDNKNFYFRNGLPQIG

VFKGSNGFEYFAPANTDANNIEGQAIRYQNRFLHLLGKIYYFGNNSKAVTGWQTINGKVYYF

MPDTAMAAAGGLFEIDGVIYFFGVDGVKAVKGLNQIGDYKYYFNSDGVMQKGFVSINDNKH

YFDDSGVMKVGYTEIDGKHFYFAENGEMQIGVFNTEDGFKYFAHHNEDLGNEEGEEISYS

GILNFNNKIYYFDDSFTAVVGWKDLEDGSKYYFDEDTAEAYIGLSLINDGQYYFNDDGIMQV

GFVTINDKVFYFSDSGIIESGVQNIDDNYFYIDDNGIVQIGVFDTSDGYKYFAPANTVNDNIYG

QAVEYSGLVRVGEDVYYFGETYTIETGWIYDMENESDKYYFNPETKKACKGINLIDDIKYYF

DEKGIMRTGLISFENNNYYFNENGEMQFGYINIEDKMFYFGEDGVMQIGVFNTPDGFKYFA

HQNTLDENFEGESINYTGWLDLDEKRYYFTDEYIAATGSVIIDGEEYYFDPDTAQLVISEHHH

HHH

SEQ ID NO: 31

- amino acid sequence of Toxin A

MSLISKEELIKLAYSIRPRENEYKTILTNLDEYNKLTTNNNENKYLQLKKLNESIDVFMN

KYKTSSRNRALSNLKKDILKEVILIKNSNTSPVEKNLHFVWIGGEVSDIALEYIKQWADI

NAEYNIKLWYDSEAFLVNTLKKAIVESSTTEALQLLEEEIQNPQFDNMKFYKKRMEFIYD

RQKRFINYYKSQINKPTVPTIDDIIKSHLVSEYNRDETVLESYRTNSLRKINSNHGIDIR

ANSLFTEQELLNIYSQELLNRGNLAAASDIVRLLALKNFGGVYLDVDMLPGIHSDLFKTI

SRPSSIGLDRWEMIKLEAIMKYKKYINNYTSENFDKLDQQLKDNFKLIIESKSEKSEIFS

KLENLNVSDLEIKIAFALGSVINQALISKQGSYLTNLVIEQVKNRYQFLNQHLNPAIESD

NNFTDTTKIFHDSLFNSATAENSMFLTKIAPYLQVGFMPEARSTISLSGPGAYASAYYDF

INLQENTIEKTLKASDLIEFKFPENNLSQLTEQEINSLWSFDQASAKYQFEKYVRDYTGG

SLSEDNGVDFNKNTALDKNYLLNNKIPSNNVEEAGSKNYVHYIIQLQGDDISYEATCNLF

SKNPKNSIIIQRNMNESAKSYFLSDDGESILELNKYRIPERLKNKEKVKVTFIGHGKDEF

NTSEFARLSVDSLSNEISSFLDTIKLDISPKNVEVNLLGCNMFSYDFNVEETYPGKLLLS

IMDKITSTLPDVNKNSITIGANQYEVRINSEGRKELLAHSGKWINKEEAIMSDLSSKEYI

FFDSIDNKLKAKSKNIPGLASISEDIKTLLLDASVSPDTKFILNNLKLNIESSIGDYIYY

EKLEPVKNIIHNSIDDLIDEFNLLENVSDELYELKKLNNLDEKYLISFEDISKNNSTYSV

RFINKSNGESVYVETEKEIFSKYSEHITKEISTIKNSIITDVNGNLLDNIQLDHTSQVNT

LNAAFFIQSLIDYSSNKDVLNDLSTSVKVQLYAQLFSTGLNTIYDSIQLVNLISNAVNDT

INVLPTITEGIPIVSTILDGINLGAAIKELLDEHDPLLKKELEAKVGVLAINMSLSIAAT

VASIVGIGAEVTIFLLPIAGISAGIPSLVNNELILHDKATSVVNYFNHLSESKKYGPLKT

-continued

EDDKILVPIDDLVISEIDFNNNSIKLGTCNILAMEGGSGHTVTGNIDHFFSSPSISSHIP

SLSIYSAIGIETENLDFSKKIMMLPNAPSRVFWWETGAVPGLRSLENDGTRLLDSIRDLY

PGKFYWRFYAFFDYAITTLKPVYEDTNIKIKLDKDTRNFIMPTITTNEIRNKLSYSFDGA

GGTYSLLLSSYPISTNINLSKDDLWIFNIDNEVREISIENGTIKKGKLIKDVLSKIDINK

NKLIIGNQTIDFSGDIDNKDRYIFLTCELDDKISLIIEINLVAKSYSLLLSGDKNYLISN

LSNTIEKINTLGLDSKNIAYNYTDESNNKYFGAISKTSQKSIIHYKKDSKNILEFYNDST

LEFNSKDFIAEDINVFMKDDINTITGKYYVDNNTDKSIDFSISLVSKNQVKVNGLYLNES

VYSSYLDFVKNSDGHHNTSNFMNLFLDNISFWKLFGFENINFVIDKYFTLVGKTNLGYVE

FICDNNKNIDIYFGEWKTSSSKSTIFSGNGRNVVVEPIYNPDTGEDISTSLDFSYEPLYG

IDRYINKVLIAPDLYTSLININTNYYSNEYYPEIIVLNPNTFHKKVNINLDSSSFEYKWS

TEGSDFILVRYLEESNKKILQKIRIKGILSNTQSFNKMSIDFKDIKKLSLGYIMSNFKSF

NSENELDRDHLGFKIIDNKTYYYDEDSKLVKGLININNSLFYFDPIEFNLVTGWQTINGK

KYYFDINTGAALTSYKIINGKHFYFNNDGVMQLGVFKGPDGFEYFAPANTQNNNIEGQAI

VYQSKFLTLNGKKYYFDNNSKAVTGWRIINNEKYYFNPNNAIAAVGLQVIDNNKYYFNPD

TAIISKGWQTVNGSRYYFDTDTAIAFNGYKTIDGKHFYFDSDCVVKIGVFSTSNGFEYFA

PANTYNNNIEGQAIVYQSKFLTLNGKKYYFDNNSKAVTGLQTIDSKKYYFNTNTAEAATG

WQTIDGKKYYFNTNTAEAATGWQTIDGKKYYFNTNTAIASTGYTIINGKHFYFNTDGIMQ

IGVFKGPNGFEYFAPANTDANNIEGQAILYQNEFLTLNGKKYYFGSDSKAVTGWRIINNK

KYYFNPNNAIAAIHLCTINNDKYYFSYDGILQNGYITIERNNFYFDANNESKMVTGVFKG

PNGFEYFAPANTHNNNIEGQAIVYQNKFLTLNGKKYYFDNDSKAVTGWQTIDGKKYYFNL

NTAEAATGWQTIDGKKYYFNLNTAEAATGWQTIDGKKYYFNTNTFIASTGYTSINGKHFY

FNTDGIMQIGVFKGPNGFEYFAPANTDANNIEGQAILYQNKFLTLNGKKYYFGSDSKAVT

GLRTIDGKKYYFNTNTAVAVTGWQTINGKKYYFNTNTSIASTGYTIISGKHFYFNTDGIM

QIGVFKGPDGFEYFAPANTDANNIEGQAIRYQNRFLYLHDNIYYFGNNSKAATGWVTIDG

NRYYFEPNTAMGANGYKTIDNKNFYFRNGLPQIGVFKGSNGFEYFAPANTDANNIEGQAI

RYQNRFLHLLGKIYYFGNNSKAVTGWQTINGKVYYFMPDTAMAAAGGLFEIDGVIYFFGV

DGVKAPGIYG

SEQ ID NO: 32

- amino acid sequence of Toxin B

MSLVNRKQLEKMANVRFRTQEDEYVAILDALEEYHNMSENTVVEKYLKLKDINSLTDIYI

DTYKKSGRNKALKKFKEYLVTEVLELKNNNLTPVEKNLHFVWIGGQINDTAINYINQWKD

VNSDYNVNVFYDSNAFLINTLKKTVVESAINDTLESFRENLNDPRFDYNKFFRKRMEIIY

DKQKNFINYYKAQREENPELIIDDIVKTYLSNEYSKEIDELNTYIEESLNKITQNSGNDV

RNFEEFKNGESFNLYEQELVERWNLAAASDILRISALKEIGGMYLDVDMLPGIQPDLFES

IEKPSSVTVDFWEMTKLEAIMKYKEYIPEYTSEHFDMLDEEVQSSFESVLASKSDKSEIF

SSLGDMEASPLEVKIAFNSKGIINQGLISVKDSYCSNLIVKQIENRYKILNNSLNPAISE

DNDFNTTTNTFIDSIMAEANADNGRFMMELGKYLRVGFFPDVKTTINLSGPEAYAAAYQD

LLMFKEGSMNIHLIEADLRNFEISKTNISQSTEQEMASLWSFDDARAKAQFEEYKRNYFE

GSLGEDDNLDFSQNIVVDKEYLLEKISSLARSSERGYIHYIVQLQGDKISYEAACNLFAK

TPYDSVLFQKNIEDSEIAYYYNPGDGEIQEIDKYKIPSIISDRPKIKLTFIGHGKDEFNT

DIFAGFDVDSLSTEIEAAIDLAKEDISPKSIEINLLGCNMFSYSINVEETYPGKLLLKVK

-continued

DKISELMPSISQDSIIVSANQYEVRINSEGRRELLDHSGEWINKEESIIKDISSKEYISF

NPKENKITVKSKNLPELSTLLQEIRNNSNSSDIELEEKVMLTECEINVISNIDTQIVEER

IEEAKNLTSDSINYIKDEFKLIESISDALCDLKQQNELEDSHFISFEDISETDEGFSIRF

INKETGESIFVETEKTIFSEYANHITEEISKIKGTIFDTVNGKLVKKVNLDTTHEVNTLN

AAFFIQSLIEYNSSKESLSNLSVAMKVQVYAQLFSTGLNTITDAAKVVELVSTALDETID

LLPTLSEGLPIIATIIDGVSLGAAIKELSETSDPLLRQEIEAKIGIMAVNLTTATTAIIT

SSLGIASGFSILLVPLAGISAGIPSLVNNELVLRDKATKVVDYFKHVSLVETEGVFTLLD

DKIMMPQDDLVISEIDFNNNSIVLGKCEIWRMEGGSGHTVTDDIDHFFSAPSITYREPHL

SIYDVLEVQKEELDLSKDLMVLPNAPNRVFAWETGWTPGLRSLENDGTKLLDRIRDNYEG

EFYWRYFAFIADALITTLKPRYEDTNIRINLDSNTRSFIVPIITTEYIREKLSYSFYGSG

GTYALSLSQYNMGINIELSESDVWIIDVDNVVRDVTIESDKIKKGDLIEGILSTLSIEEN

KIILNSHEINFSGEVNGSNGFVSLTFSILEGINAIIEVDLLSKSYKLLISGELKILMLNS

NHIQQKIDYIGFNSELQKNIPYSFVDSEGKENGFINGSTKEGLFVSELPDVVLISKVYMD

DSKPSFGYYSNNLKDVKVITKDNVNILTGYYLKDDIKISLSLTLQDEKTIKLNSVHLDES

GVAEILKFMNRKGNTNTSDSLMSFLESMNIKSIFVNFLQSNIKFILDANFIISGTTSIGQ

FEFICDENDNIQPYFIKFNTLETNYTLYVGNRQNMIVEPNYDLDDSGDISSTVINFSQKY

LYGIDSCVNKVVISPNIYTDEINITPVYETNNTYPEVIVLDANYINEKINVNINDLSIRY

VWSNDGNDFILMSTSEENKVSQVKIRFVNVFKDKTLANKLSFNFSDKQDVPVSEIILSFT

PSYYEDGLIGYDLGLVSLYNEKFYINNFGMMVSGLIYINDSLYYFKPPVNNLITGFVTVG

DDKYYFNPINGGAASIGETIIDDKNYYFNQSGVLQTGVFSTEDGFKYFAPANTLDENLEG

EAIDFTGKLIIDENIYYFDDNYRGAVEWKELDGEMHYFSPETGKAFKGLNQIGDYKYYFN

SDGVMQKGFVSINDNKHYFDDSGVMKVGYTEIDGKHFYFAENGEMQIGVFNTEDGFKYFA

HHNEDLGNEEGEEISYSGILNFNNKIYYFDDSFTAVVGWKDLEDGSKYYFDEDTAEAYIG

LSLINDGQYYFNDDGIMQVGFVTINDKVFYFSDSGIIESGVQNIDDNYFYIDDNGIVQIG

VFDTSDGYKYFAPANTVNDNIYGQAVEYSGLVRVGEDVYYFGETYTIETGWIYDMENESD

KYYFNPETKKACKGINLIDDIKYYFDEKGIMRTGLISFENNNYYFNENGEMQFGYINIED

KMFYFGEDGVMQIGVFNTPDGFKYFAHQNTLDENFEGESINYTGWLDLDEKRYYFTDEYI

AATGSVIIDGEEYYFDPDTAQLVISE

SEQ ID NO: 33

- amino acid sequence of CDTb" C39 when expressed in fusion with
GST.

LMSDWEDEDLDTDNDNIPDSYERNGYTIKDLIAVKWEDSFAEQGYKKYVSNYLESNTAGDPYTDYEKASGSFDKA

IKTEARDPLVAAYPIVGVGMEKLIISTNEHASTDQGKTVSRATTNSKTESNTAGVSVNVGYQNGFTANVTTNYSH

TTDNSTAVQDSNGESWNTGLSINKGESAYINANVRYYNTGTAPMYKVTPTTNLVLDGDTLSTIKAQENQIGNNLS

PGDTYPKKGLSPLALNTMDQFSSRLIPINYDQLKKLDAGKQIKLETTQVSGNFGTKNSSGQIVTEGNSWSDYISQ

IDSISASIILDTENESYERRVTAKNLQDPEDKTPELTIGEAIEKAFGATKKDGLLYFNDIPIDESCVELIFDDNT

ANKIKDSLKTLSDKKIYNVKLERGMNILIKTPTYFTNFDDYNNYPSTWSNVNTTNQDGLQGSANKLNGETKIKIP

MSELKPYKRYVFSGYSKDPLTSNSIIVKIKAKEEKTDYLVPEQGYTKFSYEFETTEKDSSNIEITLIGSGTTYLD

NLSITELNSTPEILDEPEVKIPTDQEIMDAHKIYEADLNENPSTGNTYINGMYFAPTQTNKEALDYIQKYRVEAT

LQYSGFKDIGTKDKEMRNYLGDPNQPKTNYVNLRSYFTGGENIMTYKKLRIYAITPDDRELLVLSVD

Remarks:
The protein tested in the cytotoxicity assay was obtained after
cleavage of the GST by PreScission protease -continued Following experimental results, it is demonstrated that the mature CDTb (without SP and pro-domain) starts at the Ser212 (in red and underlined in the sequence).

SEQ ID NO: 34

- amino acid sequence of CdtB receptor binding domain with linker in N-term of sequence, from aa 620-876 (C52)

MTNFDDYNNYPSTWSNVNTTNQDGLQGSANKLNGETKIKIPMSELKPYKRYVFSGYSKDPLTSNSIIVKIKAKEE

KTDYLVPEQGYTKFSYEFETTEKDSSNIEITLIGSGTTYLDNLSITELNSTPEILDEPEVKIPTDQEIMDAHKIY

FADLNFNPSTGNTYINGMYFAPTQTNKEALDYIQKYRVEATLQYSGFKDIGTKDKEMRNYLGDPNQPKTNYVNLR

SYFTGGENIMTYKKLRIYAITPDDRELLVLSVDGGHHHHHH

SEQ ID NO: 35

- Nucleotide sequence of C52

ATGACCAATTTTGATGATTATAACAATTATCCGAGCACTTGGAGCAATGTGAATACCACCAATCAGGATGGTCTG

CAGGGTAGCGCAAATAAACTGAATGGTGAAACCAAAATCAAAATTCCGATGAGCGAACTGAAACCGTATAAACGT

TATGTGTTTAGCGGCTATAGCAAAGATCCGCTGACCAGCAATAGCATTATTGTGAAAATCAAAGCCAAAGAAGAA

AAAACCGATTATCTGGTTCCGGAACAGGGTTATACCAAATTTAGCTATGAATTTGAAACCACCGAAAAAGATAGC

AGTAATATTGAAATTACCCTGATTGGTAGCGGCACCACCTATCTGGATAATCTGAGTATTACCGAACTGAATAGC

ACACCGGAAATTCTGGATGAACCGGAAGTGAAAATTCCGACCGATCAAGAAATTATGGATGCCCATAAAATCTAT

TTTGCCGATCTGAACTTTAATCCGAGCACCGGCAATACCTATATTAACGGCATGTATTTTGCACCGACCCAGACC

AATAAAGAAGCCCTGGATTATATTCAGAAATATCGTGTTGAAGCCACCCTGCAGTATAGCGGTTTTAAAGATATT

GGCACCAAAGATAAAGAAATGCGTAATTATCTGGGCGATCCGAATCAGCCGAAAACCAATTATGTTAATCTGCGC

AGCTATTTTACCGGTGGCGAAAACATTATGACCTACAAAAAACTGCGCATTTATGCCATTACACCGGATGATCGT

GAACTGCTGGTTCTGAGCGTTGATGGCGGTCACCACCATCATCATCATTAA

SEQ ID NO: 36

- amino acid sequence of CdtB receptor binding domain without linker in N-term of sequence, from aa 636-876 (C55)

MNTTNQDGLQGSANKLNGETKIKIPMSELKPYKRYVFSGYSKDPLTSNSIIVKIKAKEEKTDYLVPEQGYTKFSY

EFETTEKDSSNIEITLIGSGTTYLDNLSITELNSTPEILDEPEVKIPTDQEIMDAHKIYEADLNENPSTGNTYIN

GMYFAPTQTNKEALDYIQKYRVEATLQYSGFKDIGTKDKEMRNYLGDPNQPKTNYVNLRSYFTGGENIMTYKKLR

IYAITPDDRELLVLSVDGGHHHHHH

SEQ ID NO: 37

- nucleotide sequence of C55

ATGAATACCACCAATCAGGATGGTCTGCAGGGTAGCGCAAATAAACTGAATGGTGAAACCAAAATCAAAATTCCGATGAG

CGAACTGAAACCGTATAAACGTTATGTGTTTAGCGGCTATAGCAAAGATCCGCTGACCAGCAATAGCATTATTGTGAAAA

TCAAAGCCAAAGAAGAAAAAACCGATTATCTGGTTCCGGAACAGGGTTATACCAAATTTAGCTATGAATTTGAAACCACC

GAAAAAGATAGCAGTAATATTGAAATTACCCTGATTGGTAGCGGCACCACCTATCTGGATAATCTGAGTATTACCGAACT

GAATAGCACACCGGAAATTCTGGATGAACCGGAAGTGAAAATTCCGACCGATCAAGAAATTATGGATGCCCATAAAATCT

ATTTTGCCGATCTGAACTTTAATCCGAGCACCGGCAATACCTATATTAACGGCATGTATTTTGCACCGACCCAGACCAAT

AAAGAAGCCCTGGATTATATTCAGAAATATCGTGTTGAAGCCACCCTGCAGTATAGCGGTTTTAAAGATATTGGCACCAA

AGATAAAGAAATGCGTAATTATCTGGGCGATCCGAATCAGCCGAAAACCAATTATGTTAATCTGCGCAGCTATTTTACCG

GTGGCGAAAACATTATGACCTACAAAAAACTGCGCATTTATGCCATTACACCGGATGATCGTGAACTGCTGGTTCTGAGC

GTTGATGGCGGTCACCACCATCATCATCATTAA

SEQ ID NO: 38

- amino acid sequence of CDTb prodomain sequence (long, aa43-211) (C58)

MEIVNEDILPNNGLMGYYFTDEHFKDLKLMAPIKDGNLKFEEKKVDKLLDKDKSDVKSIRWTGRIIPSKDGEYTL

STDRDDVLMQVNTESTISNTLKVNMKKGKEYKVRIELQDKNLGSIDNLSSPNLYWELDGMKKIIPEENLFLRDYS

NIEKDDPFIPNNNFFDPKLM

-continued

SEQ ID NO: 39

- amino acid sequence of CDTb prodomain sequence (short, aa43-186)
(C59)
MEIVNEDILPNNGLMGYYFTDEHFKDLKLMAPIKDGNLKFEEKKVDKLLDKDKSDVKSIRWTGRIIPSKDGEYTL

STDRDDVLMQVNTESTISNTLKVNMKKGKEYKVRIELQDKNLGSIDNLSSPNLYWELDGMKKIIPEENLF

SEQ ID NO: 40

- amino acid sequence of Fusion CDTa N-term with
linker (aa44-268) to CDTb receptor binding domain
with linker in N term of sequence (aa621-876) (C60)
CDTa part of the fusion is underlined.
MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISL

EKFNEFKETIQNKLFKQDGFKDISLYEPGKGDEKPTPLLMHLKLPRNTGMLPYTNTNNVSTL

IEQGYSIKIDKIVRIVIDGKHYIKAEASVVSSLDFKDDTNFDDYNNYPSTWSNVNTTNQDGL

QGSANKLNGETKIKIPMSELKPYKRYVFSGYSKDPLTSNSIIVKIKAKEEKTDYLVPEQGYT

KFSYEFETTEKDSSNIEITLIGSGTTYLDNLSITELNSTPEILDEPEVKIPTDQEIMDAHKI

YFADLNFNPSTGNTYINGMYFAPTQTNKEALDYIQKYRVEATLQYSGFKDIGTKDKEMRNYL

GDPNQPKTNYVNLRSYFTGGENIMTYKKLRIYAITPDDRELLVLSVDGGHHHHHH

SEQ ID NO: 41

- amino acid sequence of Fusion CDTa N-term with
linker (aa44-268) to CDTb receptor binding domain
without linker in N term of sequence (aa636-876) (C61)
CDTa part of the fusion is underlined.
MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISL

EKFNEFKETIQNKLFKQDGFKDISLYEPGKGDEKPTPLLMHLKLPRNTGMLPYTNTNNVSTL

IEQGYSIKIDKIVRIVIDGKHYIKAEASVVSSLDFKDDNTTNQDGLQGSANKLNGETKIKIP

MSELKPYKRYVFSGYSKDPLTSNSIIVKIKAKEEKTDYLVPEQGYTKFSYEFETTEKDSSNI

EITLIGSGTTYLDNLSITELNSTPEILDEPEVKIPTDQEIMDAHKIYFADLNFNPSTGNTYI

NGMYFAPTQTNKEALDYIQKYRVEATLQYSGFKDIGTKDKEMRNYLGDPNQPKTNYVNLRSY

FTGGENIMTYKKLRIYAITPDDRELLVLSVDGGHHHHHH

SEQ ID NO: 42

- amino acid sequence of Fusion CDTa N-term without
linker (aa44-260) to CDTb receptor binding domain
with linker in N term of sequence (aa621-876) (C62)
CDTa part of the fusion is underlined.
MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISL

EKFNEFKETIQNKLFKQDGFKDISLYEPGKGDEKPTPLLMHLKLPRNTGMLPYTNTNNVSTL

IEQGYSIKIDKIVRIVIDGKHYIKAEASVVSTNFDDYNNYPSTWSNVNTTNQDGLQGSANKL

NGETKIKIPMSELKPYKRYVFSGYSKDPLTSNSIIVKIKAKEEKTDYLVPEQGYTKFSYEFE

TTEKDSSNIEITLIGSGTTYLDNLSITELNSTPEILDEPEVKIPTDQEIMDAHKIYFADLNF

NPSTGNTYINGMYFAPTQTNKEALDYIQKYRVEATLQYSGFKDIGTKDKEMRNYLGDPNQPK

TNYVNLRSYFTGGENIMTYKKLRIYAITPDDRELLVLSVDGGHHHHHH

SEQ ID NO: 43

- amino acid sequence of Fusion CDTa N-term without
linker (aa44-260) to CDTb receptor binding domain
without linker in N term of sequence (aa636-876) (C63)
CDTa part of the fusion is underlined.
MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISL

EKFNEFKETIQNKLFKQDGFKDISLYEPGKGDEKPTPLLMHLKLPRNTGMLPYTNTNNVSTL

-continued

IEQGYSIKIDKIVRIVIDGKHYIKAEASVVSNTTNQDGLQGSANKLNGETKIKIPMSELKPY

KRYVFSGYSKDPLTSNSIIVKIKAKEEKTDYLVPEQGYTKFSYEFETTEKDSSNIEITLIGS

GTTYLDNLSITELNSTPEILDEPEVKIPTDQEIMDAHKIYFADLNFNPSTGNTYINGMYFAP

TQTNKEALDYIQKYRVEATLQYSGFKDIGTKDKEMRNYLGDPNQPKTNYVNLRSYFTGGENI

MTYKKLRIYAITPDDRELLVLSVDGGHHHHHH

SEQ ID NO: 44

- amino acid sequence of Fusion F2- CDTb receptor binding domain with linker in N term of sequence (aa621-876) (C64)
F2 sequence is underlined.

MGWQTIDGKKYYFNTNTAIASTGYTIINGKHEYENTDGIMQIGVFKGPNGFEYFAPANTDANNIEGQAILYQNEF

LTLNGKKYYFGSDSKAVTGWRIINNKKYYFNPNNAIAAIHLCTINNDKYYFSYDGILQNGYITIERNNEYFDANN

ESKMVTGVFKGPNGFEYFAPANTHNNNIEGQAIVYQNKFLTLNGKKYYFDNDSKAVTGWQTIDGKKYYFNLNTAE

AATGWQTIDGKKYYFNLNTAEAATGWQTIDGKKYYENTNTFIASTGYTSINGKHEYENTDGIMQIGVFKGPNGFE

YFAPANTDANNIEGQAILYQNKFLTLNGKKYYFGSDSKAVTGLRTIDGKKYYFNTNTAVAVTGWQTINGKKYYFN

TNTSIASTGYTIISGKHEYENTDGIMQIGVFKGPDGFEYEAPANTDANNIEGQAIRYQNRFLYLHDNIYYFGNNS

KAATGWVTIDGNRYYFEPNTAMGANGYKTIDNKNEYERNGLPQIGVFKGSNGFEYFAPANTDANNIEGQAIRYQN

RFLHLLGKIYYFGNNSKAVTGWQTINGKVYYFMPDTAMAAAGGLNQIGDYKYYFNSDGVMQKGFVSINDNKHYFD

DSGVMKVGYTEIDGKHFYFAENGEMQIGVENTEDGEKYFAHHNEDLGNEEGEEISYSGILNFNNKIYYFDDSFTA

VVGWKDLEDGSKYYFDEDTAEAYIGLSLINDGQYYFNDDGIMQVGFVTINDKVEYESDSGIIESGVQNIDDNYFY

IDDNGIVQIGVFDTSDGYKYFAPANTVNDNIYGQAVEYSGLVRVGEDVYYFGETYTIETGWIYDMENESDKYYFN

PETKKACKGINLIDDIKYYFDEKGIMRTGLISFENNNYYFNENGEMQFGYINIEDKMFYFGEDGVMQIGVFNTPD

GFKYFAHQNTLDENFEGESINYTGWLDLDEKRYYFTDEYIAATGSVIIDGEEYYFDPDTAQLVISETNFDDYNNY

PSTWSNVNTTNQDGLQGSANKLNGETKIKIPMSELKPYKRYVFSGYSKDPLTSNSIIVKIKAKEEKTDYLVPEQG

YTKFSYEFETTEKDSSNIEITLIGSGTTYLDNLSITELNSTPEILDEPEVKIPTDQEIMDAHKIYEADLNENPST

GNTYINGMYFAPTQTNKEALDYIQKYRVEATLQYSGFKDIGTKDKEMRNYLGDPNQPKTNYVNLRSYFTGGENIM

TYKKLRIYAITPDDRELLVLSVDGGHHHHHH

SEQ ID NO: 45

- amino acid sequence of Fusion of F2 to CDTb receptor binding domain without linker in N term of sequence (aa636-876) with 2 heterogeneous Gly residues between F2 and CTDb sequences (C65)
F2 sequence is underlined.

MGWQTIDGKKYYFNTNTAIASTGYTIINGKHFYFNTDGIMQIGVFKGPNGFEYFAPANTDANNIEGQAILYQNEF

LTLNGKKYYFGSDSKAVTGWRIINNKKYYFNPNNAIAAIHLCTINNDKYYFSYDGILQNGYITIERNNFYFDANN

ESKMVTGVFKGPNGFEYFAPANTHNNNIEGQAIVYQNKFLTLNGKKYYFDNDSKAVTGWQTIDGKKYYFNLNTAE

AATGWQTIDGKKYYFNLNTAEAATGWQTIDGKKYYFNTNTFIASTGYTSINGKHFYFNTDGIMQIGVFKGPNGFE

YFAPANTDANNIEGQAILYQNKFLTLNGKKYYFGSDSKAVTGLRTIDGKKYYFNTNTAVAVTGWQTINGKKYYFN

TNTSIASTGYTIISGKHFYFNTDGIMQIGVFKGPDGFEYFAPANTDANNIEGQAIRYQNRFLYLHDNIYYFGNNS

KAATGWVTIDGNRYYFEPNTAMGANGYKTIDNKNFYFRNGLPQIGVFKGSNGFEYFAPANTDANNIEGQAIRYQN

RFLHLLGKIYYFGNNSKAVTGWQTINGKVYYFMPDTAMAAAGGLNQIGDYKYYFNSDGVMQKGFVSINDNKHYFD

DSGVMKVGYTEIDGKHFYFAENGEMQIGVFNTEDGFKYFAHHNEDLGNEEGEEISYSGILNFNNKIYYFDDSFTA

VVGWKDLEDGSKYYFDEDTAEAYIGLSLINDGQYYFNDDGIMQVGFVTINDKVFYFSDSGIIESGVQNIDDNYFY

IDDNGIVQIGVFDTSDGYKYFAPANTVNDNIYGQAVEYSGLVRVGEDVYYFGETYTIETGWIYDMENESDKYYFN

PETKKACKGINLIDDIKYYFDEKGIMRTGLISFENNNYYFNENGEMQFGYINIEDKMFYFGEDGVMQIGVFNTPD

GFKYFAHQNTLDENFEGESINYTGWLDLDEKRYYFTDEYIAATGSVIIDGEEYYFDPDTAQLVISEGGNVNTTNQ

DGLQGSANKLNGETKIKIPMSELKPYKRYVFSGYSKDPLTSNSIIVKIKAKEEKTDYLVPEQGYTKFSYEFETTE

-continued

KDSSNIEITLIGSGTTYLDNLSITELNSTPEILDEPEVKIPTDQEIMDAHKIYFADLNFNPSTGNTYINGMYFAP

TQTNKEALDYIQKYRVEATLQYSGFKDIGTKDKEMRNYLGDPNQPKTNYVNLRSYFTGGENIMTYKKLRIYAITP

DDRELLVLSVDGGHHHHHH

SEQ ID NO: 46

- amino acid sequence of CDTa without signal peptide, with two mutations (E428Q, E430Q, aa 44-463) (C67)

MVCNTTYKAPIERPEDFLKDKEKAKEWERKEAERIEQKLERSEKEALESYKKDSVEISKYSQTRNYFYDYQIEAN

SREKEYKELRNAISKNKIDKPMYVYYFESPEKFAFNKVIRTENQNEISLEKFNEFKETIQNKLFKQDGFKDISLY

EPGKGDEKPTPLLMHLKLPRNTGMLPYTNTNNVSTLIEQGYSIKIDKIVRIVIDGKHYIKAEASVVSSLDFKDDV

SKGDSWGKANYNDWSNKLTPNELADVNDYMRGGYTAINNYLISNGPVNNPNPELDSKITNIENALKREPIPTNLT

VYRRSGPQEFGLTLTSPEYDFNKLENIDAFKSKWEGQALSYPNFISTSIGSVNMSAFAKRKIVLRITIPKGSPGA

YLSAIPGYAGqYqVLLNHGSKFKINKIDSYKDGTITKLIVDATLIP

SEQ ID NO: 47

- nucleotide sequence of C67

ATGGTTTGCAATACCACCTATAAAGCACCGATTGAACGTCCGGAAGATTTTCTGAAAGATAAAGAAAAAGCCAAA

GAATGGGAACGCAAAGAAGCAGAACGTATTGAACAGAAACTGGAACGTAGCGAAAAAGAAGCACTGGAAAGCTAC

AAAAAAGATAGCGTGGAAATTTCAAAATATAGCCAGACCCGCAATTATTTCTATGATTATCAGATTGAAGCCAAT

AGCCGTGAAAAAGAATATAAAGAACTGCGCAATGCCATTAGCAAAAACAAAATTGATAAACCGATGTATGTGTAT

TATTTCGAAAGTCCGGAAAAATTTGCCTTTAACAAAGTGATTCGCACCGAAAATCAGAATGAAATTAGCCTGGAA

AAATTCAATGAATTTAAAGAAACCATTCAGAATAAACTGTTTAAACAGGATGGCTTTAAAGATATTTCACTGTAT

GAACCGGGTAAAGGTGATGAAAAACCGACACCGCTGCTGATGCATCTGAAACTGCCTCGTAATACCGGTATGCTG

CCGTATACCAATACCAATAATGTTAGCACCCTGATTGAACAGGGCTATAGCATCAAAATTGATAAAATTGTGCGC

ATTGTGATTGATGGCAAACATTATATCAAAGCCGAAGCCAGCGTTGTTTCAAGCCTGGATTTTAAAGATGATGTG

AGCAAAGGCGATAGCTGGGGTAAAGCAAACTATAATGATTGGAGCAATAAACTGACCCCGAATGAACTGGCAGAT

GTGAATGATTATATGCGTGGTGGTTATACCGCCATTAACAATTATCTGATTAGCAATGGTCCGGTGAATAATCCG

AATCCGGAACTGGATAGCAAAATTACCAATATTGAAAATGCCCTGAAACGCGAACCGATTCCGACCAATCTGACC

GTTTATCGTCGTAGCGGTCCGCAAGAATTTGGTCTGACCCTGACCAGTCCGGAATATGACTTTAACAAACTGGAA

AATATTGATGCCTTTAAAAGCAAATGGGAAGGTCAGGCACTGAGCTATCCGAACTTTATTAGCACCAGCATTGGT

AGCGTTAATATGAGCGCATTTGCCAAACGTAAAATTGTGCTGCGTATTACCATTCCGAAAGGTAGTCCGGGTGCA

TATCTGAGCGCAATTCCGGGTTATGCCGGTCAATATCAGGTTCTGCTGAATCATGGCAGCAAATTCAAAATTAAC

AAAATTGATAGCTATAAAGATGGCACCATTACCAAACTGATTGTTGATGCAACCCTGATTCCGTAA

SEQ ID NO: 48

- amino acid sequence of CDTa without signal peptide, with seven mutations (R345A, Q350A, N385A, R402A, S388F, E428Q, E430Q, aa 44-463) (C69)

MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISL

EKFNEFKETIQNKLFKQDGFKDISLYEPGKGDEKPTPLLMHLKLPRNTGMLPYTNTNNVSTL

IEQGYSIKIDKIVRIVIDGKHYIKAEASVVSSLDFKDDVSKGDSWGKANYNDWSNKLTPNEL

ADVNDYMRGGYTAINNYLISNGPVNNPNPELDSKITNIENALKREPIPTNLTVYARSGPAEF

GLTLTSPEYDFNKLENIDAFKSKWEGQALSYPAFIFTSIGSVNMSAFAKAKIVLRITIPKGS

PGAYLSAIPGYAGQYQVLLNHGSKFKINKIDSYKDGTITKLIVDATLIP

SEQ ID NO: 49

- nucleotide sequence of C69

ATGGTTTGCAATACCACCTATAAAGCACCGATTGAACGTCCGGAAGATTTTCTGAAAGATAA

AGAAAAAGCCAAAGAATGGGAACGCAAAGAAGCAGAACGTATTGAACAGAAACTGGAACGTA

-continued

GCGAAAAAGAAGCACTGGAAAGCTACAAAAAAGATAGCGTGGAAATTTCAAAATATAGCCAG

ACCCGCAATTATTTCTATGATTATCAGATTGAAGCCAATAGCCGTGAAAAAGAATATAAAGA

ACTGCGCAATGCCATTAGCAAAAACAAAATTGATAAACCGATGTATGTGTATTATTTCGAAA

GTCCGGAAAAATTTGCCTTTAACAAAGTGATTCGCACCGAAAATCAGAATGAAATTAGCCTG

GAAAAATTCAATGAATTTAAAGAAACCATTCAGAATAAACTGTTTAAACAGGATGGCTTTAA

AGATATTTCACTGTATGAACCGGGTAAAGGTGATGAAAAACCGACACCGCTGCTGATGCATC

TGAAACTGCCTCGTAATACCGGTATGCTGCCGTATACCAATACCAATAATGTTAGCACCCTG

ATTGAACAGGGCTATAGCATCAAAATTGATAAAATTGTGCGCATTGTGATTGATGGCAAACA

TTATATCAAAGCCGAAGCCAGCGTTGTTTCAAGCCTGGATTTTAAAGATGATGTGAGCAAAG

GCGATAGCTGGGGTAAAGCAAACTATAATGATTGGAGCAATAAACTGACCCCGAATGAACTG

GCAGATGTGAATGATTATATGCGTGGTGGTTATACCGCCATTAACAATTATCTGATTAGCAA

TGGTCCGGTGAATAATCCGAATCCGGAACTGGATAGCAAAATTACCAATATTGAAAATGCCC

TGAAACGCGAACCGATTCCGACCAATCTGACCGTTTATGCACGTAGCGGTCCGGCAGAATTT

GGTCTGACCCTGACCAGTCCGGAATATGACTTTAACAAACTGGAAAATATTGATGCCTTTAA

AAGCAAATGGGAAGGTCAGGCACTGAGCTATCCGGCATTTATTTTCACCAGCATTGGTAGCG

TTAATATGAGCGCATTTGCCAAAGCAAAAATTGTGCTGCGTATTACCATTCCGAAAGGTAGT

CCGGGTGCATATCTGAGCGCAATTCCGGGTTATGCCGGTCAGTATCAGGTTCTGCTGAATCA

TGGCAGCAAATTCAAAATTAACAAAATTGATAGCTATAAAGATGGCACCATTACCAAACTGA

TTGTTGATGCAACCCTGATTCCG

SEQ ID NO: 50

- amino acid sequence of CDTb without signal sequence and prodomain (mature fragment based on MS data) with Ca2+ binding motif mutation (aa212-876, mut Asp-9-11-13 Ala) (C97) 3 mutated residues in this sequence. Three Asp residues were mutated into Ala. They are highlighted in bold and underlined.

MSDWEDEDLATANANIPDSYERNGYTIKDLIAVKWEDSFAEQGYKKYVSNYLESNTAGDPYTDYEKASGSFDKAI

KTEARDPLVAAYPIVGVGMEKLIISTNEHASTDQGKTVSRATTNSKTESNTAGVSVNVGYQNGFTANVTTNYSHT

TDNSTAVQDSNGESWNTGLSINKGESAYINANVRYYNTGTAPMYKVTPTTNLVLDGDTLSTIKAQENQIGNNLSP

GDTYPKKGLSPLALNTMDQFSSRLIPINYDQLKKLDAGKQIKLETTQVSGNFGTKNSSGQIVTEGNSWSDYISQI

DSISASIILDTENESYERRVTAKNLQDPEDKTPELTIGEATEKAFGATKKDGLLYENDIPIDESCVELIFDDNTA

NKIKDSLKTLSDKKIYNVKLERGMNILIKTPTYFTNFDDYNNYPSTWSNVNTTNQDGLQGSANKLNGETKIKIPM

SELKPYKRYVFSGYSKDPLTSNSIIVKIKAKEEKTDYLVPEQGYTKFSYEFETTEKDSSNIEITLIGSGTTYLDN

LSITELNSTPEILDEPEVKIPTDQEIMDAHKIYEADLNENPSTGNTYINGMYEAPTQTNKEALDYIQKYRVEATL

QYSGFKDIGTKDKEMRNYLGDPNQPKTNYVNLRSYFTGGENIMTYKKLRIYAITPDDRELLVLSVDHHHHHH

SEQ ID NO: 51

- amino acid sequence of CDTb with prodomain removed (CDTb", aa212-876) (C55)

MSDWEDEDLDTDNDNIPDSYERNGYTIKDLIAVKWEDSFAEQGYKKYVSNYLESNTAGDPYTDYEKASGSFDKAI

KTEARDPLVAAYPIVGVGMEKLIISTNEHASTDQGKTVSRATTNSKTESNTAGVSVNVGYQNGFTANVTTNYSHT

TDNSTAVQDSNGESWNTGLSINKGESAYINANVRYYNTGTAPMYKVTPTTNLVLDGDTLSTIKAQENQIGNNLSP

GDTYPKKGLSPLALNTMDQFSSRLIPINYDQLKKLDAGKQIKLETTQVSGNEGTKNSSGQIVTEGNSWSDYISQI

DSISASIILDTENESYERRVTAKNLQDPEDKTPELTIGEATEKAFGATKKDGLLYENDIPIDESCVELIFDDNTA

NKIKDSLKTLSDKKIYNVKLERGMNILIKTPTYFTNFDDYNNYPSTWSNVNTTNQDGLQGSANKLNGETKIKIPM

SELKPYKRYVFSGYSKDPLTSNSIIVKIKAKEEKTDYLVPEQGYTKFSYEFETTEKDSSNIEITLIGSGTTYLDN

-continued

LSITELNSTPEILDEPEVKIPTDQEIMDAHKIYEADLNENPSTGNTYINGMYEAPTQTNKEALDYIQKYRVEATL

QYSGFKDIGTKDKEMRNYLGDPNQPKTNYVNLRSYFTGGENIMTYKKLRIYAITPDDRELLVLSVDHHHHHH

SEQ ID NO: 52

- amino acid sequence of CDTa without signal peptide, with five mutations (R345A, Q350A, N385A, R402A, S388F, aa 44-463) (C107)

MVCNTTYKAPIERPEDFLKDKEKAKEWERKEAERIEQKLERSEKEALESYKKDSVEISKYSQ

TRNYFYDYQIEANSREKEYKELRNAISKNKIDKPMYVYYFESPEKFAFNKVIRTENQNEISLE

KFNEFKETIQNKLFKQDGFKDISLYEPGKGDEKPTPLLMHLKLPRNTGMLPYTNTNNVSTLIE

QGYSIKIDKIVRIVIDGKHYIKAEASVVSSLDFKDDVSKGDSWGKANYNDWSNKLTPNELAD

VNDYMRGGYTAINNYLISNGPVNNPNPELDSKITNIENALKREPIPTNLTVYARSGPAEFGLT

LTSPEYDFNKLENIDAFKSKWEGQALSYPAFIFTSIGSVNMSAFAKAKIVLRITIPKGSPGAYL

SAIPGYAGEYEVLLNHGSKFKINKIDSYKDGTITKLIVDATLIPHHHHHH**

SEQ ID NO: 53

- Polynucleotide sequence of CDTa without signal peptide, with five mutations (R345A, Q350A, N385A, R402A, S388F, aa 44-463) (C107)

ATGGTTTGCAATACCACCTATAAAGCACCGATTGAACGTCCGGAAGATTTTCTGAAAGA

TAAAGAAAAAGCCAAAGAATGGGAACGCAAAGAAGCAGAACGTATTGAACAGAAACTG

GAACGTAGCGAAAAAGAAGCACTGGAAAGCTACAAAAAAGATAGCGTGGAAATTTCAAA

ATATAGCCAGACCCGCAATTATTTCTATGATTATCAGATTGAAGCCAATAGCCGTGAAAA

AGAATATAAAGAACTGCGCAATGCCATTAGCAAAAACAAAATTGATAAACCGATGTATGT

GTATTATTTCGAAAGTCCGGAAAAATTTGCCTTTAACAAAGTGATTCGCACCGAAAATCA

GAATGAAATTAGCCTGGAAAAATTCAATGAATTTAAAGAAACCATTCAGAATAAACTGT

TTAAACAGGATGGCTTTAAAGATATTTCACTGTATGAACCGGGTAAAGGTGATGA

AAAACCGACACCGCTGCTGATGCATCTGAAACTGCCTCGTAATACCGGTATGCTG

CCGTATACCAATACCAATAATGTTAGCACCCTGATTGAACAGGGCTATAGCATCA

AAATTGATAAAATTGTGCGCATTGTGATTGATGGCAAACATTATATCAAAGCCGA

AGCCAGCGTTGTTTCAAGCCTGGATTTTAAAGATGATGTGAGCAAAGGCGATAG

CTGGGGTAAAGCAAACTATAATGATTGGAGCAATAAACTGACCCCGAATGAACT

GGCAGATGTGAATGATTATATGCGTGGTGGTTATACCGCCATTAACAATTATCTG

ATTAGCAATGGTCCGGTGAATAATCCGAATCCGGAACTGGATAGCAAAATTACC

AATATTGAAAATGCCCTGAAACGCGAACCGATTCCGACCAATCTGACCGTTTATG

CACGTAGCGGTCCGGCAGAATTTGGTCTGACCCTGACCAGTCCGGAATATGACTT

TAACAAACTGGAAAATATTGATGCCTTTAAAAGCAAATGGGAAGGTCAGGCACT

GAGCTATCCGGCATTTATTTTCACCAGCATTGGTAGCGTTAATATGAGCGCATTT

GCCAAAGCAAAAATTGTGCTGCGTATTACCATTCCGAAAGGTAGTCCGGGTGCA

TATCTGAGCGCAATTCCGGGTTATGCCGGTgAaTATgAaGTTCTGCTGAATCATGG

CAGCAAATTCAAAATTAACAAAATTGATAGCTATAAAGATGGCACCATTACCAA

ACTGATTGTTGATGCAACCCTGATTCCGCACCACCATCATCATCATTAATAA

SEQ ID NO: 54

- Amino acid sequence of CDTa without signal peptide, with six mutations (R345A, Q350A, N385A, R402A, S388F, E430Q, aa 44-463) (C108)

MVCNTTYKAPIERPEDFLKDKEKAKEWERKEAERIEQKLERSEKEALESYKKDSVEI

SKYSQTRNYFYDYQIEANSREKEYKELRNAISKNKIDKPMYVYYFESPEKFAFNKVIR

-continued

TENQNEISLEKFNEFKETIQNKLFKQDGFKDISLYEPGKGDEKPTPLLMHLKLPRNTG

MLPYTNTNNVSTLIEQGYSIKIDKIVRIVIDGKHYIKAEASVVSSLDFKDDVSKGDSW

GKANYNDWSNKLTPNELADVNDYMRGGYTAINNYLISNGPVNNPNPELDSKITNIE

NALKREPIPTNLTVYARSGPAEFGLTLTSPEYDFNKLENIDAFKSKWEGQALSYPAFIF

TSIGSVNMSAFAKAKIVLRITIPKGSPGAYLSAIPGYAGEYQVLLNHGSKFKIN

KIDSYKDGTITKLIVDATLIPHHHHHH**

SEQ ID NO: 55

- Polynucleotide sequence of CDTa without
signal peptide, with six mutations (R345A,
Q350A, N385A, R402A, S388F, E430Q, aa 44-463)
(C108)

ATGGTTTGCAATACCACCTATAAAGCACCGATTGAACGTCCGGAAGATTTTCTGA

AAGATAAAGAAAAAGCCAAAGAATGGGAACGCAAAGAAGCAGAACGTATTGAA

CAGAAACTGGAACGTAGCGAAAAAGAAGCACTGGAAAGCTACAAAAAAGATAG

CGTGGAAATTTCAAAATATAGCCAGACCCGCAATTATTTCTATGATTATCAGATT

GAAGCCAATAGCCGTGAAAAAGAATATAAAGAACTGCGCAATGCCATTAGCAAA

AACAAAATTGATAAACCGATGTATGTGTATTATTTCGAAAGTCCGGAAAAATTTG

CCTTTAACAAAGTGATTCGCACCGAAAATCAGAATGAAATTAGCCTGGAAAAAT

TCAATGAATTTAAAGAAACCATTCAGAATAAACTGTTTAAACAGGATGGCTTTAA

AGATATTTCACTGTATGAACCGGGTAAAGGTGATGAAAAACCGACACCGCTGCT

GATGCATCTGAAACTGCCTCGTAATACCGGTATGCTGCCGTATACCAATACCAAT

AATGTTAGCACCCTGATTGAACAGGGCTATAGCATCAAAATTGATAAAATTGTGC

GCATTGTGATTGATGGCAAACATTATATCAAAGCCGAAGCCAGCGTTGTTTCAAG

CCTGGATTTTAAAGATGATGTGAGCAAAGGCGATAGCTGGGGTAAAGCAAACTA

TAATGATTGGAGCAATAAACTGACCCCGAATGAACTGGCAGATGTGAATGATTA

TATGCGTGGTGGTTATACCGCCATTAACAATTATCTGATTAGCAATGGTCCGGTG

AATAATCCGAATCCGGAACTGGATAGCAAAATTACCAATATTGAAAATGCCCTG

AAACGCGAACCGATTCCGACCAATCTGACCGTTTATGCACGTAGCGGTCCGGCA

GAATTTGGTCTGACCCTGACCAGTCCGGAATATGACTTTAACAAACTGGAAAATA

TTGATGCCTTTAAAAGCAAATGGGAAGGTCAGGCACTGAGCTATCCGGCATTTAT

TTTCACCAGCATTGGTAGCGTTAATATGAGCGCATTTGCCAAAGCAAAAATTGTG

CTGCGTATTACCATTCCGAAAGGTAGTCCGGGTGCATATCTGAGCGCAATTCCGG

GTTATGCCGGTgAaTATcAaGTTCTGCTGAATCATGGCAGCAAATTCAAAATTAAC

AAAATTGATAGCTATAAAGATGGCACCATTACCAAACTGATTGTTGATGCAACCC

TGATTCCGCACCACCATCATCATCATTAATAA

SEQ ID NO: 56

- Amino acid sequence of CDTa without signal
peptide, with six mutations (R345A, Q350A,
N385A, R402A, S388F, E428Q, aa 44-463) (C110

MVCNTTYKAPIERPEDFLKDKEKAKEWERKEAERIEQKLERSEKEALESYKKDSVEI

SKYSQTRNYFYDYQIEANSREKEYKELRNAISKNKIDKPMYVYYFESPEKFAFNKVIR

TENQNEISLEKFNEFKETIQNKLFKQDGFKDISLYEPGKGDEKPTPLLMHLKLPRNTG

MLPYTNTNNVSTLIEQGYSIKIDKIVRIVIDGKHYIKAEASVVSSLDFKDDVSKGDSW

GKANYNDWSNKLTPNELADVNDYMRGGYTAINNYLISNGPVNNPNPELDSKITNIE

NALKREPIPTNLTVYARSGPAEFGLTLTSPEYDFNKLENIDAFKSKWEGQALSYPAFIF

-continued

TSIGSVNMSAFAKAKIVLRITIPKGSPGAYLSAIPGYAGQYEVLLNHGSKFKIN

KIDSYKDGTITKLIVDATLIPHHHHHH**

The invention claimed is:

1. An immunogenic composition comprising a fusion protein, said fusion protein comprising a *Clostridium difficile* binary toxin a (CDTa) protein sequence covalently linked to a *Clostridium difficile* binary toxin b (CDTb) protein sequence, wherein:

(a) the CDTa protein sequence comprises the CDTa C-terminal domain and comprises an amino acid substitution that reduces CDTa enzymatic activity, and (b) the CDTb protein sequence lacks the CDTb prodomain sequence and comprises a sequence having at least 95% sequence identity to SEQ ID NO:9.

2. A vaccine comprising the immunogenic composition of claim 1 and a pharmaceutically acceptable excipient.

3. A method of preventing or treating *C. difficile* disease comprising administering the vaccine of claim 2 to a human subject.

4. The immunogenic composition of claim 1, wherein said CDTa amino acid substitution is selected from R345K, Q350A, N385A, R402A, S388F, E428Q, and E430Q, where the amino acid numbering corresponds to that of SEQ ID NO: 1.

5. An immunogenic composition comprising a fusion protein, said fusion protein comprising a *Clostridium difficile* binary toxin a (CDTa) protein sequence covalently linked to a *Clostridium difficile* binary toxin b (CDTb) protein sequence, wherein:

(a) the CDTa protein sequence comprises the CDTa C-terminal domain and comprises an amino acid substitution that reduces CDTa enzymatic activity, where the CDTa sequence is selected from a sequence having at least 95% sequence identity to SEQ ID NO:46, a sequence having at least 95% sequence identity to SEQ ID NO:48, a sequence having at least 95% sequence identity to SEQ ID NO:52, or a sequence having at least 95% sequence identity to SEQ ID NO:54, and (b) the CDTb protein sequence lacks the CDTb prodomain sequence and comprises a sequence having at least 95% sequence identity to SEQ ID NO:9.

6. The immunogenic composition of claim 1, wherein in said fusion protein, the CDTa protein sequence and CDTb protein sequence are covalently linked via a peptide linker.

7. The immunogenic composition of claim 5, wherein in said fusion protein, the CDTa protein sequence and CDTb protein sequence are covalently linked via a peptide linker.

8. A vaccine comprising the immunogenic composition of claim 5 and a pharmaceutically acceptable excipient.

9. A method of preventing or treating *C. difficile* disease comprising administering the vaccine of claim 8 to a human subject.

10. The immunogenic composition of claim 1, wherein the CDTb protein sequence lacks the CDTb prodomain sequence and comprises the sequence of amino acids 212-876 of SEQ ID NO: 3.

11. The immunogenic composition of claim 1, wherein the CDTb protein sequence lacks the CDTb prodomain sequence and comprises SEQ ID NO:9.

12. The immunogenic composition of claim 5, wherein the CDTa protein sequence comprises the CDTa C-terminal domain and comprises an amino acid substitution that reduces CDTa enzymatic activity, where the CDTa sequence is selected from SEQ ID NO: 46, SEQ ID NO: 48, SEQ ID NO: 52, or SEQ ID NO: 54.

13. The immunogenic composition of claim 5, wherein the CDTb protein sequence lacks the CDTb prodomain sequence and comprises the sequence of amino acids 212-876 of SEQ ID NO: 3.

14. The immunogenic composition of claim 5, wherein the CDTb protein sequence lacks the CDTb prodomain sequence and comprises SEQ ID NO: 9.

* * * * *